US010357577B2

(12) United States Patent
Guise et al.

(10) Patent No.: US 10,357,577 B2
(45) Date of Patent: Jul. 23, 2019

(54) BACTERIAL NITROREDUCTASE ENZYMES AND METHODS RELATING THERETO

(75) Inventors: Christopher Paul Guise, Auckland (NZ); David Francis Ackerley, Wellington (NZ); Amir Ashoorzadeh, Manukau (NZ); Janine Naomi Copp, Nelson (NZ); Jack Urquhart Flanagan, Auckland (NZ); Alexandra Marie Mowday, Auckland (NZ); Adam Vorn Patterson, Waiheke Island (NZ); Gareth Adrian Prosser, Wellington (NZ); Jeffrey Bruce Smaill, Auckland (NZ); Sophie Phillipa Syddall, Melbourne (AU); Elsie May Williams, Wellington (NZ)

(73) Assignees: AUCKLAND UNISERVICES LIMITED, Auckland (NZ); VICTORIA LINK LIMITED, Wellington (NZ)

( * ) Notice: Subject to any disclaimer, the term of this patent is extended or adjusted under 35 U.S.C. 154(b) by 105 days.

(21) Appl. No.: 13/810,434

(22) PCT Filed: Jul. 18, 2011

(86) PCT No.: PCT/NZ2011/000137
§ 371 (c)(1),
(2), (4) Date: Jul. 5, 2013

(87) PCT Pub. No.: WO2012/008860
PCT Pub. Date: Jan. 19, 2012

(65) Prior Publication Data
US 2013/0295011 A1    Nov. 7, 2013

(30) Foreign Application Priority Data

Jul. 16, 2010   (NZ) ........................... 586849

(51) Int. Cl.
| A61K 51/04 | (2006.01) |
| A61K 38/44 | (2006.01) |
| C12Q 1/26 | (2006.01) |
| A61K 47/54 | (2017.01) |
| C12N 9/02 | (2006.01) |
| C12N 9/06 | (2006.01) |

(52) U.S. Cl.
CPC .......... *A61K 51/0495* (2013.01); *A61K 38/44* (2013.01); *A61K 47/556* (2017.08); *C12N 9/0028* (2013.01); *C12N 9/0036* (2013.01); *C12Q 1/26* (2013.01); *Y02A 50/473* (2018.01)

(58) Field of Classification Search
None
See application file for complete search history.

(56) References Cited

U.S. PATENT DOCUMENTS

| 647,582 | A | 4/1900 | Bermudes et al. |
| 2,231,808 | A | 2/1941 | Augustin |
| 3,136,720 | A | 6/1964 | Baermann |
| 5,468,631 | A | 11/1995 | Zenno et al. |
| 5,633,158 | A | 5/1997 | Anlezark et al. |
| 5,777,190 | A | 7/1998 | Shah et al. |
| 5,780,585 | A | 7/1998 | Anlezark et al. |
| 5,886,190 | A * | 3/1999 | Wallace et al. ............ 548/332.5 |
| 5,958,682 | A | 9/1999 | Connors et al. |
| 5,977,065 | A | 11/1999 | Anlezark et al. |
| 6,080,849 | A | 6/2000 | Bermudes et al. |
| 6,190,657 | B1 | 2/2001 | Pawelek et al. |
| 6,416,754 | B1 | 7/2002 | Brown et al. |
| 6,447,784 | B1 | 9/2002 | Bermudes et al. |
| 6,608,037 | B2 | 8/2003 | Young et al. |
| 6,652,849 | B2 | 11/2003 | Brown et al. |
| 6,685,935 | B1 | 2/2004 | Pawelek et al. |
| 6,863,894 | B2 | 3/2005 | Bermudes et al. |
| 6,923,972 | B2 | 8/2005 | Bermudes et al. |
| 6,984,513 | B2 | 1/2006 | Brown et al. |
| 7,179,646 | B2 | 2/2007 | Young et al. |
| 7,354,592 | B2 | 4/2008 | Bermudes et al. |
| 7,498,161 | B2 | 3/2009 | Brown et al. |
| 7,514,089 | B2 | 4/2009 | Bermudes et al. |
| 2002/0054865 | A1 | 5/2002 | Fujimori et al. |
| 2002/0131973 | A1 | 9/2002 | Bagshawe et al. |

(Continued)

FOREIGN PATENT DOCUMENTS

| EP | 0618191 | 10/1994 |
| EP | 2366693 | 9/2011 |

(Continued)

OTHER PUBLICATIONS

Liu et al. Optimized clostridium-directed enzyme prodrug therapy improves the antitumor activity of the novel DNA cross-linking agent PR-104. 2008 Cancer Res. 68: 7995-8003.*

(Continued)

*Primary Examiner* — Michael G. Hartley
*Assistant Examiner* — Jennifer Lamberski
(74) *Attorney, Agent, or Firm* — Polsinelli PC

(57) ABSTRACT

The invention relates generally to bacterial nitroreductase enzymes and methods of use thereof: more particularly, although not exclusively, the enzymes have use in non-invasive imaging techniques, monitoring of therapeutic cell populations and gene-directed enzyme prodrug therapy. The invention also relates to the use of bacterial nitroreductase enzymes in radioimaging and/or ablation of biological agents and to compositions of use in such methods.

10 Claims, 57 Drawing Sheets

Specification includes a Sequence Listing.

(56) References Cited

U.S. PATENT DOCUMENTS

| | | |
|---|---|---|
| 2005/0013808 A1 | 1/2005 | Grove et al. |
| 2007/0254852 A1 | 11/2007 | Matin et al. |
| 2009/0000416 A1 | 1/2009 | Wilhelm |
| 2009/0091933 A1 | 4/2009 | Yen et al. |
| 2009/0275780 A1 | 11/2009 | Mangion |

FOREIGN PATENT DOCUMENTS

| | | | |
|---|---|---|---|
| JP | 08131176 A | * | 5/1996 |
| WO | 1993/008288 A1 | | 4/1993 |
| WO | 94/08949 | | 4/1994 |
| WO | 1995/012678 A2 | | 5/1995 |
| WO | 1996/014420 A1 | | 5/1996 |
| WO | 1996/040238 A1 | | 12/1996 |
| WO | 1997/024143 A1 | | 7/1997 |
| WO | 98/33935 | | 8/1998 |
| WO | 1998/054349 A1 | | 12/1998 |
| WO | 1999/013053 A1 | | 3/1999 |
| WO | 1999/051270 A1 | | 10/1999 |
| WO | 2000/047725 A1 | | 8/2000 |
| WO | 2001/064739 A1 | | 9/2001 |
| WO | 2003/014380 A2 | | 2/2003 |
| WO | 2003/018788 A2 | | 3/2003 |
| WO | 2003/082323 A1 | | 10/2003 |
| WO | 2003/102169 A1 | | 12/2003 |
| WO | 2004/035769 A1 | | 4/2004 |
| WO | 2005/042471 | | 5/2005 |
| WO | 2005/049844 A2 | | 6/2005 |
| WO | 2005/049845 A2 | | 6/2005 |
| WO | 2005/049846 A2 | | 6/2005 |
| WO | 2006/103452 A2 | | 10/2006 |
| WO | 2010/04/768 | | 5/2010 |

OTHER PUBLICATIONS

Vass et al. *E. coli* NfsA: an alternative nitroreductase for prodrug activation gene therapy in combination with CB1954. 2009 Br. J. Cancer 100: 1903-1911.*

Das et al. 99mTc-labeling studies of a modified metronidazole and its biodistribution in tumor bearing animal models. 2003 Nucl. Med. Biol. 30: 127-134.*

Adams GE. Hypoxia-mediated drugs for radiation and chemotherapy. 1981 Cancer 48: 696-707. (Year: 1981).*

Search Report dated Jan. 22, 2012, in Application No. PCT/NZ2011/000137.

Written Opinion dated Jan. 16, 2013, in Application No. PCT/NZ2011/000137.

International Preliminary Report on Patentability dated Jan. 16, 2013, in Application No. PCT/NZ2011/000137.

Ackerley, J.N., et al., "Selection, analysis and evolution of bacterial nitroreductase enzymes for prodrug-mediated cancer gene therapy" Queenstown Molecular Biology Week Drug Discovery Satellite, Sep. 3, 2010.

Anlezark et al., "The bioactivation of 5-(aziridin-1-yl)-2,4-dinitrobenzamide (CB1954)—I. Purification and properties of a nitroreductase enzyme from *Escherichia coli*—a potential enzyme for antibody-directed enzyme prodrug therapy (ADEPT)," Biochem. Pharmacol., 1992, vol. 44, No. 12, pp. 2289-2295 (Abstract).

Anlezark et al., "Bioactivation of dinitrobenzamide mustards by an *E. coli* B nitroreductase," Biochem Pharmacol, 1995, vol. 50, No. 5, pp. 609-618 (Abstract).

Bhaumik S. et al., "Noninvasive optical imaging of nitroductase gene-directed enzyme prodrug therapy system in living animals," Gene Ther. Mar. 2-12; vol. 19, No. 3, pp. 295-302. doi: 10.1038/gt.2011.101. Epub Jul. 14, 2011.

Guise, C., et al., "Development of dinitrobenzamide mustard prodrugs optimised for maximal bystander effect for gene therapy applications" New Zealand Society of Oncology Meeting "From Benchtop to Bedside", May 25, 2011.

Perez-Reinado, E. et al., "Regulation and Characterization of Two Nitroreductase Genes, nprA and nprB, of Rhodobacter capsulatus", Applied and Environmental Microbiology, 2005, vol. 71, No. 12, pp. 7643-7649.

Pisharath, H. et al., "Targeted ablation of beta cells in the embryonic zebrafish andreas using *E.coli* nitroreductase, Mechanisms of Development," 2007, vol. 124, pp. 21-229.

Prosser, G.A., et al., "Improving the nitroaromatic prodrug reducing activity of Bacillus subtilis YcnD: Saturation mutagenesis of the active site" Zing Biocatalysis Conference, Dec. 10, 2010.

Syddall, S. et al., "The *E.coli* nitroreductase nfsA is an efficient 2-nitroimidazole reductase: implications for non-invasive imaging of armed replicating vectors with clinical stage PET imaging agents," New Zealand Society of Oncology Meeting "From Benchtop to Bedside", May 25, 2011.

Ziemer, L.S. et al., "Noninvasive imaging of tumor hypoxia in rats using the 2-nitroimidazole 18F-EF5," European Journal of Nuclear Medicine and Molecular Imaging, 2003, vol. 30, No. 2, pp. 259-266.

Bhaumik, S., "Advances in Imaging Gene-Directed Enzyme Prodrug Therapy" Current Pharmaceutical Biotechnology, 2011, vol. 12, pp. 497-507.

Anlezark et al., "Bioactivtion of Dinitrobenzamide Mustards by an *E. coli* B Nitroreductase" Biochemical Pharmacology, 1995, vol. 50, No. 5, pp. 609-618.

Forbes, Engineering the perfect (bacterial) cancer therapy, Cancer, 2010, 10:785-794.

Knox et al., The bioactivation of 5-(azindin-1-yl)-2,4-dinitrobenzamide (CB1954)—II. A comparison of an *Escherichia coli* nitroreductase and Walker DT diaphorase, Biochem Pharmacol. Dec. 15, 1992;44(12):2297-301.

Latham et al., Prostate-specific antigen promoter/enhancer driven gene therapy for prostate cancer: construction and testing of a tissue-specific adenovirus vector, Cancer Res. Jan. 15, 2000;60(2):334-41.

Palmer et al., Virus-directed enzyme prodrug therapy: intratumoral administration of a replication-deficient adenovirus encoding nitroreductase to patients with resectable liver cancer, J Clin Oncol. May 1, 2004;22(9):1546-52. Epub Mar. 29, 2004.

Penet et al., Prodrug enzymes and their applications in image-guided therapy of cancer: tracking prodrug enzymes to minimize collateral damage, Drug Deliv Transl Res. Feb. 1, 2012;2(1):22-30.

Sekar et al., Dual-therapeutic reporter genes fusion for enhanced cancer gene therapy and imaging, Gene Ther. May 2013;20(5):529-37.

Shah et al., Inhibition of dinitropyrene mutagenicity in vitro and in vivo using *Salmonella typhimurium* and the intrasanguinous host-mediated assay, Mutat Res. Oct. 1991;253(2):181-91.

Williams et al., Nitroreductase gene-directed enzyme prodrug therapy: insights and advances toward clinical utility, Biochem J. Oct. 15, 2015;471(2):131-53.

Morin, Scintigraphic Imaging During Gene Therapy, Doctoral Thesis, The University of Alberta, Spring 1997, 174 pages.

Supplementary European Search Report for EP 11807121, dated Jun. 28, 2016, 13 pages.

* cited by examiner

Figure 10
A)
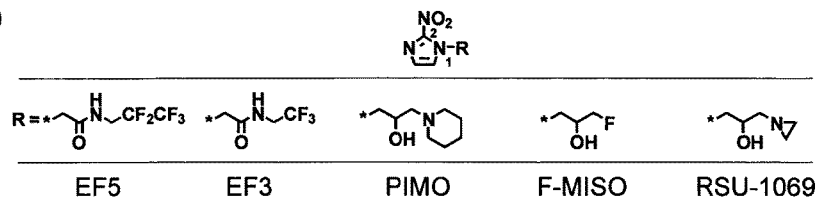
B)
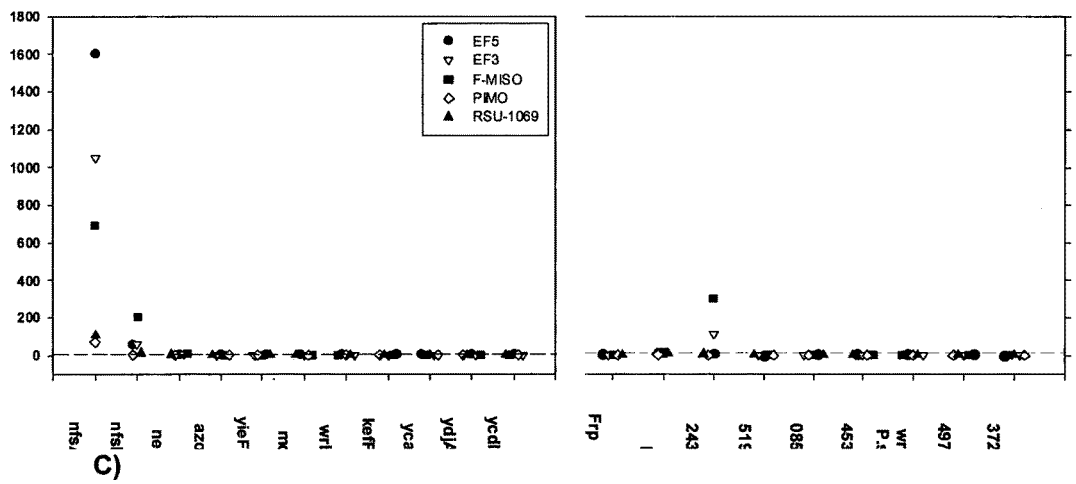
C)
| Cell line | EF5 | | EF3 | | PIMO | | F-MISO | | RSU-1069 | |
|---|---|---|---|---|---|---|---|---|---|---|
| | | WT:NT R ratio | | WT:NT R ratio | | WT:NTR ratio | | WT:NT R ratio | | WT:NT R ratio |
| WT | 8000 ±200 | | 8400 ±800 | | 1200 ±200 | | 6900 ±900 | | 43 ±1 | |
| NfsA | 5 ±0.1 | 1600 | 8 ±0.1 | 1050 | 17 ±4 | 71 | 10 ±1 | 690 | 0.4 ±0.06 | 108 |
| NfsB | 140 ±20 | 57 | 140 ±30 | 60 | 800 ±200 | 2 | 34 ±6 | 203 | 3 ±0.06 | 13 |
| YcaK | 6300 ±70 | 1 | 7400 ±300 | 1 | 1200 ±100 | 1 | 6000 ±500 | 1 | 45 ±6 | 1 |
| YieF | 5400 ±500 | 1 | 5500 ±700 | 2 | 900 ±400 | 1 | 7100 ±1700 | 1 | 23 ±8 | 2 |
| AzoR | 6400 ±1600 | 1 | 7600 ±3000 | 1 | 1300 ±100 | 1 | 4900 ±100 | 1 | 28 ±5 | 2 |
| MdaB | 7400 | 1 | 7200 ±500 | 1 | 1200 ±200 | 1 | 6100 ±2700 | 1 | 22 ±15 | 2 |
| WrbA | 4000 ±500 | 2 | 7000 ±1400 | 1 | 1900 ±500 | 1 | 8000 ±100 | 1 | 25 ±6 | 2 |
| KefF | 6300 ±1500 | 1 | 6300 ±1100 | 1 | 1300 ±200 | 1 | 7000 ±1400 | 1 | 44 ±9 | 1 |
| YcdI | 6300 ±1700 | 1 | 7400 ±1300 | 1 | 1300 ±400 | 1 | 6200 ±1200 | 1 | 52 ±13 | 1 |
| YdjA | 5000 ±1800 | 2 | 4400 ±1600 | 2 | 1400 ±400 | 1 | 4800 ±3000 | 1 | 51 ±14 | 1 |
| NemA | 2070 ±80 | 4 | 1100 ±90 | 8 | 773 ±53 | 1.5 | 248 ±34 | 28 | 8.2 ±0.8 | 5 |

Figure 12

|  | $K_m$ (μM) | $k_{cat}$ (s$^{-1}$) | $k_{cat}/K_m$ (S$^{-1}$/mM) |
|---|---|---|---|
| NfsA | 180 | 17.5 | 97 |
| NfsB | 1600 | 0.3754 | 0.24 |
| NemA | 11 | 0.1393 | 13 |
| Yief | ND[1] | ND[1] | ND[1] |
| AzoR | ND[1] | ND[1] | ND[1] |
| YcaK | ND[1] | ND[1] | ND[1] |
| MdaB | ND[1] | ND[1] | ND[1] |
| YdjA | ND[1] | ND[1] | ND[1] |
| YcdI | ND[1] | ND[1] | ND[1] |
| WrbA | ND[1] | ND[1] | ND[1] |
| KefF | ND[2] | ND[2] | ND[2] |
|  |  |  |  |
| ND[1] | No detectable activity | | |
| ND[2] | Cannot purify soluble enzyme | | |

Figure 15
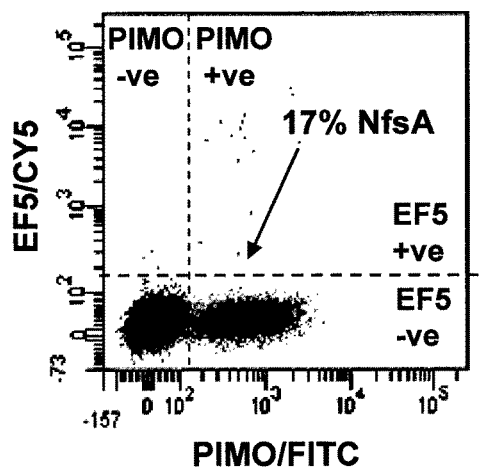 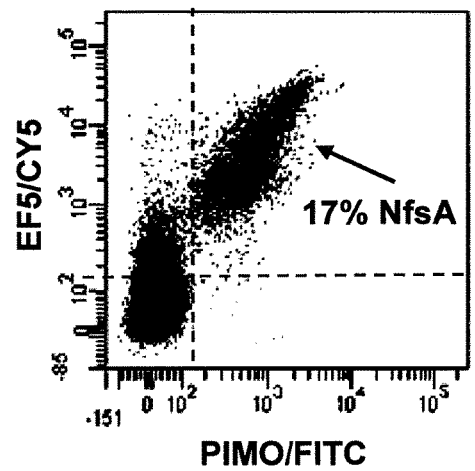

Figure 30

| Name | $TC_{10}$ (μM) | $T_CC_{10}$ (μM) | $A_CC_{10}$ (μM) | Total Conc (μM-hr) | BEE (%) | Human plasma AUC (μM-hr) | #Human AUC/ $A_CC_{10}$ ratio |
|---|---|---|---|---|---|---|---|
| EF5 | >5000 | >5000 | 141.8 | 709 | 0 (estimate) | 2000 [1] | 5.6 |
| Etanidazole | >5000 | >5000 | 975.5 | 4878 | 0 (estimate) | 35000 [2] | 7.2 |
| Metronidazole | >20000 | >20000 | 1470 | 7350 | 0 (estimate) | 77000 [3] | 10.5 |
| Misonidazole | >3000 | >3000 | 79.1 | 396 | 0 (estimate) | 25000 [4] | 63.2 |
| Nifuratel | | | | | | 0.557 [5] | |
| Nifutimox | | | | | | 18.9 [6] | |
| Nimorazole | | | | | * | >23000 [7] | |
| Nitrofurantoin | 609.3 | 671.5 | 78.6 | 393 | 0 | 9.74 [8] | 0.02 |
| Ornidazole | | | | | | 1193 [9] | |
| TH-302 | 18.9 | 1.86 | 0.09 | 0.45 | 43.4 | 51.2 [10] | 114 |
| Tinidazole | >25000 | >25000 | 438 | 2190 | 0 (estimate) | 3646 [11] | 1.7 |
| PR-104A | 59.9 | 1.71 | 1.13 | 5.65 | 89.6 | 16.9 [12] | 3 |

*Not determined as $IC_{50}$ > 100μM for NfsA
Human AUC/ $A_CC_{10}$ ratio defines the therapeutic window for single cell ablation at tissue-like cell densities as a function of achievable human plasma concentrations

Figure 52

|  | Km (µM) | $k_{cat}$ ($s^{-1}$) | $k_{cat}/Km$ ($s^{-1}$/mM) |
|---|---|---|---|
| NfsA(Ec) | 180 | 17.5 | 97.22 |
| YfkO(Bs) | 2507 | 8 | 3.27 |
| NfrA(Bs) | 390 | 12.2 | 31.28 |
| NfsA(Vv) | 252 | 40 | 160.32 |
| NfsB(Ec) | 1599 | 0.3754 | 0.23 |
| NemA(Ec) | 11 | 0.1393 | 13.27 |
| NfsA(Ck) | 413 | 48.9 | 118.40 |

Figure 53

|          | Km (µM) | $k_{cat}$ (s$^{-1}$) | $k_{cat}$/Km(s$^{-1}$/mM) |
|----------|---------|----------------------|---------------------------|
| NfsA(Ec) | 0.335   | 15.8                 | 47                        |
| NfrA(Bs) | 0.264   | 12.9                 | 49                        |
| NfsA(Ck) | 0.353   | 13.2                 | 37                        |
| NfsA(Vv) | 0.327   | 22.7                 | 69                        |
| NfsA(Vf) | 0.195   | 15.7                 | 81                        |
| CoFrp(Vh)| 0.227   | 21.8                 | 96                        |

Figure 54

| NTR | Co-subs. | $k_{cat}$ ($s^{-1}$) | $K_m$ ($\mu M$) | $k_{cat}/K_m$ ($M^{-1} s^{-1}$) | $NO_2$ pref. |
|---|---|---|---|---|---|
| NfsA (E.c) | NADPH | 12.1 | 101 | 119,900 | para |
| NfsA (S.t) | NADPH | <1 | ND | ND | para |
| NfsA (C.k) | NADPH | 17.1 | 155 | 110,300 | - |
| NfsA (K.p) | NADPH | 29.5 | 245 | 120,400 | para |
| NfsA (E.s) | NADPH | 22.0 | 99.5 | 220,800 | - |
| NfsA (V.f) | NADPH | 6.2 | 18.8 | 329,800 | - |
| NfsA (V.v) | NADPH | 24.4 | 77.7 | 314,000 | para |
| Frp (V.h) | NADPH | 17.6 | 61.3 | 287,800 | para |
| NfrA (B.s) | NADPH | 10.1 | 25.5 | 397,600 | para |
| YcnD (B.s) | NADPH | 5.15 | 10.8 | 479,100 | - |
| NfsB (E.c) | NADH | 60 | 4,490 | 13,280 | para |
| NfsB (C.k) | NADH | 34.8 | 2,060 | 16,880 | - |
| NfsB (K.p) | NADH | 90 | 1,930 | 46,610 | para |
| NfsB (V.v) | NADH | 54.5 | 541 | 100,700 | para |
| YfkO (B.s) | NADPH | 8.5 | 1,380 | 5,970 | para |
| YdgI (B.s) | NADH | 33.7 | 244 | 137,900 | para |
| MdaB (E.c) | NADPH | 0.14 | 4,290 | 33 | - |
| AzoR (E.c) | NADPH | 0.076 | 1,320 | 57 | ND |
| NemA (E.c) | NADPH | ND | ND | ND | ortho |

Figure 55

| NTR | Co-subs.[a] | $k_{cat}$ (s$^{-1}$) | $K_m$ (μM) | $k_{cat}/K_m$ (M$^{-1}$ s$^{-1}$) | NO$_2$ pref. |
|---|---|---|---|---|---|
| NfsA (E.c) | NADPH | 16 | 220 | 73,000 | 2 |
| NfsA (S.t) | NADPH | <1 | ND | ND | 2 |
| NfsA (C.k) | NADPH | 24.7 | 163 | 151,700 | ND |
| NfsA (K.p) | NADPH | 37.1 | 1,670 | 22,270 | 2 |
| NfsA (E.s) | NADPH | 25.7 | 260 | 98,880 | ND |
| NfsA (V.f) | NADPH | 13.8 | 52.5 | 262,900 | ND |
| NfsA (V.v) | NADPH | 45.2 | 210 | 215,700 | 2 |
| Frp (V.h) | NADPH | 21.7 | 99.6 | 217,600 | 2 |
| NfrA (B.s) | NADPH | 14.2 | 147 | 96,520 | 2 |
| YcnD (B.s) | NADPH | 15.2 | 35.4 | 430,800 | ND |
| NfsB (E.c) | NADH | 62 | 11,000 | 5,600 | 2, 4 (50:50) |
| NfsB (C.k) | NADH | 72.7 | 12,200 | 4,920 | ND |
| NfsB (K.p) | NADH | 204 | 21,140 | 9,630 | 2, 4 (50:50) |
| NfsB (V.v) | NADH | 72.9 | 1,260 | 58,000 | 2, 4 (25:75) |
| FraseI (V.f) | NADH | 12.4 | 903 | 13,660 | ND |
| YfkO (B.s) | NADPH | 60.2 | 2,440 | 24,740 | 4 |
| YdgI (B.s) | NADH | 7.68 | 1,780 | 4,330 | 2, 4 (60:40) |
| AzoR (E.c) | NADPH | 0.15 | 1,400 | 110 | 4 |
| NemA (E.c) | NADPH | 0.22 | 56 | 3,900 | 4 |

[a] Preferred co-substrates were used for all enzymes

Figure 57

Synthetic gene library

CCCCATATGACGCCAACCAYTGAACTTATTTGTGGCCATCGCTCCATTCGCCATTTCACTGATGAACCCATTTCCGA
AGCGCAGCGTGAGGCGATTATTAACAGCGCCCGTGCGACGTCCAGTTCCTMCTTTTTGCAGTGCAGTAGCATTATT
CGCATTACCGACAAAGCGTTACGTGAAGAACTGGTGACGCTGACCGGCGGGCAAAAACACGTAGCGCAAGCGGC
GGAGTTCTGGGTGTTCTGTGCCGACTTTAACCGCCATTTACAGATCTGTCCGGATGCTCAGCTCGGCCTGGCGRA
CAACTGTTGWTGGGTGTCGTTGATACGGCAATGATGGCGCAGAATGCATTAATCGCAGCGGAATCGCTGGGATTG
GGCGGGGTATATATCGGCGGCCTGCGCAATAATATTGAAGCGGTGACGAAACTGCTTAAATTACCGCAGCATGTT
CTGCCGCTGTTTGGGCTGTGCCTTGGCTGGCCTGCGGATAATCCGGATCTTAAGCCGCGTTTACCGGCCTCCATTTT
GGTGCATGAAAACAGCTATCAACCGCTGGATAAAGGCGCACTGGCGCAGTATGACGAGCAACTGGCGGAATATTA
CCTCACCCGTGGCAGCAATAATCGCCGGGATACCTGGAGCGATCATATCCGCCGAACAATCATTRAAGAAAGCSS
CCCATYTATTSTCGATTATTTGCACAAACAGGGTTGGGCGACGCGCTAAGTCGACCCC

Figure 59

| NTR | I5T | S41Y | E99G | L103M | K222E | R225X | F227S | PR104A | HX4 | METRO | F-MISO | EF5 | Tinidazole | CB1954 |
|---|---|---|---|---|---|---|---|---|---|---|---|---|---|---|
| 42 |  | ■ |  | ■ |  | G |  | 1.6 | 1.9 | ■ | 1.5 | 0.9 | 2.8 | 0.3 |
| 33 | ■ | ■ |  |  |  | A |  |  | 1.5 | 2.6 | 1.7 | 1.4 | ■ | 0.4 |
| 441 |  | ■ |  |  |  | A |  |  | 1.8 | 2.5 | 1.7 | 1.5 | 2.1 | 0.4 |
| 28 | ■ |  |  | ■ |  | G | ■ |  | 1.4 | ■ | 1.6 | 1.0 | ■ | 0.5 |
| 17 |  | ■ |  |  |  | P |  | 2.2 | 1.2 | ■ | 1.8 | 1.0 | ■ | ■ |
| 43 |  | ■ |  |  |  | A |  |  | 2.1 | 2.0 | ■ | ■ | 1.9 | 0.2 |
| 22C1 | ■ | ■ |  |  |  | P |  |  | ■ | 0.6 | 1.5 | 1.0 | 1.8 | 0.1 |
| 41 |  | ■ | ■ |  |  | A |  | 2.2 | ■ | 1.9 | 1.7 | 1.7 | 1.9 | 0.1 |
| 14 |  |  |  | ■ | ■ |  |  | 2.1 | 1.3 | 1.8 | 1.3 | 1.2 | 2.9 | 0.3 |
| 40 | ■ |  |  | ■ |  | A |  | 2.1 | ■ |  | 1.5 | ■ | ■ | 0.2 |
| s41y | ■ | ■ |  |  |  |  |  | 2.1 | ■ | 1.8 | ■ | ■ | ■ | 0.7 |
| wt |  |  |  |  |  |  |  | 1.0 | 1.0 | 1.0 | 1.0 | 1.0 | 1.0 | 1.0 |

Figure 60

| Poly-mutant code | IC50 value PR-104A (nM) | IC50 value SN27686 (nM) | IC50 value CB1954 ($\mu$M) | IC50 value Metronidazole (mM) |
|---|---|---|---|---|
| HCT116 Parental (Wt) | 19,000 | 20,320 | 175 | 1.5 |
| E. coli NfsA (wild-type sequence) | 21 | 24 | 0.575 | 0.49 |
| 17 [#] | 53 [#] | 46 [#] | 9.5 [#] | 4.6 [#] |
| 22 | 10 | 4 | 8.9 | >5.0 |
| 22C1 | 7 | 1 | 0.175 | 0.054 |
| 28 [#] | >200 [#] | 10 [#] | >100 [#] | 2.0 [#] |
| 40 | 12 | 11 | 1.5 | 0.30 |
| 42 [#] | >200 [#] | >100 [#] | >100 [#] | >5.0 [#] |
| 43 | 30 | 38 | 4.6 | 4.4 |

[#] NTR is unstable in HCT116 cells in vitro

BACTERIAL NITROREDUCTASE ENZYMES AND METHODS RELATING THERETO

CROSS REFERENCE TO RELATED APPLICATIONS

This application is a national phase application based on PCT/NZ2011/000137, filed Jul. 18, 2011, which claims the priority of New Zealand Patent Application No. 586849, filed Jul. 16, 2010, the content of both of which is incorporated herein by reference.

The invention relates generally to bacterial nitroreductase enzymes and methods of use thereof. More particularly, although not exclusively, said enzymes have use in non-invasive imaging techniques, monitoring of therapeutic cell populations and gene-directed enzyme prodrug therapy. The invention also relates to the use of bacterial nitroreductase enzymes in radioimaging and/or ablation of cells and/or biological agents and to compositions of use in such methods.

BACKGROUND OF THE INVENTION

Selective targeting of cancer tissues can be achieved by tumour-tropic organisms, including certain replication competent viral vectors and bacteria. Such organisms are generally antineoplastic in their own right, and a number are in clinical trials (or clinical use) as novel therapeutic agents. Ideally such agents would be introduced via systemic administration, and would "seek out" cancerous tissues. However, applications to date have been limited owing to an inability to non-invasively image the location of viruses or bacteria in the body post-administration. The self-amplifying nature and uncertain tropism for human tissues has hampered the selection and development of oncolytic viruses and bacteria.

Non-Invasive Imaging Methods for Biological Vectors

Tissue biopsies and other invasive approaches to imaging tumour-tropic biological vectors cannot be applied to all organs of the body in concert and repeated sampling is rarely clinically feasible. However, the requirement for repeat sample analysis is necessary for dynamic agents that amplify and can redistribute micro-regionally and systemically with time, and mandates a non-invasive methodology that can be applied at regular intervals. This is desirable to allow early intravenous administration of novel vectors in human clinical trials. Of note, animal toxicological models are generally considered to have poor predictive value for human tropic viruses and consequently there is a need to monitor experimental vectors thereby establishing early proof of principle in (preclinical) animal models and in human trials.

Various indirect reporter gene approaches have been tried in an attempt to monitor vector behaviour in living systems including bioluminescence, fluorescence and secreted plasma markers, none of which are considered clinically viable for various reasons including signal attenuation or lack of spatial information.

Positron Emission Tomography (PET) technology is increasingly being applied to the area of therapy development and is the most attractive method for non-invasive and comprehensive measurement of whole body vector distribution. Multiple sampling from the same patient is also possible. PET is safe, accurate and results are reproducible. It also has extremely high sensitivity to imaging probe molecules and is ideal for monitoring cellular or molecular events early in the course of the disease, during therapy, and for evaluating disease recurrence.

PET-based vector imaging has been achieved in preclinical studies for the reporter gene Herpes simplex virus thymidine kinase (HSV-tk) Bennett et al, 2001, *Nat Med* 7 (7): 859-863; Gambhir et al, 2000, *Proc Natl Acad Sci USA* 97 (6): 2785-2790; Soghomonyan et al, 2005, *Cancer Gene Ther* 12 (1): 101-108) and proof of principle studies are underway with newly designed HSV-tk PET probes (Hackman et al, 2002, *Molec Imag* 1 (1): 36-42; Jacobs et al, 2001, *Cancer Res* 61 (7): 2983-2995; Min et al, 2003, *Eur J Nuc Med Mol Imaging* 30 (11): 1547-1560; Miyagawa et al, 2008, *J Nucl Med* 49 (4): 637-648) including FHBG (9-(4-[18F]fluoro-3 hydroxymethylbutyl)guanine). However, it has been demonstrated that tumour retention of $^{18}$F-FHBG, monitored via PET, was unsuccessful in predicting HSV-1tk virus load due to tumour release of soluble phosphorylated $^{18}$F-FHBG following tumour cell oncolysis (Kuruppu et al, 2007, *Cancer Res* 67 (7): 3295-3300). In addition, imaging is hampered using current probes by excessive background signal and a lack of homogenous distribution throughout the body. Other disadvantages to known systems include laborious synthesis of the probes, that the probes can themselves be toxic, and easy degradation of probe molecules in the blood, limiting the ability for systemic administration.

Use of Bacterial Nitroreductases as Reporter Genes for Imaging

Bacterial nitroreductases (NTRs) can catalyse the reduction of certain nitroheterocyclic/nitrocarbocyclic/nitroaromatic molecules. Limited studies have been conducted on their utility as enzymes for reporter gene systems. Available publications and patents relating to imaging are restricted to the use of fluorescent probe substrates with minimal clinical utility. For example, the non-fluorescent compound 6-chloro-9-nitro-5H-benzo[a]phenoxazin-5-one (C-22220, CNOB) has been described as a fluorogenic probe for detection of nitroreductase activity (Molecular Probes Handbook, Ed. Richard P. Haugland, 10$^{th}$ Edition, 2005, p 535). *Escherichia coli* NfsB can metabolise CNOB to a fluorescent aminophenoxazine (Ex/Em 617/625 nm) and CNOB has been used for the detection of *E. coli* nfsB expression in tumour bearing nude mice injected with *E. coli* NfsB-expressing *Clostridia sporogenes* spores (Liu et al, 2008, *Cancer Res* 68 (19): 7995-8003). However, *E. coli* NfsB has limited catalytic flexibility and NfsB has previously been found to be inactive when evaluated with 2-nitroimidazole (2-NI) substrates (Anlezark et al, 1995, *Biochem Pharmacol* 50 (5): 609-618). The scarcity of characterised microbial NTR genes and their coordination with appropriate prodrug substrates is an unaddressed limitation.

The non-fluorescent 6-nitroquinoline has been described as a fluorogenic probe for the detection of *E. coli* nfsB expression in cell culture monolayers (Singleton et al, 2007, Cancer Gene Ther 14 (12): 953-967). In a further example, CytoCy5 is a cell-entrapped red fluorescent probe for *E. coli* NfsB with recently demonstrated utility in cell lines and animal models (U.S. Pat. No. 7,579,140 Bhaumik et al, 2011, Gene Ther July 14; epub ahead of print). However, despite recent research on these systems, they are still deemed to be inadequate as nitroreductase-based reporter gene systems for clinical applications due to problems including signal attenuation and lack of spatial information.

Thus it is desirable to provide alternative non-invasive imaging technologies that preferably allow for rapid, reproducible and quantitative imaging and/or that enable the monitoring of gene/vector distribution and amplitude in the same patient or animal over time. Additionally, there would be an advantage in providing imaging technologies to monitor the spatial and temporal distribution of vector systems with time in a manner that is predictive of normal tissue toxicity and antitumour efficacy.

Gene-Directed Enzyme Prodrug Therapy (GDEPT)

Gene-directed enzyme prodrug therapy (GDEPT) is a gene therapy strategy in which a therapeutic gene encodes an exogenous enzyme that will convert an administered non-toxic prodrug into an active cytotoxic derivative. GDEPT is made up of three components; the prodrug to be activated, the prodrug activating enzyme, and the delivery vector for the corresponding gene. Preferential activation of the prodrug in transduced tumour cells generates high intra-tumoural drug (activated prodrug metabolite) concentrations and therefore increases the therapeutic index of the drug.

It would be preferable to be able to utilise a single enzyme or gene product to enable both imaging and prodrug activation as imaging may directly predict the location and magnitude of prodrug activation, providing critical safety information prior to introduction of a conditionally cytotoxic therapy component.

Selectivity for tumour (over normal) tissues is predicated on the use of a biological vector, such as an oncolytic virus, that has been targeted to the tumour tissues. Therapy that utilises viral delivery vehicles is also known as virus-directed enzyme prodrug therapy (VDEPT). Alternatively, use of bacterial vectors tropic for tumour tissues, such as *Clostridia* sp., *Salmonella* sp. or *Bifidobacter* sp. is commonly termed bacterial-directed enzyme prodrug therapy (BDEPT), or in certain specific cases CDEPT (for *Clostridia*-directed enzyme prodrug therapy). These are all vector specific variants of GDEPT and are considered to be covered by this common acronym. An additional term, ADEPT, refers to antibody-directed enzyme prodrug therapy and encompasses the use of epitope-specific antibodies to guide systemically administered antibody-enzyme fusions to tumour sites in order to target prodrug activation.

The limited activity of GDEPT systems has led to the evaluation of the *E. coli* nitroreductase NfsB in combination with CB1954 (5-aziridinyl-2,4-dinitrobenzamide) and various other nitroheterocyclic/nitrocarbocyclic/nitroaromatic prodrugs (Denny, 2002, *Curr Pharm Des* 8 (15):1349-1361; Searle et al, 2004, *Clin Exp Pharmacol Physiol* 31 811-816; Singleton et al, 2007, *Cancer Gene Ther* 14 (12): 953-967). The NfsB/CB1954 combination has undergone evaluation in a VDEPT setting with some signs of activity (Palmer et al, 2004, *J Clin Oncol* 22 (9): 1546-1552). Alternate NTRs, an evolved form of *E. coli* YieF (Barak et al, *Mol Can Ther* 5 (1): 97-103) and wild-type *E. coli* NfsA (Vass et al, 2009, *Br J Cancer* 100 (12): 1903-1911; Prosser et al, 2010, *Biochem Pharmacol* 79, 678-687) have been evaluated in combination with CB1954 (and the former also with mitomycin C and CNOB (C-22220) (Thorne et al, 2009, *Mol Can Ther* 8 (2): 333-341)). *Bacillus amyloliquefaciens* YwrO and *Enterobacter cloacae* NR are also known to reduce the prodrug CB1954 (Anlezark et al, 2002, *Microbiology* 148 (Pt 1): 297-306).

The currently known and studied bacterial nitroreductase enzymes for GDEPT have not been shown to be capable of metabolising 2-nitroimidazole PET imaging agents, rendering them ineffectual as reporter genes for non-invasive imaging of gene/vector distribution and amplitude in the same patient or animal over time. Additionally, CB1954 has low potency, poor formulation characteristics, an insufficient bystander effect for meaningful therapeutic utility and is poorly tolerated in humans. *E. coli* NfsB possesses poor enzyme kinetic properties with respect to CB1954 reduction and has limited substrate flexibility. Attempts to monitor NfsB activity in murine tumour xenografts using CNOB (C-22220) have required direct intratumour injection of fluorogenic substrate. Use of nfsB-labelled virus in humans has necessitated direct intratumoural injection since monitoring of nfsB/virus distribution following systemic administration is not possible.

The ability to ablate cells without localised damage to neighbouring tissue (known as single cell ablation) is seen as a valuable safety control for enabling the elimination of a vector in the matrix, cells or tissues should this be deemed necessary. The ability to control viral (VDEPT) or bacterial (BDEPT) infection is an additional biosafety feature and is considered to be a desired design feature in replicating biological vectors. To achieve this, activation of prodrugs that provide reduced, substantially minimal or zero bystander effect is also desirable.

Thus there is a need for nitroreductases that are more catalytically efficient and which can utilise a broad array of prodrugs that are able to distribute well in tumour tissues. Further there is a need for nitroreductases that can be imaged prior to prodrug administration to determine tissue distribution since the combination of nfsB/virus and prodrug is specifically designed to be cytotoxic upon interaction.

It is an object of the invention to overcome or ameliorate at least one of the disadvantages of the prior art, or at least to provide the public with a useful choice.

SUMMARY OF THE INVENTION

In a first aspect, the invention provides a method of radioimaging and/or ablation of a cell and/or biological agent, the method comprising the steps of:
a. introduction of a nitroreductase to a subject and
b. introduction of a radiolabelled imaging probe to a subject and/or;
c. introduction of a prodrug to the subject;
    wherein the nitroreductase is capable of activating the imaging probe and the prodrug to the subject; and
    wherein the steps may be carried out concurrently or sequentially in any order; and
wherein, when the method does not include step b., the prodrug has a substantially minimal bystander effect.

In a particular embodiment, the invention provides a method of ablation of a cell and/or a biological agent comprising the steps of:
a. introduction of a nitroreductase to a subject; and
b. introduction of a prodrug to a subject; and
c. ablation of the cell and/or biological agent by the activated prodrug
    wherein the nitroreductase is expressed by the cell and/or biological agent and is capable of activating the prodrug; and
    wherein steps a. and b. may be carried out concurrently or sequentially in any order; and
    wherein the prodrug has a substantially minimal bystander effect; and
    wherein the nitroreductase is not the NfsB polypeptide from *Escherichia coli*.

In a further particular embodiment, the invention provides a method of radioimaging a cell and/or biological agent, the method comprising the steps of:
a. introduction of a nitroreductase to a subject; and
b. introduction of a radiolabelled imaging probe to a subject,
    wherein the nitroreductase is capable of activating the imaging probe; and wherein the steps may be carried out concurrently or sequentially in any order.

In a further particular embodiment, the invention provides a method of radioimaging and ablation of a cell and/or a biological agent, the method comprising the steps of:
  a. introduction of a nitroreductase to a subject; and
  b. introduction of a radiolabelled imaging probe to a subject; and
  c. introduction of a prodrug to the subject;
  wherein the nitroreductase is capable of activating the imaging probe and the prodrug; and
  wherein the steps may be carried out concurrently or sequentially in any order.

In a second aspect, the invention provides a vector that expresses a nitroreductase or expresses a gene encoding a nitroreductase, wherein the nitroreductase comprises any one of SEQ ID NO 3 to 7, 9 to 20, 22, and 24 to 90 or, has at least one amino acid substitution, insertion or deletion relative to and shares at least about 25%, about 30%, about 35%, about 40%, about 50%, about 60%, about 70%, about 80%, about 90% or greater amino acid sequence identity with any one of SEQ ID NOs 1 to 90.

In a third aspect, the invention provides an isolated nitroreductase comprising any one of SEQ ID NO 3 to 7, 9 to 20, 22, and 24 to 90 or, has at least one amino acid substitution, insertion or deletion relative to and shares at least about 25%, about 30%, about 35%, about 40%, about 50%, about 60%, about 70%, about 80%, about 90% or greater amino acid sequence identity with any one of SEQ ID NOs 1 to 90.

In a fourth aspect, the invention provides an isolated polynucleotide that encodes a nitroreductase as defined in the third aspect.

In a fifth aspect, the invention provides a composition for use with a nitroreductase in cell or biological agent radioimaging and ablation, the composition comprising an imaging probe and a prodrug as defined herein.

In a sixth aspect, the invention provides a kit for use in cell radioimaging, the kit comprising:
  a. an imaging probe as defined herein; and
  b. a vector as described in the second aspect or an isolated nitroreductase as defined in the third aspect or an isolated polynucleotide as defined in the fourth aspect.

In a seventh aspect, the invention provides a kit for use in cell radioimaging and cell ablation, the kit comprising:
  a. a composition according to the fifth aspect; and
  b. a vector as described in the second aspect or an isolated nitroreductase as defined in the third aspect or an isolated polynucleotide as defined in the fourth aspect.

In specific embodiments, the imaging probe is used for imaging a subject using Positron Emission Tomography (PET), micro-Positron Emission Tomography (micro-PET) or Single Photon Emission Tomography (SPECT) and may contain a positron-emitting nuclide such as $^{15}O$, $^{13}N$, $^{11}C$, $^{124}I$, $^{76}Br$ and $^{16}F$ or a gamma-emitting nuclide such as $^{99m}Tc$, $^{67}Ga$, $^{111}In$ and $^{123}I$.

In a particular embodiment, the imaging probe or the prodrug comprises a nitroheterocyclic, nitrocarbocyclic or a nitroaromatic compound.

In a particular embodiment, the imaging probe or the prodrug comprises a substituted or unsubstituted nitroimidazole compound including 2-nitroimidazole, 4-nitroimidazole and 5-nitroimidazole. Preferably, the prodrug is a precursor to an anti-parasitic agent.

In a particular embodiment, the imaging probe or the prodrug comprises a substituted or unsubstituted nitroimidazole compound including 2-nitroimidazole, 4-nitroimidazole and 5-nitroimidazole. In further embodiments, the imaging probe or the prodrug comprises a substituted or unsubstituted dinitrobenzamide, mononitrobenzamide, quinone, nitrofuran, a mono-nitro aromatic or compounds derived from one of the above compound groups.

In a particular embodiment, the prodrug is selected from NLCQ-1, RSU-1069, RB6145, CI-1010, Misonidazole, Etanidazole, Nimorazole, Metronidazole, Tinidazole, Ornidazole, Nitrofurantoin, Nitrofurazone, Nifuratel, Nifurtimox, Furazolidinone, SN26634, SN27857, KS119, LH7, EF5 (pentafluoroetanidazole), EF3 (trifluoroetanidazole), CB 1954, TH-302, PR-104A, SN27686, SN31609, SN32102, SN28065, SN28099, mitomycin C, porfiromycin, EO9 and RH1.

In a particular embodiment, the imaging probe is an $^{18}F$-labelled imaging probe selected from EF3, EF5, F-MISO, HX4, F-PIMO, FETNIM, FAZA, FETA, CCI-103F, or SR4554.

In a particular embodiment, the activated prodrug acts exogenously and the cell and/or biological agent undergoes ablation as a result of the bystander effect of the activated prodrug.

In a particular embodiment, the activation of the prodrug results in a substantial bystander effect when the prodrug is selected from CB 1954, TH-302, PR-104A, SN27686, SN31609, SN32102, SN28065 and SN28099.

In a particular embodiment, the prodrug and the imaging probe are the same compound. The inventors have surprisingly found that when the imaging probe is present in the matrix at a high concentration, preferably approximately 1000 times, relative to the concentration required for the purpose of imaging a cell/biological agent the probe has efficacy as a prodrug.

The probe/prodrug may be introduced to the subject in a dosage that results in the ablation of a vector and/or a cell in a concentration up to about the maximum tolerated dose (MTD) for the subject. In particular embodiments, the probe/prodrug is a 2-nitroimidazole, preferably EF5.

In a particular embodiment, the cell and/or biological agent that is ablated expresses the nitroreductase or expresses a polynucleotide that encodes a nitroreductase.

In a particular embodiment, the cell is a tumour cell.

In a particular embodiment, the activation of the prodrug results in a substantially minimal bystander effect and the prodrug may be selected from NLCQ-1, RSU-1069, CI-1010, Misonidazole, Etanidazole, Nimorazole, Metronidazole, Tinidazole, Ornidazole, Nitrofurantoin, Nitrofurazone, Nifuratel, Nifurtimox, Furazolidinone, SN26634, SN27857, KS119, LH7, EF5 (pentafluoroetanidazole) and EF3 (trifluoroetanidazole).

In a particular embodiment, a nitroreductase is expressed by a transformed cell and the sensitivity of the transformed cell to a prodrug is improved relative to a cell that does not express the nitroreductase. In a particular embodiment, the transformed cell is a stem cell, a hematopoietic stem cell or a genetically modified immune cell.

In further embodiments, the nitroreductase is expressed by a cell including a stem cell, a hematopoietic stem cell, a genetically modified immune cell or a tumour cell.

In a particular embodiment, the nitroreductase is selected from the group consisting of:
  a. a nitroreductase selected from a NfsA, NfsB, AzoR, NemA, MdaB or YwrO nitroreductase family or a mutant nitroreductase thereof, or
  b. a nitroreductase according to any one of SEQ ID Nos 1 to 90
  or a functionally equivalent nitroreductase variant thereof.

In a particular embodiment, the nitroreductase is encoded by a nitroreductase gene selected from the group consisting of:
a. a gene that encodes a nitroreductase from a NfsA, NfsB, AzoR, NemA, MdaB or YwrO nitroreductase family; or
b. a gene encoding a nitroreductase according to any one of SEQ ID Nos 1 to 90
or a functionally equivalent nitroreductase gene variant thereof.

In particular embodiments, the nitroreductase is a mutant nitroreductase which corresponds to any one of SEQ ID NO 32 to 90 or has at least one amino acid substitution, insertion or deletion relative to, and shares at least about 25%, about 30%, about 35%, about 40%, about 50%, or greater amino acid sequence identity with any one of SEQ ID Nos 1 to 31.

In a particular embodiment, the mutant nitroreductase is encoded by a gene that has undergone directed evolution wherein the method of directed evolution comprises error-prone PCR, targeted mutagenesis, targeted random mutagenesis and/or DNA shuffling strategies and the mutant nitroreductase is encoded by a gene encoding a nitroreductase according to:
a. a gene that encodes a nitroreductase from a NfsA, NfsB, AzoR, NemA, MdaB or YwrO nitroreductase family; or
b. a gene encoding a nitroreductase according to any one of SEQ ID Nos 1 to 90.

In further embodiments, the mutant nitroreductase differs to a nitroreductase from the NfsA family by a substitution, insertion or deletion in a residue corresponding to one or more of amino acid residues I5, S41, E99, L103, K222, R225, F227, L229, S33, F42, I49, G130, R133, E178, G204, R208, I220 or S224 from E. coli NfsA.

In a further embodiment, the method of the first aspect further comprises a step of imaging the imaging probe and evaluating the distribution of a cell or biological agent.

In a further embodiment, the method of the first aspect further comprises the use of more than one prodrug wherein all the prodrugs are activated by the nitroreductase enzyme. In particular embodiments, the second or subsequent prodrug may be introduced concurrently or sequentially with the first prodrug. The second or subsequent prodrug may be metronidazole, tinidazole or misonidazole.

In a particular embodiment, the vector of the second aspect may be used in the method of the first aspect.

In particular embodiments, the nitroreductase is encoded by a gene that has undergone directed evolution and further embodiments, the method of directed evolution comprises error-prone PCR, targeted mutagenesis, targeted random mutagenesis and/or DNA shuffling strategies. The nitroreductase may have undergone directed evolution from a gene encoding a nitroreductase according to any one of SEQ ID Nos. 1 to 90.

In a further embodiment, the vector comprises a mutant nitroreductase that differs to a nitroreductase from the NfsA family by a substitution, insertion or deletion in a residue corresponding to one or more of amino acid residues 15, S41, E99, L103, K222, R225, F227, L229, S33, F42, I49, G130, R133, E178, G204, R208, I220 or S224 from E. coli NfsA.

The vector of the second aspect may be any suitable vector and may be selected from the group consisting of viruses, bacteria, liposomes, nanoparticles, antibodies, human multipotent marrow stromal cells or plasmid vectors.

In particular embodiments, the vector or isolated nitroreductase is capable of:

a. catalysing the metabolism of an imaging probe; and
b. activating a prodrug by contacting the prodrug with the nitroreductase.

In an eighth aspect, the invention provides the use of an imaging probe and a nitroreductase capable of catalysing the metabolism of the imaging probe in the manufacture of a medicament for the treatment or diagnosis of a disease including cancer, Parkinson's disease, Alzheimer's disease, stroke, heart disease, rheumatological diseases or a disease treated by stem-cell transplantation, wherein the administration pattern of the imaging probe and the nitroreductase comprises concurrent administration or sequential administration in any order.

In a particular embodiment, the medicament further comprises a prodrug capable of activation by the nitroreductase and wherein the administration pattern of any combination of the imaging probe, the nitroreductase and the prodrug comprises concurrent administration of or sequential administration in any order.

In a further embodiment, the prodrug has a substantially minimal bystander effect.

In a ninth aspect, the invention provides the use of a prodrug and a nitroreductase capable of activating the prodrug in the manufacture of a medicament for the treatment or diagnosis of a disease including cancer, Parkinson's disease, Alzheimer's disease, stroke, heart disease, rheumatological diseases or a disease treated by stem-cell transplantation, wherein the administration pattern of the prodrug and the nitroreductase comprises concurrent administration or sequential administration in any order and wherein the prodrug has a substantially minimal bystander effect.

In a tenth aspect, the invention provides the use of a vector according to the second aspect, an isolated nitroreductase according to the third aspect or a composition according to the fourth aspect in the manufacture of a medicament for the treatment or diagnosis of a disease including cancer, Parkinson's disease, Alzheimer's disease, stroke, heart disease, rheumatological diseases or a disease treated by stem-cell transplantation.

In an eleventh aspect, the invention provides the use of an imaging probe and a nitroreductase capable of catalysing the metabolism of the imaging probe for the treatment or diagnosis of a disease including cancer, Parkinson's disease, Alzheimer's disease, stroke, heart disease, rheumatological diseases or a disease treated by stem-cell transplantation, wherein the administration pattern of the imaging probe and the nitroreductase comprises concurrent administration or sequential administration in any order.

In a particular embodiment, the use of the eleventh aspect further comprises the use of a prodrug capable of activation by the nitroreductase and wherein the administration pattern of any combination of the imaging probe, the nitroreductase and the prodrug comprises concurrent administration of or sequential administration in any order.

In a particular embodiment, the prodrug has a substantially minimal bystander effect.

In a twelfth aspect, the invention provides the use of a prodrug and a nitroreductase capable of activating the prodrug for the treatment or diagnosis of a disease including cancer, Parkinson's disease, Alzheimer's disease, stroke, heart disease, rheumatological diseases or a disease treated by stem-cell transplantation, wherein the administration pattern of the prodrug and the nitroreductase comprises concurrent administration or sequential administration in any order and wherein the prodrug has a substantially minimal bystander effect.

In a further aspect, the invention provides a method of ablation of a cell and/or a biological agent comprising the steps of:
 a. introduction of a nitroreductase to a subject; and
 b. introduction of a prodrug, capable of activation by the nitroreductase to the subject; and
 c. ablation of a cell and/or biological agent by the activated prodrug
 wherein steps a. and b. may be carried out concurrently or sequentially in any order; and
wherein the nitroreductase is as defined in the second, third or fourth aspects.

In a further aspect, the invention provides a method of evaluating the efficacy of a nitroreductase with a target prodrug using a plasmid vector in a bacterial chromosomal lacZ reporter strain or a plasmid-based GFP reporter strain comprising incorporating an sfiA::GFP reporter construct into a CDF-based plasmid to give a pANODuet reporter plasmid for GFP screening.

In particular embodiments of the invention, a nitroreductase or a gene encoding a nitroreductase is introduced to a cell and/or biological agent using gene-directed enzyme prodrug therapy (GDEPT), virus-directed enzyme prodrug therapy (VDEPT), bacterial-directed enzyme prodrug therapy (BDEPT), Clostridia-directed enzyme prodrug therapy (CDEPT) or antibody-directed enzyme prodrug therapy (ADEPT).

In particular embodiments of the invention, a nitroreductase or a gene encoding a nitroreductase is expressed from a vector comprising viruses, bacteria, liposomes, nanoparticles, antibodies or other genetic vectors. These enable radioimaging of their in vivo cellular localisation, replication and/or gene expression.

In a particular embodiment, the nitroreductase is introduced to a cell via human multipotent marrow stromal cells.

In a further aspect, the invention provides a kit for the evaluation of the in vivo distribution of genetic vectors such as viruses, bacteria, liposomes, antibodies, comprising:
 (a) a NTR protein as defined herein selected from the NfsA, or NemA enzyme families wherein the enzyme is capable of reducing $^{18}$F-labelled nitroaromatic PET imaging probes to a cell-entrapped form for radioimaging, and wherein the expression of the enzyme is controlled by an operably-linked promoter; and b) an $^{18}$F-labeled nitroaromatic PET imaging probe capable of being converted into a cell-entrapped form by said NfsA or NemA derived enzyme for PET or microPET imaging.

In a further aspect, the invention provides a kit for the evaluation of the in vivo distribution of therapeutic cell populations, comprising a) an isolated polynucleotide, encoding a protein derived from the NfsA or NemA enzyme families, capable of reducing $^{18}$F-labeled nitroaromatic PET imaging probes to a cell-entrapped form for PET or microPET imaging, expression of the enzyme being controlled by an operably-linked promoter; and b) an $^{18}$F-labeled nitroaromatic PET imaging probe capable of being converted into a cell-entrapped form by said NfsA or NemA derived enzyme for PET or microPET imaging.

In a further aspect, the invention provides a kit for the control of replicating biological agents such as oncolytic viruses and bacteria, comprising a) an isolated polynucleotide, encoding a protein derived from the NfsA or NemA enzyme families, capable of reducing metronidazole into an active cytotoxic compound with zero or substantially minimal bystander effect for specific and controlled ablation of those biological agents in situ with minimal harm to surrounding cells; and b) metronidazole, capable of being converted into an active cytotoxic compound with zero or substantially minimal bystander effect by said NfsA or NemA derived enzyme, as a safety control to eliminate said oncolytic biological agents as and when desired.

In a further aspect, the invention provides a kit for treatment of cancer comprising a) at least one tumour-targeting vector, which comprises an isolated polynucleotide, encoding a protein derived from the NfsA or NemA enzyme families, capable of reducing $^{18}$F-labeled nitroaromatic PET imaging probes to a cell-entrapped form for PET or microPET imaging, as well as co-metabolising one or more prodrugs into active cytotoxic compounds for therapeutic purposes, as well as co-metabolising metronidazole into an active cytotoxin with substantially minimal or zero bystander effect as a safety control; and b) an $^{18}$F-labeled nitroaromatic PET imaging probe capable of being converted into a cell-entrapped form by said NfsA or NemA derived enzyme for PET or microPET imaging; and c) one or more prodrugs capable of being converted into active cytotoxic compounds by said NfsA or NemA derived enzyme; and d) metronidazole, capable of being converted into an active cytotoxic compound with substantially minimal or zero bystander effect by said NfsA or NemA derived enzyme, as a safety control to prevent undesirable vector replication or localisation, or to eliminate residual vector at the conclusion of treatment.

In a further aspect, the invention provides a kit for evaluating and conducting gene therapy comprising a) at least one gene-delivery vector which comprises a desirable therapeutic gene payload together with an isolated polynucleotide, encoding a protein derived from the NfsA or NemA enzyme families, capable of reducing $^{18}$F-labeled nitroaromatic PET imaging probes to a cell-entrapped form for PET or microPET imaging, as well as co-metabolising metronidazole into an active cytotoxic compound with substantially minimal or zero bystander effect as a safety control; and b) an $^{18}$F-labeled nitroaromatic PET imaging probe capable of being converted into a cell-entrapped form by said NfsA or NemA derived enzyme for PET or microPET imaging; and c) metronidazole, capable of being converted into an active cytotoxic compound with substantially minimal or zero bystander effect by said NfsA or NemA derived enzyme, as a safety control to eliminate cancers arising from undesirable gene delivery events that activate oncogenes, or to eliminate residual vector at the conclusion of the therapy.

In a further aspect, the invention provides a kit for labelling cell lines comprising a) an isolated polynucleotide, encoding a protein derived from the NfsA or NemA enzyme families, capable of reducing $^{18}$F-labeled nitroaromatic PET imaging probes to a cell-entrapped form for PET or microPET imaging, as well as co-metabolising metronidazole into an active cytotoxic compound with substantially minimal or zero bystander effect for specific and controlled ablation of those cells without harm to surrounding cells; and b) an $^{18}$F-labeled nitroaromatic PET imaging probe capable of being converted into a cell-entrapped form by said NfsA or NemA derived enzyme for PET or microPET imaging; and c) metronidazole, capable of being converted into an active cytotoxic compound with substantially minimal or zero bystander effect by said NfsA or NemA derived enzyme to specifically ablate those cells and monitoring the phenotypic effects.

Preferably, the stem cells of any of the above aspects are intravenously administered via human multipotent marrow stromal cells.

In further aspects, the invention is characterised as any sequence of DNA or RNA encoding a bacterial nitroreductase, gene of interest, or a polypeptide thereof, able to perform multiple catalytic functions, including:
(a) metabolism and retention of PET probes for non-invasive imaging (bio-detection),
(b) activation of bioreductive prodrugs (bio-therapy); and
(c) activation of anti-parasitic agents to permit vector ablation (bio-control).

The NTR gene(s) may be introduced into the genome or accessory genetic material (e.g. plasmids) of any suitable vehicle (e.g. biological agent) in order to confer these multifunctional activities such that any single activity predicts for another, quantitatively, spatially and temporally. A small gene insert (typically less than 2 kb) is desirable to minimise disruption of the therapeutic vector genome, whilst the capacity to encode multiple enzymatic functions (dependent upon substrate) concurrently permits tissue detection, conditional cytotoxicity or single cell ablation, singularly or in concert.

Further aspects of the invention, which should be considered in all its novel aspects, will become apparent to those skilled in the art upon reading of the following description which provides at least one example of a practical application of the invention.

DESCRIPTION OF THE FIGURES

Embodiments of the invention will now be described, by way of example only, with reference to the accompanying drawings in which:

FIG. 10 (A) illustrates the panel of five 2-nitroimidazoles evaluated as imaging agents FIGS. 10 (B) and 10 (C) illustrates the results of evaluation of 2-nitroimidazole clinical imaging candidates with E. coli and non-E. coli NTRs. Stably-expressing cells were treated with varying concentration of 2-nitroimidazole prodrugs diluted in αMEM+5% FCS+P/S. Cells were exposed to prodrug for 18 hrs, washed and left to regrow for 5 days. $IC_{50}$ was determined as the concentration of prodrug required to inhibit cell growth by 50% of untreated controls. $IC_{50}$ values are mean for ≥2 independent experiments. WT:NTR ratio-ratio of $IC_{50}$ means from WT cells versus NTR-expressing cell lines.

FIG. 12 illustrates the purified enzyme kinetic data for eleven E. coli nitroreductases with EF5 as a substrate. Reactions contained 10 mM Tris-Cl (pH 7.0), 4% DMSO, 0.25 mM NADPH and varying EF5 concentrations. Reactions were initiated by addition of 10 μl enzyme and changes in absorbance were measured for 15 s at 340 nm on a spectrophotometer to monitor NTR-catalysed NADPH oxidation.

FIG. 14 (B) illustrates the 'NfsA phenotyping' protocol indicating the gates used to determine percentage and fluorescence of NfsA expressing cells. Cells were treated with EF5 in 3D conditions (MCL or tumour), then trypsinised and $1\times10^6$ cells were plated and incubated with 20 μM pimonidazole for 1 hr at 37° C. FIG. 14 (B) further illustrates the Phenotyping procedure and Histograms of all CY5 and FITC events, then gating of PIMO+ve cells to give EF5/CY5 activity in only NfsA-expressing cells.

FIG. 15 illustrates the results of flow cytometry analysis demonstrating the ability to precisely and selectively label nfsA-expressing HCT116 cells in intimate 3D contact with parental HCT116 (WT). Cells were treated under 3D conditions (MCL) as described in the title, then trypsinised and $1\times10^6$ cells were plated and incubated as a monolayer with 20 μM pimonidazole for 1 hr at 37° C. Dot plots demonstrating use of pimo-labelling to distinguish between total nfsA +ve and -ve and those cells labelled in 3D by EF5. Left: MCL containing 17% NfsA positive HCT116 cells (plus 83% WT) as detected by PIMO following disaggregation. Right: MCL containing 17% NfsA positive HCT116 cells which are detected by EF5 exposure in 3D with subsequent resolution by flow cytometry following disaggregation.

FIG. 16 (A) further illustrates Fluorescent microscope pictures of tumour sections, and FIG. 16 (B) illustrates flow cytometry histograms of EF5/CY5 fluorescence to confirm % NfsA expressing cells of individual tumour.

FIG. 30: Bystander efficiency summary of expanded set of compounds shown in FIG. 22 to FIG. 29 inclusive. MCLs contained either 100% HCT-116$^{WT}$ or were seeded with 75%:25% ratio of HCT116$^{WT}$/HCT 116$^{NfsA}$ cells. Exact wt:nfsA cell ratios varied between experiments as defined in individual legends. The table identifies a series of compounds with no detectable bystander effect (BEE=0%). These nil-bystander agents have potential utility as cytoprotective (biosafety) agents in clinical gene therapy procedures. Specifically, where the concentration×time (CT) of agent required to eliminate 90% of NfsA expressing cells (AcC10) is less than the concentration×time (CT) achieved in human plasma (AUC) it is anticipated the agent will provide a useful therapeutic index. * indicates not determined as $IC_{50}$>100 uM for NfsA. #Human AUC/$A_C C_{10}$ ratio defines the therapeutic window for single cell ablation at tissue-like cell densities as a function of achievable human plasma concentrations. References for human plasma AUC values are as follows:

References (column 7) for human plasma AUC values:
1. Koch C J, Hahn S M, Rockwell Jr K, Covey J M, McKenna W G, Evans S M. (2001) Pharmacokinetics of EF5 [2-(2-nitro-1-H-imidazol-1-yl)-N-(2,2,3,3,3-pentafluoropropyl) acetamide] in human patients: implications for hypoxia measurements in vivo by 2-nitroimidazoles. *Cancer Chemother Pharmacol* 48: 177-187.
2. Coleman C N, Noll L, Howes A E, Harris J R, Zakar J, Kramer R A. (1989) Initial results of a phase I trial of continuous infusion SR 2508 (etanidazole): a Radiation Therapy Oncology Group study. *Int J Radiat Oncol Biol Phys* 16: 1085-1087.
3. Urtasun R C, Chapman J D, Band P, Rabin H, Fryer C G, Sturmwind J. (1975) Phase I study of high-dose metronidazole: a specific in vivo and in vitro radiosensitizer of hypoxic cells. *Radiology* 117: 129-133.
4. Gary A J, Dische S, Adams G E, Flockhart I R, Foster J L. (1976) Clinical testing of radiosensitizer Ro-07-0582. I. Dose tolerance, serum and tumour concentrations. *Clin Radiol* 27: 151-157.
5. Li X, Li B, Ni M, Wang B, Guo R. (2007) An improved HPLC method for determination of nifuratel in human plasma and its application to pharmacokinetic studies. *Eur J Drug Metab Ph* 32(2):69-73.
6. Gonzalez-Martin G, Thambo S, Paulos C, Vasquez I, Paredes J. (1992) The pharmacokinetics of nifurtimox in chronic renal failure. *Eur J Clin Pharmacol* 42: 671-674.
7. Timothy A R, Overgaard J, Overgaard M. (1984) A phase I clinical study of nimorazole as a hypoxic radiosensitizer. *Int J Radiat Oncol Biol Phys* 10: 1765-1768.
8. Adkison K K, Vaidya S S, Lee D Y, Koo S H, Li L, Mehta A A, Gross A S, Polli J W, Lou Y, Lee E J D. (2008) The ABCG2 C421A polymorphism does not affect oral nitrofurantoin pharmacokinetics in healthy Chinese male subjects. *Br J clin Pharmacol* 66(2): 233-239.
9. Ramamurthy L, Kulkarni R D, Chauhan B L, Sharma D R, Singh A. (2002) Relative bioavailability of two brands of Ornidazole in twelve healthy volunteers. *J Assoc Physicians India* 50: 1149-1152.
10. Weiss G J, Infante J R, Chiorean E G, Borad M J, Bendall J C, Molina J R, Tibes R, Ramanathan R K, Lewandowski K, Jones S F, Lacouture M E, Langmuir V K, Lee H, Kroll S, Burris H A. (2011) Phase I study of the safety, tolerability and pharmacokinetics of TH-302, a hypoxia-activated prodrug, in patients with advanced solid malignancies. *Clin Cancer Res* 17: 2997-3004.
11. RX-list URL.
12. Patel K, Choy S S F, Hicks K O, Melink T J, Holford N H G, Wilson W R. (2010) A combined pharmacokinetic model for the hypoxia-targeted prodrug PR-104A in humans, dogs, rats and mice predicts species differences in clearance and toxicity. *Cancer Chemother Pharmacol* 67: 1145-1155.

Figure 31:
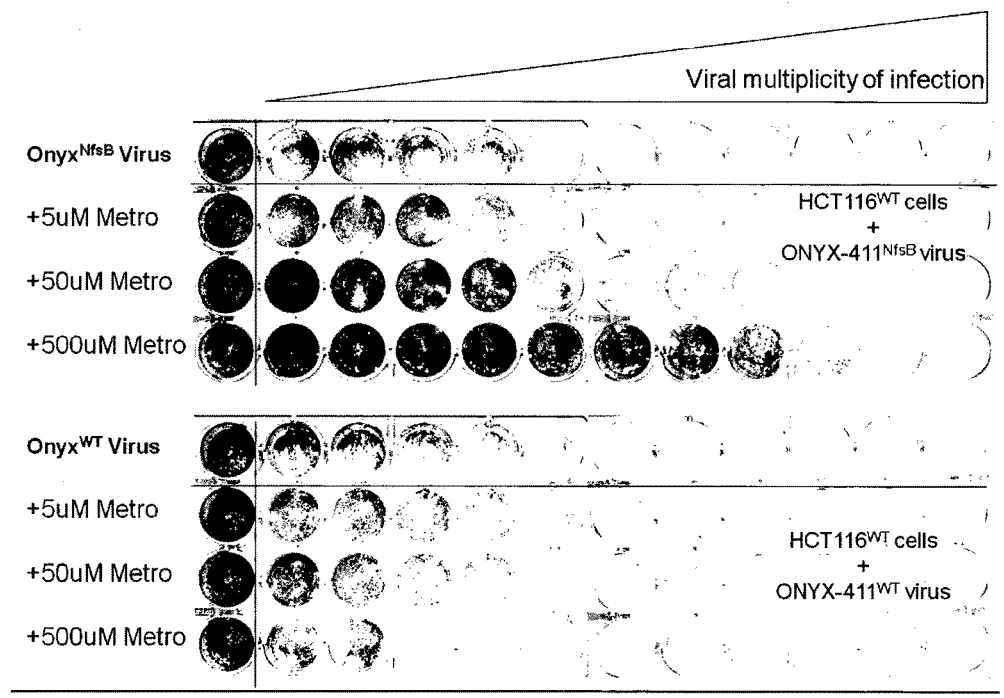

FIG. 31 illustrates the cytoprotective effects of NfsB dependent activation of metronidazole by conditionally replicating virus ONYX411$^{NfsB}$. HCT-116WT cells were seeded overnight and the top wells were infected with 0.125 MOI for ONYX411-nfsB and 1 MOI for ONYX411-WT with 2-fold serial dilutions. 24 hrs following infection media was replaced with fresh αMEM containing 2% FCS and varying concentrations of metronidazole, which was refreshed every 2 days. On day 9 wells were fixed with 10% TCA and stained with SRB and cell density analysed.

Figure 32:
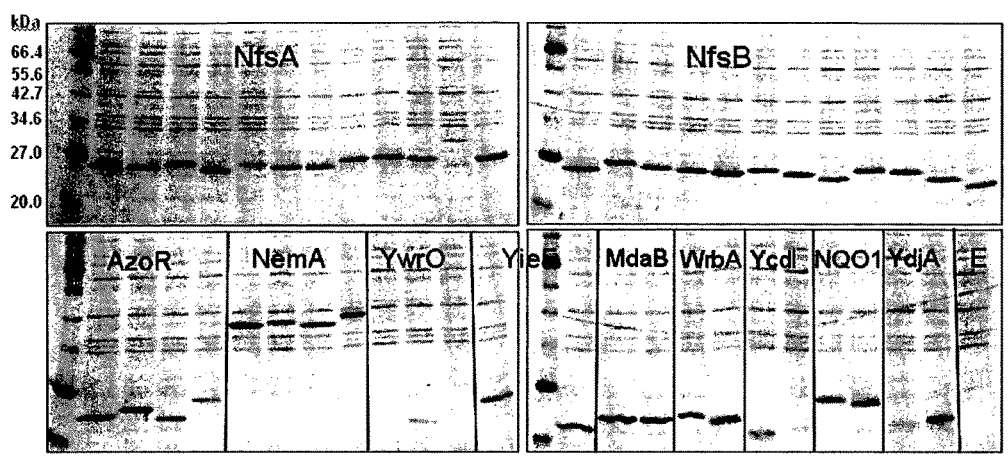

FIG. 32 illustrates SDS-PAGE analysis of expression levels of a subset of 47 NTRs from the 58-NTR core library. NTRs were expressed from pUCX in the *E. coli* reporter strain SOS-R2. The order of enzymes from left to right, top two gels then bottom two gels, is as follows: NfsA (Ec); NfsA (St); NfsA (Ck); NfsA (Kp); NfsA (Es); NfsA (Vf); NfsA (Vv); Frp (Vh); NfrA (Bs); NfsA (Li); EcD (Pp); YcnD (Bs); NfsB (Ec); NfsB (Ck); NfsB (St); NfsB (Kp); NfsB (Vv); 2432 (Pp); NfsB (Es); Frasel (Vf); NfsB (Vh); YfkO (Bs); YdgI (Bs); 5190 (Pa); AzoR (Ec); AzoR (St); AzoR (Vv); 4538 (Pp); NemA (Ec); NemA (St); NemA (Kp); NemA (Vv); YwrO (Bs); YwrO (Li); YwrO (Vf); YieF (Ec); 1204 (Pa); MdaB (Ec); MdaB (Ps); WrbA (Ec); WrbA (Ps); YdjA (Ec); YdjA (Kp); 3720 (Pp); 4975 (Pa); YcdI (Ec); YcdI (Kp). The final sample, "E", is the empty vector control; and each gel has standard markers in the left-most lane (with sizes as marked at the left of to the top left-most gel). Samples for electrophoresis were taken from a single replicate at the conclusion of an SOS assay. Samples were normalized for cell density (OD600) prior to gel loading. Expression of the remaining 8 NfsA family members, the two YcaK family members and *E. coli* KefF was demonstrated to yield visible bands on SDS-PAGE conducted in identical fashion (not shown).

Figure 33:
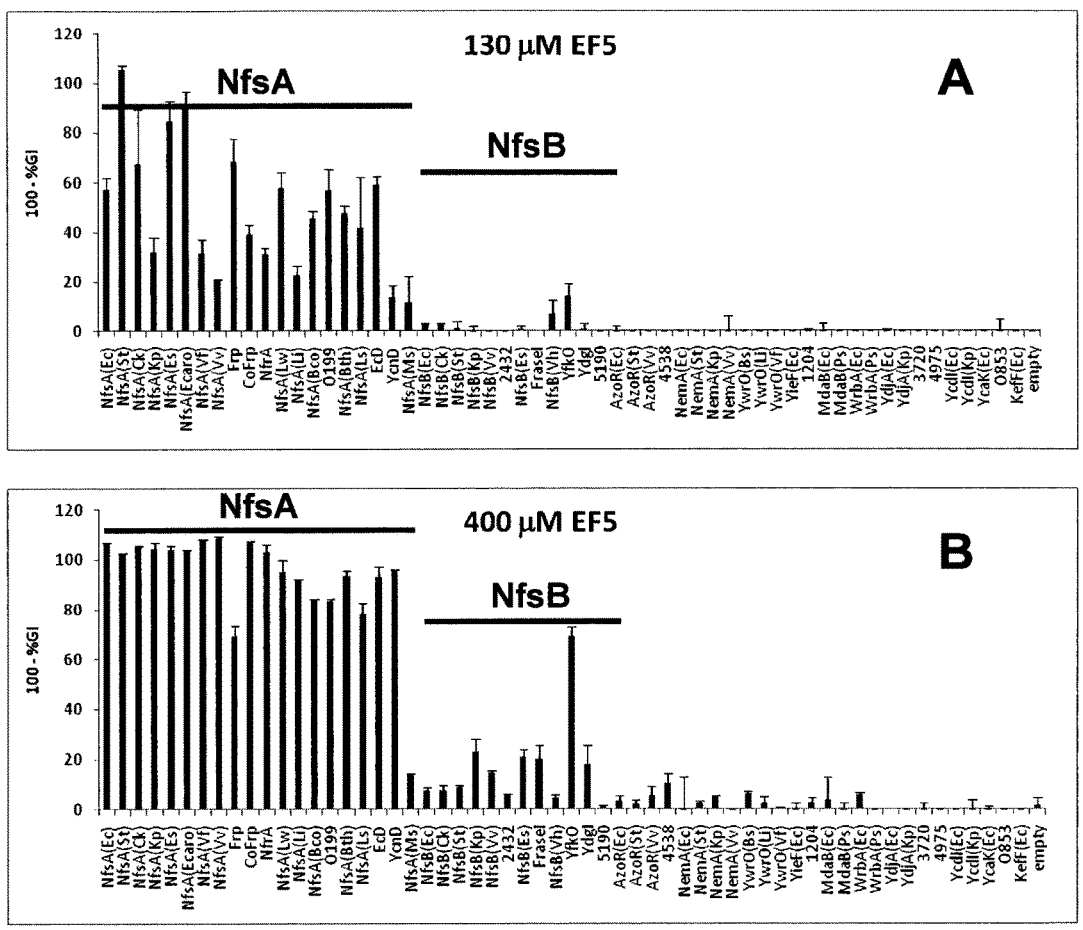

FIG. 33 (A) illustrates the metabolism of EF5 by NfsA members of the 58-membered NTR over-expression library as measured by Growth Inhibition assay. Turbidity ($OD_{600}$) of NTR over-expressing cell cultures was recorded directly before and after 4 h incubation with 130 μM EF5. Growth Inhibition (% GI) is expressed as the percentage decrease in $OD_{600}$ of challenged cells relative to unchallenged control cells for each strain post-incubation. The Y-axis presents this data in an inverse manner (100-% GI) such that positive values indicate heightened growth inhibition in the challenged culture. Data are the average of 2 independent assays and the error bars indicate ±1 standard deviation. The bars corresponding to the NfsA and NfsB family members are as marked.

FIG. 33 (B) illustrates the metabolism of EF5 by members of the 58 NTR over-expression library, measured by Growth Inhibition assay as described for FIG. 33 (A) except that cells were challenged with 400 μM EF5.

Figure 34:
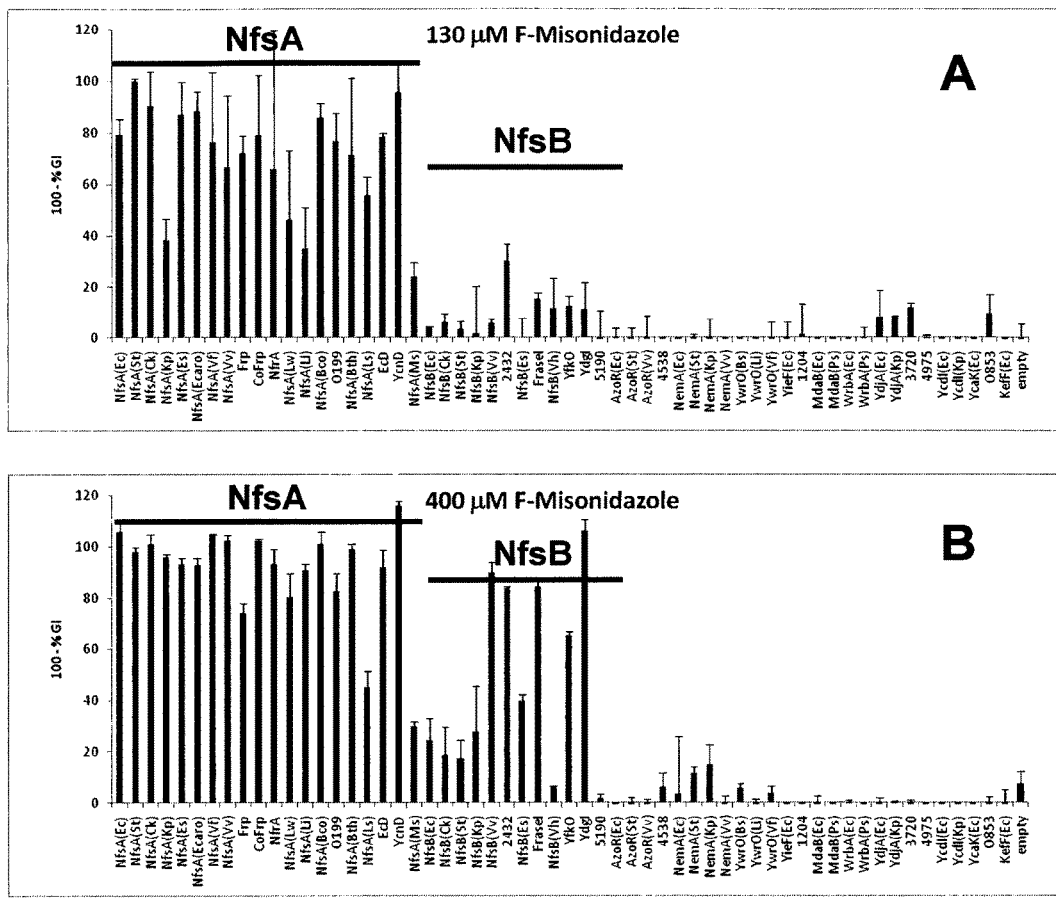

FIG. 34 (A) illustrates the metabolism of F-MISO by members of the 58 NTR over-expression library as measured by Growth Inhibition assay. Turbidity ($OD_{600}$) of NTR over-expressing cell cultures was recorded directly before and after 4 h incubation with 130p, F-MISO. Growth Inhibition (% GI) is expressed as the percentage decrease in $OD_{600}$ of challenged cells relative to unchallenged control cells for each strain post-incubation. The Y-axis presents this data in an inverse manner (100-% GI) such that positive values indicate heightened growth inhibition in the challenged culture. Data are the average of 2 independent assays and the error bars indicate ±1 standard deviation. The bars corresponding to the NfsA and NfsB family members are as marked.

FIG. 34 (B) illustrates the metabolism of F-MISO by members of the 58 NTR over-expression library as measured by Growth Inhibition assay as described for FIG. 34A except that cells were challenged with 400 μM F-MISO.

Figure 35:
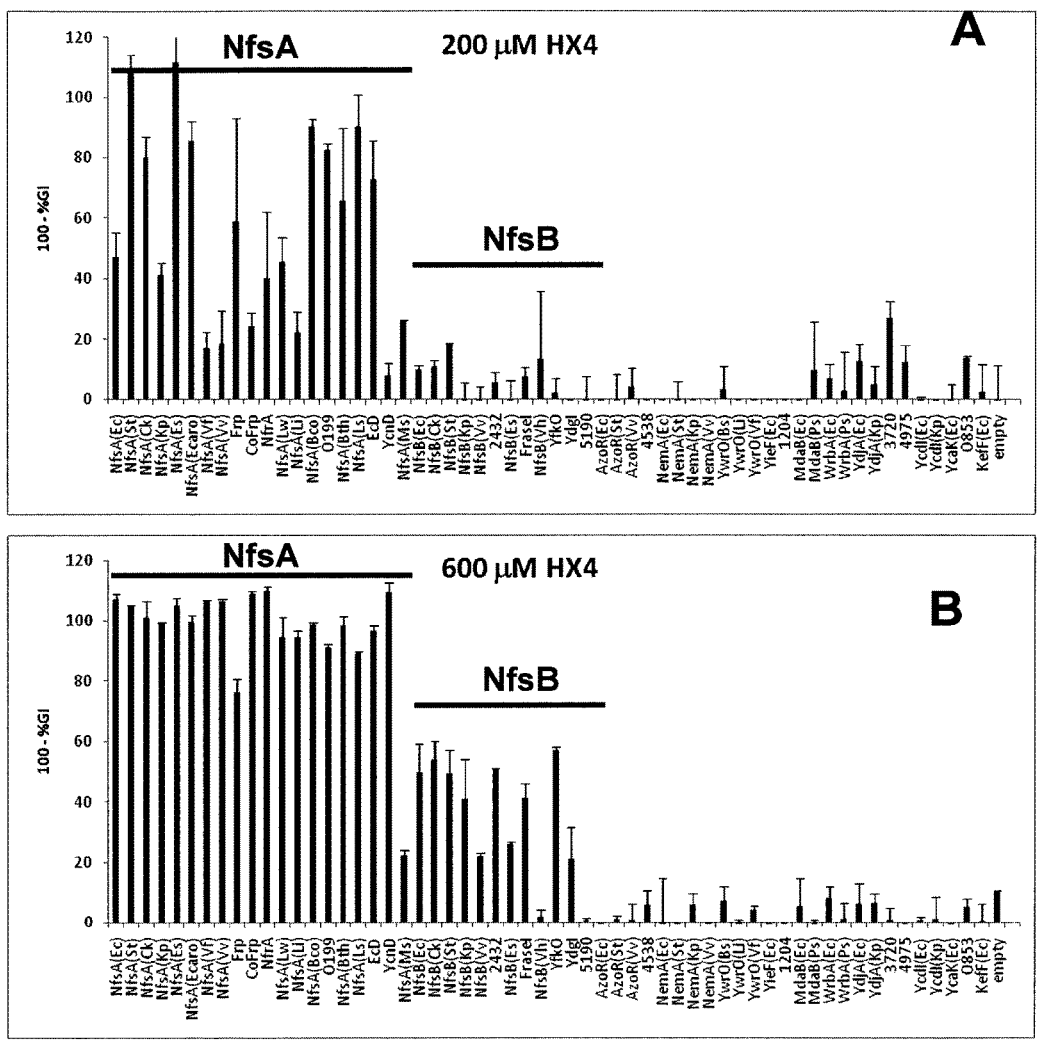

FIG. 35 (A) illustrates the metabolism of HX4 by members of the 58 NTR over-expression library as measured by Growth Inhibition assay. Turbidity ($OD_{600}$) of NTR over-expressing cell cultures was recorded directly before and after 4 h incubation with 200 μM HX4. Growth Inhibition (% GI) is expressed as the percentage decrease in $OD_{600}$ of challenged cells relative to unchallenged control cells for each strain post-incubation. The Y-axis presents this data in an inverse manner (100-% GI) such that positive values indicate heightened growth inhibition in the challenged culture. Data are the average of 2 independent assays and the error bars indicate ±1 standard deviation. The bars corresponding to the NfsA and NfsB family members are as marked.

FIG. 35 (B) illustrates the metabolism of HX4 by members of the 58 NTR over-expression library as measured by Growth Inhibition assay as described for FIG. 35A except that cells were challenged with 600 µM HX4.

Figure 36:
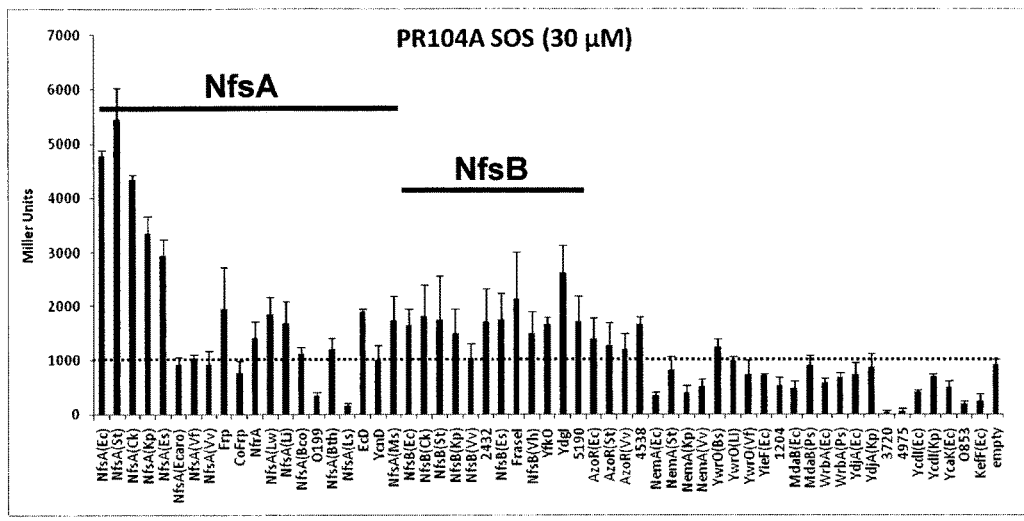

FIG. 36 illustrates the metabolism of PR-104A by members of the 58 NTR over-expression library as measured by SOS assay. The data presented is the SOS response, measured by β-galactosidase activity (in Miller units), of NTR-over-expressing $E.\ coli$ SOS-R2 after 4 h challenge with 30 µM PR-104A. Data are the average of 2 independent assays and the error bars indicate ±1 standard deviation. The red dashed line indicates the baseline activity for the empty plasmid control, and the bars corresponding to the NfsA and NfsB family members are as marked.

Figure 37:
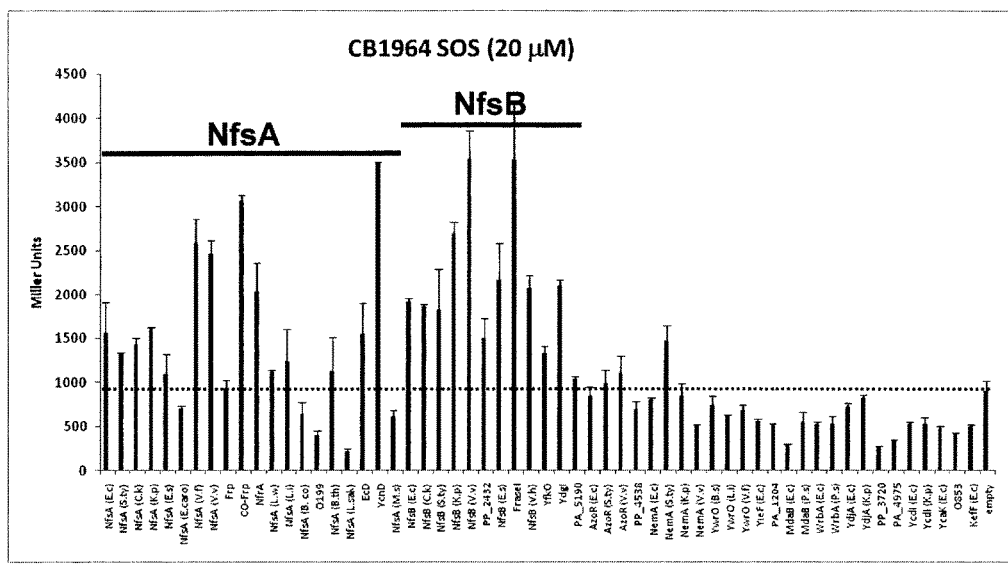

FIG. 37 illustrates the metabolism of CB1954 by members of the 58 NTR over-expression library as measured by SOS assay. The data presented is the SOS response, measured by β-galactosidase activity (in Miller units), of NTR-over-expressing $E.\ coli$ SOS-R2 after 3.5 h challenge with 20 µM CB1954. Data are the average of 2 independent assays and the error bars indicate ±1 standard deviation. The red dashed line indicates the baseline activity for the empty plasmid control, and the bars corresponding to the NfsA and NfsB family members are as marked.

Figure 38:
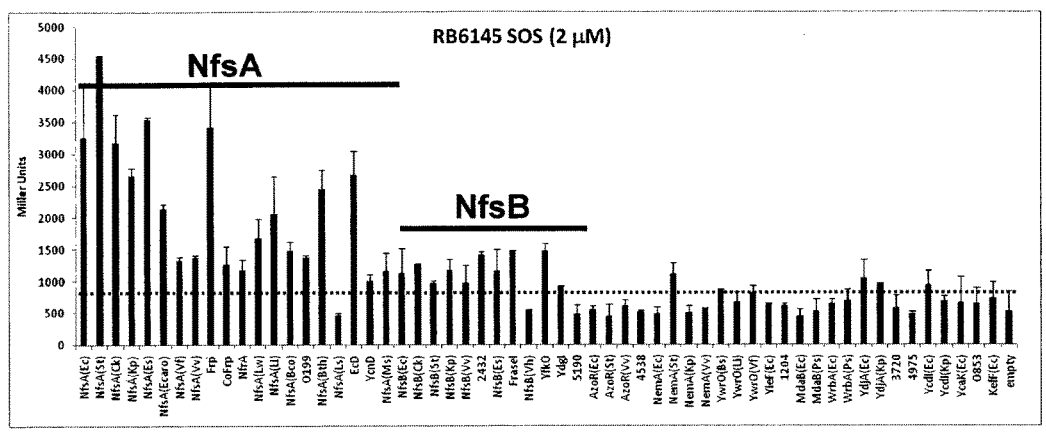

FIG. 38 illustrates the metabolism of RB6145 by members of the 58 NTR over-expression library as measured by SOS assay. The data presented is the SOS response, measured by β-galactosidase activity (in Miller units), of NTR-over-expressing $E.\ coli$ SOS-R2 after 4 h challenge with 2 µM RB6145. Data are the average of 2 independent assays and the error bars indicate ±1 standard deviation. The red dashed line indicates the baseline activity for the empty plasmid control, and the bars corresponding to the NfsA and NfsB family members are as marked.

Figure 39:
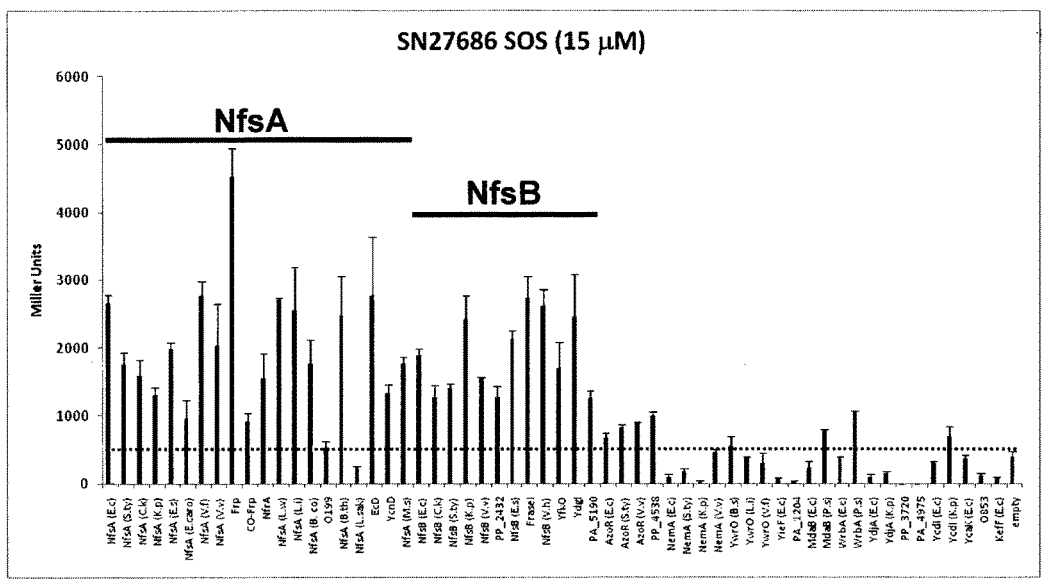

FIG. 39 illustrates the metabolism of SN27686 by members of the 58 NTR over-expression library as measured by SOS assay. The data presented is the SOS response, measured by β-galactosidase activity (in Miller units), of NTR-over-expressing $E.\ coli$ SOS-R2 after 4.5 h challenge with 15 µM SN27686. Data are the average of 2 independent assays and the error bars indicate ±1 standard deviation. The red dashed line indicates the baseline activity for the empty plasmid control, and the bars corresponding to the NfsA and NfsB family members are as marked.

Figure 40:
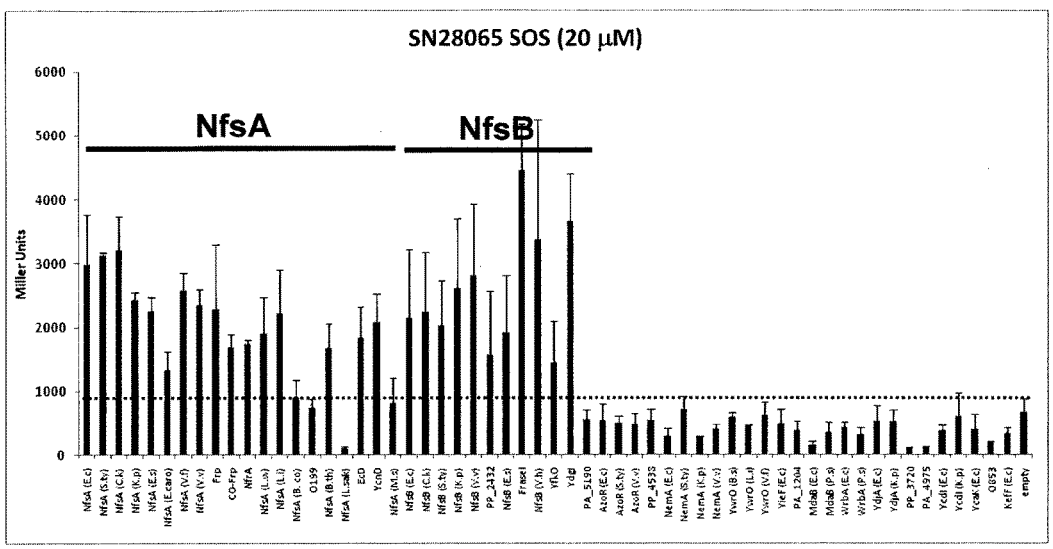

FIG. 40 illustrates the metabolism of SN28065 by members of the 58 NTR over-expression library as measured by SOS assay. The data presented is the SOS response, measured by β-galactosidase activity (in Miller units), of NTR-over-expressing $E.\ coli$ SOS-R2 after 3.5 h challenge with 20 µM SN28065. Data are the average of 2 independent assays and the error bars indicate ±1 standard deviation. The red dashed line indicates the baseline activity for the empty plasmid control, and the bars corresponding to the NfsA and NfsB family members are as marked.

Figure 41:
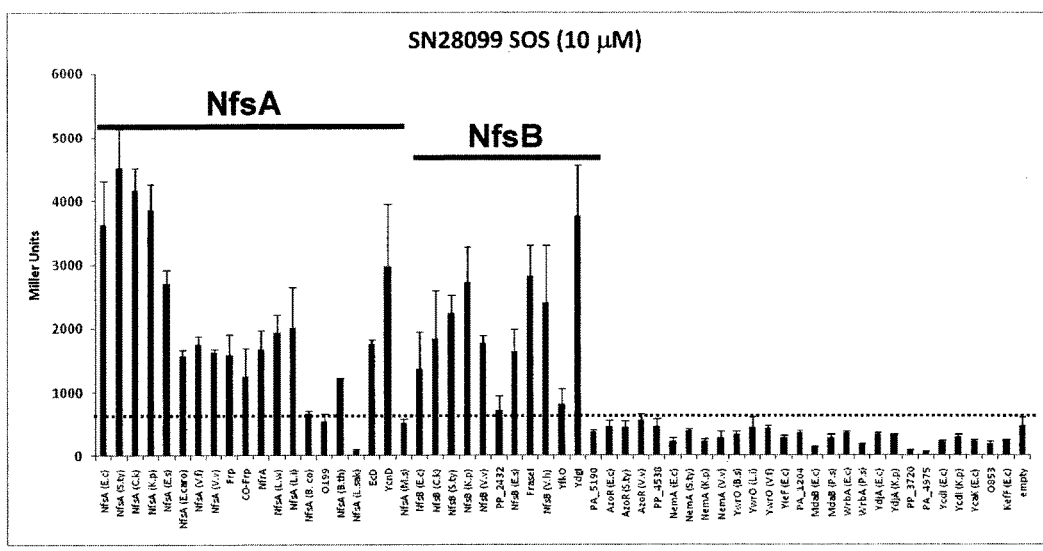

FIG. 41 illustrates the metabolism of SN28099 by members of the 58 NTR over-expression library as measured by SOS assay. The data presented is the SOS response, measured by β-galactosidase activity (in Miller units), of NTR-over-expressing $E.\ coli$ SOS-R2 after 3.5 h challenge with 10 µM SN28099. Data are the average of 2 independent assays and the error bars indicate ±1 standard deviation. The red dashed line indicates the baseline activity for the empty plasmid control, and the bars corresponding to the NfsA and NfsB family members are as marked.

Figure 42:
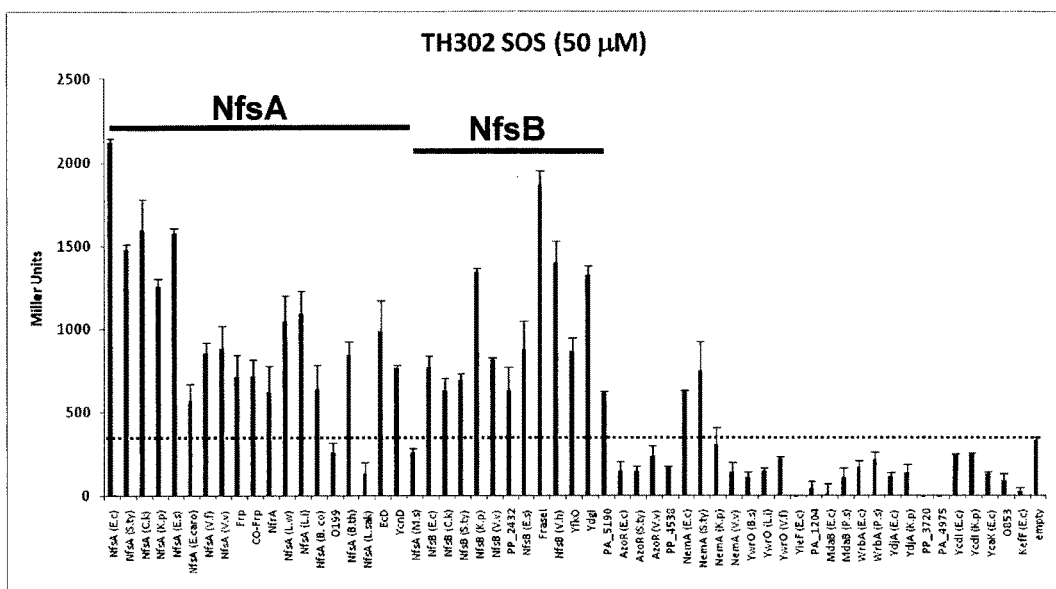

FIG. 42 illustrates metabolism of TH-302 by members of the 58 NTR over-expression library as measured by SOS assay. The data presented is the SOS response, measured by β-galactosidase activity (in Miller units), of NTR-over-expressing $E.\ coli$ SOS-R2 after 4.5 h challenge with 50 µM TH-302. Data are the average of 2 independent assays and the error bars indicate ±1 standard deviation. The red dashed line indicates the baseline activity for the empty plasmid control, and the bars corresponding to the NfsA and NfsB family members are as marked.

Figure 43:
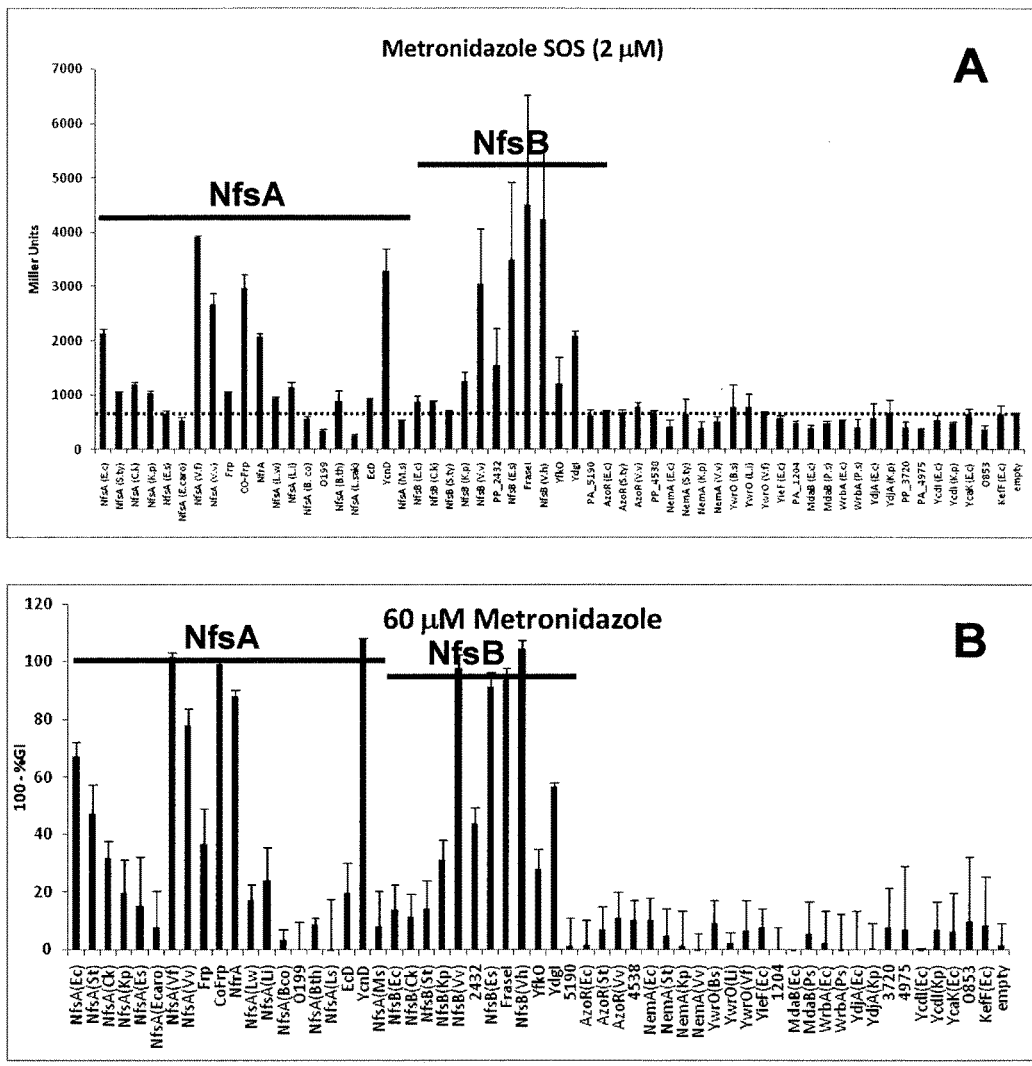

FIG. 43 (A) illustrates metabolism of metronidazole by members of the 58 NTR over-expression library as measured by SOS assay. The data presented is the SOS response, measured by β-galactosidase activity (in Miller units), of NTR-over-expressing $E.\ coli$ SOS-R2 after 3.5 h challenge with 2 µM metronidazole. Data are the average of 2 independent assays and the error bars indicate ±1 standard deviation. The red dashed line indicates the baseline activity for the empty plasmid control, and the bars corresponding to the NfsA and NfsB family members are as marked.

FIG. 43 (B) illustrates metabolism of metronidazole by members of the 58 NTR over-expression library as measured by Growth Inhibition assay. Turbidity ($OD_{600}$) of NTR over-expressing cell cultures was recorded directly before and after 4 h incubation with 60 µM metronidazole. Growth Inhibition (% GI) is expressed as the percentage decrease in $OD_{600}$ of challenged cells relative to unchallenged control cells for each strain post-incubation. The Y-axis presents this data in an inverse manner (100-% GI) such that positive values indicate heightened growth inhibition in the challenged culture. Data are the average of 2 independent assays and the error bars indicate ±1 standard deviation. The bars corresponding to the NfsA and NfsB family members are as marked.

Figure 44:
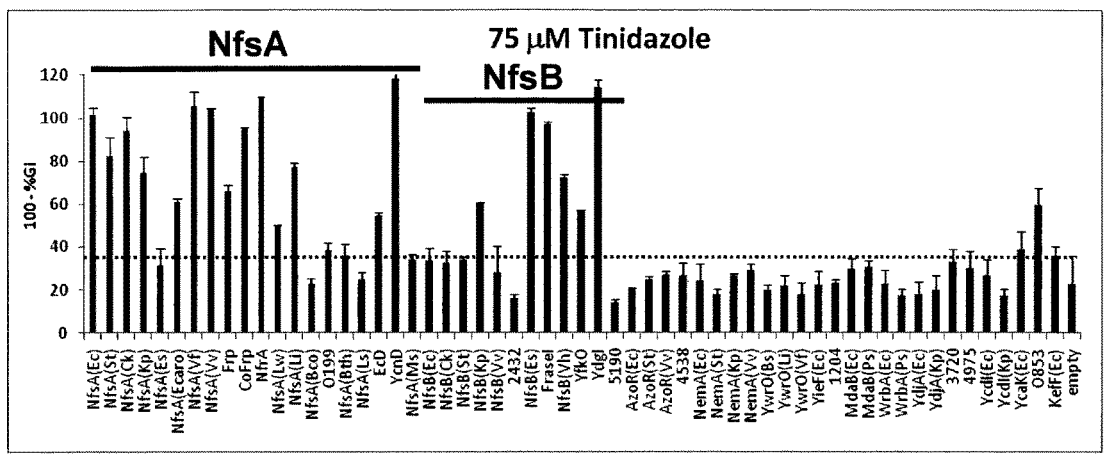

FIG. 44 illustrates metabolism of tinidazole by members of the 58 NTR over-expression library as measured by Growth Inhibition assay. Turbidity ($OD_{600}$) of NTR over-expressing cell cultures was recorded directly before and after 4 h incubation with 75 µM tinidazole. Growth Inhibition (% GI) is expressed as the percentage decrease in $OD_{600}$ of challenged cells relative to unchallenged control cells for each strain post-incubation. The Y-axis presents this data in an inverse manner (100-% GI) such that positive values indicate heightened growth inhibition in the challenged culture. Data are the average of 2 independent assays and the error bars indicate ±1 standard deviation. The red dashed line indicates the baseline activity for the empty plasmid control, and the bars corresponding to the NfsA and NfsB family members are as marked.

Figure 45:
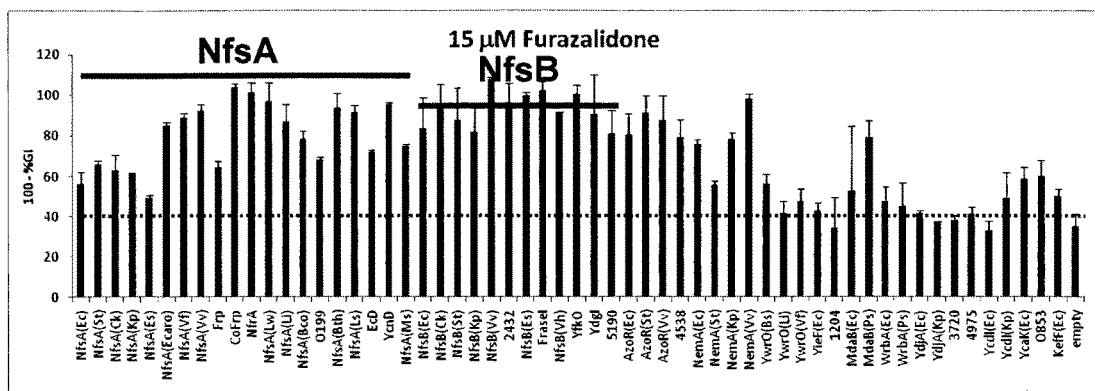

FIG. 45 illustrates metabolism of furazalidone by members of the 58 NTR over-expression library as measured by Growth Inhibition assay. Turbidity ($OD_{600}$) of NTR over-expressing cell cultures was recorded directly before and after 4 h incubation with 15 µM furazalidone. Growth Inhibition (% GI) is expressed as the percentage decrease in $OD_{600}$ of challenged cells relative to unchallenged control cells for each strain post-incubation. The Y-axis presents this data in an inverse manner (100-% GI) such that positive values indicate heightened growth inhibition in the challenged culture. Data are the average of 2 independent assays and the error bars indicate ±1 standard deviation. The red dashed line indicates the baseline activity for the empty plasmid control, and the bars corresponding to the NfsA and NfsB family members are as marked.

Figure 46:
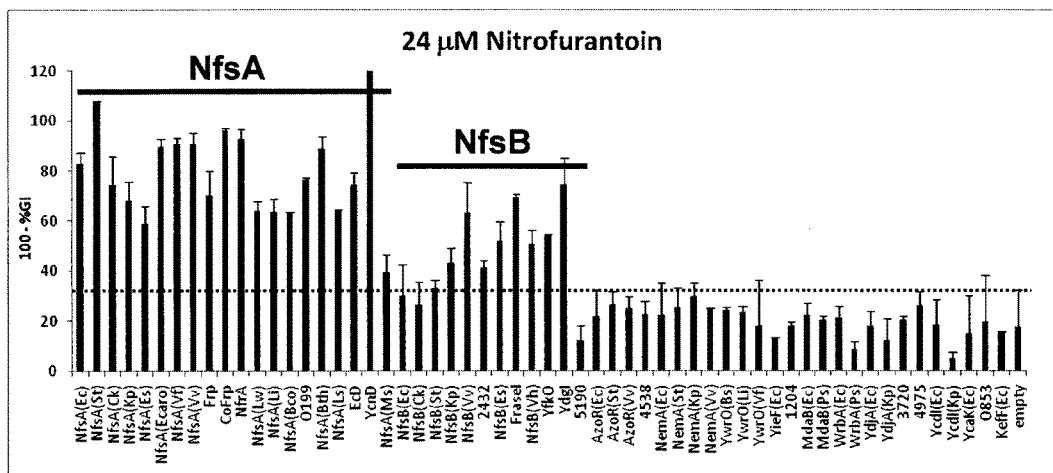

FIG. 46 illustrates metabolism of nitrofurantoin by members of the 58 NTR over-expression library as measured by Growth Inhibition assay. Turbidity ($OD_{600}$) of NTR over-expressing cell cultures was recorded directly before and after 4 h incubation with 24 µM nitrofurantoin. Growth Inhibition (% GI) is expressed as the percentage decrease in $OD_{600}$ of challenged cells relative to unchallenged control cells for each strain post-incubation. The Y-axis presents this data in an inverse manner (100-% GI) such that positive values indicate heightened growth inhibition in the challenged culture. Data are the average of 2 independent assays and the error bars indicate ±1 standard deviation. The red dashed line indicates the baseline activity for the empty plasmid control, and the bars corresponding to the NfsA and NfsB family members are as marked.

Figure 47:
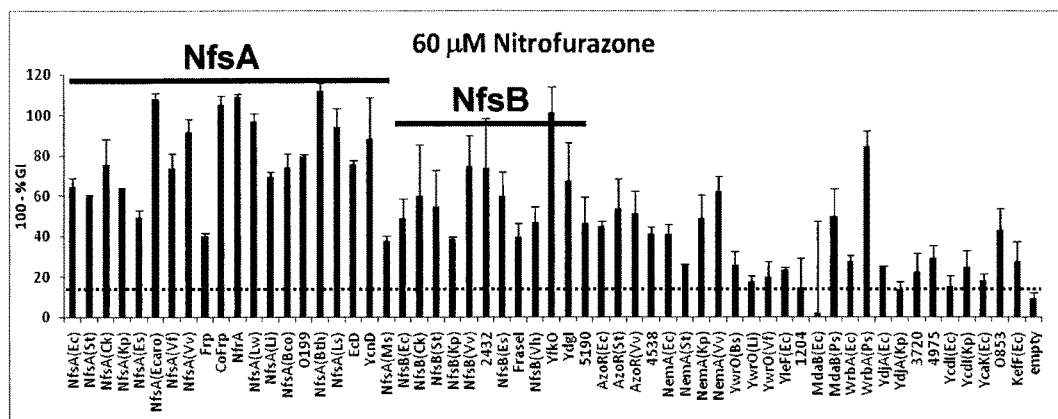

FIG. 47 illustrates metabolism of nitrofurazone by members of the 58 NTR over-expression library as measured by Growth Inhibition assay. Turbidity ($OD_{600}$) of NTR over-expressing cell cultures was recorded directly before and after 4 h incubation with 60 µM nitrofurazone. Growth Inhibition (% GI) is expressed as the percentage decrease in $OD_{600}$ of challenged cells relative to unchallenged control cells for each strain post-incubation. The Y-axis presents this data in an inverse manner (100-% GI) such that positive values indicate heightened growth inhibition in the challenged culture. Data are the average of 2 independent assays and the error bars indicate ±1 standard deviation. The red dashed line indicates the baseline activity for the empty plasmid control, and the bars corresponding to the NfsA and NfsB family members are as marked.

Figure 48:
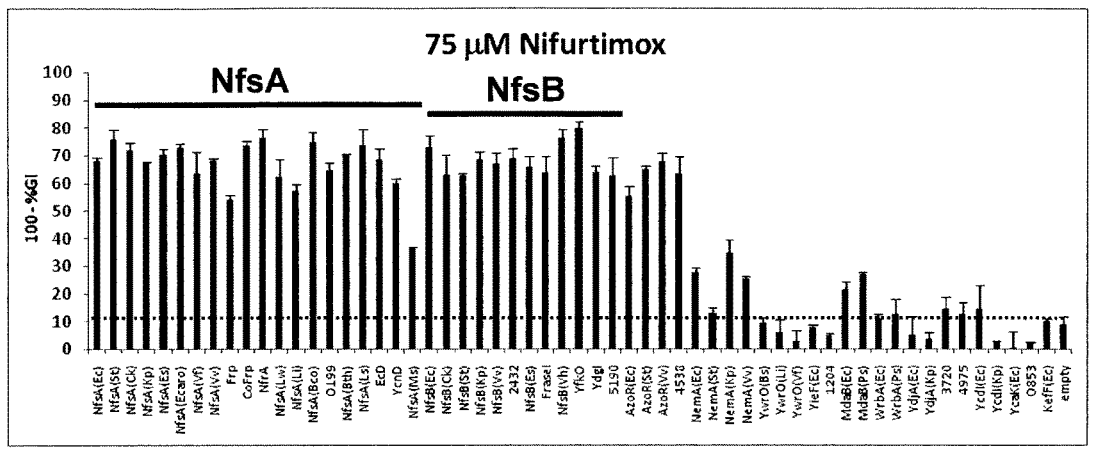

FIG. 48 illustrates metabolism of nifurtimox by members of the 58 NTR over-expression library as measured by Growth Inhibition assay. Turbidity ($OD_{600}$) of NTR over-expressing cell cultures was recorded directly before and after 4 h incubation with 75 µM nifurtimox. Growth Inhibition (% GI) is expressed as the percentage decrease in $OD_{600}$ of challenged cells relative to unchallenged control cells for each strain post-incubation. The Y-axis presents this data in an inverse manner (100-% GI) such that positive values indicate heightened growth inhibition in the challenged culture. Data are the average of 2 independent assays and the error bars indicate ±1 standard deviation. The red dashed line indicates the baseline activity for the empty plasmid control, and the bars corresponding to the NfsA and NfsB family members are as marked.

Figure 49:
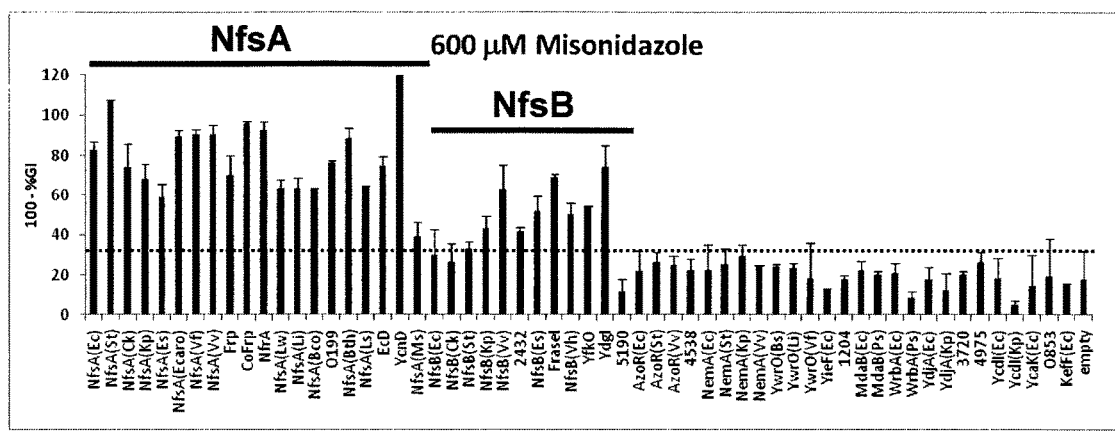

FIG. 49 illustrates metabolism of misonidazole by members of the 58 NTR over-expression library as measured by Growth Inhibition assay. Turbidity ($OD_{600}$) of NTR over-expressing cell cultures was recorded directly before and after 4 h incubation with 600 µM misonidazole. Growth Inhibition (% GI) is expressed as the percentage decrease in $OD_{600}$ of challenged cells relative to unchallenged control cells for each strain post-incubation. The Y-axis presents this data in an inverse manner (100-% GI) such that positive values indicate heightened growth inhibition in the challenged culture. Data are the average of 2 independent assays and the error bars indicate ±1 standard deviation. The red dashed line indicates the baseline activity for the empty plasmid control, and the bars corresponding to the NfsA and NfsB family members are as marked.

Figure 50:
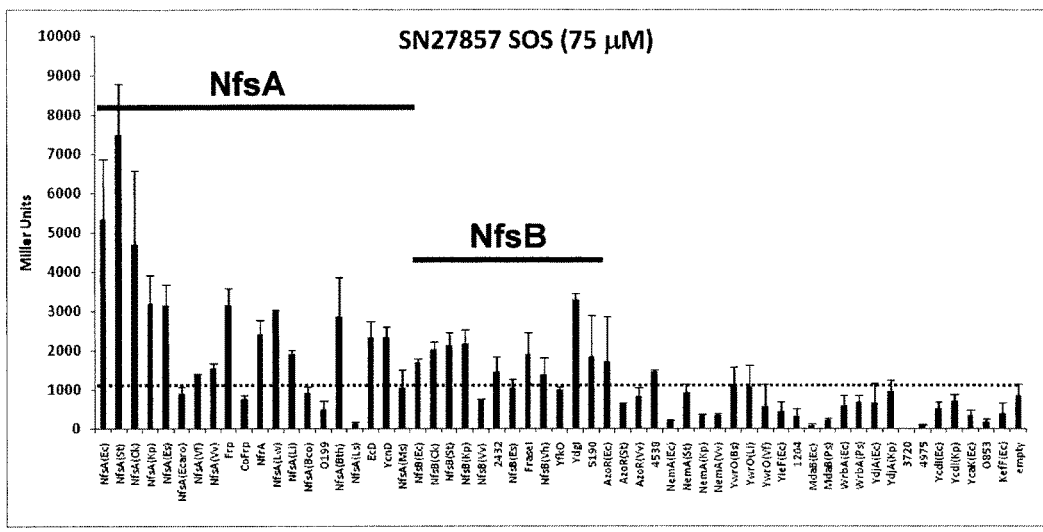

FIG. 50 illustrates the metabolism of SN27857 by members of the 58 NTR over-expression library as measured by SOS assay. The data presented is the SOS response, measured by β-galactosidase activity (in Miller units), of NTR-over-expressing E. coli SOS-R2 after 4 h challenge with 75 µM SN27857. Data are the average of 2 independent assays and the error bars indicate ±1 standard deviation. The red dashed line indicates the baseline activity for the empty plasmid control, and the bars corresponding to the NfsA and NfsB family members are as marked.

Figure 51:
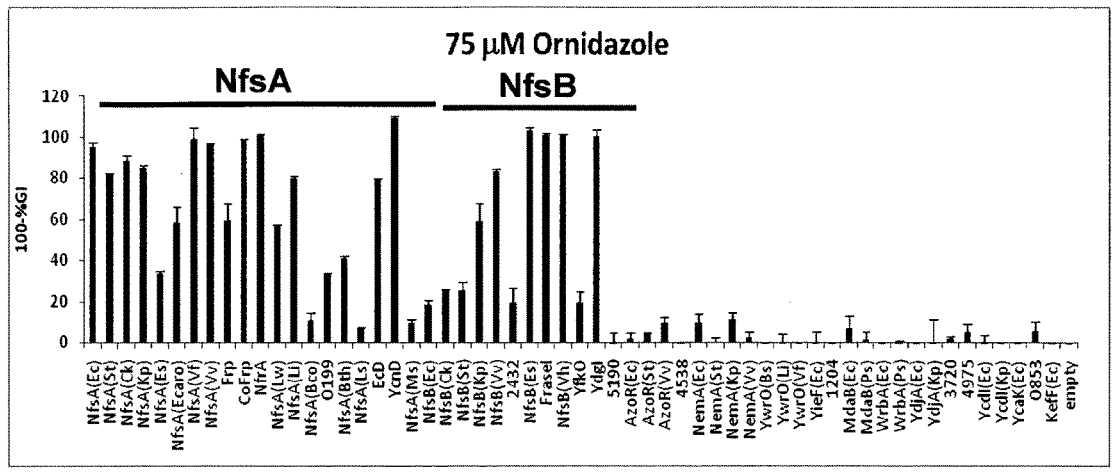

FIG. 51 illustrates metabolism of ornidazole by members of the 58 NTR over-expression library as measured by Growth Inhibition assay. Turbidity ($OD_{600}$) of NTR over-expressing cell cultures was recorded directly before and after 4 h incubation with 75 µM ornidazole. Growth Inhibition (% GI) is expressed as the percentage decrease in $OD_{600}$ of challenged cells relative to unchallenged control cells for each strain post-incubation. The Y-axis presents this data in an inverse manner (100-% GI) such that positive values indicate heightened growth inhibition in the challenged culture. Data are the average of 2 independent assays and the error bars indicate ±1 standard deviation. The bars corresponding to the NfsA and NfsB family members are as marked.

FIG. 52 illustrates purified enzyme kinetic data with EF5 for selected nitroreductases. Reactions contained 10 mM Tris-Cl (pH 7.0), 4% DMSO, 0.25 mM NADPH and varying EF5 concentrations. Reactions were initiated by addition of 10 µl enzyme and changes in absorbance were measured for 15 s at 340 nm on a spectrophotometer to monitor NTR-catalysed NADPH oxidation. NfsA family members are highlighted in bold.

FIG. 53 illustrates purified enzyme kinetic data with F-MISO for selected nitroreductases. Reactions contained 10 mM Tris-Cl (pH 7.0), 4% DMSO, 0.25 mM NADPH and varying F-MISO concentrations. Reactions were initiated by addition of 10 µl enzyme and changes in absorbance were measured for 15 s at 340 nm on a spectrophotometer to monitor NTR-catalysed NADPH oxidation.

FIG. 54 illustrates purified enzyme kinetic data with PR-104A for selected nitroreductases. Reduction of PR-104A was measured as decrease in absorbance at 400 nm ($\varepsilon$=6000 $M^{-1}$ $cm^{-1}$). All reactions were performed in 10 mM Tris-Cl buffer (pH 7.0), supplemented with 0.25 mM NAD(P)H. DMSO concentration was kept constant at 4% v/v in all reactions.

FIG. 55 illustrates purified enzyme kinetic data with CB1954 for selected nitroreductases. Reduction of CB1954 was measured at 420 nm ($\varepsilon$=6000 $M^{-1}$ $cm^{-1}$). All reactions were performed in 10 mM Tris-Cl buffer (pH 7.0), supplemented with 0.25 mM NAD(P)H. DMSO concentration was kept constant at 4% v/v in all reactions. Nitro-group reduction preference was determined by HPLC.

Figure 56:
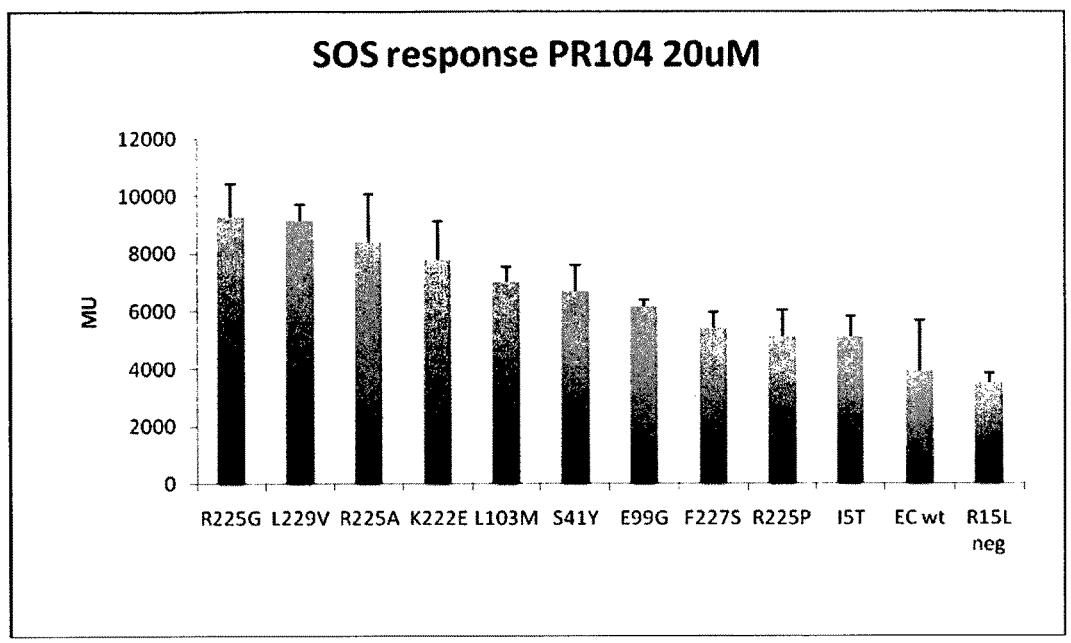

FIG. 56 illustrates the metabolism of PR-104A by single-residue mutants of NfsA(Ec) and the wild type enzyme as measured by SOS assay. R15L is a null mutant control; all other single-residue mutations were found to enhance SOS output. The data presented are Miller Units indicating the SOS response in E. coli SOS-R2 over-expressing different NfsA(Ec) variants after 3 h challenge with 20 µM PR-104A. Data are the average of 4 independent assays and error bars indicate ±1 standard deviation.

FIG. 57 illustrates the synthetic gene library that was designed using degenerate codons at each mutation site to comprise all possible combinations of wild type and preferred single-residue mutations. Redundancy codes were used to specify degenerate codons at each mutant site, such that either the wild-type NfsA(Ec) residue or the previously identified mutant residue (but no other amino acids) could potentially be specified by that codon. For example, at codon 41 the degenerate code TMC represents both TCC (specifying serine) and TAC (specifying tyrosine). The highlighted yellow sequences indicate NdeI (5' end) and SaI (3' end) restriction sequences that were incorporated to facilitate efficient cloning of the library into the pUCX plasmid vector.

Figure 58:
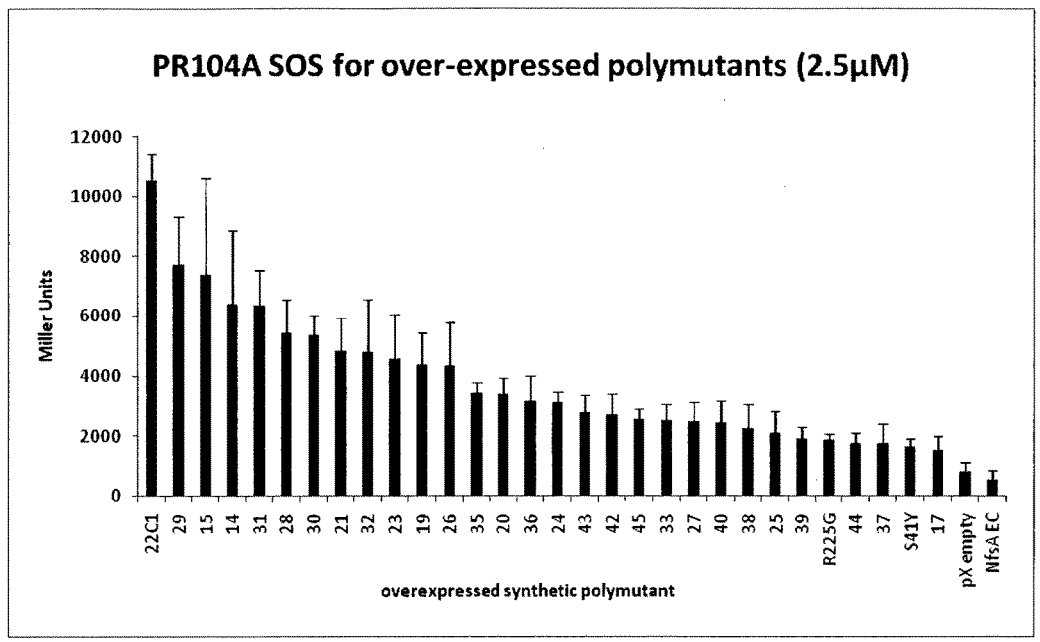

FIG. 58 illustrates the metabolism of PR-104A by poly-mutant variants of NfsA(Ec), alongside the two most active single mutant variants, the wild type enzyme and an empty plasmid control, as measured by SOS assay. The data presented are raw Miller Units indicating the SOS response in E. coli SOS-R2 over-expressing different NfsA(Ec) variants after 3 h challenge with 20 μM PR-104A. Data are the average of 4 independent assays and the error bars indicate ±1 standard deviation.

FIG. 59 illustrates the combinations of mutations identified in the ten preferred NfsA(Ec) polymutant variants and the relative sensitivities of E. coli strains expressing those polymutants to seven bioreductive compounds. Relative sensitivities for a given compound are the $IC_{50}$ of the strain expressing wild type NfsA divided by the $IC_{50}$ of the strain expressing a specific polymutant.

Polymutant codes are listed in the leftmost column. S41Y is the most generally active single-residue mutant; and "wt" is the wild type NfsA(Ec) enzyme. In the next seven columns, green shading indicates presence of that mutation in the polymutant, while white indicates the absence of that mutation (i.e. the wild type NfsA(Ec) residue was retained at that position). For mutations at position 225, the substituted residue is identified using the appropriate one-letter amino acid code. The mutation L229V was not represented in any of the preferred polymutants.

The remaining seven columns indicate the fold-increase in sensitivity (i.e. fold-decrease in measured $IC_{50}$ value) relative to wild type NfsA(Ec), for the various compounds tested. Yellow shading indicates a moderate increase in sensitivity; orange a large increase in sensitivity; and red a very large increase in sensitivity. Grey shading indicates at least a moderate loss in sensitivity relative to wild type NfsA(Ec).

FIG. 60: Anti-proliferative activity (1050 values) of four substrates against human HCT116 colon cancer cells expressing various poly-mutant NfsAs from E. coli.

DETAILED DESCRIPTION OF THE INVENTION

Definitions

EF3 also called trifluoroetanidazole, also called 2-(2-nitro-1H-imidazol-1-yl)-N-(2,2,2-trifluoroethyl)acetamide EF5 also called pentafluoroetanidazole, also called 2-(2-nitro-1H-imidazol-1-yl)-N-(2,2,3,3,3-pentafluoropropyl)acetamide F-MISO also called fluoromisonidazole, also called 1-fluoro-3-(2-nitro-1H-imidazol-1-yl)propan-2-ol HX4 also called 3-fluoro-2-(4-((2-nitro-1H-imidazol-1-yl)methyl)-1H-1,2,3-triazol-1-yl)propan-1-ol FETNIM also called 1-fluoro-4-(2-nitro-1H-imidazol-1-yl)butane-2,3-diol FAZA also called (2R,3R,4R,5R)-2-(fluoromethyl)-5-(2-nitro-1H-imidazol-1-yl)tetrahydrofuran-3,4-diol FETA also called N-(2-fluoroethyl)-2-(2-nitro-1H-imidazol-1-yl)acetamide CCI-103F also called 1-((1,1,1,3,3,3-hexafluoropropan-2-yl)oxy)-3-(2-nitro-1H-imidazol-1-yl)propan-2-ol SR4554 also called 2-(2-nitro-1H-imidazol-1-yl)-N-(3,3,3-trifluoro-2-hydroxypropyl)acetamide mitomycin C also called ((1aS,8S,8aR,8bS)-6-amino-8a-methoxy-5-methyl-4,7-dioxo-1,1a,2,4,7,8,8a,8b-octahydroazirino[2',3':3,4]pyrrolo[1,2-a]indol-8-yl)methyl carbamate Porfiromycin also called ((1aS,8S,8aR,8bS)-6-amino-8a-methoxy-1,5-dimethyl-4,7-dioxo-1,1a,2,4,7,8,8a,8b-octahydroazirino[2',3':3,4]pyrrolo[1,2-a]indol-8-yl)methyl carbamate EO9 also called (E)-5-(aziridin-1-yl)-3-(hydroxymethyl)-2-(3-hydroxyprop-1-en-1-yl)-1-methyl-1H-indole-4,7-dione RH1 also called 2,5-di(aziridin-1-yl)-3-(hydroxymethyl)-6-methylcyclohexa-2,5-diene-1,4-dione CB 1954 also called 5-(aziridin-1-yl)-2,4-dinitrobenzamide PR-104 is a phosphate ester pre-prodrug of the alcohol PR-104A. PR-104 is also called 2-((2-bromoethyl)(2,4-dinitro-6-((2-(phosphonooxy)ethyl)carbamoyl)phenyl)amino) ethyl methanesulfonate.

PR-104A also called 2-((2-bromoethyl)(2-((2-hydroxyethyl)carbamoyl)-4,6-dinitrophenyl)amino)ethyl methanesulfonate SN 27686 also called 2-(bis(2-bromoethyl)amino)-N-(2-hydroxyethyl)-3,5-dinitrobenzamide SN 31609 also called 2-(bis(2-bromoethyl)amino)-N-(2-hydroxyethyl)-N-methyl-3,5-dinitrobenzamide SN 32102 also called 2-(bis(2-bromoethyl)amino)-N-ethyl-N-(2-hydroxyethyl)-3,5-dinitrobenzamide SN 28065 also called 5-(bis(2-bromoethyl)amino)-N-(2-hydroxyethyl)-2,4-dinitrobenzamide SN 28099 also called 2-((2-bromoethyl)(5-((2-hydroxyethyl)carbamoyl)-2,4-dinitrophenyl)amino)ethyl methanesulfonate NLCQ-1 also called 7-chloro-N-(3-(2-nitro-1H-imidazol-1-yl)propyl)quinolin-4-amine TH-302 also called N,N'-bis(2-bromoethyl)-(1-methyl-2-nitro-1H-imidazol-5-yl)methyl phosphorodiamidic acid ester RSU-1069 also called 1-(aziridin-1-yl)-3-(2-nitro-1H-imidazol-1-yl)propan-2-ol CI-1010 also called 1-((2-bromoethyl)amino)-3-(2-nitro-1H-imidazol-1-yl)propan-2-ol Misonidazole also called 1-methoxy-3-(2-nitro-1H-imidazol-1-yl)propan-2-ol Etanidazole also called N-(2-hydroxyethyl)-2-(2-nitro-1H-imidazol-1-yl)acetamide Nimorazole also called 4-(2-(2-nitro-1H-imidazol-1-yl)ethyl)morpholine Metronidazole also called 2-(2-methyl-5-nitro-1H-imidazol-1-yl)ethanol Tinidazole also called 1-(2-(ethylsulfonyl)ethyl)-2-methyl-5-nitro-1H-imidazole Ornidazole also called 1-chloro-3-(2-methyl-5-nitro-1H-imidazol-1-yl)propan-2-ol Nitrofurantoin also called (E)-1-(((5-nitrofuran-2-yl)methylene)amino)imidazolidine-2,4-dione Nitrofurazone also called (E)-2-((5-nitrofuran-2-yl)methylene)hydrazinecarboxamide Nifuratel also called (E)-5-((methylthio)methyl)-3-(((5-nitrofuran-2-yl)methylene)amino)oxazolidin-2-one Nifurtimox also called (E)-3-methyl-4-(((5-nitrofuran-2-yl)methylene)amino)thiomorpholine 1,1-dioxide Furazolidinone also called (E)-3-(((5-nitrofuran-2-yl)methylene)amino)oxazolidin-2-one SN 26634 also called 5-(aziridin-1-yl)-N-(2,3-dihydroxypropyl)-2,4-dinitrobenzamide SN 27857 also called ((2-((2-hydroxyethyl)carbamoyl)-4,6-dinitrophenyl)azanediyl)bis(ethane-2,1-diyl)dimethanesulfonate KS119 also called 1-(3-hydroxy-4-nitrophenyl)ethyl 2-(2-chloroethyl)-1,2-bis(methylsulfonyl)hydrazinecarboxylate KS119W also called 1-(4-nitro-3-(phosphonooxy)phenyl)ethyl 2-(2-chloroethyl)-1,2-bis(methylsulfonyl)hydrazinecarboxylate "Nitroreductase"—an enzyme that catalyses the reduction of a nitro functional group (—$NO_2$) or quinine functional group.

"Functionally equivalent nitroreductase variant" includes mutant and polymutant nitroreductase variants as defined herein, and nitroreductase enzymes in the NfsA, NfsB, NemA, AzoR, MdaB and YwrO families or those nitroreductases that share at least 25%, preferably 30%, preferably 35%, preferably 40%, preferably 50%, preferably 60%, preferably 70%, preferably 75%, preferably 80%, preferably 85%, preferably 90%, preferably 95% or greater amino acid identity with any one of SEQ ID Nos 1 to 90, and are able to metabolise at least one of the compounds in FIG. 1,2,3, 4,5,6, or 7.

"Functionally equivalent nitroreductase gene variant"—this term encompasses a gene that encodes a "Functionally equivalent nitroreductase variant".

"Prodrug"—An inactive compound that is converted to a reactive cytotoxic metabolite once activated that may have an endogenous or exogenous effect (see bystander effect). Preferably activation occurs within target cells or within the local microenvironment by reduction or selective action of a target-cell-specific enzyme. Prodrugs may also be activated by differences in pH/oxygenation between target and non-target tissue. Prodrugs include precursors to anti-parasitic agents and examples of prodrugs may be found in FIGS. 2 to 7. As well as being activated in a cell and/or biological agent, it is also contemplated that the prodrug is activated in a matrix.

"Matrix"—this term refers to the material that may support or contain a cell and/or biological agent. The term includes a tissue or a growth medium and the matrix may be found in vivo or in vitro.

"Ablation" is to be considered in its broadest context and as well meaning the complete ceasing of the function of the target being ablated, is also intended to encompass any degree of suppression of the function of the target where the target includes but is not limited to a cell or a biological agent.

"Imaging probe" or "probe"—a compound or agent that is radioactively labelled, that may be used to detect, identify or obtain information about another substance in a sample or tissue. Imaging probes are often labelled using radioactive labels for use in non-invasive imaging (bio-detection) or radioimaging. In particular embodiments, imaging probes may be used to label particular tissues or cells for detection using Positron Emission Tomography (PET), micro-Positron Emission Tomography (micro-PET) or Single Photon Emission Tomography (SPECT). The labels for such imaging probes may comprise a positron-emitting nuclide such as $^{15}$O, $^{13}$N, $^{11}$C, $^{124}$I, $^{76}$Br and $^{18}$F or a gamma-emitting nuclide such as $^{99m}$Tc, $^{67}$Ga, $^{111}$In and $^{123}$I. The generation of the data described herein may employ "cold" versions of these imaging probes typically labelled with a stable isotope (e.g. $^{19}$F). This is for the convenience of handling the materials in the laboratory and it will be appreciated by someone skilled in the art that this data will translate directly to the radio labelled versions of the probes.

"Activation" or "metabolism" with reference to the imaging probes or prodrugs refers to the catalytic reduction process that a probe or prodrug may undergo following contact with an enzyme. The probe/prodrug may be activated/metabolised to yield alternative compounds that may have beneficial activity for imaging or therapeutic applications. The metabolites may also be retained by a cell, matrix and/or biological agent which can enable the temporal analysis of probe/prodrug distribution.

"Nitroimidazole or a derivative thereof"—this term includes substituted and unsubstituted nitroimidazole compounds including substituted and unsubstituted 2-nitroimidazole, 4-nitroimidazole, and 5-nitroimidazole compounds.

"Cell" refers to a biological sub-unit that is specialized in carrying out a particular function or functions. For the purposes of the invention as defined herein, the term "cell" also encompasses the medium in which the cell is found. For example this may mean a hypoxic region of a tumour or the cell matrix which supports the cell in vivo or in vitro.

"Biological agent" encompasses any biological unit (except cells as defined above) on which an activated prodrug may act. This term includes, but is not limited to vectors (particularly plasmid vectors), viruses (particularly adenoviruses, vaccinia virus, measles virus, picornaviruses), bacteria (particularly *Clostridium* sp. and *Salmonella* sp.), liposomes, nanoparticles, and antibodies.

"Endogenous"—as used herein, this term refers to an effect of a prodrug on the cell and/or biological agent in which the prodrug is activated.

"Exogenous"—as used herein, this term refers to an effect on a cell and/or biological agent that is external to the matrix, cell and/or biological agent in which the prodrug is activated.

"Bystander effect"—this effect is triggered by treatment of a target cell with a prodrug and refers to the secondary ablation effect on cells or tissues in the local microenvironment to the target cell/biological agent. Without wishing to be bound by theory, the bystander effect is believed to be caused by the diffusion of cytotoxic prodrug metabolites (activated prodrugs) from the site of production to affect unmodified cells exogenous to the target cell.

"Vector" encompasses any vehicle for the delivery of an enzyme or gene to a target. Examples of vectors include includes viruses, bacteria, plasmids, liposomes, nanoparticles, antibodies, human multipotent marrow stromal cells or genetic vectors but the vector may also be a cell, for example a stem cell.

"Polynucleotide"—a number of nucleotides bonded together to form a chain. A polynucleotide may be a gene that encodes a polypeptide and will usually comprise DNA and RNA nucleotides.

"Residue"—an individual amino acid in a polypeptide chain

"Wild-type"—this term means a gene or polypeptide that is not a mutant or polymutant and does not substantially differ in sequence (nucleotide or amino acid) to the gene/polypeptide found in the originating organism.

"Mutant polypeptide" or simply "mutant"—a polypeptide that differs from the wild-type polypeptide by at least one amino acid, and may differ by at least two but may differ by more amino acids while retaining substantially the same function as a nitroreductase. The sequence changes may be substitutions, insertions or deletions in one or more residues and the mutant polypeptide shares at least 25%, preferably 30%, preferably 35%, preferably 40%, preferably 50%, or greater amino acid sequence identity with any one of SEQ ID Nos 1 to 31, and is able to metabolise at least one of the compounds in FIG. 1,2,3,4,5,6, or 7. Preferably, the variant shares greater than or equal to 35% sequence identity to *E. coli* NfsA. A single-residue mutant means that the mutant differs from the wild-type polypeptide at a single residue location. This term also comprises a fragment of a nitroreductase enzyme described in any of SEQ ID Nos 1 to 31 that is able to metabolise at least one of the compounds in FIG. 1,2,3,4,5,6, or 7 wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location.

"Polymutants" or "polymutant NfsAs"—this term relates to mutants that induced substantially heightened SOS responses relative to wild type NfsA following 10 μM PR-104A challenge.

"Treatment" is to be considered in its broadest context. The term does not necessarily imply that a subject is treated until total recovery. Accordingly, "treatment" broadly includes, for example, the prevention, amelioration or management of one or more symptoms of a disorder, the severity of one or more symptoms and preventing or otherwise reducing the risk of developing secondary complications.

"Prevention" of disease should not be taken to imply that disease development is completely prevented, and include delay of disease development.

Preferred Embodiments

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The inventors have surprisingly found that known and novel nitroreductases activate (i.e. catalyse the reduction of) imaging probes. This aspect of the invention has particular utility in radioimaging nitroreductase expressing cells or biological agents which may target tumours or may be therapeutic in their own right (e.g. stem cells). Additionally, they have surprisingly identified, characterised and/or improved nitroreductase enzymes (NTRs) with the ability to activate imaging probes for use in radioimaging and also optionally to activate a prodrug. They have also found that nitroreducatases have the capacity to activate prodrugs in the local microenvironment of a target cell/biological agent may result in the ablation (which includes the suppression of the function) of the cell and/or biological agent. In some embodiments, the nitroreductase expressing cell and/or biological agent is ablated.

A gene encoding a nitroreductase enzyme can be introduced into cells (such as tumour cells) either directly as an expression plasmid (e.g. by liposome/nanoparticle delivery or gold particle bombardment) or via vector delivery (e.g. adenovirus, lentivirus, vaccinia virus). Alternatively a gene encoding a nitroreductase enzyme can be introduced into a local tissue microenvironment or the cell matrix by means of bacterial colonisation (e.g. *clostridium, salmonella, bifidobacterium*). Imaging probes can be introduced via systemic administration and can provide a means to visualise and quantify tissue colonisation and geometry thereof. Information obtained by image capture and rendering can be used to inform about the presence of target cells and also about the concurrent or delayed use of prodrug administration. The invention therefore provides a non-invasive imaging technology capable of use in both shallow and deep tissues that is able to accurately monitor the spatial and temporal distribution of cells and vector systems, providing a particular advantage in comparison to existing systems.

Activation of a prodrug can provide therapeutic cell or biological agent ablation in the image positive regions with local extension via the bystander effect. Prodrugs may be introduced to a subject by any suitable known in the art including enteral, parenteral or topical administration. A "subject" as referred to herein is intended to mean a human or other animal. Additionally, it is envisaged that the methods of the invention may be carried out in vivo or in vitro and therefore in certain embodiments the subject will be a cell or tissue in vitro. Prodrug administration may be delayed if image analysis indicates that further vector amplification and spread is required or would be advantageous. Further imaging probe use may be mandated at later time points, to identify an optimal prodrug administration schedule. Alternatively, if image capture and rendering indicates a requirement for vector removal or silencing, an ablation substrate may be applied concurrently. If ablation should be required at the completion of therapy, use of an ablation substrate may be delayed until the completion of treatment. Thus imaging the catalytic activity of a single nitroreductase enzyme can provide high quality, real time information in a clinical setting and inform on the temporal use of prodrug (for therapeutic and/or ablatory effects) either concurrently or sequentially. Repeated imaging to monitor the course of treatment is advantageous and may allow for protocol modification over time.

The activation of a radiolabelled imaging probe provides a highly accurate way to detect, identify or obtain spatial and temporal information about a substance in a sample or tissue. Imaging probes are labelled using radioactive labels for use in non-invasive radioimaging. In particular embodiments, they are used as probes to label particular tissues for detection using Positron Emission Tomography (PET), micro-Positron Emission Tomography (micro-PET) or Single Photon Emission Tomography (SPECT) or other radioimaging systems. In further embodiments, the metabolism/retention of the probe can be used for non-invasive whole-body imaging of tumour-tropic vectors. In particular embodiments, nitroheterocyclic, nitrocarbocyclic or nitroaromatic compounds are used as imaging probes. In other embodiments, the probe may comprise a substituted or unsubstituted imidazole ring. In yet further embodiments, the probe may comprise a substituted or unsubstituted nitroimidazole compound including 2-nitroimidazoles (FIG. 1), 4-nitroimidazoles or 5-nitroimidazoles. In further particular embodiments, the imaging probe comprises an $^{18}$F-labelled probe selected from EF3, EF5, F-MISO, HX4, F-PIMO, FETNIM, FAZA, FETA, CCI-103F, or SR4554.

These imaging probes are able to be reduced by nitroreductase enzymes of the invention and have particular utility in PET imaging as probes for imaging of hypoxic tumour regions. Reduction of these compounds results in their metabolism and cellular entrapment (retention), and the radiolabelled probes can therefore be visualised by PET a few hours after administration once the non-entrapped compounds have been eliminated from the body. In hypoxic zones, bioreduction of these agents is catalysed by oxygen-sensitive human enzymes which have a weak affinity for the probes. However, by employing the nitroreductases of the present invention, effective cellular imaging of nitroreductase-expressing cells can be achieved without significant background resulting from tissue hypoxia. This enables the improved monitoring of the localisation and replication of tumour-tropic agents that have been labelled with such nitroreductases. This ability also allows improved accuracy of identification of the extent of target cells at a variety of depths thus providing the user with a distinct advantage over current options.

It is envisaged that imaging could be conducted before, during and/or after prodrug treatment to monitor the effect of prodrug on total vector activity and tissue biodistribution. A further key advantage of the invention defined herein is the dynamic nature in which the imaging probe can directly report vector-prodrug interactions. This direct reporting is only made possible by the fact that a single gene product (i.e. the nitroreductase) is able to metabolise both imaging probe and prodrug.

Furthermore, it is envisaged that the prodrug and probe may be introduced to the subject as a single composition, or as separate components from a kit or like unit either concurrently or sequentially in any order. Additionally, the nitroreductase or the vector expressing the nitroreductase may be introduced with the prodrug and/or probe concurrently or sequentially in any order. Such compositions when used in imaging applications with a nitroreductase form an aspect of the present invention. The ability to image and target cells using a single composition, for use with a single NTR able to metabolise both components of the composition provides a useful option for the user. In particular embodiments, the composition comprises a probe and prodrug and the prodrug will predominantly be present in a much higher concentration relative to the probe. Since the probe is radioactively labelled, it is prudent to administer this component in a concentration that is as low as reasonably achievable. The concentration of the prodrug will depend on the nature of the prodrug used and the amount required to achieve a therapeutic effect once activated by the nitroreductase. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like, and the treatment required. In particular embodiments, the prodrug:imaging probe concentration ratio will be approximately 10000:1 to 100:1. In certain embodiments, the composition comprises at least one prodrug and at least one imaging probe in the form of a pharmaceutically acceptable salt of the prodrug/probe, a hydrate thereof, or a solvate of any of the foregoing. The composition can include a pharmaceutically acceptable diluent, carrier, excipient and/or adjuvant of any of the foregoing. The choice of diluent, carrier, excipient and/or adjuvant can depend upon, among other factors, the desired mode of administration. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The compositions can additionally include lubricating agents such as talc, magnesium stearate, and mineral oil, wetting agents, emulsifying and suspending agents, preserving agents such as methyl- and propylhydroxy-benzoates, sweetening agents, pH adjusting and buffering agents, toxicity adjusting agents, flavoring agents, and the like. The compositions can be formulated so as to provide quick, sustained or delayed release of the active ingredient after administration to the patient by employing procedures known in the art. A composition can be formulated in unit dosage form, each dosage comprising a physically discrete unit suitable as a unitary dosage for humans and other mammals, each unit containing a predetermined quantity of active material calculated to produce the desired therapeutic effect, in association with a suitable pharmaceutical excipient, diluent, carrier and/or adjuvant. Use of such compositions of standard components in the treatment or diagnosis of diseases such as cancer, Parkinson's disease, Alzheimer's disease, stroke, heart disease, rheumatological diseases or a disease treated by stem-cell transplantation is therefore a part of the present invention. The use of these compositions or combinations of compounds to prepare medicaments for use in such diagnosis or treatments is also a part of the invention.

The inventors have demonstrated that 5-nitroimidazole (5-NI) compounds are metabolised by NTRs of the invention. In further embodiments use of radiolabelled 4-nitroimidazole (4-NI) or 5-nitroimidazole (5-NI) probes coupled with NTRs can be employed for NTR reporter gene/probe technologies. An advantage of this approach is the more negative reduction potential of the 4-NI or 5-NI relative to 2-NI which lowers single-electron affinity thereby minimising or eliminating hypoxia dependent metabolism in humans. The absence of human metabolic reduction underlies the utility of 4-NI and 5-NI, such as metronidazole or tinidazole, as specific anti-parasitic agents and permits a more exclusive relationship between exogenous NTR and probe substrate.

The invention also provides an NTR that has the capacity to activate a prodrug such as those shown in FIGS. 2 to 7. In a particular embodiment, the activation of the prodrug can yield cytotoxic compounds that ablate (i.e. suppress the function of, or kill) cells or biological agents such as tumour cells. A number of the prodrugs able to be activated by an NTR of the invention were developed independently as stand-alone bioreductive cytotoxins. NTRs of the invention have utility in GDEPT, VDEPT, BDEPT, CDEPT and ADEPT methods. Specific examples of prodrugs with utility in the invention include nitroheterocyclic, nitrocarbocyclic and nitroaromatic compounds as well as dinitrobenzamides (FIG. 2), mononitrobenzamides, quinones (FIG. 3), nitroimidazoles (FIG. 4), 5-nitroimidazoles (FIG. 5), nitrofurans (FIG. 6) and mono-nitro aromatics (FIG. 7) or compounds derived from one of the above compound groups.

It will be understood by one of skill in the art that NTRs of the invention have utility in activating further prodrugs that are not specifically exemplified in the figures.

In a further embodiment, the NTRs described in the current invention may be used in conjunction with radiolabelled imaging probes, preferably substituted or unsubstituted nitroimidazole(s) as a reporter-gene technology to noninvasively monitor cell transplantation and trafficking. This would be done by transplanting/trafficking cells which express an NTR then introducing an image probe to determine the distribution of the cells both spatially and temporally. Imaging can be used to monitor different properties of cellular trafficking, including metastasis, stem cell transplantation, engraftment of hematopoietic stem cells or genetically modified immune cells. Methodological approaches can include ex-vivo transfection with reintroduction or use of tumour-tropic biological vectors to 'seek out' and label otherwise occult disease (disease that is hidden or lacking in significant symptoms).

The use of the NTRs of the present invention to render stem cells avid for nitroimidazole PET probes technologies represents an important biomarker technology to monitor the success of treatments. Stem-cell transplantation has application in a wide variety of human diseases, including Parkinson's disease, Alzheimer's disease, stroke, heart disease and rheumatological diseases. In addition, intravenously administered human multipotent marrow stromal cells target cancers in vivo and may have the potential to serve as vehicles for the delivery of anticancer therapies (Nakamizo A et al., 2005, *Cancer Res.* 65:3307-3318).

Analysis of stem-cell survival in vivo ideally requires non-invasive longitudinal monitoring to determine the fate and migratory behaviour of the stem cells. The dependence on intracellular cofactors such as NADPH provides a useful measure of the metabolic integrity of the cell population under study and when the reporter gene is integrated into the cellular chromosomes it becomes inheritable. This permits tracking of cell proliferation and viability over time. It is envisaged that the NTRs of the present invention have utility for the treatment of the above mentioned diseases and in monitoring and development of treatments for those diseases.

The inventors envisage that NTRs may be incorporated into a stem cell or a vector selective for a stem cell to render the stem cell sensitive to single cell ablation by a suitable prodrug. This use would enable the control and selective ablation of introduced cells to prevent uncontrolled growth (e.g. tumour formation) or to restrict the growth of therapeutic cells to a particular location. This use, especially combined with the use of the NTR as a way to metabolise an imaging probe represents a potentially useful technology to improve the accuracy and ensure the safety of novel treatments, often with unknown outcomes.

Once activated, the prodrugs may suppress or ablate a target cell and/or biological agent. The target cell/biological agent that is ablated may either directly express a nitroreductase or be present in the local microenvironment of the cell/biological agent that expresses an NTR. It is envisaged that the target cell/biological agent local tissue microenvironment may be colonised regionally by tumour-tropic bacterium (e.g. *Clostridium* sp, *Salmonella* sp, *Bifidobacterium* sp).

The ability of activated prodrugs to diffuse from the site of production and ablate unmodified cells in the local microenvironment is termed the "bystander effect" and is an important determinant of the overall efficacy of any prodrug activating system. This makes it possible to target a large proportion of the tumour mass with a relatively small number of nitroreductase expressing cells/biological agents and means that the non-uniform distribution of the vector can be ameliorated. Prodrug activating systems each possess bystander effect efficiencies of varying magnitude and mechanism, dependent at least in part, on the tissue penetration capacity of the active cytotoxin in the microenvironment in which it is generated.

Bystander effects can be quantified according to methods described in Wilson et al, 2002, *Cancer Res.* 62:1425-1432, by employing a 3D multicellular layer (MCL) composed of a minority (1%) of NTR-expressing 'activator' cells, mixed with a majority (99%) of parental (wild-type) 'target' cells. The prodrug concentrations for 10% survival ($C_{10}$) of target cells (wild-type cells) grown without activators (T), and targets in co-culture ($T_C$) and activators (NTR-expressing cells) in co-culture ($A_C$) can be determined. The bystander effect of a test prodrug is measured by the bystander effect efficiency which can be calculated using the algorithm ((Log $C_{10}$T−Log $C_{10}T_C$)/(Log $C_{10}$T−Log $C_{10}A_C$)). A BEE value of less than about 15%, less than about 10%, less than about 5%, less than about 1% or zero is considered "substantially minimal", whilst a BEE value of greater than about 50%, about 60%, about 70% is considered "substantial".

It has been found that NTRs when used in the methods of the invention in combination with specific prodrugs exhibit a surprisingly high bystander effect efficiency which is a feature that is associated with markedly enhanced therapeutic efficacy in vivo. Additionally, a large bystander effect is considered advantageous in many GDEPT settings as it ensures a more homogeneous exposure to cytotoxic metabolites.

Among known dinitro substrates are the dinitrobenzamide mustard prodrugs (Anlezark et al, 1995*Biochem. Pharmacol.*, 50 (5): 609-18) and the dinitrobenzamideaziridine prodrugs (Anlezark et al, 1992 *Biochem. Pharmacol.*, 44 (12): 2289-95) exemplified by PR-104A and CB1954, respectively. It is also envisaged that mono nitro substrates are able to be metabolised by nitroreductases of the invention due to their similar structure and reactive properties. Known mono-nitro substrates include mono-nitrobenzylcarbamate prodrugs of enediyne and aniline mustard cytotoxins (Hay et al, 1995 *Bioorg Med Chem Lett*, 5 (23): 2829-34), Hay et al, 2003 *J. Med. Chem.* 46 (25), 5533-5545), 2-nitroimidazol-5-yl carbamate prodrugs of the potent minor groove alkylating agent amino-seco-CBI-TMI (Hay et al, 1999 *Bioorg. Med. Chem. Lett.* 9 (15): 2237-2242), mono-nitro prodrugs of aseco-cyclopropylindole alkylating agent (Tercel et al, 1996, *Bioorg. Med. Chem. Lett.* 6 (22): 2741-2744), mono-nitrobenzylphosphoramide mustards prodrugs (Jiang et al, 2006, J. Med. Chem. 49 (14), 4333-4343) and 4-methylsulfonyl-2-nitrobenzamide mustard prodrugs (Atwell et al, 2007, *J. Med. Chem.* 50 (6): 1197-1212).

The methods and compounds of the present invention are of particular use where it is desirable to maximise the bystander effect of an activated prodrug. The inventors have shown that a number of prodrugs result in a substantial bystander effect. Such prodrugs that result in a substantial bystander effect include CB 1954, PR-104A, TH-302, SN27686, SN31609, SN32102, SN28065 and SN28099.

Whereas desirable anti-cancer prodrugs have strong "bystander" effects, the ability to ablate individual cells expressing a cognate NTR without localised damage to neighbouring tissue (known as single cell ablation) is seen as a valuable safety control for enabling the elimination of the NTR-expressing vector in the matrix, cells or tissues should this be deemed necessary. The ability to control viral (VD-EPT) or bacterial (BDEPT) infection is an additional biosafety feature and is considered to be a desired design feature in replicating biological vectors. To achieve this, activation of prodrugs that provide reduced, substantially minimal or zero bystander effect is also desirable.

Prodrug conditional single cell ablation may also be employed to improve the sensitivity of cells (such as transplanted stem cells, engrafted hematopoietic stem cells or genetically modified immune cells) to cell ablation by use of a vector selective for the cell or by direct modification of the cell to express an NTR of the invention. This minimises the unpredictable side effects that may result from uncontrolled spread of the modified cells. Methods that may benefit from the use of NTR expressing vectors/cells include ex-vivo transfection with systemic reintroduction, or cell selective in vivo methods of gene transfer. Such techniques have use in the treatment of a wide variety of human diseases, including Parkinson's disease, Alzheimer's disease, stroke, heart disease, rheumatological diseases and diseases treated by stem-cell transplantation.

The inventors have found that NTRs are effective in reducing a range of prodrugs that are able to be used for single cell ablation and consequently have utility in the treatment of the above diseases. 5-nitroimidazole prodrugs metronidazole and tinidazole (FIG. 5), have been demonstrated to be examples of prodrugs that lack any measurable bystander effect, giving them the unique capacity to act as a specific "off switch"—ablating cells expressing a cognate NTR without localised damage to neighbouring tissue (FIG. 30). The 2-nitroimidazole based prodrugs RSU-1069 (or RB6145/CI-1010) (FIG. 4), also lack any measurable bystander effect and are equally suitable for this purpose.

Figure 1:
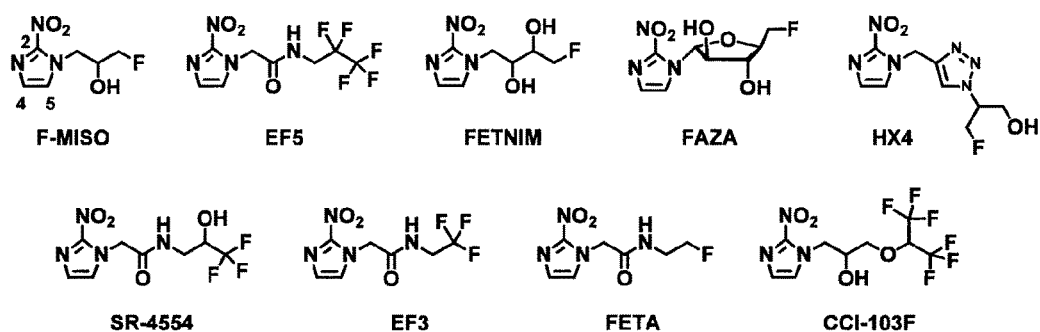
FIG. 1 illustrates $^{18}F$ PET imaging agents based on substituted 2-nitroimidazoles.
Figure 2:
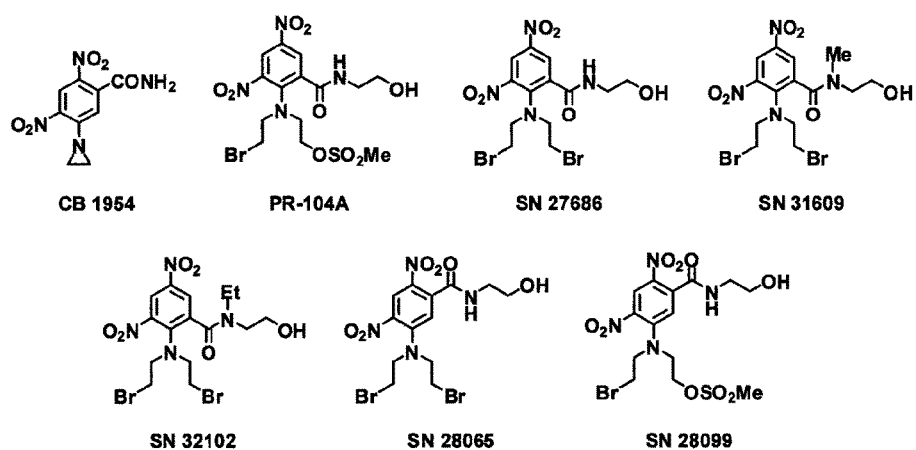
FIG. 2 illustrates dinitrobenzamide prodrugs.
Figure 3:
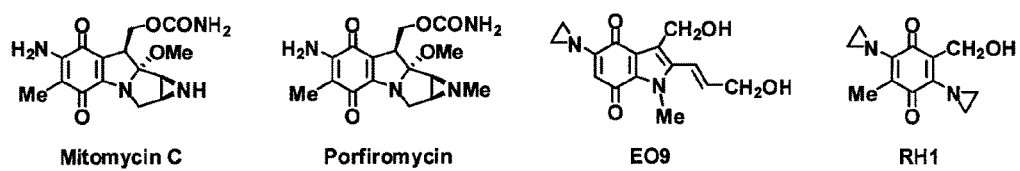
FIG. 3 illustrates quinone-derived prodrugs.
Figure 4:
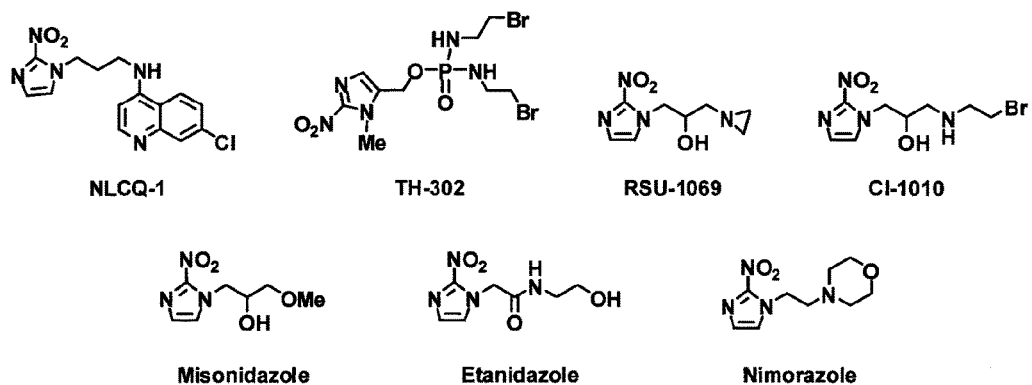
FIG. 4 illustrates substituted 2-nitroimidazole prodrugs.
Figure 5:
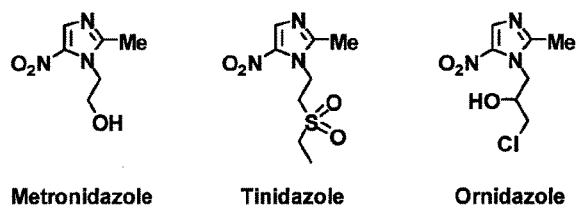
FIG. 5 illustrates 5-nitroimidazole prodrugs.
Figure 6:
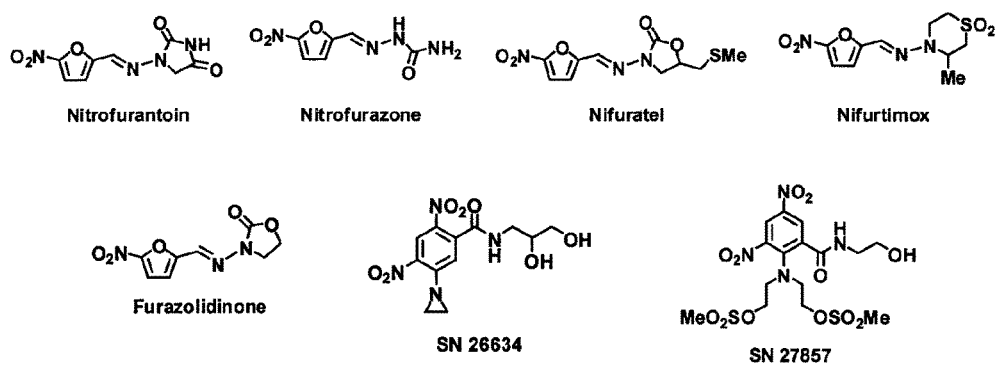
FIG. 6 illustrates structures of 5-nitrofurans, and dinitrobenzamide prodrugs including the aziridinyl dinitrobenzamide SN 26634 and the dinitrobenzamide bis-mesylate mustard SN 27857.
Figure 7:
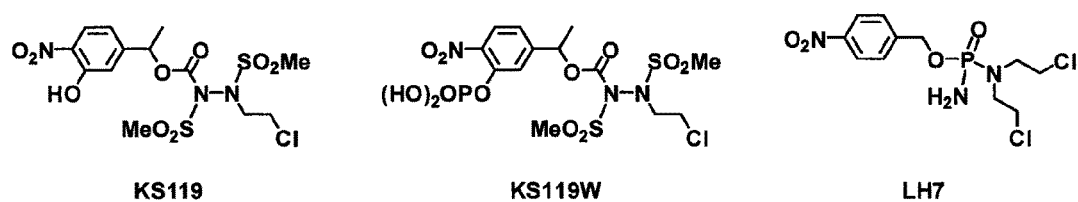
FIG. 7 illustrates mono-nitroaromatic prodrugs

Enzymes and methods of the present invention are therefore of particular use where it is desirable to minimise the bystander effect of an activated prodrug. It was found by the inventors that a number of prodrugs result in a substantially minimal bystander effect. Such prodrugs that result in a substantially minimal bystander effect include NLCQ-1, RSU-1069, CI-1010, Misonidazole, Etanidazole, Nimorazole, Metronidazole, Tinidazole, Ornidazole, Nitrofurantoin, Nitrofurazone, Nifuratel, Nifurtimox, Furazolidinone, SN26634, SN27857, KS119, LH7, EF5 (pentafluoroetanidazole), (cold, i.e. radiolabel free) EF5 (pentafluoroetanidazole) and EF3 (trifluoroetanidazole) (FIGS. 6 and 30).

Figure 23:
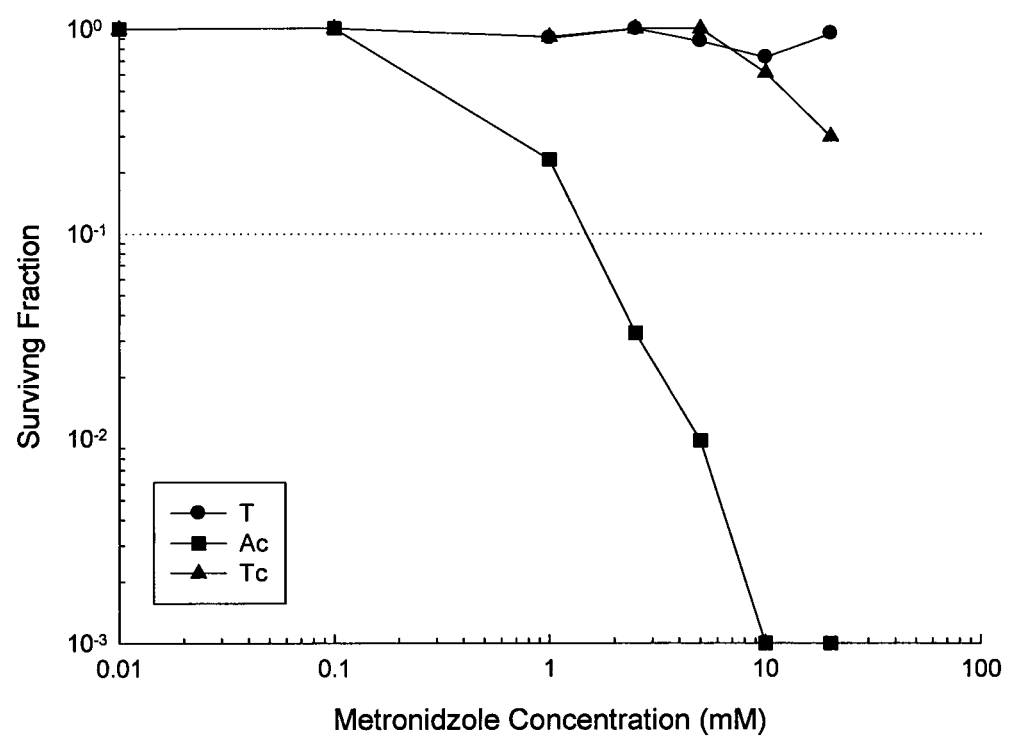
FIG. 23 illustrates NfsA-dependent activation of metronidazole in an MCL bystander experiment. It includes a representative bystander efficiency graph which illustrates that metronidazole is unable to produce any bystander effect. Metronidazole dose-response curves for hyperoxic (95% $O_2$) multicellular layers (MCLs) of HCT116-WT (parental) 'target' cells in the absence (T) and presence (Tc) of nitroreductase NfsA-expressing HCT116 'activator' cells (A). MCLs are composed of 'targets only' (T) or as intimate mixtures of 32% activators (A) and 68% targets (Tc). Displacement of the Target cell survival curve to the left (T to Tc) is indicative of the presence of a cytotoxic metabolite(s) able to diffusible out of the sensitive activator (A) cell population. The prodrug concentrations for 10% survival ($C_{10}$) of target cells (wild-type cells) grown without activators (T), targets in co-culture ($T_C$) and activators (nfsA-expressing cells) in co-culture ($A_C$) were determined by interpolation. BEE—Bystander effect efficiency calculates the drugs bystander effect: $((\text{Log } C_{10}T - \text{Log } C_{10}T_C)/(\text{Log } C_{10}T - \text{Log } C_{10}A_C))$. The estimated bystander effect efficiency is 0% at concentrations achievable in α-MEM+10% fetal bovine serum (FBS).

The inventors have also surprisingly found that in a further aspect of the invention, the probe also acts as a prodrug. 2-NI probes (e.g. EF5), when administered at a high dose when compared to the dose used for the purpose of PET imaging, can selectively ablate NTR-expressing cells. It is envisaged that NTRs may also be used to target cells for selective ablation using the presence of one or more further suitable prodrugs. The dosage required to enable ablation is preferably approximately the maximum tolerated dose (MTD) for the subject. "High dose" may also relate to the achievable concentrations in human plasma using 'cold' (radiolabel-free) EF5 administration. At 0.7 mM-hr cold EF5 provides 90% loss of viability for nfsA expressing HCT116 cells (FIGS. 23 and 30). A concentration-time of 0.89 mM-hr is readily achieved in human plasma following administration of cold EF5 (9 mg/kg). A dose of 21 mg/kg can be safely injected without any toxicities and will provide a plasma AUC of 2 mM-hr (Koch et al., Can Chemother Pharmacol, 2001, 48:177-187). A 1000-fold lower concentration (0.1%) of radio labelled drug 18F-EF5 is administered for PET imaging and will not result in cell ablation (Koch et al., 2010, Eur J Nucl Med Mol Imaging, 37:2048-2059).

Where the probe also acts as a prodrug, it is contemplated that one or more further prodrugs may be administered at the same or different timepoint in order to modulate the therapeutic effect.

It is also contemplated that where a probe has detectable cytotoxic effects, the prodrug/probe may be imaged using standard techniques to determine the extent of the cytotoxic effect. This measurement can lead to the determination of the bystander effect for the prodrug.

Nitroreductase Families in Bacteria

Figure 8:
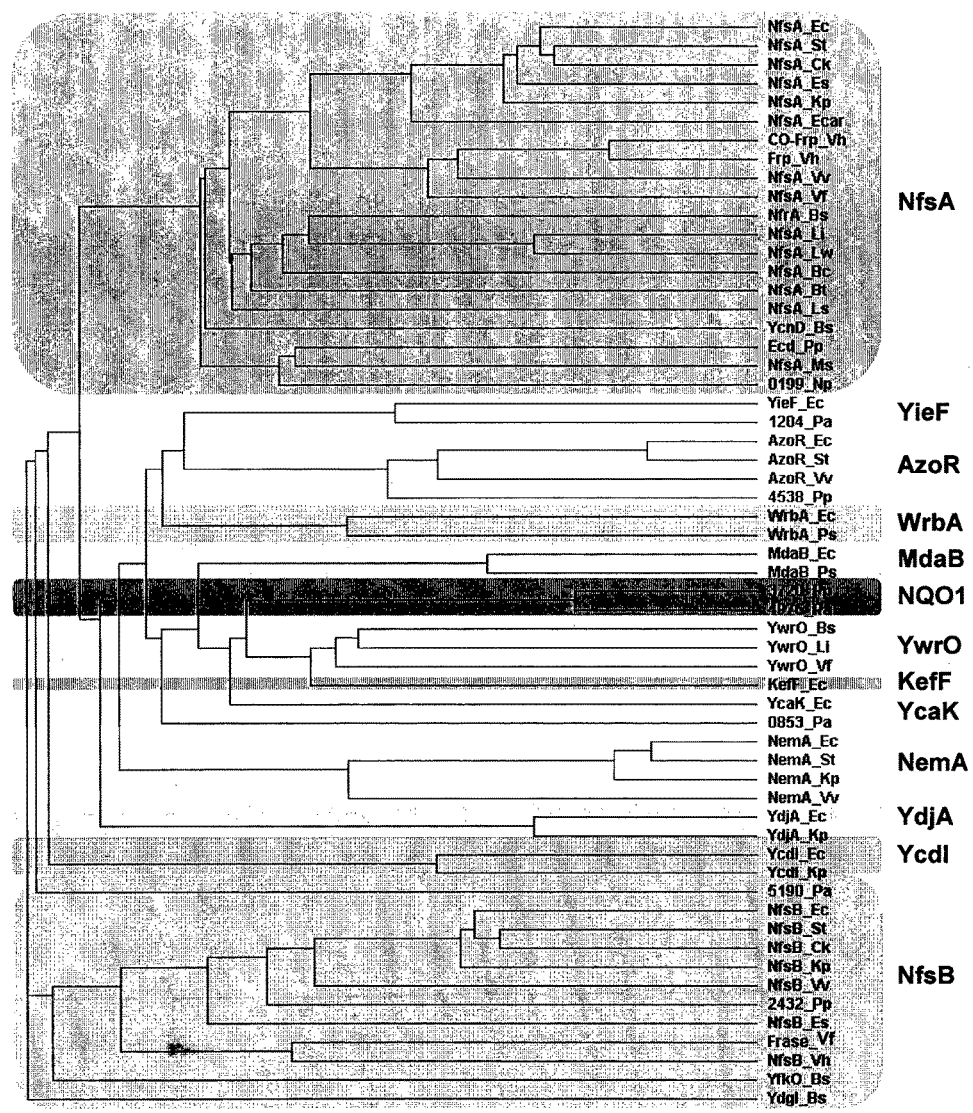
FIG. 8 illustrates fifty eight NTR candidates from thirteen bacterial enzyme families. Candidate NTRs were identified and chosen based on amino-acid sequence homology to the 11 previously identified E. coli enzymes (NfsA, YieF, AzoR, WrbA, MdaB, KefF, YcaK, NemA, YdjA, Ycd1 & NfsB), human NQ01 or YwrO from Bacillus amyloliquefaciens using Basic Local Alignment Search Tool (BLAST). Amino-acid identity limits were set at a minimum of 25%. Sequences in this figure were aligned using CLUSTALW.

To date 13 candidate NTR families have been identified (the basis for identification of 11 of these is described in Prosser et al, 2010, *Biochemical Pharmacology*, 79, 678-687; a $12^{th}$ is based on shared identity with *B. amyloliquefaciens* YwrO; and the $13^{th}$ is based on shared identity with mammalian NQO1, which is able to metabolise CB1954; (Belinsky and Jaiswal, 1993, *Cancer Metastasis Rev* 12 (2): 103-117) with homologues identified across 19 bacterial species (FIG. 8). Of these, the inventors have shown that 6 families ("NfsA", "NfsB", "NemA", "AzoR", "MdaB" and "YwrO") contain members with verified nitroreductase activity.

The NTRs identified in the present invention all share at least 35% sequence identity with NfsA from *E. coli* across a full-enzyme sequence alignment of at least 240 amino acids. However, it will be appreciated by one of skill in the art that a lower sequence identity may also provide functionally equivalent variants and such variants are intended to be included within the scope of the invention.

Membership of one of the above six nitroreductase families is defined as an enzyme that shares at least 25%, preferably 30%, preferably 35%, preferably 40%, preferably 50%, preferably 60%, preferably 70%, preferably 75%, preferably 80%, preferably 85%, preferably 90%, preferably 95% or greater amino acid identity with *E. coli* NfsA, *E. coli* NfsB, *E. coli* NemA, *E. coli* AzoR, *E. coli* MdaB or *B. amyloliquefaciens* YwrO, and is able to metabolise at least one of the compounds pictured in FIG. 1,2,3,4,5,6, or 7.

In some embodiments a fragment of a nitroreductase polypeptide defined herein may be utilised. Fragments include truncated forms of the polypeptide, where deletions may be from about 1 to about 5, to about 10, to about 15, to about 20, to about 25 amino acids, and may extend from residue 1 through 25 at either terminus of the polypeptide, comprising deletions of any length within the region; or may be at an internal location.

Nitroreductase Polypeptides

The invention also provides a nitroreductase polypeptide or a polynucleotide encoding a nitroreductase, wherein the nitroreductase is able to activate (i.e. to catalyse the reduction of) an imaging probe and activate a prodrug. The gene encoding the nitroreductase may be introduced into the genome or accessory genetic material (e.g. plasmids) of any suitable vector (e.g. viruses, bacteria, nanoparticles, liposomes, antibodies or other genetic vectors) in order to express the nitroreductase and confer these functions. It is also envisaged that any single activity predicts for another, quantitatively, spatially and temporally. This enables radioimaging of the vector's in vivo cellular localisation, replication and/or gene expression and means that the extent of a cell expressing a nitroreductase may be imaged and selectively ablated using the same nitroreductase simultaneously or sequentially. A small gene insert (typically less than 2 kb) is desirable to minimise disruption of the therapeutic vector genome, whilst the capacity to encode multiple enzymatic functions (dependent upon substrate) concurrently permits tissue detection, conditional cytotoxicity or single cell ablation, singularly or in concert.

The inventors have cloned and assembled a phylogenetically diverse library of 85 nitroreductase candidates from 19 bacterial species, representing 13 different enzyme families. These bacterial NTR enzymes have been screened for their ability to co-metabolise nitroimidazole imaging probes (bioimaging) and bioreductive prodrugs (bio-therapy, bio-control) and several families of interest have been identified.

In order to screen novel NTR candidates, the inventors have also developed several novel screening assays to efficiently identify functional NTRs. The first is an SOS/DNA damage *E. coli* reporter strain (lacZ, GFP), which utilised modified forms of existing SOS reporter strains. NTR over-expression in SOS reporter strains can be used to evaluate efficacy with a target prodrug as described in Prosser et al, 2010, *Biochem Pharmacol* 79, 678-687. To allow NTR over-expression in these strains a ColE1-based plasmid vector was developed. Improvements in sensitivity were achieved through transfer of an sfiA::GFP reporter construct into a CDF-based plasmid (which contains a compatible origin of replication with the NTR-over-expressing plasmid) to give pANODuet reporter plasmid for GFP screening. In addition, nfsA, nfsB, azoR, and nemA genes were deleted to minimise background metabolism, and the tolC gene deleted to minimise efflux of test compounds in both the SOS-R2 and SOS-R3 reporter strains. In addition, the nitro-blue tetrazolium/iodonitrotetrazolium chloride assay was optimised to detect non-cytotoxic substrates by monitoring NAD(P)H cofactor consumption assays (FIG. 9) as originally described by Glieder and Meinhold (*Methods in Molecular Biology*, Volume 230, Directed Enzyme Evolution, Eds. F. H. Arnold and G. Georgiou, Humana Press Inc., Totowa, N.J., 2003, pp. 157-170.). Bacterial growth inhibition (GI) and $IC_{50}$ assays were also developed and utilised as described herein.

The above assays have considerable advantages over those previously known or used in the art and have utility in screening nitroreductase enzymes, evaluating the efficacy of an NTR with a target prodrug and for selecting nitroreductase enzymes suitable to be used in the methods described herein.

The nitroreductase enzymes identified herein are able to metabolise one or more of a broad range of nitroheterocyclic/nitrocarbocycle/nitroaromatic substrates and in particular embodiments both 2-nitroimidazole PET imaging agents as well as nitroheterocyclic/nitrocarbocycle/nitroaromatic prodrugs such as those in FIGS. 2 to 7. This enables both imaging and conditionally cytotoxic prodrug activation by a single gene product. Such dual-utility enzymes have considerable advantages over the prior art as previously described.

Nitroreductases that have been identified with the desired dual functionality include the NfsA and NfsB families. An expanded/targeted sub-library of 20 NfsA and 12 NfsB enzymes has been created. The inventors have surprisingly discovered that reduction of prodrugs such as PR-104A, TH-302 and metronidazole is a general property of both the NfsA and NfsB families, and that the NfsA enzymes are uniquely efficient in metabolism of imaging probes which may have PET imaging potential. NfsB enzymes also possess this functionality although to a more limited degree. *E. coli*-based screens as described herein have been developed to enable rapid assessment of activity with both prodrug and imaging probes. Candidate NTRs with utility in the present invention, particularly with the capacity to activate bioimaging agents as well as prodrugs, include, but are not limited to, the orthologous and wild type enzymes of NfsA from *Escherichia coli* (NfsA or NfsA(Ec)), NfsA from *Salmonella enterica* serovar Typhi Ty2 (NfsA(St)), NfsA from *Citrobacter koseri* (NfsA(Ck)), NfsA from *Klebsiella pneumoniae* (NfsA(Kp)), NfsA from *Enterobacter sakazakii* (NfsA(Es)), NfsA from *Vibrio fischeri* (NfsA(Vf)), NfsA from *Vibrio vulnificus* (NfsA(Vv)), Frp from different strains of *Vibrio harveyi* (Frp or Co-Frp), NfrA from *Bacillus subtilis* (NfrA or NfrA(Bs)), NfsA from *Listeria innocua* (NfsA(Li)), Ecd from *Pseudomonas putida* (Ecd or Ecd (Pp)), YcnD from *Bacillus subtilis* (YcnD or YcnD(Bs)), NfsA from *Erwinia carotovora* (NfsA(Ecaro)), NfsA from *Lactobacillus sakei* (NfsA(Ls)), NfsA from *Bacillus coagulans* (NfsA(Bc)), NfsA from *Listeria welshmerii* (NfsA (Lw)), NfsA from *Bacillus thuringeinsis* (NfsA(Bt)), NfsA from *Mycobacterium smegmatis* (NfsA(Ms)), NfsA from *Nostoc punctiforme* gene product 0199 (NfsA(Np), 0199, or 0199(Np)), NfsB from *Escherichia coli* (NfsB or NfsB(Ec)), NfsB from *Citrobacter koseri* (NfsB (Ck)); NfsB from *Salmonella enterica* serovar Typhi Ty2 (NfsB (St)); NfsB from *Klebsiella pneumoniae* (NfsB (Kp)); NfsB from *Vibrio vulnificus* (NfsB (Vv)); *Pseudomonas putida* gene product 2432 (2432 or 2432(Pp)); NfsB from *Enterobacter sakazakii* (NfsB (Es)); Flavin Reductase I from *Vibrio fischeri* (Frasel or Frasel(Vf)); NfsB from *Vibrio harveyi* (NfsB (Vh)); YfkO from *Bacillus subtilis* (YfkO or YfkO(Bs)); YdgI from *Bacillus subtilis* (YdgI or YdgI(Bs)); *Pseudomonas aeruginosa* PAO1 gene product 5190 (5190 or 5190(Pa))

In particular embodiments, the wild-type NfsA protein from *E. coli*; homologues from related bacteria; variants derived therefrom; or a combination thereof may be used.

The sequences of nitroreductases of use in the present invention are presented in the Sequence Listing appended to this specification.

```
The sequence of wild-type NfsA from E. coli (strain W3110) designated as SEQ ID
NO: 1 is as follows:
MTPTIELICGHRSIRHFTDEPISEAQREAIINSARATSSSSFLQCSSIIRITDKALREELV

TLTGGQKHVAQAAEFWVFCADFNRHLQICPDAQLGLAEQLLLGVVDTAMMAQNALI

AAESLGLGGVYIGGLRNNIEAVTKLLKLPQHVLPLFGLCLGWPADNPDLKPRLPASIL

VHENSYQPLDKGALAQYDEQLAEYYLTRGSNNRRDTWSDHIRRTIIKESRPFILDYL

HKQGWATR

NfsA(St) (from Salmonella enterica serovar Typhi Ty2) designated as SEQ ID NO: 2
is as follows:
MSPTIELLCGHRSIRHFTDEPVTDAQREAIIAAARSTSSSSFLQCSSIIRITDRALREAL

VPLTGGQKHVAQAAEFWVFCADFNRHLQICPDAQLGLAEQLLLGVVDTAMMGQNA

LTAAESLGLGGVYISGIRNNIESVTELLKLPKHVLPLFGLCLGWPADNPDLKPRLPAE

LVVHENQYQPLDEKLLARYDEQLAEYYLTRGSNTRRDTWSDHIRRTLIKENRPFILE

YLHKQGWATR

NfsA(Ck) (from Citrobacter koseri ATCC 27156) designated as SEQ ID NO: 3 is as
follows:
MTPTIDLIRGHRSIRHFTDEPISDAQRESIIAAARGTSSSSFLQCSSIIRITDKAMREAL

VPLTGGQKHVAQAAEFWVFCADFNRHLQICPDAQLGLAEQLLLGTVDTAMMGQNA

LTAAESLGLGGVYIGGIRNHIEAVTERLKLPKYVLPLFGLCLGWPADNPGVKPRLPA

ELVVHENHYQPVDAALLAQYDEQIAEYYLTRDSNTRRDTWSDHIRRTIIKENRPFILD

YLHKQGWATR
```

-continued

NfsA(Kp) (from *Klebsiella pneumoniae* subspecies *pneumoniae* ATCC 13883)
designated as SEQ ID NO: 4 is as follows:
MTPTIELLRSHRSIRHFTDAPVSDEQRAEIIASAQAASTSSFLQCTSIIRITDPALRERL

VPLTGGQQHVAQAAEFWVFCADFNRHLQICPQAQLGLAEQLLIGVVDTALLAQNAL

TAAESLGLGGVYIGGLRNSIEAVTELLELPQHVLPLFGLCLGWPADNPDIKPRMPAA

MLVHENRYQPLDNALLAEYDEQLAHYYLSRGSNARRDTWSDHIRRTIVKESRPFILD

YLHKQGWATR

NfsA(Es) (from *Enterobacter sakazakii* ATCC BAA-894) designated as SEQ ID NO: 5
is as follows:
MGKLSLAFQHTRNKENVMTPTIELLCSHRSIRHYTDEPISDAQREAIIHAAQSASSSS

FLQCSSIIRVTDRAMREQLVTLTGGQPHVAKAAEFWVFCADFNRHLQICPDAQLGL

AEQLLLGVVDTAMLGQNALVAAESLGLGGVYIGGIRNSIEAVTELLGLPKHVLPLFGL

CLGWPADNPQVKPRMPAGLMVHENRYQPVDRELLAEYDEEIADYYLHRDSNARR

DTWSDQIRRTIIKENRPFILDYLHKQGWATR

NfsA(Vf) (from *Vibrio fischeri*, NZ isolate) designated as SEQ ID NO: 6 is
as follows:
MNPVIDTILEHRSIRSFTNEPISKEQLDTIISAGIAASSSSLLQVNSIIRITDKEKRKALVE

LSGGQPYVEGAAEFLVFCIDFQRHYEMNPEIKAEFTELTLIGAVDAGIMAQNCLLAA

ESMGLGGVYIGGLRTNAQGVDDLLELPKNTAVLFGMCLGYPNQAPQKKPRLSPDVI

VHENSYQPLDKSKIDEYDEIMQSYYATRSTNQKQSSWSEQITGKLSQESRPHIKGY

LNNKGLAIK

NfsA(Vv) (from *Vibrio vulnificus*, NZ isolate) designated as SEQ ID NO: 7 is
as follows:
MNAVIDTLLSHRSIRKFTDQAITPEQLDTIIRAGLAASSSSLLQVVSIIRITDPAKRQQL

AELAGPQHYVETAAEFLVFCIDYQRHATLNSEVQAGFTELTLIGAVDAGIMAQNCLL

AAESMGLGGVYIGGLRNKAAEVDALLELPPFSAVLFGMCLGHPDQDPDLKPRLPAE

VILHENHYQPLDLNKVEQYDQTMLDYYGKRSSNQKQASWSEQVTGKLAGESRPHI

LPYLHSKGLATK

CoFrp (Flavin Reductase P from *Vibrio harveyi*, accession no. AAA21331)
designated as SEQ ID NO: 8 is as follows:
MNNTIETILAHRSIRKFTAVPITDEQRQTIIQAGLAASSSSMLQVVSIVRVTDSEKRNE

LAQFAGNQAYVESAAEFLVFCIDYQRHATINPDVQADFTELTLIGAVDSGIMAQNCLL

AAESMGLGGVYIGGLRNSAAQVDELLGLPENSAVLFGMCLGHPDQNPEVKPRLPA

HVVVHENQYQELNLDDIQSYDQTMQAYYASRTSNQKLSTWSQEVTGKLAGESRPH

ILPYLNSKGLAKR

Frp (Flavin Reductase P from *Vibrio harveyi*, accession no. Q56691) designated
as SEQ ID NO: 9 is as follows:
MNNTIETILAHRSIRKFTAVPITDEQRQTIIQAGLAASSSSMLQVVSIVRVTDSEKRKQ

LAQFAGNQAYIESAAEFLVFCIDYQRHATINPDVQADFTELTLIGAVDSGIMAQNCLL

AAESMGLGGVYIGGLRNSAAQVDKLLGLPENSAVLFGMCLGHPDQNPEVKPRLPA

HVVVHENQYQELNLDDIQSYDQTMQAYYASSTSNQKLSSWSQEVTGKLAGESRPH

ILPYLNSKGLAKR

NfrA(Bs) (from *Bacillus subtilis*, subspecies *subtilis*, NZ isolate) designated
as SEQ ID NO: 10 is as follows:
MNNTIETILNHRSIRSFTDQLLTAEEIDILVKSAQAASTSSYVQAYSIIGVSDPEKKREL

SVLAGNQPYVENNGHFFVFCADLHRHQKLAEEKGENISELLENTEMFMVSLIDAALA

-continued

AQNMSVAAESMGLGICYIGGIRNELDKVTEVLQTPDHVLPLFGLAVGHPANLSGKKP

RLPKQAVYHENTYNVNADDFRDTMNAYDQTISDYYRERTNGQREETWSDQILNFM

KQKPRTYLNDYVKEKGFNKN

NfsA(Li) (from *Listeria innocua* ATCC 33090) designated as SEQ ID NO:11 is as follows:
MNQAIDAILGHYSVRNFEDKALTEEELALLIKSAQAASTSSFVQAYSIIGITDKKIREQI

SAIAGNQPYTVQTGQLFIFVADLARHQAILEEHQVDTAALETSEKWLVSIIDAALAAQ

NMAVAAESLGFGICFIGGIRNDVGQIAEILDLPPYTMPLFGLTIGHPIKGKEKAKPRLP

QDLVYHENTYQKMNPATLAEYDEQIKTYYDERTAGKRVEGWSEQIARGLGRKSRL

DLKDFLQKQHLNQK

Ecd (from *Pseudomonas putida* KT2440) designated as SEQ ID NO: 12 is as follows:
MSLQDEALKAWQARYGEPANLPAADTVIAQMLQHRSVRAYSDLPVDEQMLSWAIA

AAQSASTSSNLQAWSVLAVRDRERLARLARLSGNQRHVEQAPLFLVWLVDWSRLR

RLARTLQAPTAGIDYLESYTVGVVDAALAAQNAALAFEAQGLGIVYIGGMRNHPEAM

SEELGLPNDTFAVFGMCVGHPDPAQPAEIKPRLAQSVVLHRERYEATEAEAVSVAA

YDRRMSDFQHRQQRENRSWSSQAVERVKGADSLSGRHRLRDALNTLGFGLR

YcnD (from *Bacillus subtilis*, subspecies *subtilis*, NZ isolate) designated as SEQ ID NO: 13 is as follows:
MNEVIKSLTDHRSIRSYTDEPVAKEQLDQIIQAVQSAPTSINGQQVTVITVQDKERKK

KISELSGGQPWIDQAPVFLLFCADFNRAKIALEDLNDIKMEITNGLESVLVGAVDAGI

ALGTATAAAESLGLGTVPIGAVRGNPQELIELLELPKYVFPVSGLVIGHPADRSAKKP

RLPQEAVNYQETYLNQDELTSYIQAYDEKMSEYMNKRTNGKETRNWSQGIASYYE

RLYYPHIREMLEKQGFKVEK

NfsA(Ecaro) (from *Erwinia carotovora*, subspecies *carotovora*, NZ isolate) designated as SEQ ID NO: 14 is as follows:
MIPTIDLLQRHRSIRAFTSQAVTDEQRHAIIASAQSASSSSFLQCSSIIRITDPAVRETLI

HYTGEQAYVAQAAEFWVFCADFHRHVEIFPQAETGLAEQLLIGCVDTAIMAQNALV

AAESLGLGGVFIGGIRNRIADVTQLLQLPTLVIPLFGLCLGHPDAEPQLKPRMPTAM

MLHENVYQPLDRDVLAQYDQQMVEYYLQRTGSRRESWSEHVELTLKKELRPFMLD

YLHQQGWAIR

NfsA(Ls) (from *Lactobacillus sakei*, NZ isolate) designated as SEQ ID NO: 15 is as follows:
MSDLIAQMQHHVSVRNFEATPLSAEVKQQLIAAAQSGSSSNFVQAFSIIEVTDLALR

TEIATISNSASYVNQTGTFYVFVADLYRQASMLKAQGQSLAGIQNMEALLVASVDTTI

AAEDMAVAAESLGLGICYIGGIRNDIARVAELLGLPEYTVPLFGLTVGIPKTKNQVKP

RLPQINQVAQNQYPRAQFADLKQYDQQIADYYANRGSNQQQADWISKNLDFFSAP

RRPEVGAFLKKQGFTLA

NfsA(Bco) (from *Bacillus coagulans* ATCC 7050) designated as SEQ ID NO: 16 is as follows:
MNTIIETILNHRSIRHYEDRPLSDEQIRLIVESAQAAATSHFVQAYTILGIQDPGRKQR

LAELTGNRHVGTCGHLLIFCADLHKHALAAEMEGVDAQDTLETTEKFMVALIDTALA

AQNAALAAESMGLGICYVGGLRNRLPEVAELLKIPQYVLPLFAMTIGYPADPSAKKP

RMAAEHVYFEDEYPADERLLRDLKEYNETVSQYYTKRTDGKRNDTWTGQMAQFF

KEPSRVFMKEFVEHQGFDKK

NfsA(Lw) (from *Listeria welshmerii* ATCC 35897) designated as SEQ ID NO: 17 is as follows:
MNQAIDAILGHYSVRKFEDKSLTEEELSLLIKSAQAASTSSFVQAYSIIGITDKEVRKQI

SLVAGNQPYTVQTGQLFIFVADLARHHAILEEFQVDTEALETSEKWLVSVIDAALAA

QNMAIAAESLGFGICYIGGIRNNVEQISKILDLPPYTMPLFGLTVGHPVVDKEKAKPR

LPQSLVYHENTYQKTNPTILADYDEQIKMYYNERTAGKRIEGWSEQMARGLGQKNR

LDLKAFLEKQHLNQK

NfsA(Bth) (from *Bacillus thuringeinsis* NZ isolate) designated as SEQ ID NO: 18 is as follows:
MNEMIHKMEQHVSVRKYKEESIPKDVVEKMVHAAQHAASSHFVQAYSVIYVTDQEL

KAKLAELSGNRHVKDCAAFFVCCADLKRLEIACEKHSTEIKHEGVEDFIVATVDASLF

AQNLALAAESLGYGICYIGGIRNNPREVSELLHLPDKVYPVFGMTVGVPDEEHGVKP

RLPVAAVLHENGYDEQKYDELLNEYDETMNAYYKERPSNKKNVTWTESMSSFMSK

EKRMHMKEFLSERGLNKK

NfsA(Ms) (from *Mycobacterium smegmatis* MC$^2$155) designated as SEQ ID NO: 19 is as follows:
MTVIARYADVDATLGVHSDTLALQLAHRSVRKFLPDAVSDEHLSALVAAAQSAATSS

NLQPWSVVAVRDPQRKARLAVLAKNQQFINDAPLFLVWVADLGRARRIAERAGVPL

DGADYLETTIIGFVDTALAAQNAVLAAESLGLGTVFVGAIRNHPEEVAAELGLPPSAV

ATFGLAVGFPDPTENAGIKPRLPREAVLHHEQYDAQTADSHVPAYDERLADYNTRH

GLTGTWSERVLARLAGPQSLSGRHLLRTQLERLGLGIR

NfsA(Np) (NfsA from *Nostoc punctiforme*, Australian isolate) designated as SEQ ID NO: 20 is as follows:
MPLQMELVLVIKYRKIWELIMTNPIELLRSRYGEIPFNPEEWNDSLTALLSHRSIRSYL

SDPLPEGTLELLIAAAQSASTSSNLQTWSVVAVEDPECKEELSKLAGNQAHIKQVPL

FLVWLADLARLSYVADSRGISHDALEYLEMFVMATIDATLAAQNAAVAAESLGLGTV

YIGGIRNHPQEVAEILNLPSSVYAVFGLCVGYPNPEVEAAIKPRLPQSAVLHRETYKL

SEQEEAIAHYNDIIKEFYTEQKMNVPGDWSEHSAQRIATVESLRGRDRLREVLNHLG

FKLL

NfsB from *E. coli* (strain W3110) designated as SEQ ID NO:21 is as follows:
MDIISVALKRHSTKAFDASKKLTPEQAEQIKTLLQYSPSSTNSQPWHFIVASTEEGKA

RVAKSAAGNYVFNERKMLDASHVVVFCAKTAMDDVWLKLVVDQEDADGRFATPEA

KAANDKGRKFFADMHRKDLHDDAEWMAKQVYLNVGNFLLGVAALGLDAVPIEGFD

AAILDAEFGLKEKGYTSLVVVPVGHHSVEDFNATLPKSRLPQNITLTEV

NfsB(Ck) (from *Citrobacter koseri* ATCC 27156) designated as SEQ ID NO: 22 is as follows:
MDIVSVALKRYSTKAFDPSKQLTADEAEKLKTLLQYSPSSTNSQPWHFIVASTEEGK

ARVAKSAAGNFVFNERKMLDASHVVVFCAKTAMDDAWLDRVVDQEDADGRFATP

EAKAANNKGRRFFADLHRRDLKDDDQWMAKQVYLNVGNFLLGVAAMGLDAVPIEG

FDAAVLDAEFGLKEKGYTSLVVVPVGHHSVEDFNATLPKSRLPQETTLTEV

NfsB(St) (from *Salmonella enterica* serovar Typhi Ty2) designated as SEQ ID NO: 23 is as follows:
MDIVSVALKRYSTKAFDPSKKLTAEEADKVKTLLQYSPSSTNSQPWHFIVASTEEGK

ARVAKSAAGNYTFNERKMLDASHVVVFCAKTAMDDAWLQRVVDQEDADGRFATP

EAKAANDKGRRFFADMHRVSLKDDHQWMAKQVYLNVGNFLLGVAAMGLDAVPIE

GFDAEVLDAEFGLKEKGYTSLVVVPVGHHSIEDFNAGLPKSRLPLETTLTEV

-continued

NfsB(Kp) (from *Klebsiella pneumoniae* subspecies *pneumoniae* ATCC 13883)
designated as SEQ ID NO: 24 is as follows:
MDIVSVALKRYSTKAFDATKKLTAGEAEQLKTLLQYSPSSTNSQPWHFIVASTDEGK

ARVAKAASGTYVFNERKILDASHVVVFCAKTAMDDAWLQRVVDQEEADGRFATPD

AKAANHKGRTFFADMHRKELKDDDQWMAKQVYLNVGNFLLGVAAMGLDAVPIEGV

DFAILDEEFDLKAQGYTSLVVVPVGHHSAEDFNATLPKSRLPQSTTITEI

NfsB(Vv) (from *Vibrio vulnificus*, NZ isolate) designated as SEQ ID NO: 25
is as follows:
MTIVQAAQSRYSTKAFDASRKLPEEKVAAVKELIRMSASSVNSQPWHFIVASSEEG

KARIAKATQGGFAFNERKILDASHVVVFCAKTAIDEAYLLDLLESEDKDGRFADVEAK

NGMHAGRSFFVNMHRFDLKDAHHWMEKQVYLNVGTLLLGASAMEIDAVPIEGFDA

KVLDEEFGLREKGFTSVVIVPLGYHSEDDFNAKLPKSRWSAETVFTEI

2432(Pp) (from *Pseudomonas putida* KT2440) designated as SEQ ID NO: 26
is as follows:
MDTVSLAKRRYTTKAYDASRRIPQATVDALLEQLRHSPSSVNSQPWHFIVADTAEG

KALLAKSTAEGYAYNTQKLLDASHVIVFCTRTEMTEEHLNAVLDQEAADGRFRDEQ

ARAGQNQSRRHYVNLHRFDQKDVQHWMEKQTYLALGTALLGAAAHGLDATPIEGF

DSKVLDAELGLRERGFTSVVILSLGYRSEADFNAGLNKSRLPASQVFTFL

NfsB(Es) (from *Enterobacter sakazakii* ATCC BAA-894) designated as
SEQ ID NO: 27 is as follows:
MNLNEIIRTRHTSKAYDNSRKLTAEQQQELLDLLRFSPSSVNSQPWHFFAVTTEEG

KAQILPALMDANQVKAKNAAMTVVFTIKEELNEAHLLQLLEKEQQDGRYDSEEARA

ANDKGRRFFVGLNSETPEQQREWMTRQAYLALGFLLLGAAAMGLDATPIEGFHPE

KMDEVLGLKEKGLCSVVVATIGYRSDADFNATLPKSRLDQDVVITQL

FraseI(Vf) (from *Vibrio fischeri*, NZ isolate) designated as SEQ ID NO: 28
is as follows:
MTHPIIHDLENRYTSKKYDPSKKVSQEDLAVLLEALRLSASSINSQPWKFIVIESDAA

KQRMHDSFANMHQFNQPHIKACSHVILFANKLSYTRDDYDVVLSKAVADKRITEEQ

KEAAFASFKFVELNCDENGEHKAWTKPQAYLALGNALHTLARLNIDSTTMEGIDPEL

LSEIFADELKGYECHVALAIGYHHPSEDYNASLPKSRKAFEDVITIL

YfkO(Bs) (from *Bacillus subtilis*, subspecies *subtilis*, NZ isolate)
designated as SEQ ID NO: 29 is as follows:
MADLKTQILDAYNFRHATKEFDPNKKVSDSDFEFILETGRLSPSSLGLEPWKFVVVQ

NPEFREKLREYTWGAQKQLPTASHFVLILARTAKDIKYNADYIKRHLKEVKQMPQDV

YEGYLSKTEEFQKNDLHLLESDRTLFDWASKQTYIALGNMMTAAAQIGVDSCPIEGF

QYDHIHRILEEEGLLENGSFDISVMVAFGYRVRDPRPKTRSAVEDVVKWV

Ydgi(Bs) (from *Bacillus subtilis*, subspecies *subtilis*, NZ isolate)
designated as SEQ ID NO: 30 is as follows:
MIKTNDFMEIMKGRRSIRNYDPAVKISKEEMTEILEEATTAPSSVNAQPWRFLVIDSP

EGKEKLAPLASFNQTQVTTSSAVIAVFADMNNADYLEEIYSKAVELGYMPQEVKDR

QIAALTAHFEKLPAQVNRETILIDGGLVSMQLMLTARAHGYDTNPIGGYDKENIAETF

GLDKERYVPVMLLSIGKAADEGYASYRLPIDTIAEWK

5190(Pa) (from *Pseudomonas aeruginosa* PA01) designated as SEQ ID NO: 31
is as follows:
MHIEDAVRSRRAIKGYDSSFSLTREEKDHLLDLALHAPSAFNLQHVRLVEVSDPQLR

VQLREVAWDQAQVTDAAMLVVVCAQLDSWERNAQRVWDGAPEAVQAFMAGAIDT

YYRGKPQVQRDEAMRSCGLLAQTLMLVARGQGLDSCPMDGFDFDAVARLINLPDN

HVIGLMVAVGKKAVEPWPRSGKLPREELVIRDRF

Directed Evolution of Nitroreductase Enzymes

The sequence of the NTR polypeptide may be altered in various ways known in the art to generate changes in sequence through a process of directed evolution such as error-prone PCR, targeted mutagenesis and/or DNA shuffling strategies.

Targeted mutagenesis refers to targeting a specific amino acid so that it is changed to another specific amino acid, whereas targeted random mutagenesis refers to targeting a specific amino acid so that it is randomly changed to any of the 20 possible proteinogenic amino acids The mutant polypeptide will usually be substantially similar to the sequences provided herein, i.e. will differ by at least one amino acid, and may differ by at least two but may differ by more amino acids while retaining substantially the same function. Where changes are introduced by shuffling or any other means of random mutation method, the amino acid differences may be greater. The sequence changes may be substitutions, insertions or deletions. Scanning mutations that systematically introduce alanine, or other residues, may be used to determine key amino acids.

In one embodiment of the invention, the polypeptide comprises an amino acid substitution at the position corresponding to amino acid R225 of E. coli NfsA. It will be understood by one of skill in the art that the corresponding amino acid can be identified and substituted in homologous polypeptides by alignment of the two sequences using conventional algorithms, e.g. BLASTN, CLUSTALW, and the like.

In another embodiment of the invention, the polypeptide comprises an amino acid substitution at the position corresponding to amino acid F227 of E. coli NfsA.

In another embodiment of the invention, the polypeptide comprises an amino acid substitution at the position corresponding to amino acid 15 of E. coli NfsA.

In another embodiment of the invention, the polypeptide comprises an amino acid substitution at the position corresponding to amino acid K222 of E. coli NfsA.

In another embodiment of the invention, the polypeptide comprises an amino acid substitution at the position corresponding to amino acid L229 of E. coli NfsA.

In another embodiment of the invention, the polypeptide comprises an amino acid substitution at the position corresponding to amino acid S41 of E. coli NfsA.

In another embodiment of the invention, the polypeptide comprises an amino acid substitution at the position corresponding to amino acid E99 of E. coli NfsA.

In another embodiment of the invention, the polypeptide comprises an amino acid substitution at the position corresponding to amino acid L103 of E. coli NfsA.

In another embodiment of the invention, the polypeptide comprises an amino acid substitution at the position corresponding to amino acid S33 of E. coli NfsA.

In another embodiment of the invention, the polypeptide comprises an amino acid substitution at the position corresponding to amino acid F42 of E. coli NfsA.

In another embodiment of the invention, the polypeptide comprises an amino acid substitution at the position corresponding to amino acid 149 of E. coli NfsA.

In another embodiment of the invention, the polypeptide comprises an amino acid substitution at the position corresponding to amino acid G130 of E. coli NfsA.

In another embodiment of the invention, the polypeptide comprises an amino acid substitution at the position corresponding to amino acid R133 of E. coli NfsA.

In another embodiment of the invention, the polypeptide comprises an amino acid substitution at the position corresponding to amino acid G204 of E. coli NfsA.

In another embodiment of the invention, the polypeptide comprises an amino acid substitution at the position corresponding to amino acid R208 of E. coli NfsA.

In another embodiment of the invention, the polypeptide comprises an amino acid substitution at the position corresponding to amino acid 1220 of E. coli NfsA.

In another embodiment of the invention, the polypeptide comprises an amino acid substitution at the position corresponding to amino acid S224 of E. coli NfsA.

All "polymutant" and "single mutant" sequences are derived from organism Escherichia coli (strain W3110)

```
Polymutant 14 designated as
                                                              SEQ ID NO: 32
MTPTTELICGHRSIRHFTDEPISEAQREAIINSARATSSSYFLQCSSIIRITDKALREEL

VTLTGGQKHVAQAAEFWVFCADFNRHLQICPDAQLGLAEQLLMGVVDTAMMAQNA

LIAAESLGLGGVYIGGLRNNIEAVTKLLKLPQHVLPLFGLCLGWPADNPDLKPRLPAS

ILVHENSYQPLDKGALAQYDEQLAEYYLTRGSNNRRDTWSDHIRRTIIEESRPSILDY

LHKQGWATR

Polymutant 15 designated as
                                                              SEQ ID NO: 33
MTPTIELICGHRSIRHFTDEPISEAQREAIINSARATSSSYFLQCSSIIRITDKALREELV

TLTGGQKHVAQAAEFWVFCADFNRHLQICPDAQLGLAGQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESRPSILDY

LHKQGWATR

Polymutant 17 designated as
                                                              SEQ ID NO: 34
MTPTTELICGHRSIRHFTDEPISEAQREAIINSARATSSSYFLQCSSIIRITDKALREEL

VTLTGGQKHVAQAAEFWVFCADFNRHLQICPDAQLGLAEQLLLGVVDTAMMAQNA

LIAAESLGLGGVYIGGLRNNIEAVTKLLKLPQHVLPLFGLCLGWPADNPDLKPRLPAS
```

ILVHENSYQPLDKGALAQYDEQLAEYYLTRGSNNRRDTWSDHIRRTIIKESPPSILDY

LHKQGWATR

Polymutant 19 designated as
SEQ ID NO: 35

MTPTTELICGHRSIRHFTDEPISEAQREAIINSARATSSSYFLQCSSIIRITDKALREEL

VTLTGGQKHVAQAAEFWVFCADFNRHLQICPDAQLGLAEQLLMGVVDTAMMAQNA

LIAAESLGLGGVYIGGLRNNIEAVTKLLKLPQHVLPLFGLCLGWPADNPDLKPRLPAS

ILVHENSYQPLDKGALAQYDEQLAEYYLTRGSNNRRDTWSDHIRRTIIKESPPSILDY

LHKQGWATR

Polymutant 20 designated as
SEQ ID NO: 36

MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIEESGPSILDY

LHKQGWATR

Polymutant 21 designated as
SEQ ID NO: 37

MTPTIELICGHRSIRHFTDEPISEAQREAIINSARATSSSYFLQCSSIIRITDKALREELV

TLTGGQKHVAQAAEFWVFCADFNRHLQICPDAQLGLAGQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIEESRPSILDY

LHKQGWATR

Polymutant 22 designated as
SEQ ID NO: 38

MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESRPSILDY

LHKQGWATR

Polymutant 23 designated as
SEQ ID NO: 39

MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESGPSILDY

LHKQGWATR

Polymutant 24 designated as
SEQ ID NO: 40

MTPTTELICGHRSIRHFTDEPISEAQREAIINSARATSSSSFLQCSSIIRITDKALREEL

VTLTGGQKHVAQAAEFWVFCADFNRHLQICPDAQLGLAEQLLMGVVDTAMMAQNA

LIAAESLGLGGVYIGGLRNNIEAVTKLLKLPQHVLPLFGLCLGWPADNPDLKPRLPAS

ILVHENSYQPLDKGALAQYDEQLAEYYLTRGSNNRRDTWSDHIRRTIIEESPPSILDY

LHKQGWATR

-continued

Polymutant 25 designated as
SEQ ID NO: 41
MTPTIELICGHRSIRHFTDEPISEAQREAIINSARATSSSYFLQCSSIIRITDKALREELV
TLTGGQKHVAQAAEFWVFCADFNRHLQICPDAQLGLAEQLLLGVVDTAMMAQNALI
AAESLGLGGVYIGGLRNNIEAVTKLLKLPQHVLPLFGLCLGWPADNPDLKPRLPASIL
VHENSYQPLDKGALAQYDEQLAEYYLTRGSNNRRDTWSDHIRRTIIEES A PFILDYL
HKQGWATR Polymutant 26 designated as
SEQ ID NO: 42
MTPTIELICGHRSIRHFTDEPISEAQREAIINSARATSSSYFLQCSSIIRITDKALREELV
TLTGGQKHVAQAAEFWVFCADFNRHLQICPDAQLGLAEQLLMGVVDTAMMAQNAL
IAAESLGLGGVYIGGLRNNIEAVTKLLKLPQHVLPLFGLCLGWPADNPDLKPRLPASI
LVHENSYQPLDKGALAQYDEQLAEYYLTRGSNNRRDTWSDHIRRTIIEESRPFILDY
LHKQGWATR Polymutant 27 designated as
SEQ ID NO: 43
MTPTIELICGHRSIRHFTDEPISEAQREAIINSARATSSSYFLQCSSIIRITDKALREELV
TLTGGQKHVAQAAEFWVFCADFNRHLQICPDAQLGLAGQLLLGVVDTAMMAQNALI
AAESLGLGGVYIGGLRNNIEAVTKLLKLPQHVLPLFGLCLGWPADNPDLKPRLPASIL
VHENSYQPLDKGALAQYDEQLAEYYLTRGSNNRRDTWSDHIRRTIIKESAPSILDYL
HKQGWATR Polymutant 28 designated as
SEQ ID NO: 44
MTPTTELICGHRSIRHFTDEPISEAQREAIINSARATSSSYFLQCSSIIRITDKALREEL
VTLTGGQKHVAQAAEFWVFCADFNRHLQICPDAQLGLAEQLLMGVVDTAMMAQNA
LIAAESLGLGGVYIGGLRNNIEAVTKLLKLPQHVLPLFGLCLGWPADNPDLKPRLPAS
ILVHENSYQPLDKGALAQYDEQLAEYYLTRGSNNRRDTWSDHIRRTIIKESGPSILDY
LHKQGWATR Polymutant 29 designated as
SEQ ID NO: 45
MTPTTELICGHRSIRHFTDEPISEAQREAIINSARATSSSYFLQCSSIIRITDKALREEL
VTLTGGQKHVAQAAEFWVFCADFNRHLQICPDAQLGLAEQLLMGVVDTAMMAQNA
LIAAESLGLGGVYIGGLRNNIEAVTKLLKLPQHVLPLFGLCLGWPADNPDLKPRLPAS
ILVHENSYQPLDKGALAQYDEQLAEYYLTRGSNNRRDTWSDHIRRTIIEES A PFILDY
LHKQGWATR Polymutant 30 designated as
SEQ ID NO: 46
MTPTIELICGHRSIRHFTDEPISEAQREAIINSARATSSSYFLQCSSIIRITDIKALREELV
TLTGGQKHVAQAAEFWVFCADFNRHLQICPDAQLGLAEQLLLGVVDTAMMAQNALI
AAESLGLGGVYIGGLRNNIEAVTKLLKLPQHVLPLFGLCLGWPADNPDLKPRLPASIL
VHENSYQPLDKGALAQYDEQLAEYYLTRGSNNRRDTWSDHIRRTIIKESAPSILDYL
HKQGWATR Polymutant 31 designated as
SEQ ID NO: 47
MTPTIELICGHRSIRHFTDEPISEAQREAIINSARATSSSYFLQCSSIIRITDKALREELV
TLTGGQKHVAQAAEFWVFCADFNRHLQICPDAQLGLAGQLLMGVVDTAMMAQNAL

```
IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESGPFIVDY

LHKQGWATR
```

Polymutant 32 designated as
                                          SEQ ID NO: 48
```
MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTVVSDHIRRTIIEESRPSIVDY

LHKQGWATR
```

Polymutant 33 designated as
                                          SEQ ID NO: 49
```
MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESAPSILDY

LHKQGWATR
```

Polymutant 35 designated as
                                          SEQ ID NO: 50
```
MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESGPFIVDY

LHKQGWATR
```

Polymutant 36 designated as
                                          SEQ ID NO: 51
```
MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIEESPPFILDY

LHKQGWATR
```

Polymutant 37 designated as
                                          SEQ ID NO: 52
```
MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESPPFILDY

LHKQGWATR
```

Polymutant 38 designated as
                                          SEQ ID NO: 53
```
MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESGPSIVDY

LHKQGWATR
```

-continued

Polymutant 39 designated as
SEQ ID NO: 54
MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLLGVVDTAMMAQNALI

AAESLGLGGVYIGGLRNNIEAVTKLLKLPQHVLPLFGLCLGWPADNPDLKPRLPASIL

VHENSYQPLDKGALAQYDEQLAEYYLTRGSNNRRDTWSDHIRRTIIEESPPSILDYL

HKQGWATR

Polymutant 40 designated as
SEQ ID NO: 55
MTPTTELICGHRSIRHFTDEPISEAQREAIINSARATSSSYFLQCSSIIRITDKALREEL

VTLTGGQKHVAQAAEFWVFCADFNRHLQICPDAQLGLAEQLLLGVVDTAMMAQNA

LIAAESLGLGGVYIGGLRNNIEAVTKLLKLPQHVLPLFGLCLGWPADNPDLKPRLPAS

ILVHENSYQPLDKGALAQYDEQLAEYYLTRGSNNRRDTWSDHIRRTIIEESAPFILDY

LHKQGWATR

Polymutant 42 designated as
SEQ ID NO: 56
MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESGPSILDY

LHKQGWATR

Polymutant 43 designated as
SEQ ID NO: 57
MTPTTELICGHRSIRHFTDEPISEAQREAIINSARATSSSYFLQCSSIIRITDKALREEL

VTLTGGQKHVAQAAEFWVFCADFNRHLQICPDAQLGLAEQLLLGVVDTAMMAQNA

LIAAESLGLGGVYIGGLRNNIEAVTKLLKLPQHVLPLFGLCLGWPADNPDLKPRLPAS

ILVHENSYQPLDKGALAQYDEQLAEYYLTRGSNNRRDTWSDHIRRTIIKESAPSILDY

LHKQGWATR

Polymutant 44 designated as
SEQ ID NO: 58
MMPTIELICGHRSIRHFTDEPISEAQREAIINSARATSSSYFLQCSSIIRITDKALREEL

VTLTGGQKHVAQAAEFWVFCADFNRHLQICPDAQLGLAEQLLLGVVDTAMMAQNA

LIAAESLGLGGVYIGGLRNNIEAVTKLLKLPQHVLPLFGLCLGWPADNPDLKPRLPAS

ILVHENSYQPLDKGALAQYDEQLAEYYLTRGSNNRRDTWSDHIRRTIIKESAPFILDY

LHKQGWATR

Polymutant 45 designated as
SEQ ID NO: 59
MTPTIELICGHRSIRHFTDEPISEAQREAIINSARATSSSYFLQCSSIIRITDKALREELV

TLTGGQKHVAQAAEFWVFCADFNRHLQICPDAQLGLAGQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESAPSILDY

LHKQGWATR

Polymutant 441 designated as
SEQ ID NO: 60
MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLLGVVDTAMMAQNALI

```
                                                       -continued
AAESLGLGGVYIGGLRNNIEAVTKLLKLPQHVLPLFGLCLGWPADNPDLKPRLPASIL

VHENSYQPLDKGALAQYDEQLAEYYLTRGSNNRRDTWSDHIRRTIIKESAPFILDYL

HKQGWATR

Polymutant 22P designated as
                                                                  SEQ ID NO: 61
MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESPPSILDY

LHKQGWATR

Polymutant 22G designated as
                                                                  SEQ ID NO: 62
MTPTIELICGHRSIRHFTDEPISEAQREAIINSARATSSSYFLQCSSIIRITDKALREELV

TLTGGQKHVAQAAEFWVFCADFNRHLQICPDAQLGLAGQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESRPSILDY

LHKQGWATR

Polymutant 22GP designated as
                                                                  SEQ ID NO: 63
MTPTIELICGHRSIRHFTDEPISEAQREAIINSARATSSSYFLQCSSIIRITDKALREELV

TLTGGQKHVAQAAEFWVFCADFNRHLQICPDAQLGLAGQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDIVVSDHIRRTIIKESPPSILDY

LHKQGWATR

Single mutant sequences from Escherichia coli (strain W3110):
Single mutant I5T designated as
                                                                  SEQ ID NO: 64
MTPTTELICGHRSIRHFTDEPISEAQREAIINSARATSSSSFLQCSSIIRITDKALREEL

VTLTGGQKHVAQAAEFWVFCADFNRHLQICPDAQLGLAEQLLLGVVDTAMMAQNA

LIAAESLGLGGVYIGGLRNNIEAVTKLLKLPQHVLPLFGLCLGWPADNPDLKPRLPAS

ILVHENSYQPLDKGALAQYDEQLAEYYLTRGSNNRRDTWSDHIRRTIIKESRPFILDY

LHKQGWATR

Single mutant S41Y designated as
                                                                  SEQ ID NO: 65
MTPTIELICGHRSIRHFTDEPISEAQREAIINSARATSSSYFLQCSSIIRITDKALREELV

TLTGGQKHVAQAAEFWVFCADFNRHLQICPDAQLGLAEQLLLGVVDTAMMAQNALI

AAESLGLGGVYIGGLRNNIEAVTKLLKLPQHVLPLFGLCLGWPADNPDLKPRLPASIL

VHENSYQPLDKGALAQYDEQLAEYYLTRGSNNRRDTWSDHIRRTIIKESRPFILDYL

HKQGWATR

Single mutant E99G designated as
                                                                  SEQ ID NO: 66
MTPTIELICGHRSIRHFTDEPISEAQREAIINSARATSSSYFLQCSSIIRITDKALREELV

TLTGGQKHVAQAAEFWVFCADFNRHLQICPDAQLGLAGQLLLGVVDTAMMAQNALI

AAESLGLGGVYIGGLRNNIEAVTKLLKLPQHVLPLFGLCLGWPADNPDLKPRLPASIL

VHENSYQPLDKGALAQYDEQLAEYYLTRGSNNRRDTWSDHIRRTIIKESRPFILDYL

HKQGWATR
```

Single mutant L103M designated as
SEQ ID NO: 67
MTPTIELICGHRSIRHFTDEPISEAQREAIINSARATSSSSFLQCSSIIRITDKALREELV

TLTGGQKHVAQAAEFWVFCADFNRHLQICPDAQLGLAEQLLMGVVDTAMMAQNAL

IAAESLGLGGVYIGGLRNNIEAVTKLLKLPQHVLPLFGLCLGWPADNPDLKPRLPASI

LVHENSYQPLDKGALAQYDEQLAEYYLTRGSNNRRDTWSDHIRRTIIKESRPFILDY

LHKQGWATR

Single mutant K222E designated as
SEQ ID NO: 68
MTPTIELICGHRSIRHFTDEPISEAQREAIINSARATSSSSFLQCSSIIRITDKALREELV

TLTGGQKHVAQAAEFWVFCADFNRHLQICPDAQLGLAEQLLLGVVDTAMMAQNALI

AAESLGLGGVYIGGLRNNIEAVTKLLKLPQHVLPLFGLCLGWPADNPDLKPRLPASIL

VHENSYQPLDKGALAQYDEQLAEYYLTRGSNNRRDTWSDHIRRTIIEESRPFILDYL

HKQGWATR

Single mutant R225A designated as
SEQ ID NO: 69
MTPTIELICGHRSIRHFTDEPISEAQREAIINSARATSSSSFLQCSSIIRITDKALREELV

TLTGGQKHVAQAAEFWVFCADFNRHLQICPDAQLGLAEQLLLGVVDTAMMAQNALI

AAESLGLGGVYIGGLRNNIEAVTKLLKLPQHVLPLFGLCLGWPADNPDLKPRLPASIL

VHENSYQPLDKGALAQYDEQLAEYYLTRGSNNRRDTWSDHIRRTIIKESAPFILDYL

HKQGWATR

Single mutant R225G designated as
SEQ ID NO: 70
MTPTIELICGHRSIRHFTDEPISEAQREAIINSARATSSSSFLQCSSIIRITDKALREELV

TLTGGQKHVAQAAEFWVFCADFNRHLQICPDAQLGLAEQLLLGVVDTAMMAQNALI

AAESLGLGGVYIGGLRNNIEAVTKLLKLPQHVLPLFGLCLGWPADNPDLKPRLPASIL

VHENSYQPLDKGALAQYDEQLAEYYLTRGSNNRRDTWSDHIRRTIIKESGPFILDYL

HKQGWATR

Single mutant R225P designated as
SEQ ID NO: 71
MTPTIELICGHRSIRHFTDEPISEAQREAIINSARATSSSSFLQCSSIIRITDKALREELV

TLTGGQKHVAQAAEFWVFCADFNRHLQICPDAQLGLAEQLLLGVVDTAMMAQNALI

AAESLGLGGVYIGGLRNNIEAVTKLLKLPQHVLPLFGLCLGWPADNPDLKPRLPASIL

VHENSYQPLDKGALAQYDEQLAEYYLTRGSNNRRDTWSDHIRRTIIKESPPFILDYL

HKQGWATR

Single mutant F227S designated as
SEQ ID NO: 72
MTPTIELICGHRSIRHFTDEPISEAQREAIINSARATSSSSFLQCSSIIRITDKALREELV

TLTGGQKHVAQAAEFWVFCADFNRHLQICPDAQLGLAEQLLLGVVDTAMMAQNALI

AAESLGLGGVYIGGLRNNIEAVTKLLKLPQHVLPLFGLCLGWPADNPDLKPRLPASIL

VHENSYQPLDKGALAQYDEQLAEYYLTRGSNNRRDTWSDHIRRTIIKESRPSILDYL

HKQGWATR

Single mutant L229V designated as
SEQ ID NO: 73
MTPTIELICGHRSIRHFTDEPISEAQREAIINSARATSSSSFLQCSSIIRITDKALREELV

TLTGGQKHVAQAAEFWVFCADFNRHLQICPDAQLGLAEQLLLGVVDTAMMAQNALI

-continued

```
AAESLGLGGVYIGGLRNNIEAVTKLLKLPQHVLPLFGLCLGWPADNPDLKPRLPASIL

VHENSYQPLDKGALAQYDEQLAEYYLTRGSNNRRDTWSDHIRRTIIKESRPFIVDYL

HKQGWATR
```

Further mutants with enhanced efficacy in prodrug and/or probe metabolism:
NfsA(Vv) (from *Vibrio vulnificus*, NZ isolate) mutant A33T designated as
SEQ ID NO: 74

```
MNAVIDTLLSHRSIRKFTDQAITPEQLDTIIRTGLAASSSSLLQVVSIIRITDPAKRQQL

AELAGPQHYVETAAEFLVFCIDYQRHATLNSEVQAGFTELTLIGAVDAGIMAQNCLL

AAESMGLGGVYIGGLRNKAAEVDALLELPPFSAVLFGMCLGHPDQDPDLKPRLPAE

VILHENHYQPLDLNKVEQYDQTMLDYYGKRSSNQKQASWSEQVTGKLAGESRPHI

LPYLHSKGLATK
```

NfsA(Vv) (from *Vibrio vulnificus*, NZ isolate) mutant L42C designated as
SEQ ID NO: 75

```
MNAVIDTLLSHRSIRKFTDQAITPEQLDTIIRAGLAASSSSCLQVVSIIRITDPAKRQQL

AELAGPQHYVETAAEFLVFCIDYQRHATLNSEVQAGFTELTLIGAVDAGIMAQNCLL

AAESMGLGGVYIGGLRNKAAEVDALLELPPFSAVLFGMCLGHPDQDPDLKPRLPAE

VILHENHYQPLDLNKVEQYDQTMLDYYGKRSSNQKQASWSEQVTGKLAGESRPHI

LPYLHSKGLATK
```

NfsA(Vv) (from *Vibrio vulnificus*, NZ isolate) mutant L42M designated as
SEQ ID NO: 76

```
MNAVIDTLLSHRSIRKFTDQAITPEQLDTIIRAGLAASSSSMLQVVSIIRITDPAKRQQL

AELAGPQHYVETAAEFLVFCIDYQRHATLNSEVQAGFTELTLIGAVDAGIMAQNCLL

AAESMGLGGVYIGGLRNKAAEVDALLELPPFSAVLFGMCLGHPDQDPDLKPRLPAE

VILHENHYQPLDLNKVEQYDQTMLDYYGKRSSNQKQASWSEQVTGKLAGESRPHI

LPYLHSKGLATK
```

NfsA(Vv) (from *Vibrio vulnificus*, NZ isolate) mutant L42R designated as
SEQ ID NO: 77

```
MNAVIDTLLSHRSIRKFTDQAITPEQLDTIIRAGLAASSSSRLQVVSIIRITDPAKRQQL

AELAGPQHYVETAAEFLVFCIDYQRHATLNSEVQAGFTELTLIGAVDAGIMAQNCLL

AAESMGLGGVYIGGLRNKAAEVDALLELPPFSAVLFGMCLGHPDQDPDLKPRLPAE

VILHENHYQPLDLNKVEQYDQTMLDYYGKRSSNQKQASWSEQVTGKLAGESRPHI

LPYLHSKGLATK
```

NfsA(Vv) (from *Vibrio vulnificus*, NZ isolate) mutant E178A designated as
SEQ ID NO: 78

```
MNAVIDTLLSHRSIRKFTDQAITPEQLDTIIRAGLAASSSSLLQVVSIIRITDPAKRQQL

AELAGPQHYVETAAEFLVFCIDYQRHATLNSEVQAGFTELTLIGAVDAGIMAQNCLL

AAESMGLGGVYIGGLRNKAAEVDALLELPPFSAVLFGMCLGHPDQDPDLKPRLPAE

VILHANHYQPLDLNKVEQYDQTMLDYYGKRSSNQKQASWSEQVTGKLAGESRPHI

LPYLHSKGLATK
```

NfsA(Vv) (from *Vibrio vulnificus*, NZ isolate) mutant L220D designated as
SEQ ID NO: 79

```
MNAVIDTLLSHRSIRKFTDQAITPEQLDTIIRAGLAASSSSLLQVVSIIRITDPAKRQQL

AELAGPQHYVETAAEFLVFCIDYQRHATLNSEVQAGFTELTLIGAVDAGIMAQNCLL

AAESMGLGGVYIGGLRNKAAEVDALLELPPFSAVLFGMCLGHPDQDPDLKPRLPAE

VILHENHYQPLDLNKVEQYDQTMLDYYGKRSSNQKQASWSEQVTGKDAGESRPHI

LPYLHSKGLATK
```

-continued

NfsA(Vv) (from *Vibrio vulnificus*, NZ isolate) mutant L220G designated as
SEQ ID NO: 80
MNAVIDTLLSHRSIRKFTDQAITPEQLDTIIRAGLAASSSSLLQVVSIIRITDPAKRQQL

AELAGPQHYVETAAEFLVFCIDYQRHATLNSEVQAGFTELTLIGAVDAGIMAQNCLL

AAESMGLGGVYIGGLRNKAAEVDALLELPPFSAVLFGMCLGHPDQDPDLKPRLPAE

VILHENHYQPLDLNKVEQYDQTMLDYYGKRSSNQKQASWSEQVTGKGAGESRPHI

LPYLHSKGLATK

NfsA(Vv) (from *Vibrio vulnificus*, NZ isolate) mutant S224V designated as
SEQ ID NO: 81
MNAVIDTLLSHRSIRKFTDQAITPEQLDTIIRAGLAASSSSLLQVVSIIRITDPAKRQQL

AELAGPQHYVETAAEFLVFCIDYQRHATLNSEVQAGFTELTLIGAVDAGIMAQNCLL

AAESMGLGGVYIGGLRNKAAEVDALLELPPFSAVLFGMCLGHPDQDPDLKPRLPAE

VILHENHYQPLDLNKVEQYDQTMLDYYGKRSSNQKQASWSEQVTGKLAGEVRPHI

LPYLHSKGLATK

NfsA(Vv) (from *Vibrio vulnificus*, NZ isolate) mutant S224D designated as
SEQ ID NO: 82
MNAVIDTLLSHRSIRKFTDQAITPEQLDTIIRAGLAASSSSLLQVVSIIRITDPAKRQQL

AELAGPQHYVETAAEFLVFCIDYQRHATLNSEVQAGFTELTLIGAVDAGIMAQNCLL

AAESMGLGGVYIGGLRNKAAEVDALLELPPFSAVLFGMCLGHPDQDPDLKPRLPAE

VILHENHYQPLDLNKVEQYDQTMLDYYGKRSSNQKQASWSEQVTGKLAGEDRPHI

LPYLHSKGLATK

NfsA(St) (from *Salmonella enterica* serovar Typhi Ty2) mutant I49F
designated as
SEQ ID NO: 83
MSPTIELLCGHRSIRHFTDEPVTDAQREAIIAAARSTSSSSFLQCSSIFRITDRALREA

LVPLTGGQKHVAQAAEFWVFCADFNRHLQICPDAQLGLAEQLLLGVVDTAMMGQN

ALTAAESLGLGGVYISGIRNNIESVTELLKLPKHVLPLFGLCLGWPADNPDLKPRLPA

ELVVHENQYQPLDEKLLARYDEQLAEYYLTRGSNTRRDTWSDHIRRTLIKENRPFIL

EYLHKQGWATR

NfsA(St) (from *Salmonella enterica* serovar Typhi Ty2) mutant S130G
designated as
SEQ ID NO: 84
MSPTIELLCGHRSIRHFTDEPVTDAQREAIIAAARSTSSSSFLQCSSIIRITDRALREAL

VPLTGGQKHVAQAAEFWVFCADFNRHLQICPDAQLGLAEQLLLGVVDTAMMGQNA

LTAAESLGLGGVYIGGIRNNIESVTELLKLPKHVLPLFGLCLGWPADNPDLKPRLPAE

LVVHENQYQPLDEKLLARYDEQLAEYYLTRGSNTRRDTWSDHIRRTLIKENRPFILE

YLHKQGWATR

NfsA(St) (from *Salmonella enterica* serovar Typhi Ty2) mutant R133S
designated as
SEQ ID NO: 85
MSPTIELLCGHRSIRHFTDEPVTDAQREAIIAAARSTSSSSFLQCSSIIRITDRALREAL

VPLTGGQKHVAQAAEFWVFCADFNRHLQICPDAQLGLAEQLLLGVVDTAMMGQNA

LTAAESLGLGGVYISGISNNIESVTELLKLPKHVLPLFGLCLGWPADNPDLKPRLPAE

LVVHENQYQPLDEKLLARYDEQLAEYYLTRGSNTRRDTWSDHIRRTLIKENRPFILE

YLHKQGWATR

NfsA(St) (from *Salmonella enterica* serovar Typhi Ty2) mutant G204A
designated as
SEQ ID NO: 86
MSPTIELLCGHRSIRHFTDEPVTDAQREAIIAAARSTSSSSFLQCSSIIRITDRALREAL

VPLTGGQKHVAQAAEFWVFCADFNRHLQICPDAQLGLAEQLLLGVVDTAMMGQNA

-continued

LTAAESLGLGGVYISGIRNNIESVTELLKLPKHVLPLFGLCLGWPADNPDLKPRLPAE

LVVHENQYQPLDEKLLARYDEQLAEYYLTRASNTRRDTWSDHIRRTLIKENRPFILE

YLHKQGWATR

NfsA(St) (from Salmonella enterica serovar Typhi Ty2) mutant R225C
designated as
SEQ ID NO: 87
MSPTIELLCGHRSIRHFTDEPVTDAQREAIIAAARSTSSSSFLQCSSIIRITDRALREAL

VPLTGGQKHVAQAAEFWVFCADFNRHLQICPDAQLGLAEQLLLGVVDTAMMGQNA

LTAAESLGLGGVYISGIRNNIESVTELLKLPKHVLPLFGLCLGWPADNPDLKPRLPAE

LVVHENQYQPLDEKLLARYDEQLAEYYLTRGSNTRRDTWSDHIRRTLIKENCPFILE

YLHKQGWATR

NfrA(Bs) (from Bacillus subtilis, subspecies subtilis, NZ isolate)
mutant R234P designated as
SEQ ID NO: 88
MNNTIETILNHRSIRSFTDQLLTAEEIDILVKSAQAASTSSYVQAYSIIGVSDPEKKREL

SVLAGNQPYVENNGHFFVFCADLHRHQKLAEEKGENISELLENTEMFMVSLIDAALA

AQNMSVAAESMGLGICYIGGIRNELDKVTEVLQTPDHVLPLFGLAVGHPANLSGKKP

RLPKQAVYHENTYNVNADDFRDTMNAYDQTISDYYRERTNGQREETWSDQILNFM

KQKPPTYLNDYVKEKGFNKN

NfrA(Bs) (from Bacillus subtilis, subspecies subtilis, NZ isolate)
mutant R234T designated as
SEQ ID NO: 89
MNNTIETILNHRSIRSFTDQLLTAEEIDILVKSAQAASTSSYVQAYSIIGVSDPEKKREL

SVLAGNQPYVENNGHFFVFCADLHRHQKLAEEKGENISELLENTEMFMVSLIDAALA

AQNMSVAAESMGLGICYIGGIRNELDKVTEVLQTPDHVLPLFGLAVGHPANLSGKKP

RLPKQAVYHENTYNVNADDFRDTMNAYDQTISDYYRERTNGQREETWSDQILNFM

KQKPTTYLNDYVKEKGFNKN

NfrA(Bs) (from Bacillus subtilis, subspecies subtilis, NZ isolate)
mutant R234L designated as
SEQ ID NO: 90
MNNTIETILNHRSIRSFTDQLLTAEEIDILVKSAQAASTSSYVQAYSIIGVSDPEKKREL

SVLAGNQPYVENNGHFFVFCADLHRHQKLAEEKGENISELLENTEMFMVSLIDAALA

AQNMSVAAESMGLGICYIGGIRNELDKVTEVLQTPDHVLPLFGLAVGHPANLSGKKP

RLPKQAVYHENTYNVNADDFRDTMNAYDQTISDYYRERTNGQREETWSDQILNFM

KQKPLTYLNDYVKEKGFNKN

The inventors have demonstrated that *E. coli* NfsA can be engineered through directed evolution to yield mutant nitroreductases with improved activity in activating/metabolising multiple prodrugs and imaging probes. Thus, a skilled person would have a reasonable scientific expectation that modification of the residues stated above could be used to derive further effective novel mutant nitroreductases from other NfsA family members from different species or strains. Similarly, the invention provides mutant NfsB nitroreductases with improved properties and it is expected that NfsB mutants derived from a number of organisms selected according to the methods defined herein would have similarly improved properties over the wild-type enzymes. Directed evolution could also be employed with the other NTR families and sequences defined in the specification to improve their activity with individual or multiple prodrugs as well as imaging probes. In a further aspect, the invention provides a method of ablation of a cell and/or a biological agent comprising the steps of:
d. introduction of a nitroreductase of the invention to a subject; and
e. introduction of a prodrug to a subject; and
f. ablation of a cell and/or biological agent by the activated prodrug
wherein steps a. and b. may be carried out concurrently or sequentially in any order.

Examples

Material and Methods

Purified Enzyme Kinetics:
For EF5 and other 2-NI bio-imaging agents, steady-state enzyme kinetics with purified NTRs were assessed spectrophotometrically at 340 nm to monitor NTR catalyzed NADPH oxidation. The molar extinction co-efficient of NADPH (6,220 M$^{-1}$ cm$^{-1}$) was used for the calculation of enzyme activity. For PR-104A, reduction was measured directly at 400 nm (ε=6,000 M$^{-1}$ cm$^{-1}$); and for CB1954, reduction was measured directly at 420 nm (ε=1,200 M$^{-1}$ cm$^{-1}$). Reactions were performed in 100 μl in UVettes (Eppendorf), using the 2 mm light path length. Reactions contained 10 mM Tris-Cl (pH 7.0), 4% DMSO, 0.25 mM NADPH and varying EF5 or PR-104A concentrations. Reactions were initiated by addition of 10 μl enzyme and changes in absorbance were measured for 15 s (during linearity). For calculation of $K_m$ and $k_{cat}$, substrate concentrations were varied from ~0.2×$K_m$ to 5×$K_m$. Non-linear regression analysis and Michaelis-Menten curve fitting was performed using Sigmaplot 10.0 (Systat Software Inc.).

Expression of NTRs in human HCT116 cells:

Isolated NTR gene sequences were subject to PCR and introduced in the bicistronic plasmid F579 via Gateway cloning (Invitrogen) as described by Prosser et al. (2010, *Biochem Pharmacol*, 79, 678-687). Stably transfected cell lines were created by transfection of the relevant plasmid using FuGENE 6 Transfection Reagent (Roche). Transfected cell populations were maintained by passage in puromycin Monolayer Antiproliferative Assays:

Cells were passaged in alpha-Minimal Essential Media, (αMEM; Gibco) supplemented with 5% FBS, (GIBCO NZ) without antibiotics. Cell were passaged for <3 months from frozen stocks and confirmed *Mycoplasma* free (PCR-ELISA; Roche Diagnostics). Cells were aliquoted into the 96-well plate (100 μL/well) and cells were left to attach (≥4 hrs). Stock drug solutions were prepared in DMSO and stored at −80° C. Aliquots were thawed and diluted to required concentration with αMEM. Study compounds were added to the top-well, and diluted down the plate in 3-fold serial dilutions using a multichannel pipette and placed in a 37° C., 5% $CO_2$ incubator for 4 or 18 hrs. After incubation wells were washed free of drug and left for 5 days in a 37° C., 5% $CO_2$ incubator. After this time cells were fixed by addition of cold 40% trichloroacetic acid (Merck KGaA) to each well, to give a final concentration of 10%. Plates were left for 1 hour (4° C.) and rinsed with water prior to staining with 0.4% sulforhodamine B (SRB; Sigma-Aldrich) in 1% acetic acid (30 min, dark). Plates were rinsed (1% acetic acid) and stain in 10 mM unbuffered Tris. Plates were read on an ELx 808 Absorbance Microplate Reader (Bio-Tek Instruments). Absorbance was measured at 490 nm and 450 nm (final absorbance 490-450). A dose-response curve was fitted using KC4 microplate data analysis software (KC4™ V3.4, Bio-Tek), and concentration of agent required to inhibit cell growth by 50% (relative to untreated control) was calculated ($IC_{50}$ value). $IC_{50}$ values are mean for ≥2 independent experiments. Interexperimental $IC_{50}$ ratio of parental HCT116 versus NTR expressing HCT116 clonal cell lines (WT:NTR ratio) were calculated and displayed in FIG. 10 and FIG. 17.

Figure 20:
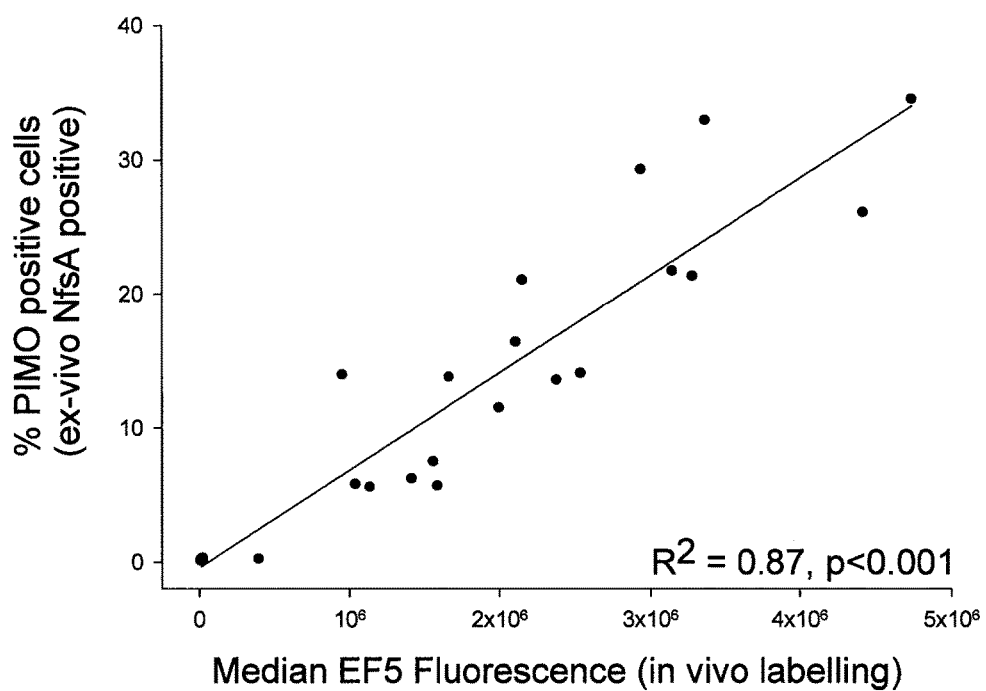
FIG. 20 illustrates the in vivo relationship between tumour EF5 binding and number of NfsA-positive cells as determined by ex-vivo (in vitro) PIMO labelling. The graph demonstrates that increasing EF5 retention is strongly correlated with total tumour NfsA activity. Mixed HCT116 human tumour xenografts were established in NIHIII nude mice by subcutaneous injection of mixtures of WT:NfsA cells using fixed ratios of 0%, 1%, 3%, 5%, 10%, 15% or 25% A *E. coli* NfsA expressing cells. Mice bearing these established mixed tumours were treated with PR-104 (325 mg/kg; ip). Three hours later EF5 (30 mg/kg, ip) was administered and after two hours tumour tissue was excised and subjected to enzymatic disaggregation to form a single cell suspension. 1×10⁶ cells plated post-treatment as a monolayer and incubated with 100 µM PIMO for one hour at 37° C. The PIMO and EF5 antibodies are conjugated to different fluorophores (PIMO to FITC (Em. 518 nm) and EF5 to CY5 (Em. 670-700 nm) allowing concurrent evaluation of single cells for both PIMO and EF5 adduct retention by flow cytometry.
Figure 21:
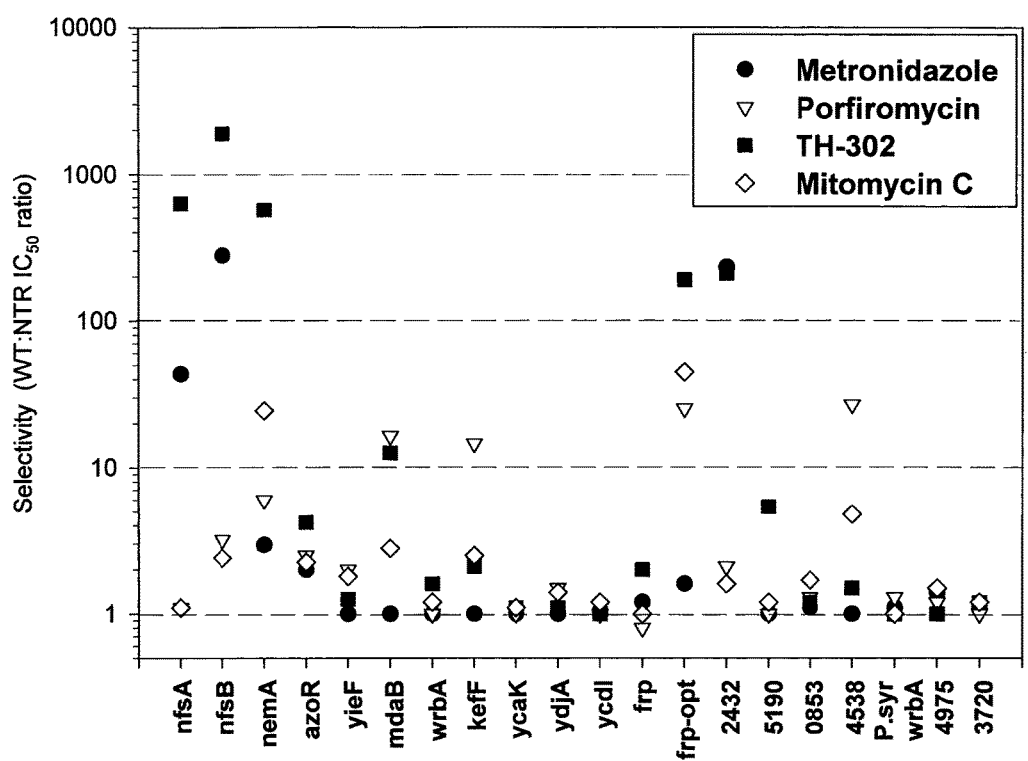
FIG. 21 illustrates antiproliferative activity ($IC_{50}$ value) of prodrug candidates with *E. coli* and non-*E. coli* nitroreductases. Stably-expressing cells were treated with varying concentration of prodrug diluted in αMEM+5% FCS+P/S. Cells were exposed to prodrug for 18 hrs, washed and left to regrow for 5 days. $IC_{50}$ was determined as the concentration of prodrug required to inhibit cell growth by 50% of untreated controls. $IC_{50}$ values are mean for ≥2 independent experiments. WT:NTR ratio-interexperimental ratio of $IC_{50}$ means from WT cells versus NTR-expressing cell lines.

Multicellular Layers (MCLs):

Millicell-CM membrane inserts (Millipore) were coated in calf-skin collagen type III (Sigma-Aldrich) to facilitate cell attachment. Single cell suspensions of cell lines (1×10$^6$ cells/0.5 ml) were seeded into the inserts and grown as described (Wilson et al., 2002, *Cancer Res.* 62:1425-1432). After 3 days MCLs were taken and exposed to study compound for 5 hrs (in presence 95% $O_2$/5% $CO_2$ to eliminate endogenous one-electron reductase activity). After exposure, inserts were disaggregated (0.07% trypsin, 10 min, 37° C., followed by 100 μg/ml DNAase I (Sigma-Aldrich). Cells were counted, resuspended and plated in P60 dishes to determine clonogenic survival. To discriminate clonogenic activator (NTR+) from target (NTR−) colonies cells were plated in non-selective medium (total cells) and medium containing 1 μM puromycin (activator cells). Colonies were grown in a 37° C. 5% $CO_2$ incubator for 10 days before staining with methylene blue (2 g/liter in 50% v/v aqueous ethanol). Colonies containing >50 cells were counted as clonogenic survivors. Surviving fractions for each population was calculated as the plating efficiency for drug-treated MCLs/untreated controls. The drug concentrations for 10% survival ($C_{10}$) of target cells grown without activators (T), targets in co-culture ($T_c$) and activators in co-culture ($A_c$) was determined by interpolation. Bystander effect efficiency (BEE) was calculated as (Log $C_{10}$T−Log $C_{10}T_c$)/(Log $C_{10}$T−Log $C_{10}A_c$) as shown in FIGS. 20 and 21.

Flow Cytometry:

In vitro: 1×10$^6$ cells were drug treated (EF5 or PIMO) for 1-2 hrs, harvested by trypsinisation, fixed with 4% buffered PFA (pH 7.4, 1 hr). In vivo: Tumour xenograft cells were isolated by enzymatic dissociation (2.5 mg/ml pronase, 1 mg/ml collagenase and 0.2 mg/ml DNAse) and immediately fixed with 4% buffered PFA (pH 7.4, 1 hr). and transferred to 70% ethanol (−20° C., overnight). Cells were resuspended in 1% BSA/PBS and permeabilised with 0.2% Triton X-100 (30 min, RT), blocked in 10% BSA/PBS (30 min, RT) and resuspended in primary antibody for 2 hr (37° C.). The primary antibody was either anti-EF5 mouse monoclonal (ELK 3.51) conjugated with CY5 or Alexa-488 diluted to 100 μg/ml in blocking buffer (according to instruction in Koch C., 2008, Rad Res, 169 (6): 677-688) or Hypoxy-probe-1 (Chemicon Int) mouse monoclonal anti-pimonidazole antibody (clone 4.3.11.3) conjugated with FITC and diluted 1:100 in blocking buffer. Cells were washed in blocking buffer and resuspended in blocking buffer containing 100 μg/ml RNAase and analysed using a Becton Dickinson FACscan flow cytometer (MA, USA) with Cell Quest software using forward scatter and side scatter to gate out cell debris and tumour cells. Integrated fluorescence measurements were recorded for 30,000 single non-debris events. Fluorescence was measured at 530±20 (FITC and Alexa Fluor 488) and 670-700 (CY5) as shown in FIGS. 11, 13, 14 and 15).

Fluorescence Microscopy:

In vitro: 3-4 drops of cell suspension prepared for flow cytometry was added to a cytospin chamber containing a poly-I-lysine coated slide and spun for 5 minutes at low acceleration (500 rpm) in a cytospinner. Cells were left to dry and mounted with coverslips using Prolong Gold antifade (Invitrogen) and sealed with nail varnish.

In vivo: mice were treated with 60 mg/kg EF5 (ip) and left for 24 hrs. Tumour tissue was excised, fixed in 10% formalin dissolved in PBS (48 h), transferred to 70% ethanol and embedded in paraffin. Sections (5 μm) were cut, mounted onto poly-L-lysine coated glass slides and heat fixed for 1 h at 60° C. Sections were dewaxed, rehydrated, washed in Milli-Q water and then rinsed in 0.01 M Tris buffered saline (TBS, pH 7.4). Antigen retrieval was achieved by boiling samples in 10 mM sodium citrate buffer pH 6 for 25 min. Sections were washed with TBS containing 0.1% Tween-20 (TBS-T) and blocked with 1% mouse serum in TBS. After rinsing, the samples were incubated for 2 hr at room temperature with 100 μg/ml anti-EF5 (Alexa-488) primary antibody diluted in PBS containing 0.2% Tween-20. After rinsing in with TBS-T the coverslips were mounted with Prolong Gold antifade (Invitrogen) and sealed with nail varnish. Following completion of the fluorescent imaging the coverslips were removed and the sections were stained with haematoxylin and eosin (H&E). Slides were viewed on an Eclipse TE2000-E inverted fluorescent microscope (Nikon, Japan). Images were analysed and overlaid using Adobe Photoshop software (Adobe Photoshop 4.0).

Cytopathic Effect Assay:

HCT-116WT cells were seeded overnight and the top wells were infected with 0.125 MOI of the replication competent adenovirus ONYX411-nfsB and 1 MOI for ONYX411-WT with 2-fold serial dilutions ((Singleton et al, 2007, *Cancer Gene Ther* 14 (12): 953-967). 24 hrs following infection media was replaced with fresh αMEM containing 2% FCS and varying concentrations of metronidazole, which was refreshed every 2 days. On day 9 wells were fixed with 10% TCA and stained with SRB and cell density analysed.

Figure 18:
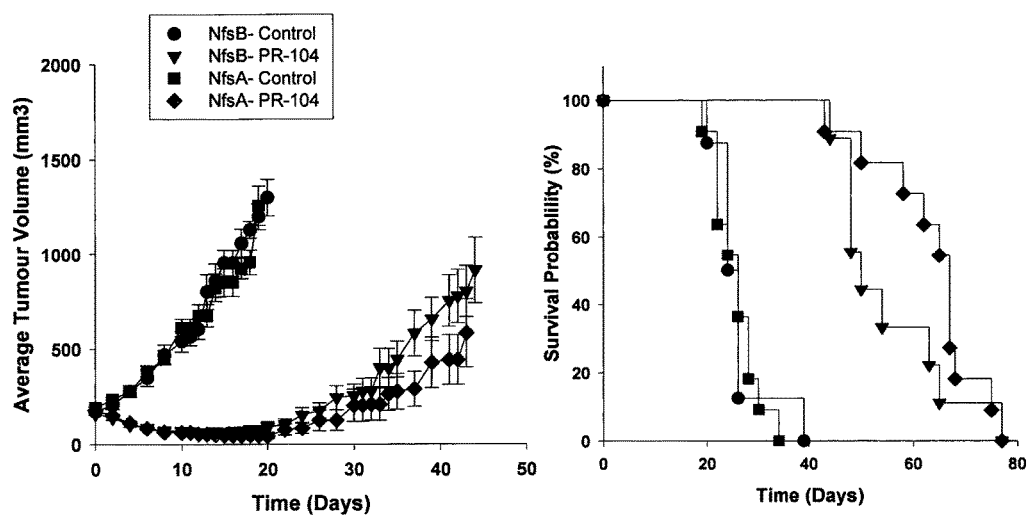
FIG. 18 illustrates in vivo activity of PR-104 in 25% nfsB or 25% nfsA tumours. Average tumour volume and Kaplan-Meier growth plots for tumours grown subcutaneously on NIH-III mice. Tumours were composed of either 25% HCT-$116^{nfsB}$/75% HCT-$116^{WT}$ or 25% HCT-$116^{nfsA}$/75% HCT-$116^{WT}$. When tumours reached 7 mm² mice (n=8-11 per group) were randomly assigned to a treatment group and injected with a single dose (i.p.) of PBS (control) or PR-104 (1000 µmol/kg). Tumour measurements were recorded twice weekly and mice were culled when tumours exceeded a mean diameter of 15 mm².

Tumour Xenograft Growth:

Specific pathogen-free female homozygous NIH-III nude mice (CrI:NIH-Lyst$^{bg}$Foxn1$^{nu}$Btk$^{xid}$; Charles River Laboratories) were housed in Techniplast microisolator cages and fed Harlan Teklad diet 2018i. Growth Delay Animals weighed 16-25 g and ranged from 6-12 weeks of age at the time of tumour inoculation. Tumours were grown s.c. in the flank of the mice by inoculating cells grown in tissue culture (total of $10^7$ cells in 100 μL αMEM consisting of 25% nfsA or 25% nfsB expressing HCT116 cells, balance 75% HCT116-WT cells). Tumours were monitored using electronic calipers and mice were randomised into treatment groups once their tumours reached 7×7 mm in diameter. Tumour size and body weight were determined three times weekly. Tumour volume was calculated as $\pi (l \times w^2)/6$, where l is the major axis and w is the perpendicular minor axis. DNBMs were formulated on the day of dosing and kept in foil wrapped sterile tubes out of direct fluorescent light. Animals were culled 80 days after start of treatment, when mean tumour diameter exceeded 15 mm (survival endpoint) or when body weight loss exceeded 15% of pre-treatment value. Average tumour volume for each treatment group and Kaplan-Meier plots were constructed (FIG. 18). The median time for tumours to increase in volume 4-fold relative to pretreatment volume (RTV-4) was determined, and the specific growth delay (SGD) was calculated as the percentage increase in RTV-4 for treated versus control groups. This variable normalises for differences in tumour volume at treatment and for differences in control tumour growth rates. Relative tumour volume ×4 for each group was used for statistical analysis and was calculated by Dunn's one-way ANOVA (SigmaStat v3.0).

Nitroreductase Over-Expression:

Candidate nitroreductase genes were cloned into and expressed from the bacterial expression plasmid pUCX, which was derived from pUC19 by addition of the lacI gene, tac promoter, lac operator, RBS region and rrnB terminator sequence, as described in (Prosser et al, 2010, *Biochemical Pharmacology* 79, 678-687).

SDS-PAGE:

Evaluation of protein expression levels from pUCX in SOS-R2, as well as purity of His-tagged purified proteins was assessed by SDS-PAGE, using the methods of (Laemmli, 1970, *Nature* 227, 680-685). Samples for assessing expression levels from pUCX in SOS-R2 were taken from un-challenged wells of completed SOS-assays, as described below. Cultures were lysed by addition of SDS to 2% final concentration prior to electrophoresis.

SOS-Assay:

SOS-R2 was derived from SOS reporter strain SOS-R1 (as described in Prosser et al, 2010, *Biochemical Pharmacology* 79, 678-687) by deletion of the endogenous nfsA, nfsB, nemA and azoR genes. Overnight cultures of SOS-R2 pUCX::ntr strains to be tested were set up in LB+100 μg ml$^{-1}$ Ampicillin, 0.4% glucose in 96 well plates and incubated at 30° C., 200 rpm. The assay was commenced by inoculation of 195 μl fresh assay media (LB+100 μg ml$^{-1}$ Ampicillin, 0.2% glucose, 50 μM IPTG) with 15 μl of overnight, in individual wells of a 96-well plate. Plates were incubated at 30° C., 200 rpm for 3.5 h (pre-challenge period), following which cultures were diluted 1:2 by splitting 50:50 into fresh assay media (+DMSO to 0.5% final concentration) and fresh challenge media (assay media+drug to desired concentration, DMSO to 0.5% final concentration) to final volumes of 200 μl each. Plates were then returned to the incubator for an additional 3 h (challenge period), at the conclusion of which culture turbidity was measured by absorbance at 600 nm. For measurement of β-galactosidase activity, 10 μl aliquots from each well were added to 90 μl of 40 mM Na phosphate buffer pH 7.0 and 50 ml ZOB buffer (Alksne et al, 2000, *Antimicrob Agents Chemother* 44, 1418-1427) which was incubated at 37° C. without shaking for 20-40 min until sufficient color development from the o-nitrophenyl-b-D-galactopyranoside substrate was observed. Reactions were terminated by addition of 50 ml of 1 M $Na_2CO_3$. Absorbance readings at 420 and 550 nm were recorded and Miller units were calculated by the Miller equation (Miller J H, 1972, *Experiments in molecular genetics*, Cold Spring Harbor, N.Y., p. 466).

Nitro-Blue Tetrazolium (NBT) NADPH Depletion Assays:

Individual microtiter plate wells containing 200 μl LB+amp, 0.4% glucose were inoculated with SOS-R2 pUCX::ntr and incubated overnight at 30° C., 200 rpm. Ten μl of the overnight culture were used to inoculate 190 μl of fresh assay media (LB+amp, 0.05 mM IPTG, 0.2% glucose) and incubated at 30° C., 200 rpm for 6 h. Crude cell lysates were prepared using BugBuster® Protein Extraction Reagent (Novagen) in a 1:1 (v/v) ratio at room temperature for 30 min. To monitor cofactor consumption, replicate 200 μl reactions containing 0.25% DMSO, 100 mM K phosphate buffer pH 8.0, either 50 μl or 10 uL of crude cell lysate ±150 uM EF5 were prepared, initiated by addition of 200 uM NADPH, and allowed to proceed at room temperature for 10 or 45 minutes. Reactions were halted by addition of 50 μl NBT solution (2 mg·ml$^{-1}$ NBT, 0.3 mg·ml$^{-1}$ phenazine methosulfate, 100 mM K phosphate buffer pH 8.0). Levels of formazan production, corresponding to the amount of NADPH remaining in each well, were quantified by measuring absorbance at 590 nm.

Growth Inhibition Assay:

Individual microtiter plate wells containing 200 μl LB+amp, 0.4% glucose were inoculated with SOS-R2 pUCX::ntr strains and incubated overnight at 30° C., 200 rpm. Ten μl of the overnight culture were used to inoculate 190 μl of fresh assay media (LB+amp, 0.05 mM IPTG, 0.2% glucose) and incubated at 30° C., 200 rpm for 3 h. The 200 μl culture was split into 100 μl duplicates which were supplemented with either 100 μl challenge media (assay media+250 uM EF5+2% DMSO) or 100 μl control media (assay media+2% DMSO). Initial $OD_{600}$ readings were recorded and then plates incubated at 30° C., 200 rpm for 4 h after which final $OD_{600}$ readings were taken and used to calculate strains respective growth inhibition in EF5 presence.

Protein Purification:

Recombinant his6-tagged NTRs were purified by nickel-affinity chromatography as described by Novagen. For kinetic assays, eluted fractions were supplemented with a 5-fold excess molar ratio of pure FMN and incubated on ice for at least 1 h before buffer-exchange into 40 mM Tris-Cl (pH 7.0) using a 5 ml HiTrap™ desalting column (GE Healthcare). Protein concentrations were calculated using the DC protein assay kit (BIORAD) and enzyme purity was confirmed by SDS-PAGE. Purified proteins were stored at 4° C. and all reactions were performed within 1-2 weeks of initial purification, to prevent loss of enzyme activity through degradation or precipitation.

HPLC:

1. Identification of CB1954 nitroreduction products. Reactions of 100 μL containing 10 mM Tris-Cl pH 7.0, 200 μM CB1954, 1 mM NAD(P)H and initiated by addition of 0.5-2 μM purified enzyme were incubated for 10-30 min at room temperature before being stopped by addition of 1 volume ice-cold 100% methanol. Samples were immediately transferred to −80° C. for at least 1 h to precipitate proteins, followed by centrifugation at 12,000 g for 10 min at 4° C. The supernatant was then diluted 1:20 in 45 mM formate buffer pH 6.5 containing 2.5% methanol and 100 μL of each sample was analysed by reverse phase-HPLC employing an Agilent 1100 system with an Alltima™ C8 5μ 150×2.1 mm column. The mobile phase used 45 mM formate buffer (pH 6.5) as aqueous and 80% acetonitrile as organic. Assay conditions consisted of 4 min at 5% organic, a linear increase to 50% organic from 4-19 mins, and a further gradient increase to 70% organic for 2 min. Flow rate was constant at 0.3 mL min$^{-1}$. The eluate was monitored at 262 nm. Elution profiles from NTR-CB1954 reactions were compared against pure standards of each potential metabolite: CB1954, its 2- and 4-hydroxylamines (2-/4-NHOH), and 2- and 4-amines (2-/4-NH2).

2. Identification of PR-104A Nitroreduction Products

Reactions with PR-104A as substrate were set up and carried out identically to those outlined for CB1954, above. Following centrifugation, samples were diluted 1:20 in 45 mM formate buffer pH 4.5, 20% methanol. Column type used and volume of sample employed were the same as for CB1954. The mobile phase used 45 mM formate buffer (pH 4.5) as aqueous and 80% MeCN as organic. Assay conditions consisted of 4 min at 20% organic, a linear increase to 100% organic over the following 21 min, followed by an extra 1 min at 100% organic. Flow rate was constant at 0.3 mL Bacterial IC50 Measurements:

Ten ml of overnight culture of SOS-R2 over-expressing a target nitroreductase were used to inoculate fresh control or challenged cultures at a serially-diluted range of compound concentrations and a total of 2% DMSO in each culture. These were incubated at 30° C., 200 rpm for 4 h, and IC50 values were calculated by comparing the OD600 challenged cultures to those of the same unchallenged strain.

Directed Evolution:

1. Error prone PCR using Mutazyme polymerase (Stratagene) was used to create mutagenesis libraries at low and medium mutagenesis rates as per the manufacturer's instructions. Libraries were cloned into pUCX, electroporated into the GFP reporter strain SOS-R3 and stored at −80° C. Aliquots were thawed and used to inoculate overnight cultures (LB+100 μg ml$^{-1}$ Ampicillin, 50 μg ml$^{-1}$ Spectinomycin, 0.4% glucose) which were incubated at 30° C., 200 rpm. The GFP assay was commenced by inoculation of 195 μl fresh assay media (LB+100 μg ml$^{-1}$ Ampicillin, 50 μg ml$^{-1}$ Spectinomycin, 0.2% glucose, 50 μM IPTG) with 15 μl of overnight culture in individual wells of a 96-well plate. Plates were incubated at 30° C., 200 rpm for 3.5 h (pre-challenge period), following which cultures were diluted 1:2 by splitting 50:50 into fresh assay media (+DMSO to 0.5% final concentration) and fresh challenge media (assay media+drug to desired concentration, DMSO to 0.5% final concentration) to final volumes of 200 μl each in duplicate. Plates were then returned to the incubator for an additional 6-12 h (challenge period) and GFP expression was monitored at excitation 488 nm/emission 509 nm. When sufficient GFP induction was observed (1.5-3 fold increase in GFP expression compared to the DMSO control), cultures were collected by centrifugation (30 s, 14,000 rpm), washed 5 times with phosphate buffered saline (PBS) and sorted on a FACSVantage DiVa (Becton Dickinson). The most fluorescent 0.5% of cells were collected in 300 μl LB+0.4% glucose and incubated for 1 h at 30° C., 200 rpm before they were plated on LB agar amended with 100 μg ml$^{-1}$ Ampicillin, 50 μg ml$^{-1}$ Spectinomycin. Colonies were used to inoculate individual wells of a 96-well plate and subsequently tested as described above to confirm GFP expression.

2. Structural modelling was used to predict active site residues that interact with PR-104A based on the solved crystal structure for *E. coli* NfsA (Kobori et al, 2001, *J Biol Chem* 276 (4): 2816-2823). Mutagenesis libraries were created for each target residue using the QuikChange mutagenesis method (Stratagene) and targeted NNK degenerate primers. Libraries were cloned into pUCX, transformed into SOS-R2 and screened using the LacZ SOS assay as previously described.

Results

Figure 9:
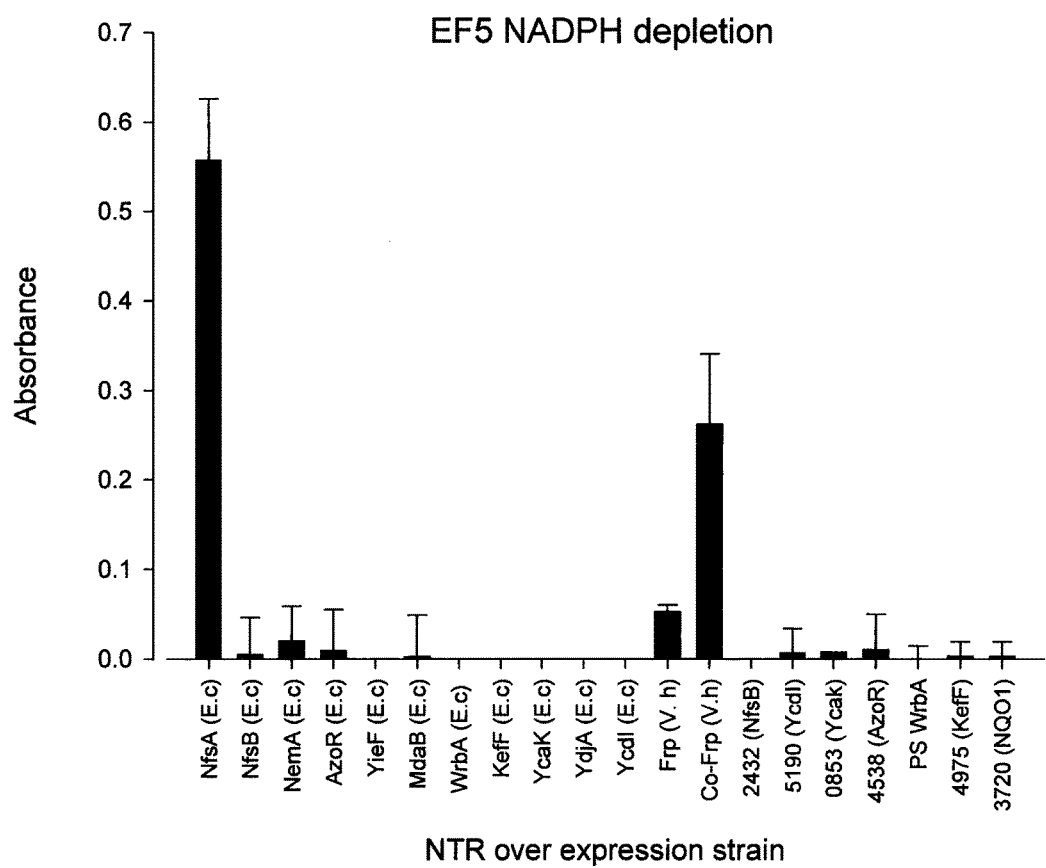
FIG. 9 illustrates reduction of EF5 by 11 E. coli and 9 non-E. coli NTRs, as measured by NBT assay. Crude cell lysates (10 μl) were incubated with 150 μM EF5 and 200 μM NADPH for 10 mins. Addition of NBT post-incubation yielded formazan dye in proportion to the amount of NADPH remaining in each well, which was quantified by measuring absorbance at $OD_{590}$. Plotted values indicate the extent of EF5 metabolism by each NTR over-expressing strain and were derived by subtracting the $OD_{590}$ of EF5-challenged lysates (chal) from the $OD_{590}$ of unchallenged duplicate controls (unchal). Data are the average of 2 independent assays and the error bars indicate ±1 standard error of the mean (SEM).

For pilot studies, eleven genes encoding putative NTRs were identified in *E. coli* as described (Prosser et al, 2010, *Biochem Pharmacol* 79, 678-687). Nine additional NTRs were also selected to provide a final panel of 20 candidates. The 20 NTRs were then introduced into an *E. coli* host reporter strain with multigene knockouts (nfsA and nfsB genes). NAD(P)H cofactor consumption was monitored using a nitro-blue tetrazolium assay. *E. coli* NfsA was shown to be catalytically superior to all other 19 NTRs (FIG. 9).

The 20 NTRs were next introduced into the human cell line HCT116 and stable NTR expressing cell populations were established by selection. Consistent with the *E. coli* EF5 NBT assay, only HCT116 cells expressing *E. coli* NfsA demonstrated substantial sensitivity to all five members of the panel of 2-Nls (FIG. 10). *E. coli* NfsA was markedly superior to the other 19 NTRs demonstrating a maximum growth inhibitory effect with EF5 (1600-fold WT:NTR ratio). *E. coli* NfsB and NfsB homologue *P. putida* 2432 cells displayed a modest sensitivity to only a single 2-nitroimidazole example, F-MISO.

Figure 11:
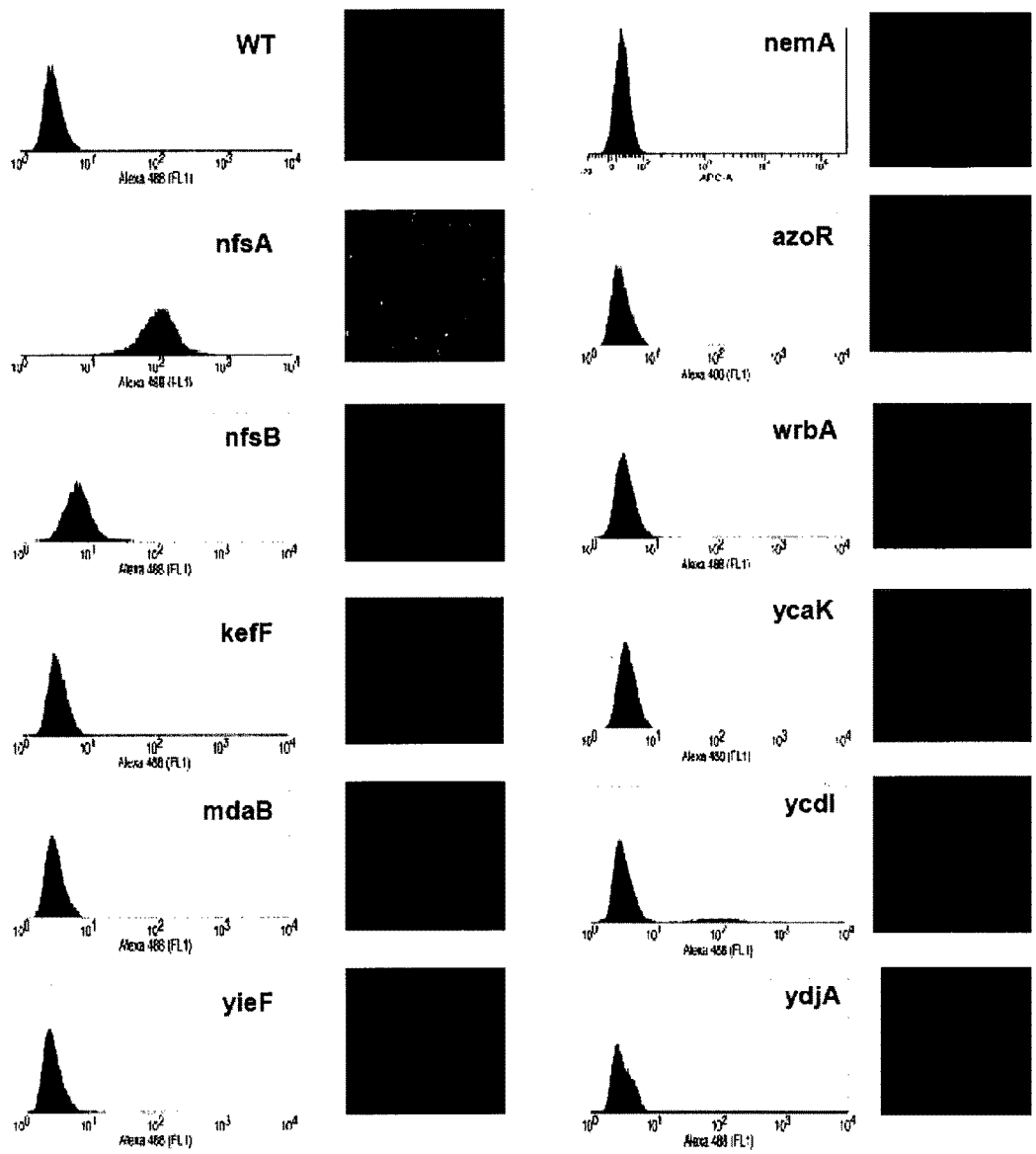
FIG. 11 illustrates the results of flow cytometry analysis and fluorescent imaging of stably-expressing E. coli NTR cells after in vitro EF5 exposure. $1\times10^6$ cells were seeded into a 6-well plate and incubated with 20 μM EF5 for 2 hrs at 37° C. Cells were fixed and stained, then analysed by flow cytometry and imaged using a Nikon2000 fluorescent microscope.

Next, functional metabolism and cellular retention of EF5 by 11 *E. coli* NTRs was evaluated directly by immunocytochemistry. The 11 stably expressing cell lines were incubated with 20 μM EF5 for 2 h under aerobic conditions. Activity of the eleven *E. coli* enzymes was measured by flow cytometry and fluorescent microscopy of the same samples (FIG. 11). NfsA alone provided the greatest retention of EF5 as judged by flow cytometry or fluorescent microscopy, an observation that was entirely consistent with the antiproliferative screen (FIG. 10). Of note, the fluorescent images of EF5 activation in the nfsA-expressing cells were overexposed (1 sec) to enable visualisation of the other inactive cell lines. As expected, NfsB was only able to confer minor EF5 retention compared to the parental cells.

To confirm the dominance of NfsA, enzyme kinetics of the 11 *E. coli* NTRs were performed using EF5 as the substrate (FIG. 12). Purified enzyme was incubated with varying concentrations of EF5 and 0.25 mM NADPH with enzyme kinetics calculated from spectrophotometric measurements of cofactor consumption at 340 nm. *E. coli* NfsA exhibited the highest $k_{cat}$ and $k_{cat}/K_m$ ratio. supporting observations from the antiproliferative, flow cytometry and immunocytochemical data.

Figure 13:
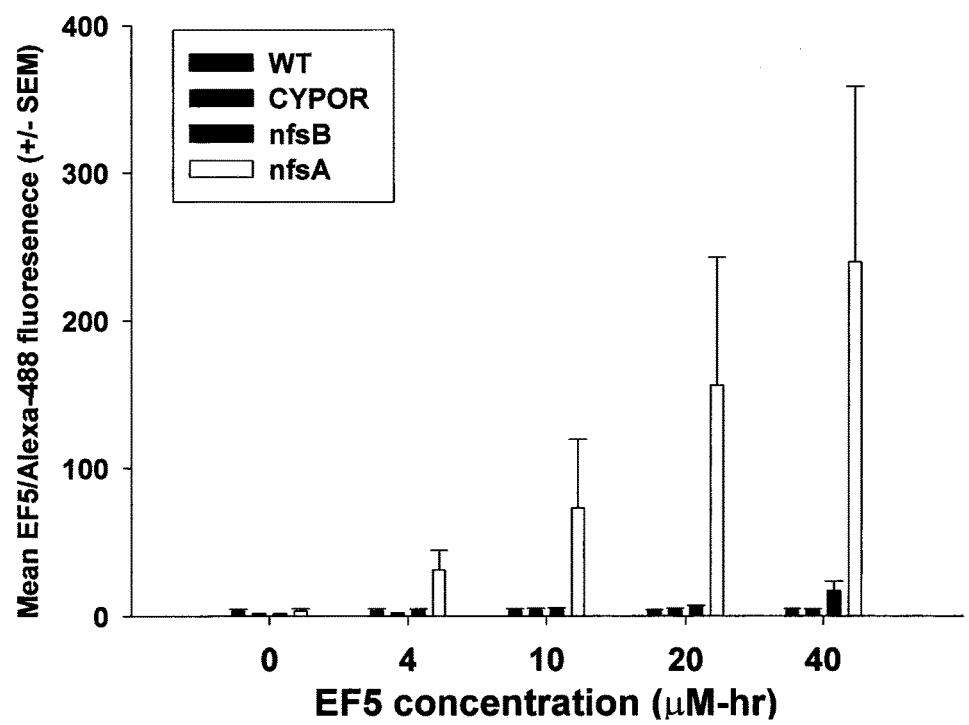
FIG. 13 illustrates the results of flow cytometry analysis of HCT-116 cells stably expressing E. coli NfsA and NfsB after in vitro dose-response to EF5 exposure. $1\times10^6$ cells were incubated with varying concentrations of EF5 in oxic conditions. Samples were fixed and stained with EF5 antibody Alexa 488 ELK3.51 at 100 μg/ml. Samples were then analysed on a Becton Dickinson FACscan flow cytometer. Values are mean±SEM of two independent experiments. Representative histograms at multiple EF5 dose levels.

Stably expressing NfsA cells were grown as a monolayer and incubated with increasing concentrations of EF5 under oxic conditions (FIG. 13). The results were compared against EF5 labelling achieved in HCT-116 parental cells and stable cell populations expressing *E. coli* NfsB or human cytochrome P450 reductase (CYPOR), an endogenous enzyme well described for its role in hypoxic metabolism of nitroaromatics, including 2-NIs (Patterson et al, 1997, *Br J Cancer* 76 (10): 1338-1347; Patterson et al, 2002, *Gene Ther* 9 (14): 946-954). NfsA cells were clearly superior with respect to retention of EF5 at all concentrations tested. NfsB and CYPOR showed minimal activity towards EF5.

Figure 14:
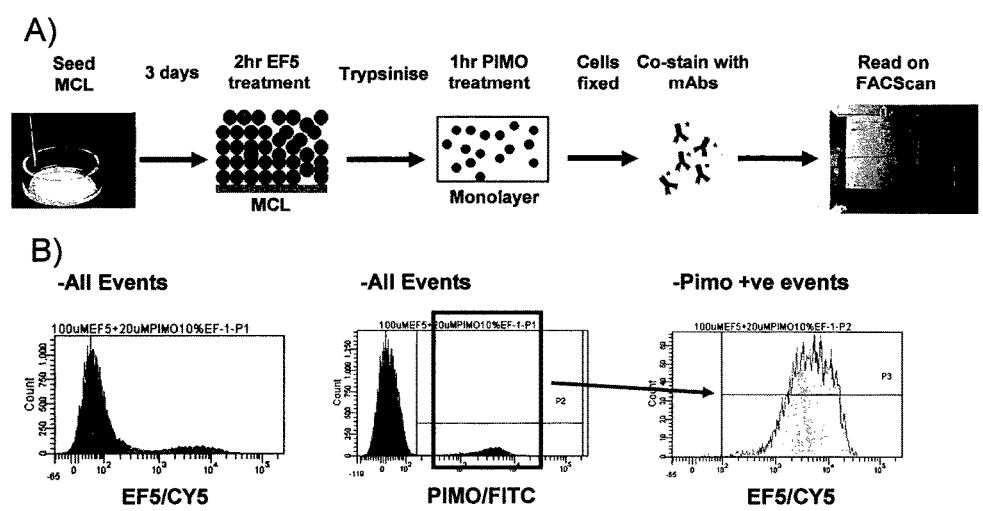
FIG. 14 (A) illustrates a schematic representation of multicellular layer preparation.

To establish whether a sub-population of NfsA positive cells could be clearly and exclusively labelled in a three dimensional (3D) tissue-like structure, parental and NfsA expressing HCT116 cells were co-cultured for 3 days as intimate mixtures in permeable, collagen coated inserts. These multicellular layers (MCLs) were exposed to EF5, disaggregated and NfsA expressing cells were identified by plating the cells post-treatment as a monolayer and incubating with 20 µM pimonidazole (PIMO) for 1 hr at 37° C. (FIG. 14). Retention of EF5 and PIMO was detected by Cy5 and FITC conjugated monoclonal antibodies, respectively. Employing this 3D approach, with subsequent 2D PIMO labelling to identify NfsA-expressing cells, it is demonstrated that it is possible to use EF5 to accurately and selectively label a discrete sub-population of NfsA cells (17%) growing within a dominant WT population (83%), thus demonstrating the precision of this novel biomarker method (FIG. 15).

Figure 16A:
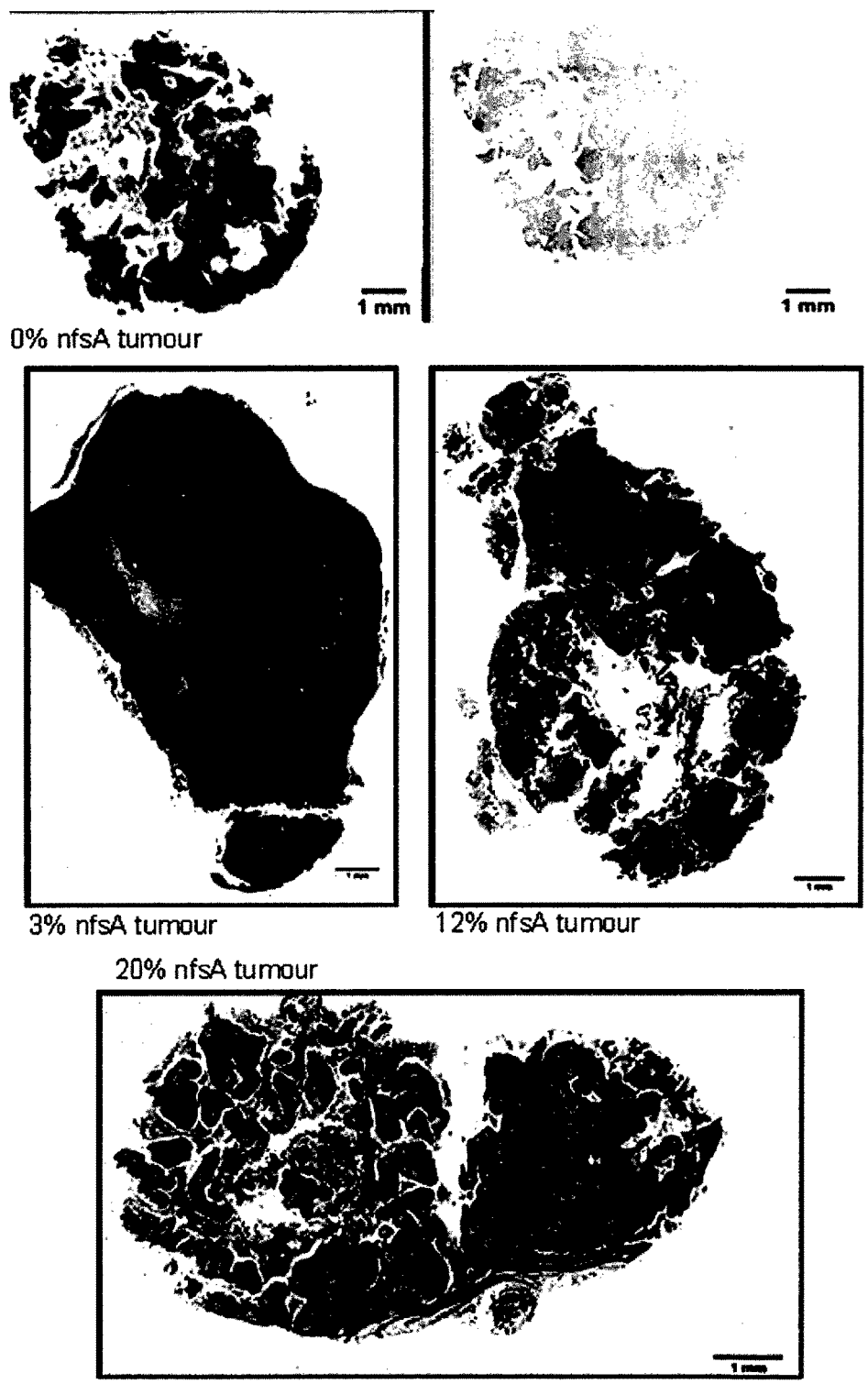
FIG. 16 (A) illustrates immunohistochemical detection of EF5 binding in human tumour xenografts harbouring 0%, 3%, 12% or 20% HCT-116$^{nfsA}$ expressing cells.
Figure 16B:
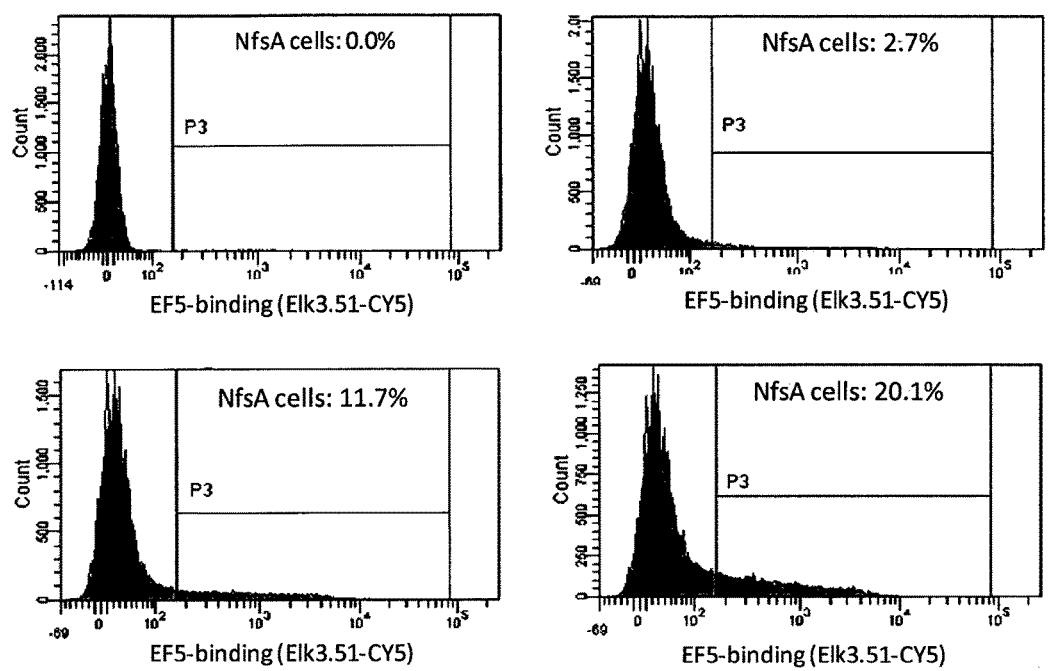

To illustrate the spatial distribution of EF5 activation various mixed HCT116 xenografts were analysed by immunohistochemistry using a Nikon 2000E inverted fluorescent microscope. The acquisition/exposure time remained constant for all tumour sections (0.5 s). The fluorescent and H&E images were taken on the same section and were overlaid using Adobe Photoshop software. The difference in EF5 retention between nfsA-expressing cells and hypoxic tumour cells was assessed (FIG. 16). EF5 retention in nfsA-expressing cells was clearly superior to EF5 retention from hypoxic activation in HCT-116 parental cells. The distribution of EF5 was relatively homogenous across the 10% nfsA tumour sections. Consistent with the flow cytometry of the MCLs, microscopic examination demonstrated EF5 labelling of a discrete subpopulation of tumour cells within the larger sections of the tumour.

Figure 17:
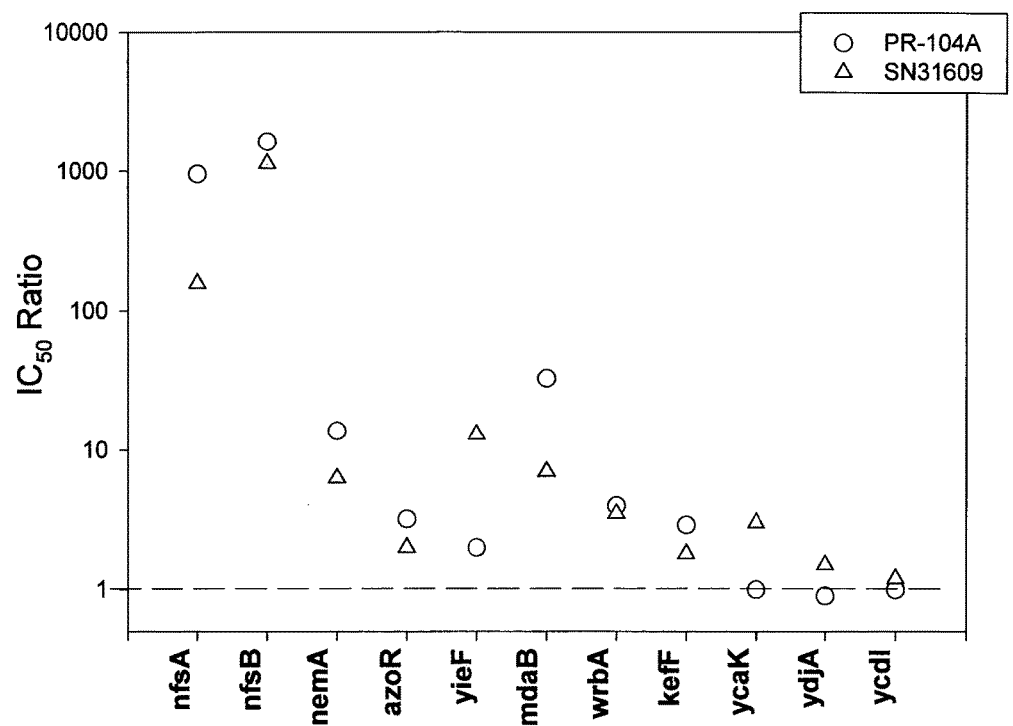
FIG. 17 illustrates antiproliferative $IC_{50}$ evaluation of PR-104A and SN31609 with 11 *E. coli* NTRs. Stably-expressing cells were treated with varying concentration of prodrug diluted in αMEM+5% FCS+P/S. Cells were exposed to prodrug for 18 hrs, washed and left to regrow for 5 days. $IC_{50}$ was determined as the concentration of prodrug required to inhibit cell growth by 50% of untreated controls. $IC_{50}$ values are mean for ≥2 independent experiments. WT:NTR ratio-inter-experimental ratio of $IC_{50}$ from WT cells versus NTR-expressing cell lines.

Since the dual imaging agent/prodrug activation capabilities of a preferred NTR are a key element to the preferred NTR for GDEPT applications, the set of 11 *E. coli* NTRs were evaluated using the DNBM candidates PR-104A and SN31609 in a low cell density proliferation assay. *E. coli* NfsB and NfsA produced significant activation of PR-104A and SN31609 indicating similar potential for prodrug conditional cytotoxicity (FIG. 17). To confirm this observation in vivo, nude mice were inoculated with 1×10⁷ cells containing either 25% NCT-116$^{nfsB}$/75% HCT-116$^{WT}$ or 25% HCT-116$^{nfsA}$/75% HCT-116$^{WT}$ cells. When tumours reached mean tumour diameter of 7 mm mice were administered (i.p.) a single dose of phosphate buffered saline (PBS) or the DNBM prodrug PR-104 (1000 µmol/kg). The growth of the xenografts was monitored and animals were culled when tumours reached endpoint (mean tumour diameter>15 mm).

The PR-104 dependent growth delay produced in tumours composed of 25% nfsB or nfsA-expressing cells were similar, with no statistically significant difference (FIG. 18). Thus NfsA is identified as a promising candidate for GDEPT with metabolism capabilities for both the prodrug PR-104 and the 2-NI probes, including EF5.

Figure 19:
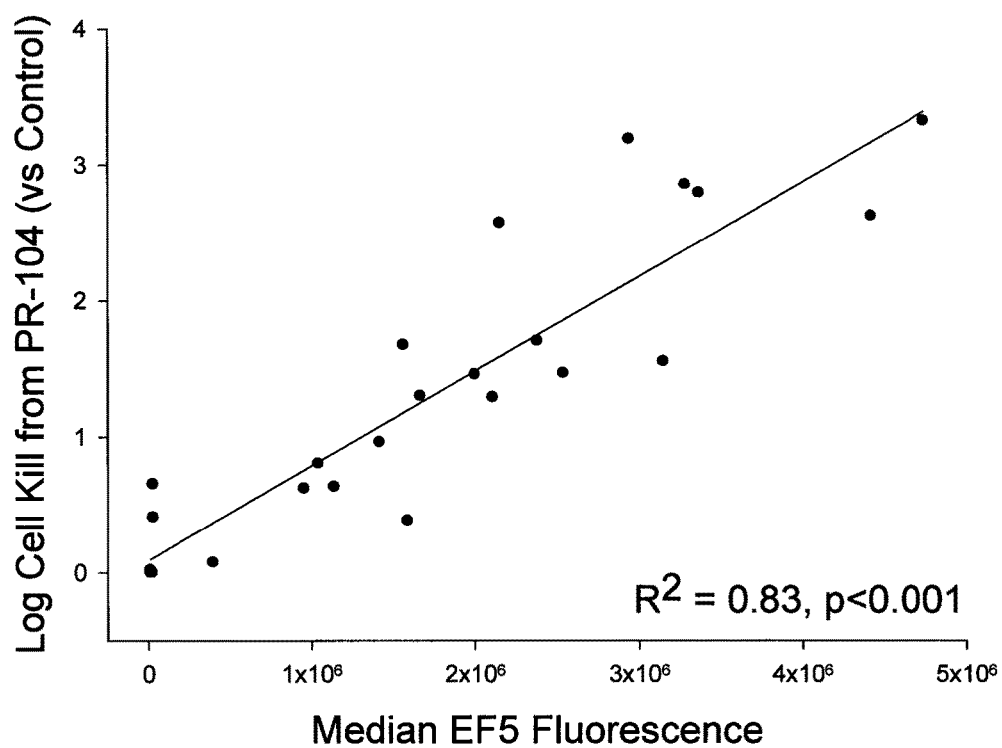
FIG. 19 illustrates the in vivo relationship between tumour EF5 binding and sensitivity to PR-104. The graph demonstrates that increasing EF5 retention that arises from increasing NfsA expression predicts total cell sensitivity of all tumour cells to PR-104 (i.e. death of NfsA positive plus NfsA negative bystander cells). Mixed HCT116 human tumour xenografts were established in NIHIII nude mice by subcutaneous injection of mixtures of WT:NfsA cells using fixed ratios of 0%, 1%, 3%, 5%, 10%, 15% or 25% *E. coli* NfsA expressing cells. Mice bearing these established mixed tumours were treated with PR-104 (325 mg/kg; ip). Three hours later EF5 (30 mg/kg, ip) was administered to label NfsA-positive cells and after a further two hours tumour tissue was excised and subjected to enzymatic disaggregation to form a single cell suspension. Cell survival was measured by clonogenic endpoint and EF5 retention by immunohistochemistry with flow cytometric quantification.

A preferred aspect of non-invasive imaging of therapeutic NTR genes is an ability to prospectively predict response to subsequent cytotoxic prodrug treatment. To test the relationship between tumour EF5 binding and sensitivity to PR-104 mixed HCT116 human tumour xenografts were established in NIHIII nude mice by subcutaneous injection of mixtures of WT:NfsA cells using fixed ratios of 0%, 1%, 3%, 5%, 10%, 15% or 25% *E. coli* NfsA expressing cells (FIG. 19). Mice bearing these established mixed tumours were treated with PR-104 (325 mg/kg; ip) and labelled with the PET imaging agent EF5 (30 mg/kg, ip). Single cell suspensions were prepared from excised tumours and surviving fraction was measured on day 10 by colony count. In parallel, total bound EF5 was measured by immunocytochemical detection with flow cytometric detection. Across a series of tumours harbouring a range of WT:NfsA cell mixtures, total EF5 binding was found to correlate with global tumour cell sensitivity to PR-104 ($r^2$=0.83; p<0.001). The results in FIG. 19 indicate tumour retention of EF5 following NfsA metabolism is predictive of overall tumour cell survival following PR-104 treatment.

To confirm whether EF5 retention was able to accurately measure the proportion of NfsA expressing cells in each mixed tumour the relationship between total tumour EF5 binding and subsequent ex-vivo PIMO labelling of NfsA-positive cells was determined (FIG. 20). Human tumour xenografts harbouring mixtures of WT:NfsA cells at fixed ratios (0%, 1%, 3%, 5%, 10%, 15% or 25% *E. coli* NfsA expressing cells) were treated with EF5 (30 mg/kg, ip) and a single cell suspension was subsequently prepared and incubated with 100 µM PIMO in monolayer for one hour at 37° C. The PIMO and EF5 antibodies are conjugated to different fluorophores (PIMO to FITC (Em. 518 nm) and EF5 to CY5 (Em. 670-700 nm) allowing concurrent evaluation of single cells for both PIMO and EF5 adduct retention by flow cytometry. The results in FIG. 20 show that EF5 is able to detect NfsA positive cells in tumours in a manner that is not impeded my the diffusion-limited microenvironment of the tumour, since subsequent PIMO exposure as a single cell monolayer correlated well ($r^2$=0.83; p<0.001). Thus EF5 can detect NfsA expression in a three dimensional tumour mass in a manner that is linear with total NfsA positive cell count.

To assess the spectrum of prodrug activation, the broader HCT116 20 NTR library was evaluated against 7 additional prodrugs. The sensitivity of HCT116 cells expressing each of the bacterial NTRs was determined using an in vitro proliferation assay. *E. coli* NfsA and NfsB were highly active for many of the 7 prodrugs (>10-fold sensitivity to TH-302, metronidazole, SN 29428, SN 30548), with *E. coli* AzoR, *V. fischeri* Frp, *P. putida* 2432, and *P. putida* 5190 showing some selective prodrug activation (FIG. 21).

Figure 22:
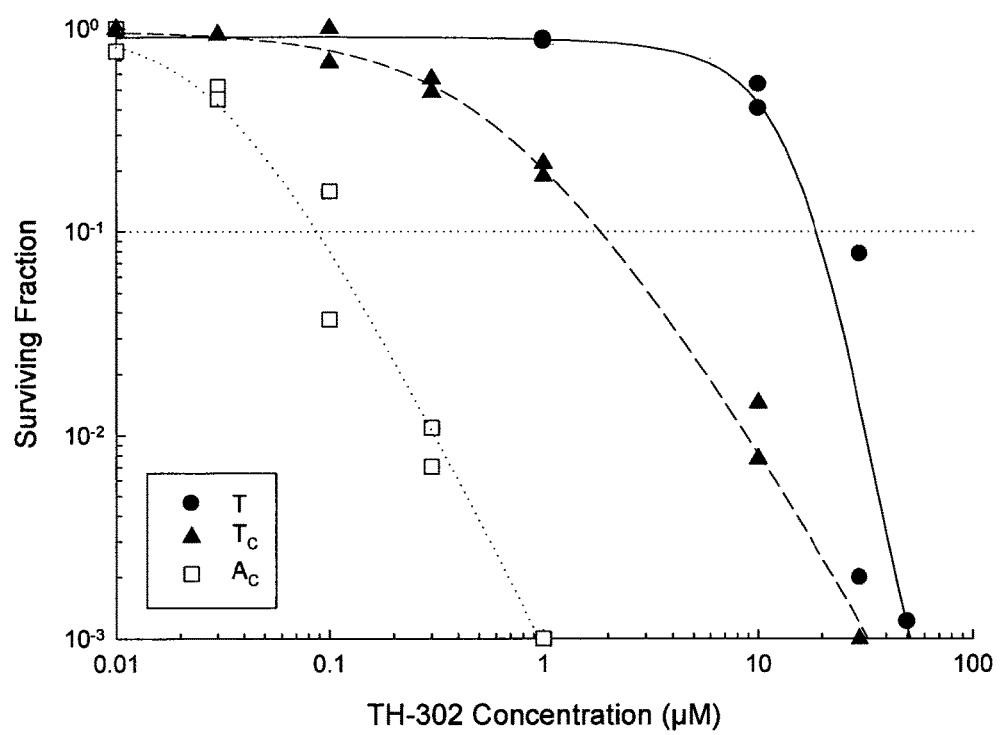
FIG. 22 illustrates NfsA-dependent activation of TH-302 in an MCL bystander experiment. It includes a representative bystander efficiency graph. TH-302 dose-response curves for hyperoxic (95% $O_2$) multicellular layers (MCLs) of HCT116-WT (parental) 'target' cells in the absence (T) and presence (Tc) of nitroreductase NfsA-expressing HCT116 'activator' cells (A). MCLs are composed of 'targets only' (T) or as intimate mixtures of 29% (±4%) NfsA activators (A) and 71% targets (Tc). Displacement of the Target cell survival curve to the left (T to Tc) is indicative of the presence of a cytotoxic metabolite(s) able to diffusible out of the sensitive activator (A) cell population. The prodrug concentrations for 10% survival ($C_{10}$) of target cells (wild-type cells) grown without activators (T), targets in co-culture ($T_C$) and activators (nfsA-expressing cells) in co-culture ($A_C$) were determined by interpolation. BEE-Bystander effect efficiency calculates the drugs bystander effect: $((\text{Log } C_{10}T - \text{Log } C_{10}T_C)/(\text{Log } C_{10}T - \text{Log } C_{10}A_C))$. The calculated bystander effect efficiency is 43.4%.

To assess the produg TH-302, a 25% nfsB-expressing ($A_C$) HCT116 population was grown in the 3D MCL with 75% parental cell (HCT116 WT) as described by Wilson et al. (2002, *Cancer Res*. 62:1425-1432) (FIG. 22). Greater than 90% sterilisation of the nfsA-expressing cells in the MCL model was achieved following incubation with just 90 nM TH-302. The NfsA negative cells were 210-fold less sensitive to TH-302, with a $C_{10}$ of 18.9 uM. NfsA negative cells in co-culture were sensitised to TH-302 with a $C_{10}$ of 1.86 uM. A bystander effect was observed (BEE value=43%).

In an otherwise identical experiment using metronidazole in the place of TH-302, metronidazole was demonstrated to elicit a zero bystander property, indicating the activated metabolite(s) do not diffuse out of the cell of origin. This is a desirable feature for controlled single cell ablation (FIG. 23).

Figure 24:
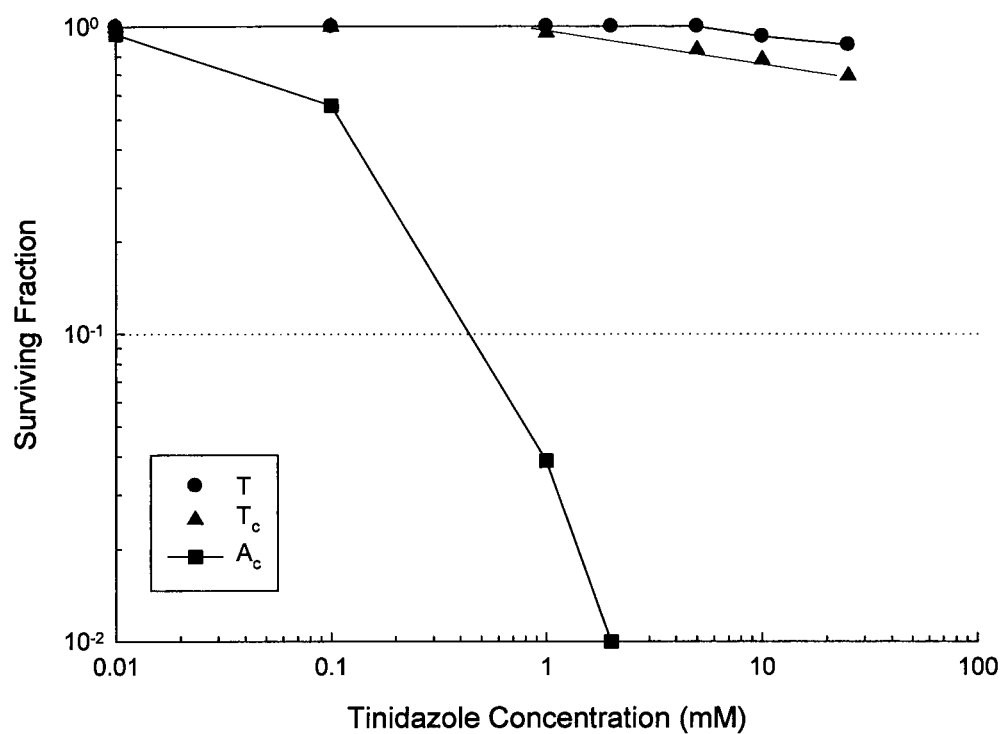
FIG. 24 illustrates NfsA-dependent activation of tinidazole in an MCL bystander experiment. It includes a representative bystander efficiency graph which illustrates that tinidazole is unable to produce any bystander effect. Tinidazole dose-response curves for hyperoxic (95% $O_2$) multicellular layers (MCLs) of HCT116-WT (parental) 'target' cells in the absence (T) and presence (Tc) of nitroreductase NfsA-expressing HCT116 'activator' cells (A). MCLs are composed of 'targets only' (T) or as intimate mixtures of 16% activators (A) and 84% targets (Tc). Displacement of the Target cell survival curve to the left (T to Tc) is indicative of the presence of a cytotoxic metabolite(s) able to diffusible out of the sensitive activator (A) cell population. The prodrug concentrations for 10% survival ($C_{10}$) of target cells (wild-type cells) grown without activators (T), targets in co-culture ($T_C$) and activators (nfsA-expressing cells) in co-culture ($A_C$) were determined by interpolation. BEE—Bystander effect efficiency calculates the drugs bystander effect: $((\text{Log } C_{10}T - \text{Log } C_{10}T_C)/(\text{Log } C_{10}T - \text{Log } C_{10}A_C))$. The estimated bystander effect efficiency is 0% at concentrations achievable in α-MEM+10% fetal bovine serum (FBS).

In an otherwise identical experiment, tinidazole was demonstrated to elicit a zero bystander property, indicating the activated metabolite(s) do not diffuse out of the cell of origin. This is a desirable feature for controlled single cell ablation (FIG. 24).

Figure 25:
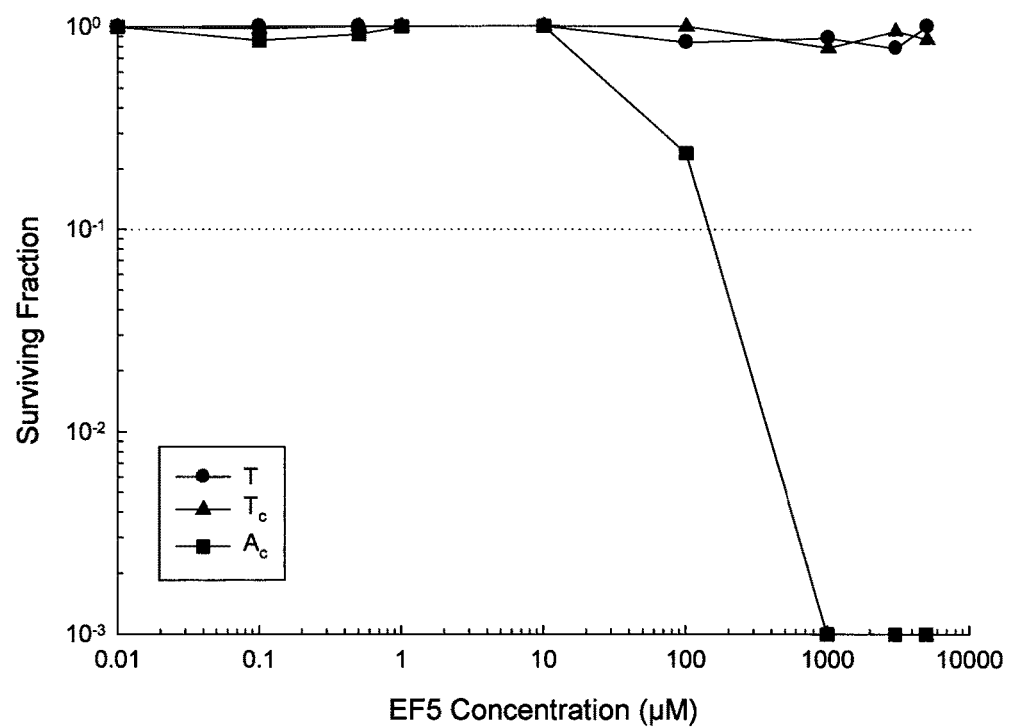
FIG. 25 illustrates NfsA-dependent activation of EF5 (pentafluoro-etanidazole) in an MCL bystander experiment. It includes a representative bystander efficiency graph which illustrates that EF5 is unable to produce any bystander effect. EF5 dose-response curves for hyperoxic (95% $O_2$) multicellular layers (MCLs) of HCT116-WT (parental) 'target' cells in the absence (T) and presence (Tc) of nitroreductase NfsA-expressing HCT116 'activator' cells (A). MCLs are composed of 'targets only' (T) or as intimate mixtures of 18% activators (A) and 82% targets (Tc). Displacement of the Target cell survival curve to the left (T to Tc) is indicative of the presence of a cytotoxic metabolite(s) able to diffusible out of the sensitive activator (A) cell population. The prodrug concentrations for 10% survival ($C_{10}$) of target cells (wild-type cells) grown without activators (T), targets in co-culture ($T_C$) and activators (nfsA-expressing cells) in co-culture ($A_C$) were determined by interpolation. BEE—Bystander effect efficiency calculates the drugs bystander effect: ((Log $C_{10}$T–Log $C_{10}T_C$)/(Log $C_{10}$T–Log $C_{10}A_C$)). The estimated bystander effect efficiency is 0% at concentrations achievable in α-MEM+10% fetal bovine serum (FBS).

In an otherwise identical experiment, EF5 was demonstrated to elicit a zero bystander property, indicating the activated metabolite(s) do not diffuse out of the cell of origin. This is a desirable feature for controlled single cell ablation (FIG. 25).

Figure 26:
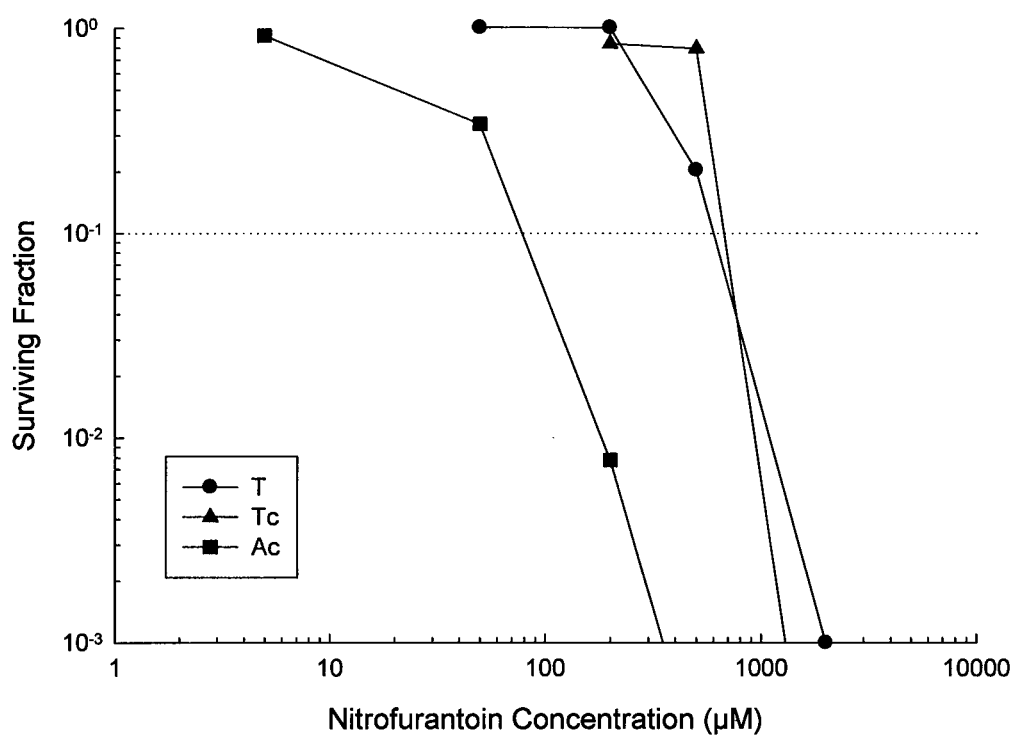
FIG. 26 illustrates NfsA-dependent activation of nitrofurantoin in an MCL bystander experiment. It includes a representative bystander efficiency graph which illustrates that nitrofurantoin is unable to produce any bystander effect. Nitrofurantoin dose-response curves for hyperoxic (95% $O_2$) multicellular layers (MCLs) of HCT116-WT (parental) 'target' cells in the absence (T) and presence (Tc) of nitroreductase NfsA-expressing HCT116 'activator' cells (A). MCLs are composed of 'targets only' (T) or as intimate mixtures of 11% activators (A) and 89% targets (Tc). Displacement of the Target cell survival curve to the left (T to Tc) is indicative of the presence of a cytotoxic metabolite(s) able to diffusible out of the sensitive activator (A) cell population. The prodrug concentrations for 10% survival ($C_{10}$) of target cells (wild-type cells) grown without activators (T), targets in co-culture ($T_C$) and activators (nfsA-expressing cells) in co-culture ($A_C$) were determined by interpolation. BEE-Bystander effect efficiency calculates the drugs bystander effect: ((Log $C_{10}$T–Log $C_{10}T_C$)/(Log $C_{10}$T–Log $C_{10}A_C$)). The calculated bystander effect efficiency is 0%.

In an otherwise identical experiment, nitrofurantoin was demonstrated to elicit a zero bystander property, indicating the activated metabolite(s) do not diffuse out of the cell of origin. This is a desirable feature for controlled single cell ablation (FIG. 26).

Figure 27:
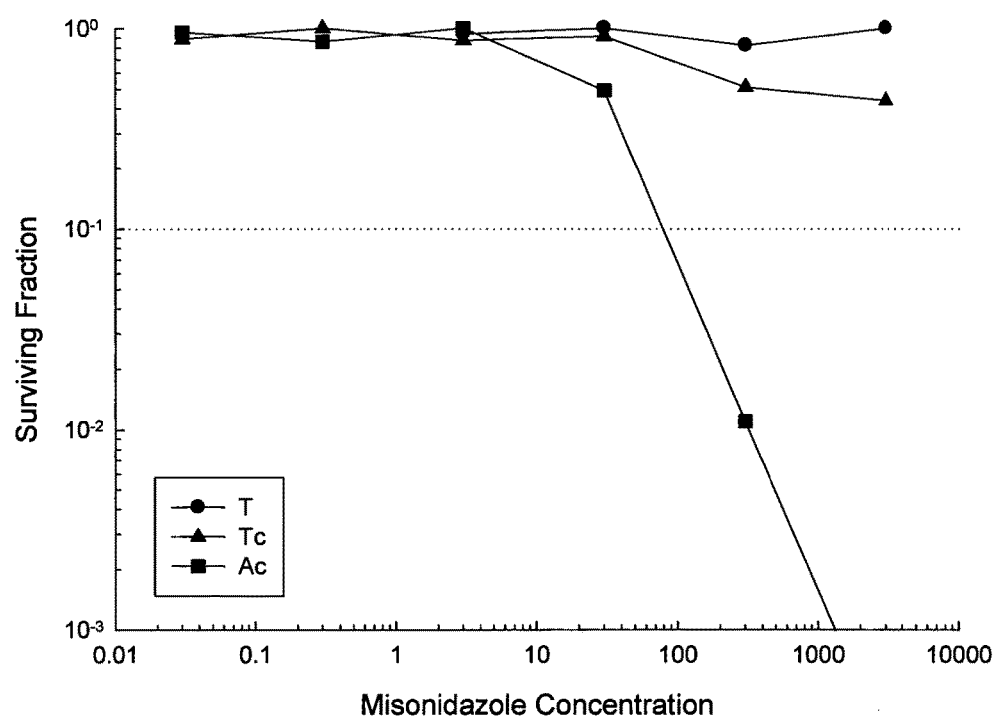
FIG. 27 illustrates NfsA-dependent activation of misonidazole in an MCL bystander experiment. It includes a representative bystander efficiency graph which illustrates that misonidazole is unable to produce any bystander effect. Misonidazole dose-response curves for hyperoxic (95% $O_2$) multicellular layers (MCLs) of HCT116-WT (parental) 'target' cells in the absence (T) and presence (Tc) of nitroreductase NfsA-expressing HCT116 'activator' cells (A). MCLs are composed of 'targets only' (T) or as intimate mixtures of 21% activators (A) and 79% targets (Tc). Displacement of the Target cell survival curve to the left (T to Tc) is indicative of the presence of a cytotoxic metabolite(s) able to diffusible out of the sensitive activator (A) cell population. The prodrug concentrations for 10% survival ($C_{10}$) of target cells (wild-type cells) grown without activators (T), targets in co-culture ($T_C$) and activators (nfsA-expressing cells) in co-culture ($A_C$) were determined by interpolation. BEE-Bystander effect efficiency calculates the drugs bystander effect: ((Log $C_{10}$T–Log $C_{10}T_C$)/(Log $C_{10}$T–Log $C_{10}A_C$)). The estimated bystander effect efficiency is 0% at concentrations achievable in α-MEM+10% fetal bovine serum (FBS).

In an otherwise identical experiment, misonidazole was demonstrated to elicit a zero bystander property, indicating the activated metabolite(s) do not diffuse out of the cell of origin. This is a desirable feature for controlled single cell ablation (FIG. 27).

Figure 28:
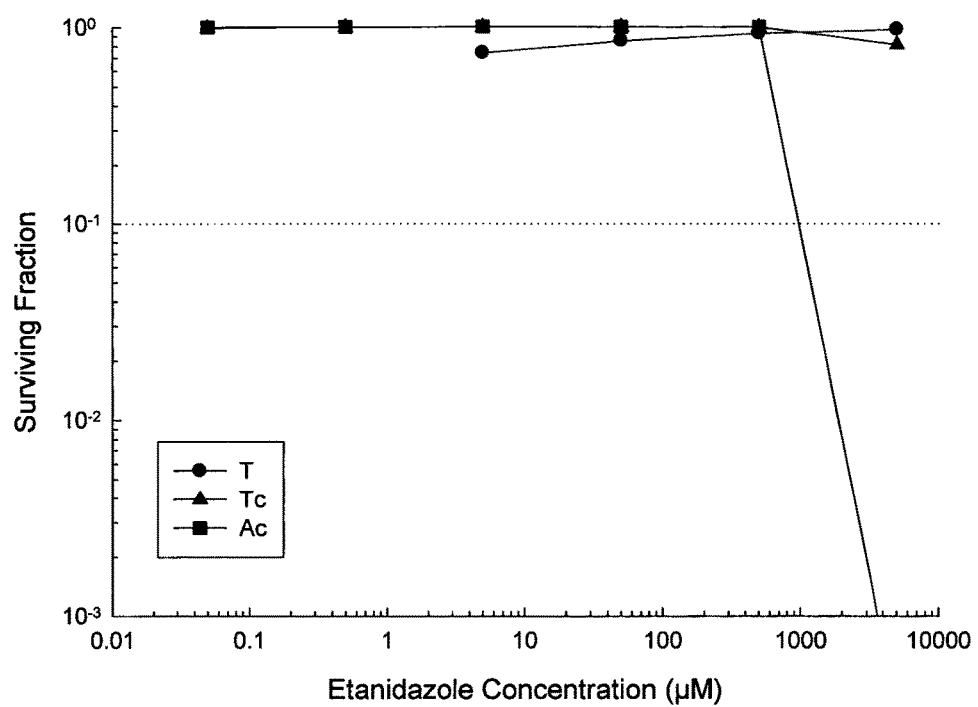
FIG. 28 illustrates NfsA-dependent activation of etanidazole in an MCL bystander experiment. It includes a representative bystander efficiency graph which illustrates that etanidazole is unable to produce any bystander effect. Etanidazole dose-response curves for hyperoxic (95% $O_2$) multicellular layers (MCLs) of HCT116-WT (parental) 'target' cells in the absence (T) and presence (Tc) of nitroreductase NfsA-expressing HCT116 'activator' cells (A). MCLs are composed of 'targets only' (T) or as intimate mixtures of 11% activators (A) and 89% targets (Tc). Displacement of the Target cell survival curve to the left (T to Tc) is indicative of the presence of a cytotoxic metabolite(s) able to diffusible out of the sensitive activator (A) cell population. The prodrug concentrations for 10% survival ($C_{10}$) of target cells (wild-type cells) grown without activators (T), targets in co-culture ($T_C$) and activators (nfsA-expressing cells) in co-culture ($A_C$) were determined by interpolation. BEE-Bystander effect efficiency calculates the drugs bystander effect: ((Log $C_{10}$T–Log $C_{10}T_C$)/(Log $C_{10}$T–Log $C_{10}A_C$)). The estimated bystander effect efficiency is 0% at concentrations achievable in α-MEM+10% fetal bovine serum (FBS).

In an otherwise identical experiment, etanidazole was demonstrated to elicit a zero bystander property, indicating the activated metabolite(s) do not diffuse out of the cell of origin. This is a desirable feature for controlled single cell ablation (FIG. 28).

Figure 29:
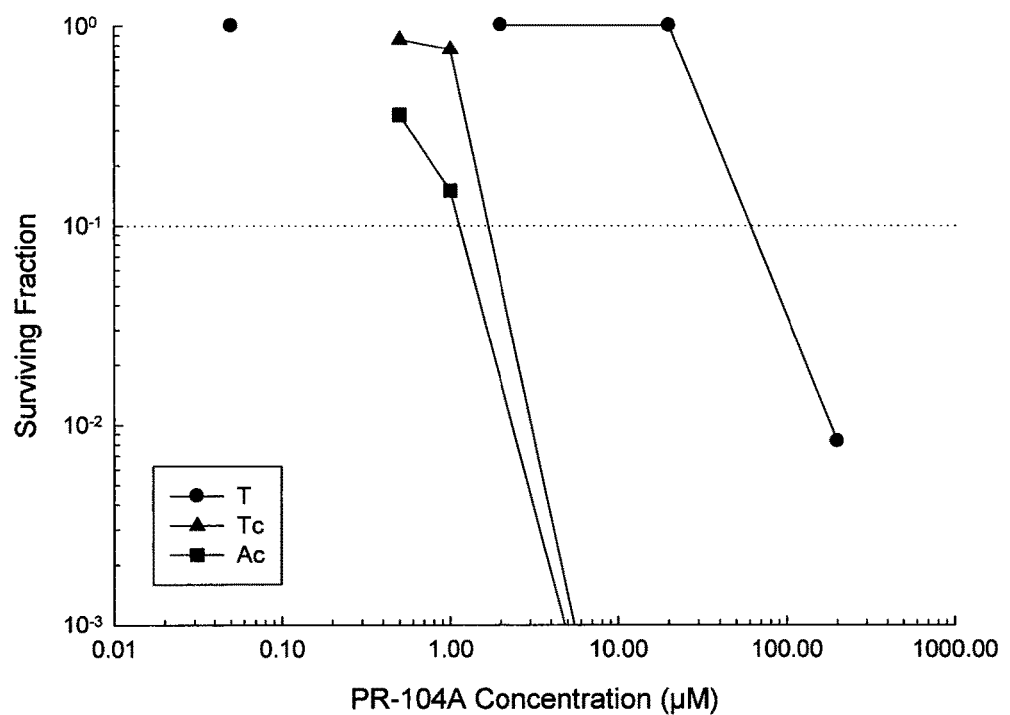
FIG. 29 illustrates NfsA-dependent activation of PR-104A in an MCL bystander experiment. It includes a representative bystander efficiency graph which illustrates that PR-104A possesses a robust bystander effect. PR-104A dose-response curves for hyperoxic (95% $O_2$) multicellular layers (MCLs) of HCT116-Wt (parental) 'target' cells in the absence (T) and presence (Tc) of nitroreductase NfsA-expressing HCT116 'activator' cells (A). MCLs are composed of 'targets only' (T) or as intimate mixtures of 21% activators (A) and 79% targets (Tc). Displacement of the Target cell survival curve to the left (T to Tc) is indicative of the presence of a cytotoxic metabolite(s) able to diffusible out of the sensitive activator (A) cell population. The prodrug concentrations for 10% survival ($C_{10}$) of target cells (wild-type cells) grown without activators (T), targets in co-culture ($T_C$) and activators (nfsA-expressing cells) in co-culture ($A_C$) were determined by interpolation. BEE—Bystander effect efficiency calculates the drugs bystander effect: ((Log $C_{10}$T–Log $C_{10}T_C$)/(Log $C_{10}$T–Log $C_{10}A_C$)). The estimated bystander effect efficiency is 89% at concentrations achievable in α-MEM+10% fetal bovine serum (FBS).

In an otherwise identical experiment, PR-104A was demonstrated to elicit a marked bystander property, indicating the activated metabolite(s) readily diffuse out of the cell of origin (FIG. 29).

A summary of data from FIG. 23 to FIG. 29 is provided with appropriate comparison with achievable human plasma concentrations (FIG. 30).

One concern is that viral virulence may not be contained within the target tumour. Using a cytopathic effect assay it is seen that replicating adenovirus engineered to express *E. coli* NfsB is highly sensitive to metronidazole. Consequently infected cells can be protected from the oncolytic effects of the virus in vitro (FIG. 31). A reduction in oncolytic activity was clearly evident in the 50-500 μM range of metronidazole exposure in the ONYX-411$^{NfsB}$ infected cells. This was in contrast to the results seen with the ONYX-411$^{WT}$ infected cells, in which no inhibitory effects were observed. This indicates that NfsB-dependent activation of metronidazole was responsible for the increase in cell density rather than the metronidazole itself. Importantly the 50 μM exposure in which the protective effect were demonstrated is equivalent to a human AUC of 1.2 mM-hr which is achievable in humans (Dilger et al, *J Clin Pharmacol* 47 (12): 1532-1539). Thus metronidazole can serve as an effective antiviral agent in this context.

Having established that the expression of candidate NTRs in *E. coli* assays were predictive of human cell line activities we next examined the broader pattern of co-metabolism of examples of 2-NI bio-imaging agents, bio-therapy prodrugs, and bio-control agents using a broader library of NTRs (FIG. 8). Here 58 NTRs were cloned and over-expressed in *E. coli* and their expression validated as demonstrated in FIG. 32. This NTR library was subject to evaluation in the NBT, growth inhibition, and/or SOS chromotest assays with respect to the 2-NI bio-imaging agents EF5 (FIG. 33), F-MISO (FIG. 34), and HX4 (FIG. 35); the bio-therapy prodrugs PR-104A (FIG. 36), CB1954 (FIG. 37), RB6145 (FIG. 38), SN27686 (FIG. 39), SN28065 (FIG. 40), SN28099 (FIG. 41), and TH-302 (FIG. 42); and the bio-control agents metronidazole (FIG. 43), tinidazole (FIG. 44), furazalidone (FIG. 45), nitrofurantoin (FIG. 46), nitrofurazone (FIG. 47), nifurtimox (FIG. 48), misonidazole (FIG. 49), SN27857 (FIG. 50) and ornidazole (FIG. 60). It was observed that members of the NfsA family are the most consistently active with compounds from each of these functional classes and hence are the most desirable candidates for multi-substrate utility. Nonetheless, NfsB family members are also consistently active with both bio-therapy prodrugs and bio-control agents. Furthermore, although *E. coli* NfsB was previously judged to be inactive with 2-NI substrates (Anlezark et al, 1995, Biochem Pharmacol 50 (5): 609-618; Bailey et al., 1996, Gene Ther 3 (12): 1143-1150), we have conclusively demonstrated that this enzyme is surprisingly able to exhibit substantial activity with both HX4 and F-MISO at elevated substrate concentrations (FIGS. 34B, 35B). We have also shown that other previously untested NfsB orthologues are even more efficient in this regard than NfsB(Ec), and exhibit substantial activity with all three 2-NI PET imaging agents tested in this study, in particular F-MISO (FIGS. 33B, 34B, 35B). This observation is novel and unexpected, and indicates that NfsB family members may also prove effective enzymes for multi-substrate utility, particularly if engineered to further enhance their activity with 2-NI bio-imaging agents. Mechanisms by which this could be achieved are demonstrated below.

Activity of selected NfsA and NfsB family members with EF5 (FIG. 52), F-MISO (FIG. 53), PR-104A (FIG. 54) and CB1954 (FIG. 55) was confirmed by purified protein kinetic assays.

To demonstrate the ability to improve metabolism of preferred substrates by directed evolution NfsA(Ec) was selected as a target NTR, with a primary goal of enhancing PR-104A metabolism by this enzyme. To achieve this, an additional *E. coli* SOS reporter strain (SOS-R3) was developed, similar to SOS-R2 in that it lacks endogenous copies of the to/C, nfsA, nfsB, nemA and azoR genes, but with an inducible green fluorescent protein (gfp) gene rather than lacZ under control of the sfiA promoter. To maximise reporter gene output the sfiA-gfp gene construct was cloned into the pANODuet plasmid rather than being chromosomally integrated (as with SOS-R2). This enabled a large randomly-mutated library of NfsA variants to be created by error-prone PCR (epPCR), cloned into pUCX, and screened in high-throughput to recover the most fluorescent 0.5% of cells using fluorescence-activated cell sorting (FACS). This fully random approach was augmented by semi-random targeted mutagenesis of active site residues predicted by structural modelling to interact with PR-104A, based on the solved crystal structure for *E. coli* NfsA (Kobori et al, 2001, *J Biol Chem* 276 (4): 2816-2823). A total of ten different single-residue mutations (I5T, S41Y, E99G, L103M, K222E, R225A, R225G, R225P, F227S and L229V) were recovered that yielded a heightened SOS sensitivity to 20 μM PR-104A challenge relative to wild type NfsA(Ec) in the SOS-R2 reporter strain (FIG. 56).

A synthetic gene library (GenScript, Piscataway, N.J.) comprising all possible combinations of the ten NfsA single-residue mutations (FIG. 56) was cloned into pUCX and screened in SOS-R2 to recover combinatorial variants containing multiple mutations with additive or synergistic effect on PR-104A metabolism. A total of 2,100 colonies were screened (allowing for a cloning efficiency of 85%, this was anticipated to provide 95% coverage of all the ($2^9$) possible mutational combinations in the library). At this stage the concentration of PR-104A used in the screening assays was reduced to 10 µM, to preferentially select for variants with decreased Km (likely to be most active at clinically relevant prodrug concentrations).

Thirty three variants that induced substantially heightened SOS responses to 10 µM PR-104A challenge were recovered. These 33 enzyme variants are hereafter referred to as the preferred "polymutant NfsAs" or "polymutants", and are each referred to by a two-digit "polymutant code". The 33 polymutants were re-screened and compared to wild type and the two most active single-residue mutants (S41Y and R225G) at 2.5 µM PR-104A, at which concentration the activity of wild type NfsA cannot be differentiated from the empty plasmid control (FIG. 58).

Promising variants were then subjected to a detailed $IC_{50}$ analysis to measure the impact of PR-104A-centred evolution on their activity with a range of compounds of particular interest: PR-104A, CB1954, EF5, F-MISO, HX4, Metronidazole and Tinidazole. Based on these results 10 preferred polymutant genes were sequenced to identify the combinations of mutations that they contained. The ten preferred NfsA variants had the polymutant codes 14, 17, 22, 28, 33, 40, 41, 42, 43, and 44 (it subsequently it transpired that the original 22 and 44 were in fact mixed gene populations; the more active variants derived from each were re-named 22C1 and 441, respectively, while the less active clones retained the previous polymutant codes 22 and 44). The combinations of single-residue mutations present in each of the preferred ten polymutants is illustrated in FIG. 59, alongside a "heatmap" of their $IC_{50}$ sensitivities with the compounds tested relative to S41Y and wild type NfsA. The single-residue mutation L229V was not represented in any of the preferred polymutants, despite being present in randomly selected "quality control" sequencing of the library and being one of the more active single-residue mutations. This suggests that the mutation L229V does not synergise with the other single-residue mutations in the synthetic gene library.

The inventors note that evolution for improved PR-104A metabolism generally (but not exclusively) had a beneficial effect on metabolism of other nitroaromatic compounds as measured by $IC_{50}$ assay in ntr-overexpressing *E. coli* cells. Thus, directed evolution of NfsB family members might reasonably be expected to yield variants exhibiting substantially improved metabolism for bio-imaging compounds as well as prodrugs, particularly if a 2-NI masked cytotoxin like the prodrug RB6145 is used as a primary compound for screening and selection of enhanced variants.

A series of poly-mutant NfsA(Ec) genes (polymutant codes 17, 22P, 22GP, 28, 40, 42, and 43) were cloned into a mammalian expression plasmid and expressed in stable polyclonal HCT116 cell line populations. Anti-proliferative activity assays were performed employing a range of potential substrates of interest, as listed in FIG. 60. The concentrations required to inhibit cell growth by 50% (IC50 value) were calculated from the resulting dose-response curves. The IC50 values provide evidence of marked sensitivity relative to HCT116 wildtype cells and improved activity relative cells expressing NfsA wildtype sequence. In some examples (polymutant codes 17, 28, 42) expression was not sufficiently stable in HCT116 cells to permit accurate estimates of sensitivity.

In subsequent directed evolution studies using NfsA(Vv), NfsA(St) and NfrA(Bs) as templates for epPCR-based evolution, additional single residue mutations that confer enhanced metabolism of PR-104A were identified. Specific mutations identified in NfsA(Vv) are A33T, L42C, L42M, L42R, E178A, L220D, L220G, S224V, and S224D. Specific mutations identified in NfsA(St) are I49F, S130G, R133S, G204A, and R225C. Specific mutations identified in NfrA (Bs) are R234P, R234T and R234L. In ClustalW alignments with NfsA(Ec) the numbers of each of the mutated residues for NfsA(Vv) and NfsA(St) are identical to the numbering for NfsA(Ec). For NfrA(Bs) residue R234 aligns with residue R225 of NfsA(Ec). Thus, it is likely that previously untested/unrecovered mutations at residues S33, F42, I49, G130, R133, E178, G204, R208, I220, S224 of NfsA(Ec) might also yield single-residue mutants with improved PR-104A metabolism relative to wild type NfsA(Ec).

This research identifies NfsA family members as preferred nitroreductases capable of activating nitroheterocyclic/nitrocarbocyclic/nitroaromatic PET imaging agents in addition to reduced, substantially minimal or zero bystander "bio-control" substrates and bioreductive prodrugs and this family of enzymes is the primary subject of the present invention although we note that wild-type or more preferably evolved NfsB family members may also have utility in this regard.

It will be appreciated that the compounds of the invention may occur in different geometric and enantiomeric forms, and that both pure forms and mixtures of these compounds are included.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

The invention may be said broadly to consist in the parts, elements and features referred to or indicated in the specification, individually or collectively, in any or all combinations of two or more of said parts, elements or features.

Wherein the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention.

SEQUENCE LISTING

<160> NUMBER OF SEQ ID NOS: 90

<210> SEQ ID NO 1
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 1

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Ser Phe Leu Gln Cys Ser Ser Ile
            35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
                100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Lys Glu Ser
    210                 215                 220

Arg Pro Phe Ile Leu Asp Tyr Leu His Lys Gln Gly Trp Ala Thr Arg
225                 230                 235                 240

<210> SEQ ID NO 2
<211> LENGTH: 240
<212> TYPE: PRT
<213> ORGANISM: Salmonella enterica
<220> FEATURE:
<221> NAME/KEY: misc_feature
<223> OTHER INFORMATION: serovar Typhi Ty2

<400> SEQUENCE: 2

Met Ser Pro Thr Ile Glu Leu Leu Cys Gly His Arg Ser Ile Arg His
1               5                   10                  15

Phe Thr Asp Glu Pro Val Thr Asp Ala Gln Arg Glu Ala Ile Ile Ala
                20                  25                  30

Ala Ala Arg Ser Thr Ser Ser Ser Phe Leu Gln Cys Ser Ser Ile
            35                  40                  45

Ile Arg Ile Thr Asp Arg Ala Leu Arg Glu Ala Leu Val Pro Leu Thr

Gly Gly Gln Lys His Val Ala Gln Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Gly
            100                 105                 110

Gln Asn Ala Leu Thr Ala Ala Glu Ser Leu Gly Leu Gly Gly Val Tyr
                115                 120                 125

Ile Ser Gly Ile Arg Asn Asn Ile Glu Ser Val Thr Glu Leu Leu Lys
        130                 135                 140

Leu Pro Lys His Val Leu Pro Leu Phe Gly Leu Cys Leu Gly Trp Pro
145                 150                 155                 160

Ala Asp Asn Pro Asp Leu Lys Pro Arg Leu Pro Ala Glu Leu Val Val
                165                 170                 175

His Glu Asn Gln Tyr Gln Pro Leu Asp Glu Lys Leu Leu Ala Arg Tyr
            180                 185                 190

Asp Glu Gln Leu Ala Glu Tyr Tyr Leu Thr Arg Gly Ser Asn Thr Arg
        195                 200                 205

Arg Asp Thr Trp Ser Asp His Ile Arg Arg Thr Leu Ile Lys Glu Asn
210                 215                 220

Arg Pro Phe Ile Leu Glu Tyr Leu His Lys Gln Gly Trp Ala Thr Arg
225                 230                 235                 240

<210> SEQ ID NO 3
<211> LENGTH: 240
<212> TYPE: PRT
<213> ORGANISM: Citrobacter koseri
<220> FEATURE:
<221> NAME/KEY: misc_feature
<223> OTHER INFORMATION: ATCC 27156

<400> SEQUENCE: 3

Met Thr Pro Thr Ile Asp Leu Ile Arg Gly His Arg Ser Ile Arg His
1               5                   10                  15

Phe Thr Asp Glu Pro Ile Ser Asp Ala Gln Arg Glu Ser Ile Ile Ala
                20                  25                  30

Ala Ala Arg Gly Thr Ser Ser Ser Phe Leu Gln Cys Ser Ser Ile
            35                  40                  45

Ile Arg Ile Thr Asp Lys Ala Met Arg Glu Ala Leu Val Pro Leu Thr
        50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Thr Val Asp Thr Ala Met Met Gly
            100                 105                 110

Gln Asn Ala Leu Thr Ala Ala Glu Ser Leu Gly Leu Gly Gly Val Tyr
                115                 120                 125

Ile Gly Gly Ile Arg Asn His Ile Glu Ala Val Thr Glu Arg Leu Lys
        130                 135                 140

Leu Pro Lys Tyr Val Leu Pro Leu Phe Gly Leu Cys Leu Gly Trp Pro
145                 150                 155                 160

Ala Asp Asn Pro Gly Val Lys Pro Arg Leu Pro Ala Glu Leu Val Val
                165                 170                 175

His Glu Asn His Tyr Gln Pro Val Asp Ala Ala Leu Leu Ala Gln Tyr
                180                 185                 190

Asp Glu Gln Ile Ala Glu Tyr Tyr Leu Thr Arg Asp Ser Asn Thr Arg
            195                 200                 205

Arg Asp Thr Trp Ser Asp His Ile Arg Arg Thr Ile Ile Lys Glu Asn
        210                 215                 220

Arg Pro Phe Ile Leu Asp Tyr Leu His Lys Gln Gly Trp Ala Thr Arg
225                 230                 235                 240

<210> SEQ ID NO 4
<211> LENGTH: 240
<212> TYPE: PRT
<213> ORGANISM: Klebsiella pneumoniae
<220> FEATURE:
<221> NAME/KEY: misc_feature
<223> OTHER INFORMATION: subspecies pneumoniae ATCC 13883

<400> SEQUENCE: 4

Met Thr Pro Thr Ile Glu Leu Leu Arg Ser His Arg Ser Ile Arg His
1               5                   10                  15

Phe Thr Asp Ala Pro Val Ser Asp Glu Gln Arg Ala Glu Ile Ile Ala
            20                  25                  30

Ser Ala Gln Ala Ala Ser Thr Ser Ser Phe Leu Gln Cys Thr Ser Ile
        35                  40                  45

Ile Arg Ile Thr Asp Pro Ala Leu Arg Glu Arg Leu Val Pro Leu Thr
    50                  55                  60

Gly Gly Gln Gln His Val Ala Gln Ala Ala Glu Phe Trp Val Phe Cys
65                  70                  75                  80

Ala Asp Phe Asn Arg His Leu Gln Ile Cys Pro Gln Ala Gln Leu Gly
                85                  90                  95

Leu Ala Glu Gln Leu Leu Ile Gly Val Val Asp Thr Ala Leu Leu Ala
            100                 105                 110

Gln Asn Ala Leu Thr Ala Ala Glu Ser Leu Gly Leu Gly Gly Val Tyr
        115                 120                 125

Ile Gly Gly Leu Arg Asn Ser Ile Glu Ala Val Thr Glu Leu Leu Glu
    130                 135                 140

Leu Pro Gln His Val Leu Pro Leu Phe Gly Leu Cys Leu Gly Trp Pro
145                 150                 155                 160

Ala Asp Asn Pro Asp Ile Lys Pro Arg Met Pro Ala Ala Met Leu Val
                165                 170                 175

His Glu Asn Arg Tyr Gln Pro Leu Asp Asn Ala Leu Leu Ala Glu Tyr
            180                 185                 190

Asp Glu Gln Leu Ala His Tyr Tyr Leu Ser Arg Gly Ser Asn Ala Arg
        195                 200                 205

Arg Asp Thr Trp Ser Asp His Ile Arg Arg Thr Ile Val Lys Glu Ser
    210                 215                 220

Arg Pro Phe Ile Leu Asp Tyr Leu His Lys Gln Gly Trp Ala Thr Arg
225                 230                 235                 240

<210> SEQ ID NO 5
<211> LENGTH: 257
<212> TYPE: PRT
<213> ORGANISM: Enterobacter sakazakii
<220> FEATURE:
<221> NAME/KEY: misc_feature
<223> OTHER INFORMATION: ATCC BAA-894

<400> SEQUENCE: 5

Met Gly Lys Leu Ser Leu Ala Phe Gln His Thr Arg Asn Lys Glu Asn
1               5                   10                  15

Val Met Thr Pro Thr Ile Glu Leu Leu Cys Ser His Arg Ser Ile Arg
            20                  25                  30

His Tyr Thr Asp Glu Pro Ile Ser Asp Ala Gln Arg Glu Ala Ile Ile
            35                  40                  45

His Ala Ala Gln Ser Ala Ser Ser Ser Phe Leu Gln Cys Ser Ser
    50                  55                  60

Ile Ile Arg Val Thr Asp Arg Ala Met Arg Glu Gln Leu Val Thr Leu
65                  70                  75                  80

Thr Gly Gly Gln Pro His Val Ala Lys Ala Ala Glu Phe Trp Val Phe
                85                  90                  95

Cys Ala Asp Phe Asn Arg His Leu Gln Ile Cys Pro Asp Ala Gln Leu
                100                 105                 110

Gly Leu Ala Glu Gln Leu Leu Leu Gly Val Val Asp Thr Ala Met Leu
            115                 120                 125

Gly Gln Asn Ala Leu Val Ala Ala Glu Ser Leu Gly Leu Gly Gly Val
    130                 135                 140

Tyr Ile Gly Gly Ile Arg Asn Ser Ile Glu Ala Val Thr Glu Leu Leu
145                 150                 155                 160

Gly Leu Pro Lys His Val Leu Pro Leu Phe Gly Leu Cys Leu Gly Trp
                165                 170                 175

Pro Ala Asp Asn Pro Gln Val Lys Pro Arg Met Pro Ala Gly Leu Met
                180                 185                 190

Val His Glu Asn Arg Tyr Gln Pro Val Asp Arg Glu Leu Leu Ala Glu
            195                 200                 205

Tyr Asp Glu Glu Ile Ala Asp Tyr Tyr Leu His Arg Asp Ser Asn Ala
    210                 215                 220

Arg Arg Asp Thr Trp Ser Asp Gln Ile Arg Arg Thr Ile Ile Lys Glu
225                 230                 235                 240

Asn Arg Pro Phe Ile Leu Asp Tyr Leu His Lys Gln Gly Trp Ala Thr
                245                 250                 255

Arg

<210> SEQ ID NO 6
<211> LENGTH: 240
<212> TYPE: PRT
<213> ORGANISM: Vibrio fischeri
<220> FEATURE:
<221> NAME/KEY: misc_feature
<223> OTHER INFORMATION: NZ isolate

<400> SEQUENCE: 6

Met Asn Pro Val Ile Asp Thr Ile Leu Glu His Arg Ser Ile Arg Ser
1               5                   10                  15

Phe Thr Asn Glu Pro Ile Ser Lys Glu Gln Leu Asp Thr Ile Ile Ser
            20                  25                  30

Ala Gly Ile Ala Ala Ser Ser Ser Leu Leu Gln Val Asn Ser Ile
        35                  40                  45

Ile Arg Ile Thr Asp Lys Glu Lys Arg Lys Ala Leu Val Glu Leu Ser
    50                  55                  60

Gly Gly Gln Pro Tyr Val Glu Gly Ala Ala Glu Phe Leu Val Phe Cys
65                  70                  75                  80

Ile Asp Phe Gln Arg His Tyr Glu Met Asn Pro Glu Ile Lys Ala Glu
                85                  90                  95

```
Phe Thr Glu Leu Thr Leu Ile Gly Ala Val Asp Ala Gly Ile Met Ala
            100                 105                 110

Gln Asn Cys Leu Leu Ala Ala Glu Ser Met Gly Leu Gly Gly Val Tyr
        115                 120                 125

Ile Gly Gly Leu Arg Thr Asn Ala Gln Gly Val Asp Asp Leu Leu Glu
    130                 135                 140

Leu Pro Lys Asn Thr Ala Val Leu Phe Gly Met Cys Leu Gly Tyr Pro
145                 150                 155                 160

Asn Gln Ala Pro Gln Lys Lys Pro Arg Leu Ser Pro Asp Val Ile Val
                165                 170                 175

His Glu Asn Ser Tyr Gln Pro Leu Asp Lys Ser Lys Ile Asp Glu Tyr
            180                 185                 190

Asp Glu Ile Met Gln Ser Tyr Tyr Ala Thr Arg Ser Thr Asn Gln Lys
        195                 200                 205

Gln Ser Ser Trp Ser Glu Gln Ile Thr Gly Lys Leu Ser Gln Glu Ser
    210                 215                 220

Arg Pro His Ile Lys Gly Tyr Leu Asn Asn Lys Gly Leu Ala Ile Lys
225                 230                 235                 240

<210> SEQ ID NO 7
<211> LENGTH: 240
<212> TYPE: PRT
<213> ORGANISM: Vibrio vulnificus
<220> FEATURE:
<221> NAME/KEY: misc_feature
<223> OTHER INFORMATION: NZ isolate

<400> SEQUENCE: 7

Met Asn Ala Val Ile Asp Thr Leu Leu Ser His Arg Ser Ile Arg Lys
1               5                   10                  15

Phe Thr Asp Gln Ala Ile Thr Pro Glu Gln Leu Asp Thr Ile Ile Arg
            20                  25                  30

Ala Gly Leu Ala Ala Ser Ser Ser Leu Leu Gln Val Val Ser Ile
        35                  40                  45

Ile Arg Ile Thr Asp Pro Ala Lys Arg Gln Gln Leu Ala Glu Leu Ala
    50                  55                  60

Gly Pro Gln His Tyr Val Glu Thr Ala Ala Glu Phe Leu Val Phe Cys
65                  70                  75                  80

Ile Asp Tyr Gln Arg His Ala Thr Leu Asn Ser Glu Val Gln Ala Gly
                85                  90                  95

Phe Thr Glu Leu Thr Leu Ile Gly Ala Val Asp Ala Gly Ile Met Ala
            100                 105                 110

Gln Asn Cys Leu Leu Ala Ala Glu Ser Met Gly Leu Gly Gly Val Tyr
        115                 120                 125

Ile Gly Gly Leu Arg Asn Lys Ala Ala Glu Val Asp Ala Leu Leu Glu
    130                 135                 140

Leu Pro Pro Phe Ser Ala Val Leu Phe Gly Met Cys Leu Gly His Pro
145                 150                 155                 160

Asp Gln Asp Pro Asp Leu Lys Pro Arg Leu Pro Ala Glu Val Ile Leu
                165                 170                 175

His Glu Asn His Tyr Gln Pro Leu Asp Leu Asn Lys Val Glu Gln Tyr
            180                 185                 190

Asp Gln Thr Met Leu Asp Tyr Tyr Gly Lys Arg Ser Ser Asn Gln Lys
        195                 200                 205

Gln Ala Ser Trp Ser Glu Gln Val Thr Gly Lys Leu Ala Gly Glu Ser
    210                 215                 220
```

Arg Pro His Ile Leu Pro Tyr Leu His Ser Lys Gly Leu Ala Thr Lys
225                 230                 235                 240

<210> SEQ ID NO 8
<211> LENGTH: 240
<212> TYPE: PRT
<213> ORGANISM: Vibrio harveyi
<300> PUBLICATION INFORMATION:
<308> DATABASE ACCESSION NUMBER: Genbank/Accession no. AAA21331
<309> DATABASE ENTRY DATE: 1994-09-03
<313> RELEVANT RESIDUES IN SEQ ID NO: (1)..(240)

<400> SEQUENCE: 8

Met Asn Asn Thr Ile Glu Thr Ile Leu Ala His Arg Ser Ile Arg Lys
1               5                   10                  15

Phe Thr Ala Val Pro Ile Thr Asp Glu Gln Arg Gln Thr Ile Ile Gln
            20                  25                  30

Ala Gly Leu Ala Ala Ser Ser Ser Met Leu Gln Val Val Ser Ile
        35                  40                  45

Val Arg Val Thr Asp Ser Glu Lys Arg Asn Glu Leu Ala Gln Phe Ala
50                  55                  60

Gly Asn Gln Ala Tyr Val Glu Ser Ala Ala Glu Phe Leu Val Phe Cys
65                  70                  75                  80

Ile Asp Tyr Gln Arg His Ala Thr Ile Asn Pro Asp Val Gln Ala Asp
                85                  90                  95

Phe Thr Glu Leu Thr Leu Ile Gly Ala Val Asp Ser Gly Ile Met Ala
            100                 105                 110

Gln Asn Cys Leu Leu Ala Ala Glu Ser Met Gly Leu Gly Gly Val Tyr
        115                 120                 125

Ile Gly Gly Leu Arg Asn Ser Ala Ala Gln Val Asp Glu Leu Leu Gly
    130                 135                 140

Leu Pro Glu Asn Ser Ala Val Leu Phe Gly Met Cys Leu Gly His Pro
145                 150                 155                 160

Asp Gln Asn Pro Glu Val Lys Pro Arg Leu Pro Ala His Val Val Val
                165                 170                 175

His Glu Asn Gln Tyr Gln Glu Leu Asn Leu Asp Asp Ile Gln Ser Tyr
            180                 185                 190

Asp Gln Thr Met Gln Ala Tyr Tyr Ala Ser Arg Thr Ser Asn Gln Lys
        195                 200                 205

Leu Ser Thr Trp Ser Gln Glu Val Thr Gly Lys Leu Ala Gly Glu Ser
    210                 215                 220

Arg Pro His Ile Leu Pro Tyr Leu Asn Ser Lys Gly Leu Ala Lys Arg
225                 230                 235                 240

<210> SEQ ID NO 9
<211> LENGTH: 240
<212> TYPE: PRT
<213> ORGANISM: Vibrio harveyi
<300> PUBLICATION INFORMATION:
<308> DATABASE ACCESSION NUMBER: UniProtKB/Accession no. Q56691
<309> DATABASE ENTRY DATE: 1998-07-15
<313> RELEVANT RESIDUES IN SEQ ID NO: (1)..(240)

<400> SEQUENCE: 9

Met Asn Asn Thr Ile Glu Thr Ile Leu Ala His Arg Ser Ile Arg Lys
1               5                   10                  15

Phe Thr Ala Val Pro Ile Thr Asp Glu Gln Arg Gln Thr Ile Ile Gln
            20                  25                  30

```
Ala Gly Leu Ala Ala Ser Ser Ser Met Leu Gln Val Ser Ile
            35                  40                  45

Val Arg Val Thr Asp Ser Glu Lys Arg Lys Gln Leu Ala Gln Phe Ala
 50                  55                  60

Gly Asn Gln Ala Tyr Ile Glu Ser Ala Ala Glu Phe Leu Val Phe Cys
 65                  70                  75                  80

Ile Asp Tyr Gln Arg His Ala Thr Ile Asn Pro Asp Val Gln Ala Asp
                 85                  90                  95

Phe Thr Glu Leu Thr Leu Ile Gly Ala Val Asp Ser Gly Ile Met Ala
            100                 105                 110

Gln Asn Cys Leu Leu Ala Ala Glu Ser Met Gly Leu Gly Gly Val Tyr
            115                 120                 125

Ile Gly Gly Leu Arg Asn Ser Ala Ala Gln Val Asp Lys Leu Leu Gly
130                 135                 140

Leu Pro Glu Asn Ser Ala Val Leu Phe Gly Met Cys Leu Gly His Pro
145                 150                 155                 160

Asp Gln Asn Pro Glu Val Lys Pro Arg Leu Pro Ala His Val Val Val
                165                 170                 175

His Glu Asn Gln Tyr Gln Glu Leu Asn Leu Asp Asp Ile Gln Ser Tyr
            180                 185                 190

Asp Gln Thr Met Gln Ala Tyr Tyr Ala Ser Ser Thr Ser Asn Gln Lys
            195                 200                 205

Leu Ser Ser Trp Ser Gln Glu Val Thr Gly Lys Leu Ala Gly Glu Ser
210                 215                 220

Arg Pro His Ile Leu Pro Tyr Leu Asn Ser Lys Gly Leu Ala Lys Arg
225                 230                 235                 240

<210> SEQ ID NO 10
<211> LENGTH: 249
<212> TYPE: PRT
<213> ORGANISM: Bacillus subtilis
<220> FEATURE:
<221> NAME/KEY: misc_feature
<223> OTHER INFORMATION: subspecies subtilis, NZ isolate

<400> SEQUENCE: 10

Met Asn Asn Thr Ile Glu Thr Ile Leu Asn His Arg Ser Ile Arg Ser
 1               5                  10                  15

Phe Thr Asp Gln Leu Leu Thr Ala Glu Glu Ile Asp Ile Leu Val Lys
             20                  25                  30

Ser Ala Gln Ala Ala Ser Thr Ser Ser Tyr Val Gln Ala Tyr Ser Ile
            35                  40                  45

Ile Gly Val Ser Asp Pro Glu Lys Lys Arg Glu Leu Ser Val Leu Ala
 50                  55                  60

Gly Asn Gln Pro Tyr Val Glu Asn Asn Gly His Phe Phe Val Phe Cys
 65                  70                  75                  80

Ala Asp Leu His Arg His Gln Lys Leu Ala Glu Glu Lys Gly Glu Asn
                 85                  90                  95

Ile Ser Glu Leu Leu Glu Asn Thr Glu Met Phe Met Val Ser Leu Ile
            100                 105                 110

Asp Ala Ala Leu Ala Ala Gln Asn Met Ser Val Ala Ala Glu Ser Met
            115                 120                 125

Gly Leu Gly Ile Cys Tyr Ile Gly Gly Ile Arg Asn Glu Leu Asp Lys
130                 135                 140

Val Thr Glu Val Leu Gln Thr Pro Asp His Val Leu Pro Leu Phe Gly
145                 150                 155                 160
```

Leu Ala Val Gly His Pro Ala Asn Leu Ser Gly Lys Lys Pro Arg Leu
            165                 170                 175

Pro Lys Gln Ala Val Tyr His Glu Asn Thr Tyr Asn Val Asn Ala Asp
            180                 185                 190

Asp Phe Arg Asp Thr Met Asn Ala Tyr Asp Gln Thr Ile Ser Asp Tyr
        195                 200                 205

Tyr Arg Glu Arg Thr Asn Gly Gln Arg Glu Gly Thr Trp Ser Asp Gln
    210                 215                 220

Ile Leu Asn Phe Met Lys Gln Lys Pro Arg Thr Tyr Leu Asn Asp Tyr
225                 230                 235                 240

Val Lys Glu Lys Gly Phe Asn Lys Asn
            245

<210> SEQ ID NO 11
<211> LENGTH: 246
<212> TYPE: PRT
<213> ORGANISM: Listeria innocua
<220> FEATURE:
<221> NAME/KEY: misc_feature
<223> OTHER INFORMATION: ATCC 33090

<400> SEQUENCE: 11

Met Asn Gln Ala Ile Asp Ala Ile Leu Gly His Tyr Ser Val Arg Asn
1               5                   10                  15

Phe Glu Asp Lys Ala Leu Thr Glu Glu Leu Ala Leu Leu Ile Lys
            20                  25                  30

Ser Ala Gln Ala Ala Ser Thr Ser Ser Phe Val Gln Ala Tyr Ser Ile
            35                  40                  45

Ile Gly Ile Thr Asp Lys Lys Ile Arg Glu Gln Ile Ser Ala Ile Ala
        50                  55                  60

Gly Asn Gln Pro Tyr Thr Val Gln Thr Gly Gln Leu Phe Ile Phe Val
65                  70                  75                  80

Ala Asp Leu Ala Arg His Gln Ala Ile Leu Glu Glu His Gln Val Asp
                85                  90                  95

Thr Ala Ala Leu Glu Thr Ser Glu Lys Trp Leu Val Ser Ile Ile Asp
            100                 105                 110

Ala Ala Leu Ala Ala Gln Asn Met Ala Val Ala Ala Glu Ser Leu Gly
        115                 120                 125

Phe Gly Ile Cys Phe Ile Gly Gly Ile Arg Asn Asp Val Gly Gln Ile
    130                 135                 140

Ala Glu Ile Leu Asp Leu Pro Pro Tyr Thr Met Pro Leu Phe Gly Leu
145                 150                 155                 160

Thr Ile Gly His Pro Ile Lys Gly Lys Glu Lys Ala Lys Pro Arg Leu
                165                 170                 175

Pro Gln Asp Leu Val Tyr His Glu Asn Thr Tyr Gln Lys Met Asn Pro
            180                 185                 190

Ala Thr Leu Ala Glu Tyr Asp Glu Gln Ile Lys Thr Tyr Tyr Asp Glu
        195                 200                 205

Arg Thr Ala Gly Lys Arg Val Glu Gly Trp Ser Glu Gln Ile Ala Arg
    210                 215                 220

Gly Leu Gly Arg Lys Ser Arg Leu Asp Leu Lys Asp Phe Leu Gln Lys
225                 230                 235                 240

Gln His Leu Asn Gln Lys
            245

<210> SEQ ID NO 12
<211> LENGTH: 274
<212> TYPE: PRT
<213> ORGANISM: Pseudomonas putida
<220> FEATURE:
<221> NAME/KEY: misc_feature
<223> OTHER INFORMATION: strain KT2440

<400> SEQUENCE: 12

Met Ser Leu Gln Asp Glu Ala Leu Lys Ala Trp Gln Ala Arg Tyr Gly
1               5                   10                  15

Glu Pro Ala Asn Leu Pro Ala Ala Asp Thr Val Ile Ala Gln Met Leu
            20                  25                  30

Gln His Arg Ser Val Arg Ala Tyr Ser Asp Leu Pro Val Asp Glu Gln
        35                  40                  45

Met Leu Ser Trp Ala Ile Ala Ala Gln Ser Ala Ser Thr Ser Ser
    50                  55                  60

Asn Leu Gln Ala Trp Ser Val Leu Ala Val Arg Asp Arg Glu Arg Leu
65                  70                  75                  80

Ala Arg Leu Ala Arg Leu Ser Gly Asn Gln Arg His Val Glu Gln Ala
                85                  90                  95

Pro Leu Phe Leu Val Trp Leu Val Asp Trp Ser Arg Leu Arg Arg Leu
            100                 105                 110

Ala Arg Thr Leu Gln Ala Pro Thr Ala Gly Ile Asp Tyr Leu Glu Ser
        115                 120                 125

Tyr Thr Val Gly Val Val Asp Ala Ala Leu Ala Ala Gln Asn Ala Ala
130                 135                 140

Leu Ala Phe Glu Ala Gln Gly Leu Gly Ile Val Tyr Ile Gly Gly Met
145                 150                 155                 160

Arg Asn His Pro Glu Ala Met Ser Glu Glu Leu Gly Leu Pro Asn Asp
                165                 170                 175

Thr Phe Ala Val Phe Gly Met Cys Val Gly His Pro Asp Pro Ala Gln
            180                 185                 190

Pro Ala Glu Ile Lys Pro Arg Leu Ala Gln Ser Val Val Leu His Arg
        195                 200                 205

Glu Arg Tyr Glu Ala Thr Glu Ala Glu Ala Val Ser Val Ala Ala Tyr
210                 215                 220

Asp Arg Arg Met Ser Asp Phe Gln His Arg Gln Gln Arg Glu Asn Arg
225                 230                 235                 240

Ser Trp Ser Ser Gln Ala Val Glu Arg Val Lys Gly Ala Asp Ser Leu
                245                 250                 255

Ser Gly Arg His Arg Leu Arg Asp Ala Leu Asn Thr Leu Gly Phe Gly
            260                 265                 270

Leu Arg

<210> SEQ ID NO 13
<211> LENGTH: 249
<212> TYPE: PRT
<213> ORGANISM: Bacillus subtilis
<220> FEATURE:
<221> NAME/KEY: misc_feature
<223> OTHER INFORMATION: subspecies subtilis, NZ isolate

<400> SEQUENCE: 13

Met Asn Glu Val Ile Lys Ser Leu Thr Asp His Arg Ser Ile Arg Ser
1               5                   10                  15

Tyr Thr Asp Glu Pro Val Ala Lys Glu Gln Leu Asp Gln Ile Ile Gln
            20                  25                  30

Ala Val Gln Ser Ala Pro Thr Ser Ile Asn Gly Gln Gln Val Thr Val
                35                  40                  45

Ile Thr Val Gln Asp Lys Glu Arg Lys Lys Ile Ser Glu Leu Ser
 50                  55                  60

Gly Gly Gln Pro Trp Ile Asp Gln Ala Pro Val Phe Leu Leu Phe Cys
 65                  70                  75                  80

Ala Asp Phe Asn Arg Ala Lys Ile Ala Leu Glu Asp Leu Asn Asp Ile
                85                  90                  95

Lys Met Glu Ile Thr Asn Gly Leu Glu Ser Val Leu Val Gly Ala Val
                100                 105                 110

Asp Ala Gly Ile Ala Leu Gly Thr Ala Thr Ala Ala Glu Ser Leu
                115                 120                 125

Gly Leu Gly Thr Val Pro Ile Gly Ala Val Arg Gly Asn Pro Gln Glu
 130                 135                 140

Leu Ile Glu Leu Leu Glu Leu Pro Lys Tyr Val Phe Pro Val Ser Gly
 145                 150                 155                 160

Leu Val Ile Gly His Pro Ala Asp Arg Ser Ala Lys Lys Pro Arg Leu
                165                 170                 175

Pro Gln Glu Ala Val Asn Tyr Gln Glu Thr Tyr Leu Asn Gln Asp Glu
                180                 185                 190

Leu Thr Ser Tyr Ile Gln Ala Tyr Asp Glu Lys Met Ser Glu Tyr Met
                195                 200                 205

Asn Lys Arg Thr Asn Gly Lys Glu Thr Arg Asn Trp Ser Gln Gly Ile
 210                 215                 220

Ala Ser Tyr Tyr Glu Arg Leu Tyr Tyr Pro His Ile Arg Glu Met Leu
225                 230                 235                 240

Glu Lys Gln Gly Phe Lys Val Glu Lys
                245

<210> SEQ ID NO 14
<211> LENGTH: 239
<212> TYPE: PRT
<213> ORGANISM: Erwinia carotovora
<220> FEATURE:
<221> NAME/KEY: misc_feature
<223> OTHER INFORMATION: subspecies carotovora, NZ isolate

<400> SEQUENCE: 14

Met Ile Pro Thr Ile Asp Leu Leu Gln Arg His Arg Ser Ile Arg Ala
 1               5                  10                  15

Phe Thr Ser Gln Ala Val Thr Asp Glu Gln Arg His Ala Ile Ile Ala
                20                  25                  30

Ser Ala Gln Ser Ala Ser Ser Ser Phe Leu Gln Cys Ser Ser Ile
                35                  40                  45

Ile Arg Ile Thr Asp Pro Ala Val Arg Glu Thr Leu Ile His Tyr Thr
 50                  55                  60

Gly Glu Gln Ala Tyr Val Ala Gln Ala Ala Glu Phe Trp Val Phe Cys
 65                  70                  75                  80

Ala Asp Phe His Arg His Val Glu Ile Phe Pro Gln Ala Glu Thr Gly
                85                  90                  95

Leu Ala Glu Gln Leu Leu Ile Gly Cys Val Asp Thr Ala Ile Met Ala
                100                 105                 110

Gln Asn Ala Leu Val Ala Ala Glu Ser Leu Gly Leu Gly Gly Val Phe
                115                 120                 125

Ile Gly Gly Ile Arg Asn Arg Ile Ala Asp Val Thr Gln Leu Leu Gln

```
            130                 135                 140
Leu Pro Thr Leu Val Ile Pro Leu Phe Gly Leu Cys Leu Gly His Pro
145                 150                 155                 160

Asp Ala Glu Pro Gln Leu Lys Pro Arg Met Pro Thr Ala Met Met Leu
                165                 170                 175

His Glu Asn Val Tyr Gln Pro Leu Asp Arg Asp Val Leu Ala Gln Tyr
            180                 185                 190

Asp Gln Gln Met Val Glu Tyr Tyr Leu Gln Arg Thr Gly Ser Arg Arg
        195                 200                 205

Glu Ser Trp Ser Glu His Val Glu Leu Thr Leu Lys Lys Glu Leu Arg
    210                 215                 220

Pro Phe Met Leu Asp Tyr Leu His Gln Gln Gly Trp Ala Ile Arg
225                 230                 235

<210> SEQ ID NO 15
<211> LENGTH: 245
<212> TYPE: PRT
<213> ORGANISM: Lactobacillus sakei
<220> FEATURE:
<221> NAME/KEY: misc_feature
<223> OTHER INFORMATION: NZ isolate

<400> SEQUENCE: 15

Met Ser Asp Leu Ile Ala Gln Met Gln His His Val Ser Val Arg Asn
1               5                   10                  15

Phe Glu Ala Thr Pro Leu Ser Ala Glu Val Lys Gln Gln Leu Ile Ala
                20                  25                  30

Ala Ala Gln Ser Gly Ser Ser Asn Phe Val Gln Ala Phe Ser Ile
            35                  40                  45

Ile Glu Val Thr Asp Leu Ala Leu Arg Thr Glu Ile Ala Thr Ile Ser
        50                  55                  60

Asn Ser Ala Ser Tyr Val Asn Gln Thr Gly Thr Phe Tyr Val Phe Val
65                  70                  75                  80

Ala Asp Leu Tyr Arg Gln Ala Ser Met Leu Lys Ala Gly Gln Ser
                85                  90                  95

Leu Ala Gly Ile Gln Asn Met Glu Ala Leu Leu Val Ala Ser Val Asp
            100                 105                 110

Thr Thr Ile Ala Ala Glu Asp Met Ala Val Ala Ala Glu Ser Leu Gly
        115                 120                 125

Leu Gly Ile Cys Tyr Ile Gly Gly Ile Arg Asn Asp Ile Ala Arg Val
    130                 135                 140

Ala Glu Leu Leu Gly Leu Pro Glu Tyr Thr Val Pro Leu Phe Gly Leu
145                 150                 155                 160

Thr Val Gly Ile Pro Lys Thr Lys Asn Gln Val Lys Pro Arg Leu Pro
                165                 170                 175

Gln Ile Asn Gln Val Ala Gln Asn Gln Tyr Pro Arg Ala Gln Phe Ala
            180                 185                 190

Asp Leu Lys Gln Tyr Asp Gln Gln Ile Ala Asp Tyr Tyr Ala Asn Arg
        195                 200                 205

Gly Ser Asn Gln Gln Gln Ala Asp Trp Thr Ser Lys Asn Leu Asp Phe
    210                 215                 220

Phe Ser Ala Pro Arg Arg Pro Glu Val Gly Ala Phe Leu Lys Lys Gln
225                 230                 235                 240

Gly Phe Thr Leu Ala
                245
```

```
<210> SEQ ID NO 16
<211> LENGTH: 247
<212> TYPE: PRT
<213> ORGANISM: Bacillus coagulans
<220> FEATURE:
<221> NAME/KEY: misc_feature
<223> OTHER INFORMATION: ATCC 7050

<400> SEQUENCE: 16

Met Asn Thr Ile Ile Glu Thr Ile Leu Asn His Arg Ser Ile Arg His
1               5                   10                  15

Tyr Glu Asp Arg Pro Leu Ser Asp Glu Gln Ile Arg Leu Ile Val Glu
            20                  25                  30

Ser Ala Gln Ala Ala Thr Ser His Phe Val Gln Ala Tyr Thr Ile
        35                  40                  45

Leu Gly Ile Gln Asp Pro Gly Arg Lys Gln Arg Leu Ala Glu Leu Thr
50                  55                  60

Gly Asn Arg His Val Gly Thr Cys Gly His Leu Leu Ile Phe Cys Ala
65                  70                  75                  80

Asp Leu His Lys His Ala Leu Ala Ala Glu Met Glu Gly Val Asp Ala
                85                  90                  95

Gln Asp Thr Leu Glu Thr Thr Glu Lys Phe Met Val Ala Leu Ile Asp
            100                 105                 110

Thr Ala Leu Ala Ala Gln Asn Ala Ala Leu Ala Ala Glu Ser Met Gly
        115                 120                 125

Leu Gly Ile Cys Tyr Val Gly Gly Leu Arg Asn Arg Leu Pro Glu Val
130                 135                 140

Ala Glu Leu Leu Lys Ile Pro Gln Tyr Val Leu Pro Leu Phe Ala Met
145                 150                 155                 160

Thr Ile Gly Tyr Pro Ala Asp Pro Ser Ala Lys Lys Pro Arg Met Ala
                165                 170                 175

Ala Glu His Val Tyr Phe Glu Asp Glu Tyr Pro Ala Asp Glu Arg Leu
            180                 185                 190

Leu Arg Asp Leu Lys Glu Tyr Asn Glu Thr Val Ser Gln Tyr Tyr Thr
        195                 200                 205

Lys Arg Thr Asp Gly Lys Arg Asn Asp Thr Trp Thr Gly Gln Met Ala
210                 215                 220

Gln Phe Phe Lys Glu Pro Ser Arg Val Phe Met Lys Glu Phe Val Glu
225                 230                 235                 240

His Gln Gly Phe Asp Lys Lys
                245

<210> SEQ ID NO 17
<211> LENGTH: 246
<212> TYPE: PRT
<213> ORGANISM: Listeria welshmerii
<220> FEATURE:
<221> NAME/KEY: misc_feature
<223> OTHER INFORMATION: ATCC 35897

<400> SEQUENCE: 17

Met Asn Gln Ala Ile Asp Ala Ile Leu Gly His Tyr Ser Val Arg Lys
1               5                   10                  15

Phe Glu Asp Lys Ser Leu Thr Glu Glu Leu Ser Leu Leu Ile Lys
            20                  25                  30

Ser Ala Gln Ala Ala Ser Thr Ser Ser Phe Val Gln Ala Tyr Ser Ile
        35                  40                  45
```

```
Ile Gly Ile Thr Asp Lys Glu Val Arg Lys Gln Ile Ser Leu Val Ala
         50                  55                  60

Gly Asn Gln Pro Tyr Thr Val Gln Thr Gly Gln Leu Phe Ile Phe Val
 65                  70                  75                  80

Ala Asp Leu Ala Arg His His Ala Ile Leu Glu Glu Phe Gln Val Asp
                 85                  90                  95

Thr Glu Ala Leu Glu Thr Ser Glu Lys Trp Leu Val Ser Val Ile Asp
                100                 105                 110

Ala Ala Leu Ala Ala Gln Asn Met Ala Ile Ala Ala Glu Ser Leu Gly
            115                 120                 125

Phe Gly Ile Cys Tyr Ile Gly Gly Ile Arg Asn Asn Val Glu Gln Ile
130                 135                 140

Ser Lys Ile Leu Asp Leu Pro Pro Tyr Thr Met Pro Leu Phe Gly Leu
145                 150                 155                 160

Thr Val Gly His Pro Val Val Asp Lys Glu Lys Ala Lys Pro Arg Leu
                165                 170                 175

Pro Gln Ser Leu Val Tyr His Glu Asn Thr Tyr Gln Lys Thr Asn Pro
                180                 185                 190

Thr Ile Leu Ala Asp Tyr Asp Glu Gln Ile Lys Met Tyr Tyr Asn Glu
                195                 200                 205

Arg Thr Ala Gly Lys Arg Ile Glu Gly Trp Ser Glu Gln Met Ala Arg
210                 215                 220

Gly Leu Gly Gln Lys Asn Arg Leu Asp Leu Lys Ala Phe Leu Glu Lys
225                 230                 235                 240

Gln His Leu Asn Gln Lys
                245
```

<210> SEQ ID NO 18
<211> LENGTH: 244
<212> TYPE: PRT
<213> ORGANISM: Bacillus thuringeinsis
<220> FEATURE:
<221> NAME/KEY: misc_feature
<223> OTHER INFORMATION: NZ isolate

<400> SEQUENCE: 18

```
Met Asn Glu Met Ile His Lys Met Glu Gln His Val Ser Val Arg Lys
 1               5                  10                  15

Tyr Lys Glu Glu Ser Ile Pro Lys Asp Val Glu Lys Met Val His
                 20                  25                  30

Ala Ala Gln His Ala Ala Ser Ser His Phe Val Gln Ala Tyr Ser Val
             35                  40                  45

Ile Tyr Val Thr Asp Gln Glu Leu Lys Ala Lys Leu Ala Glu Leu Ser
 50                  55                  60

Gly Asn Arg His Val Lys Asp Cys Ala Ala Phe Val Cys Cys Ala
 65                  70                  75                  80

Asp Leu Lys Arg Leu Glu Ile Ala Cys Glu Lys His Ser Thr Glu Ile
                 85                  90                  95

Lys His Glu Gly Val Glu Asp Phe Ile Val Ala Thr Val Asp Ala Ser
                100                 105                 110

Leu Phe Ala Gln Asn Leu Ala Leu Ala Ala Glu Ser Leu Gly Tyr Gly
            115                 120                 125

Ile Cys Tyr Ile Gly Gly Ile Arg Asn Asn Pro Arg Glu Val Ser Glu
130                 135                 140

Leu Leu His Leu Pro Asp Lys Val Tyr Pro Val Phe Gly Met Thr Val
145                 150                 155                 160
```

```
Gly Val Pro Asp Glu Glu His Gly Val Lys Pro Arg Leu Pro Val Ala
                165                 170                 175

Ala Val Leu His Glu Asn Gly Tyr Asp Glu Gln Lys Tyr Asp Glu Leu
            180                 185                 190

Leu Asn Glu Tyr Asp Glu Thr Met Asn Ala Tyr Tyr Lys Glu Arg Pro
        195                 200                 205

Ser Asn Lys Lys Asn Val Thr Trp Thr Glu Ser Met Ser Ser Phe Met
    210                 215                 220

Ser Lys Glu Lys Arg Met His Met Lys Glu Phe Leu Ser Glu Arg Gly
225                 230                 235                 240

Leu Asn Lys Lys

<210> SEQ ID NO 19
<211> LENGTH: 265
<212> TYPE: PRT
<213> ORGANISM: Mycobacterium smegmatis
<220> FEATURE:
<221> NAME/KEY: misc_feature
<223> OTHER INFORMATION: strain MC2155

<400> SEQUENCE: 19

Met Thr Val Ile Ala Arg Tyr Ala Asp Val Asp Ala Thr Leu Gly Val
1               5                   10                  15

His Ser Asp Thr Leu Ala Leu Gln Leu Ala His Arg Ser Val Arg Lys
            20                  25                  30

Phe Leu Pro Asp Ala Val Ser Asp Glu His Leu Ser Ala Leu Val Ala
        35                  40                  45

Ala Ala Gln Ser Ala Ala Thr Ser Ser Asn Leu Gln Pro Trp Ser Val
    50                  55                  60

Val Ala Val Arg Asp Pro Gln Arg Lys Ala Arg Leu Ala Val Leu Ala
65                  70                  75                  80

Lys Asn Gln Gln Phe Ile Asn Asp Ala Pro Leu Phe Leu Val Trp Val
                85                  90                  95

Ala Asp Leu Gly Arg Ala Arg Arg Ile Ala Glu Arg Ala Gly Val Pro
            100                 105                 110

Leu Asp Gly Ala Asp Tyr Leu Glu Thr Thr Ile Ile Gly Phe Val Asp
        115                 120                 125

Thr Ala Leu Ala Ala Gln Asn Ala Val Leu Ala Ala Glu Ser Leu Gly
    130                 135                 140

Leu Gly Thr Val Phe Val Gly Ala Ile Arg Asn His Pro Glu Glu Val
145                 150                 155                 160

Ala Ala Glu Leu Gly Leu Pro Pro Ser Ala Val Ala Thr Phe Gly Leu
                165                 170                 175

Ala Val Gly Phe Pro Asp Pro Thr Glu Asn Ala Gly Ile Lys Pro Arg
            180                 185                 190

Leu Pro Arg Glu Ala Val Leu His His Glu Gln Tyr Asp Ala Gln Thr
        195                 200                 205

Ala Asp Ser His Val Pro Ala Tyr Asp Glu Arg Leu Ala Asp Tyr Asn
    210                 215                 220

Thr Arg His Gly Leu Thr Gly Thr Trp Ser Glu Arg Val Leu Ala Arg
225                 230                 235                 240

Leu Ala Gly Pro Gln Ser Leu Ser Gly Arg His Leu Leu Arg Thr Gln
                245                 250                 255

Leu Glu Arg Leu Gly Leu Gly Ile Arg
            260                 265
```

<210> SEQ ID NO 20
<211> LENGTH: 292
<212> TYPE: PRT
<213> ORGANISM: Nostoc punctiforme
<220> FEATURE:
<221> NAME/KEY: misc_feature
<223> OTHER INFORMATION: Australian isolate

<400> SEQUENCE: 20

```
Met Pro Leu Gln Met Glu Leu Val Leu Val Ile Lys Tyr Arg Lys Ile
1               5                   10                  15

Trp Glu Leu Ile Met Thr Asn Pro Ile Glu Leu Leu Arg Ser Arg Tyr
            20                  25                  30

Gly Glu Ile Pro Phe Asn Pro Glu Glu Trp Asn Asp Ser Leu Thr Ala
        35                  40                  45

Leu Leu Ser His Arg Ser Ile Arg Ser Tyr Leu Ser Asp Pro Leu Pro
    50                  55                  60

Glu Gly Thr Leu Glu Leu Leu Ile Ala Ala Gln Ser Ala Ser Thr
65                  70                  75                  80

Ser Ser Asn Leu Gln Thr Trp Ser Val Val Ala Val Glu Asp Pro Glu
                85                  90                  95

Cys Lys Glu Glu Leu Ser Lys Leu Ala Gly Asn Gln Ala His Ile Lys
            100                 105                 110

Gln Val Pro Leu Phe Leu Val Trp Leu Ala Asp Leu Ala Arg Leu Ser
        115                 120                 125

Tyr Val Ala Asp Ser Arg Gly Ile Ser His Asp Ala Leu Glu Tyr Leu
    130                 135                 140

Glu Met Phe Val Met Ala Thr Ile Asp Ala Thr Leu Ala Ala Gln Asn
145                 150                 155                 160

Ala Ala Val Ala Ala Glu Ser Leu Gly Leu Gly Thr Val Tyr Ile Gly
                165                 170                 175

Gly Ile Arg Asn His Pro Gln Glu Val Ala Glu Ile Leu Asn Leu Pro
            180                 185                 190

Ser Ser Val Tyr Ala Val Phe Gly Leu Cys Val Gly Tyr Pro Asn Pro
        195                 200                 205

Glu Val Glu Ala Ala Ile Lys Pro Arg Leu Pro Gln Ser Ala Val Leu
    210                 215                 220

His Arg Glu Thr Tyr Lys Leu Ser Glu Gln Glu Ala Ile Ala His
225                 230                 235                 240

Tyr Asn Asp Ile Ile Lys Glu Phe Tyr Thr Glu Gln Lys Met Asn Val
                245                 250                 255

Pro Gly Asp Trp Ser Glu His Ser Ala Gln Arg Ile Ala Thr Val Glu
            260                 265                 270

Ser Leu Arg Gly Arg Asp Arg Leu Arg Glu Val Leu Asn His Leu Gly
        275                 280                 285

Phe Lys Leu Leu
    290
```

<210> SEQ ID NO 21
<211> LENGTH: 217
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 21

```
Met Asp Ile Ile Ser Val Ala Leu Lys Arg His Ser Thr Lys Ala Phe
1               5                   10                  15

Asp Ala Ser Lys Lys Leu Thr Pro Glu Gln Ala Glu Gln Ile Lys Thr
            20                  25                  30

Leu Leu Gln Tyr Ser Pro Ser Ser Thr Asn Ser Gln Pro Trp His Phe
                35                  40                  45

Ile Val Ala Ser Thr Glu Glu Gly Lys Ala Arg Val Ala Lys Ser Ala
    50                  55                  60

Ala Gly Asn Tyr Val Phe Asn Glu Arg Lys Met Leu Asp Ala Ser His
65                  70                  75                  80

Val Val Val Phe Cys Ala Lys Thr Ala Met Asp Asp Val Trp Leu Lys
                85                  90                  95

Leu Val Val Asp Gln Glu Asp Ala Asp Gly Arg Phe Ala Thr Pro Glu
                100                 105                 110

Ala Lys Ala Ala Asn Asp Lys Gly Arg Lys Phe Phe Ala Asp Met His
            115                 120                 125

Arg Lys Asp Leu His Asp Asp Ala Glu Trp Met Ala Lys Gln Val Tyr
130                 135                 140

Leu Asn Val Gly Asn Phe Leu Gly Val Ala Ala Leu Gly Leu Asp
145                 150                 155                 160

Ala Val Pro Ile Glu Gly Phe Asp Ala Ala Ile Leu Asp Ala Glu Phe
                165                 170                 175

Gly Leu Lys Glu Lys Gly Tyr Thr Ser Leu Val Val Pro Val Gly
                180                 185                 190

His His Ser Val Glu Asp Phe Asn Ala Thr Leu Pro Lys Ser Arg Leu
            195                 200                 205

Pro Gln Asn Ile Thr Leu Thr Glu Val
            210                 215

<210> SEQ ID NO 22
<211> LENGTH: 217
<212> TYPE: PRT
<213> ORGANISM: Citrobacter koseri
<220> FEATURE:
<221> NAME/KEY: misc_feature
<223> OTHER INFORMATION: ATCC 27156

<400> SEQUENCE: 22

Met Asp Ile Val Ser Val Ala Leu Lys Arg Tyr Ser Thr Lys Ala Phe
1               5                   10                  15

Asp Pro Ser Lys Gln Leu Thr Ala Asp Glu Ala Glu Lys Leu Lys Thr
            20                  25                  30

Leu Leu Gln Tyr Ser Pro Ser Ser Thr Asn Ser Gln Pro Trp His Phe
                35                  40                  45

Ile Val Ala Ser Thr Glu Glu Gly Lys Ala Arg Val Ala Lys Ser Ala
    50                  55                  60

Ala Gly Asn Phe Val Phe Asn Glu Arg Lys Met Leu Asp Ala Ser His
65                  70                  75                  80

Val Val Val Phe Cys Ala Lys Thr Ala Met Asp Asp Ala Trp Leu Asp
                85                  90                  95

Arg Val Val Asp Gln Glu Asp Ala Asp Gly Arg Phe Ala Thr Pro Glu
                100                 105                 110

Ala Lys Ala Ala Asn Asn Lys Gly Arg Arg Phe Phe Ala Asp Leu His
            115                 120                 125

Arg Arg Asp Leu Lys Asp Asp Asp Gln Trp Met Ala Lys Gln Val Tyr
```

```
Leu Asn Val Gly Asn Phe Leu Leu Gly Val Ala Ala Met Gly Leu Asp
145                 150                 155                 160

Ala Val Pro Ile Glu Gly Phe Asp Ala Ala Val Leu Asp Ala Glu Phe
                165                 170                 175

Gly Leu Lys Glu Lys Gly Tyr Thr Ser Leu Val Val Pro Val Gly
            180                 185                 190

His His Ser Val Glu Asp Phe Asn Ala Thr Leu Pro Lys Ser Arg Leu
            195                 200                 205

Pro Gln Glu Thr Thr Leu Thr Glu Val
            210                 215
```

<210> SEQ ID NO 23
<211> LENGTH: 217
<212> TYPE: PRT
<213> ORGANISM: Salmonella enterica
<220> FEATURE:
<221> NAME/KEY: misc_feature
<223> OTHER INFORMATION: serovar Typhi Ty2

<400> SEQUENCE: 23

```
Met Asp Ile Val Ser Val Ala Leu Lys Arg Tyr Ser Thr Lys Ala Phe
1               5                   10                  15

Asp Pro Ser Lys Lys Leu Thr Ala Glu Glu Ala Asp Lys Val Lys Thr
                20                  25                  30

Leu Leu Gln Tyr Ser Pro Ser Ser Thr Asn Ser Gln Pro Trp His Phe
            35                  40                  45

Ile Val Ala Ser Thr Glu Glu Gly Lys Ala Arg Val Ala Lys Ser Ala
50                  55                  60

Ala Gly Asn Tyr Thr Phe Asn Glu Arg Lys Met Leu Asp Ala Ser His
65                  70                  75                  80

Val Val Val Phe Cys Ala Lys Thr Ala Met Asp Asp Ala Trp Leu Gln
                85                  90                  95

Arg Val Val Asp Gln Glu Asp Ala Asp Gly Arg Phe Ala Thr Pro Glu
                100                 105                 110

Ala Lys Ala Ala Asn Asp Lys Gly Arg Arg Phe Phe Ala Asp Met His
            115                 120                 125

Arg Val Ser Leu Lys Asp Asp His Gln Trp Met Ala Lys Gln Val Tyr
130                 135                 140

Leu Asn Val Gly Asn Phe Leu Leu Gly Val Ala Ala Met Gly Leu Asp
145                 150                 155                 160

Ala Val Pro Ile Glu Gly Phe Asp Ala Glu Val Leu Asp Ala Glu Phe
                165                 170                 175

Gly Leu Lys Glu Lys Gly Tyr Thr Ser Leu Val Val Pro Val Gly
            180                 185                 190

His His Ser Ile Glu Asp Phe Asn Ala Gly Leu Pro Lys Ser Arg Leu
            195                 200                 205

Pro Leu Glu Thr Thr Leu Thr Glu Val
            210                 215
```

<210> SEQ ID NO 24
<211> LENGTH: 217
<212> TYPE: PRT
<213> ORGANISM: Klebsiella pneumoniae
<220> FEATURE:
<221> NAME/KEY: misc_feature
<223> OTHER INFORMATION: subspecies pneumoniae ATCC 13883

<400> SEQUENCE: 24

```
Met Asp Ile Val Ser Val Ala Leu Lys Arg Tyr Ser Thr Lys Ala Phe
1               5                   10                  15

Asp Ala Thr Lys Lys Leu Thr Ala Gly Glu Ala Glu Gln Leu Lys Thr
            20                  25                  30

Leu Leu Gln Tyr Ser Pro Ser Thr Asn Ser Gln Pro Trp His Phe
        35                  40                  45

Ile Val Ala Ser Thr Asp Glu Gly Lys Ala Arg Val Ala Lys Ala Ala
50                  55                  60

Ser Gly Thr Tyr Val Phe Asn Glu Arg Lys Ile Leu Asp Ala Ser His
65                  70                  75                  80

Val Val Val Phe Cys Ala Lys Thr Ala Met Asp Asp Ala Trp Leu Gln
                85                  90                  95

Arg Val Val Asp Gln Glu Glu Ala Asp Gly Arg Phe Ala Thr Pro Asp
            100                 105                 110

Ala Lys Ala Ala Asn His Lys Gly Arg Thr Phe Phe Ala Asp Met His
        115                 120                 125

Arg Lys Glu Leu Lys Asp Asp Gln Trp Met Ala Lys Gln Val Tyr
    130                 135                 140

Leu Asn Val Gly Asn Phe Leu Leu Gly Val Ala Ala Met Gly Leu Asp
145                 150                 155                 160

Ala Val Pro Ile Glu Gly Val Asp Phe Ala Ile Leu Asp Glu Phe
                165                 170                 175

Asp Leu Lys Ala Gln Gly Tyr Thr Ser Leu Val Val Pro Val Gly
        180                 185                 190

His His Ser Ala Glu Asp Phe Asn Ala Thr Leu Pro Lys Ser Arg Leu
        195                 200                 205

Pro Gln Ser Thr Thr Ile Thr Glu Ile
        210                 215
```

<210> SEQ ID NO 25
<211> LENGTH: 217
<212> TYPE: PRT
<213> ORGANISM: Vibrio vulnificus
<220> FEATURE:
<221> NAME/KEY: misc_feature
<223> OTHER INFORMATION: NZ Isolate

<400> SEQUENCE: 25

```
Met Thr Ile Val Gln Ala Ala Gln Ser Arg Tyr Ser Thr Lys Ala Phe
1               5                   10                  15

Asp Ala Ser Arg Lys Leu Pro Glu Glu Lys Val Ala Ala Val Lys Glu
            20                  25                  30

Leu Ile Arg Met Ser Ala Ser Ser Val Asn Ser Gln Pro Trp His Phe
        35                  40                  45

Ile Val Ala Ser Ser Glu Glu Gly Lys Ala Arg Ile Ala Lys Ala Thr
50                  55                  60

Gln Gly Gly Phe Ala Phe Asn Glu Arg Lys Ile Leu Asp Ala Ser His
65                  70                  75                  80

Val Val Val Phe Cys Ala Lys Thr Ala Ile Asp Glu Ala Tyr Leu Leu
                85                  90                  95

Asp Leu Leu Glu Ser Glu Asp Lys Asp Gly Arg Phe Ala Asp Val Glu
            100                 105                 110

Ala Lys Asn Gly Met His Ala Gly Arg Ser Phe Phe Val Asn Met His
        115                 120                 125
```

```
Arg Phe Asp Leu Lys Asp Ala His His Trp Met Glu Lys Gln Val Tyr
        130                 135                 140

Leu Asn Val Gly Thr Leu Leu Gly Ala Ser Ala Met Glu Ile Asp
145                 150                 155                 160

Ala Val Pro Ile Glu Gly Phe Asp Ala Lys Val Leu Asp Glu Phe
                165                 170                 175

Gly Leu Arg Glu Lys Gly Phe Thr Ser Val Ile Val Pro Leu Gly
                180                 185                 190

Tyr His Ser Glu Asp Asp Phe Asn Ala Lys Leu Pro Lys Ser Arg Trp
            195                 200                 205

Ser Ala Glu Thr Val Phe Thr Glu Ile
    210                 215
```

<210> SEQ ID NO 26
<211> LENGTH: 217
<212> TYPE: PRT
<213> ORGANISM: Pseudomonas putida
<220> FEATURE:
<221> NAME/KEY: misc_feature
<223> OTHER INFORMATION: strain KT2440

<400> SEQUENCE: 26

```
Met Asp Thr Val Ser Leu Ala Lys Arg Arg Tyr Thr Thr Lys Ala Tyr
1               5                   10                  15

Asp Ala Ser Arg Arg Ile Pro Gln Ala Thr Val Asp Ala Leu Leu Glu
                20                  25                  30

Gln Leu Arg His Ser Pro Ser Ser Val Asn Ser Gln Pro Trp His Phe
            35                  40                  45

Ile Val Ala Asp Thr Ala Glu Gly Lys Ala Leu Leu Ala Lys Ser Thr
50                  55                  60

Ala Glu Gly Tyr Ala Tyr Asn Thr Gln Lys Leu Leu Asp Ala Ser His
65                  70                  75                  80

Val Ile Val Phe Cys Thr Arg Thr Glu Met Thr Glu Glu His Leu Asn
                85                  90                  95

Ala Val Leu Asp Gln Glu Ala Ala Asp Gly Arg Phe Arg Asp Glu Gln
                100                 105                 110

Ala Arg Ala Gly Gln Asn Gln Ser Arg Arg His Tyr Val Asn Leu His
            115                 120                 125

Arg Phe Asp Gln Lys Asp Val Gln His Trp Met Glu Lys Gln Thr Tyr
        130                 135                 140

Leu Ala Leu Gly Thr Ala Leu Leu Gly Ala Ala His Gly Leu Asp
145                 150                 155                 160

Ala Thr Pro Ile Glu Gly Phe Asp Ser Lys Val Leu Asp Ala Glu Leu
                165                 170                 175

Gly Leu Arg Glu Arg Gly Phe Thr Ser Val Val Ile Leu Ser Leu Gly
                180                 185                 190

Tyr Arg Ser Glu Ala Asp Phe Asn Ala Gly Leu Asn Lys Ser Arg Leu
            195                 200                 205

Pro Ala Ser Gln Val Phe Thr Phe Leu
    210                 215
```

<210> SEQ ID NO 27
<211> LENGTH: 214
<212> TYPE: PRT
<213> ORGANISM: Enterobacter sakazakii
<220> FEATURE:
<221> NAME/KEY: misc_feature
<223> OTHER INFORMATION: ATCC BAA-894

<400> SEQUENCE: 27

Met Asn Leu Asn Glu Ile Ile Arg Thr Arg His Thr Ser Lys Ala Tyr
1               5                   10                  15

Asp Asn Ser Arg Lys Leu Thr Ala Glu Gln Gln Gln Glu Leu Leu Asp
            20                  25                  30

Leu Leu Arg Phe Ser Pro Ser Ser Val Asn Ser Gln Pro Trp His Phe
        35                  40                  45

Phe Ala Val Thr Thr Glu Glu Gly Lys Ala Gln Ile Leu Pro Ala Leu
50                  55                  60

Met Asp Ala Asn Gln Val Lys Ala Lys Asn Ala Ala Met Thr Val Val
65                  70                  75                  80

Phe Thr Ile Lys Glu Glu Leu Asn Glu Ala His Leu Leu Gln Leu Leu
                85                  90                  95

Glu Lys Glu Gln Gln Asp Gly Arg Tyr Asp Ser Glu Glu Ala Arg Ala
            100                 105                 110

Ala Asn Asp Lys Gly Arg Arg Phe Phe Val Gly Leu Asn Ser Glu Thr
        115                 120                 125

Pro Glu Gln Gln Arg Glu Trp Met Thr Arg Gln Ala Tyr Leu Ala Leu
130                 135                 140

Gly Phe Leu Leu Leu Gly Ala Ala Met Gly Leu Asp Ala Thr Pro
145                 150                 155                 160

Ile Glu Gly Phe His Pro Glu Lys Met Asp Glu Val Leu Gly Leu Lys
                165                 170                 175

Glu Lys Gly Leu Cys Ser Val Val Ala Thr Ile Gly Tyr Arg Ser
            180                 185                 190

Asp Ala Asp Phe Asn Ala Thr Leu Pro Lys Ser Arg Leu Asp Gln Asp
        195                 200                 205

Val Val Ile Thr Gln Leu
        210

<210> SEQ ID NO 28
<211> LENGTH: 218
<212> TYPE: PRT
<213> ORGANISM: Vibrio fischeri
<220> FEATURE:
<221> NAME/KEY: misc_feature
<223> OTHER INFORMATION: NZ Isolate

<400> SEQUENCE: 28

Met Thr His Pro Ile Ile His Asp Leu Glu Asn Arg Tyr Thr Ser Lys
1               5                   10                  15

Lys Tyr Asp Pro Ser Lys Lys Val Ser Gln Glu Asp Leu Ala Val Leu
            20                  25                  30

Leu Glu Ala Leu Arg Leu Ser Ala Ser Ser Ile Asn Ser Gln Pro Trp
        35                  40                  45

Lys Phe Ile Val Ile Glu Ser Asp Ala Ala Lys Gln Arg Met His Asp
50                  55                  60

Ser Phe Ala Asn Met His Gln Phe Asn Gln Pro His Ile Lys Ala Cys
65                  70                  75                  80

Ser His Val Ile Leu Phe Ala Asn Lys Leu Ser Tyr Thr Arg Asp Asp
                85                  90                  95

Tyr Asp Val Val Leu Ser Lys Ala Val Ala Asp Lys Arg Ile Thr Glu
            100                 105                 110

Glu Gln Lys Glu Ala Ala Phe Ala Ser Phe Lys Phe Val Glu Leu Asn
        115                 120                 125

```
Cys Asp Glu Asn Gly Glu His Lys Ala Trp Thr Lys Pro Gln Ala Tyr
            130                 135                 140

Leu Ala Leu Gly Asn Ala Leu His Thr Leu Ala Arg Leu Asn Ile Asp
145                 150                 155                 160

Ser Thr Thr Met Glu Gly Ile Asp Pro Glu Leu Leu Ser Glu Ile Phe
                165                 170                 175

Ala Asp Glu Leu Lys Gly Tyr Glu Cys His Val Ala Leu Ala Ile Gly
                180                 185                 190

Tyr His His Pro Ser Glu Asp Tyr Asn Ala Ser Leu Pro Lys Ser Arg
                195                 200                 205

Lys Ala Phe Glu Asp Val Ile Thr Ile Leu
            210                 215

<210> SEQ ID NO 29
<211> LENGTH: 221
<212> TYPE: PRT
<213> ORGANISM: Bacillus subtilis
<220> FEATURE:
<221> NAME/KEY: misc_feature
<223> OTHER INFORMATION: subspecies subtilis, NZ isolate

<400> SEQUENCE: 29

Met Ala Asp Leu Lys Thr Gln Ile Leu Asp Ala Tyr Asn Phe Arg His
1               5                   10                  15

Ala Thr Lys Glu Phe Asp Pro Asn Lys Lys Val Ser Asp Ser Asp Phe
                20                  25                  30

Glu Phe Ile Leu Glu Thr Gly Arg Leu Ser Pro Ser Ser Leu Gly Leu
            35                  40                  45

Glu Pro Trp Lys Phe Val Val Val Gln Asn Pro Glu Phe Arg Glu Lys
50                  55                  60

Leu Arg Glu Tyr Thr Trp Gly Ala Gln Lys Gln Leu Pro Thr Ala Ser
65                  70                  75                  80

His Phe Val Leu Ile Leu Ala Arg Thr Ala Lys Asp Ile Lys Tyr Asn
                85                  90                  95

Ala Asp Tyr Ile Lys Arg His Leu Lys Glu Val Lys Gln Met Pro Gln
                100                 105                 110

Asp Val Tyr Glu Gly Tyr Leu Ser Lys Thr Glu Glu Phe Gln Lys Asn
            115                 120                 125

Asp Leu His Leu Leu Glu Ser Asp Arg Thr Leu Phe Asp Trp Ala Ser
            130                 135                 140

Lys Gln Thr Tyr Ile Ala Leu Gly Asn Met Met Thr Ala Ala Ala Gln
145                 150                 155                 160

Ile Gly Val Asp Ser Cys Pro Ile Glu Gly Phe Gln Tyr Asp His Ile
                165                 170                 175

His Arg Ile Leu Glu Glu Glu Gly Leu Leu Glu Asn Gly Ser Phe Asp
                180                 185                 190

Ile Ser Val Met Val Ala Phe Gly Tyr Arg Val Arg Asp Pro Arg Pro
            195                 200                 205

Lys Thr Arg Ser Ala Val Glu Asp Val Val Lys Trp Val
210                 215                 220

<210> SEQ ID NO 30
<211> LENGTH: 209
<212> TYPE: PRT
<213> ORGANISM: Bacillus subtilis
<220> FEATURE:
<221> NAME/KEY: misc_feature
```

<223> OTHER INFORMATION: subspecies subtilis, NZ isolate

<400> SEQUENCE: 30

```
Met Ile Lys Thr Asn Asp Phe Met Glu Ile Met Lys Gly Arg Arg Ser
1               5                   10                  15

Ile Arg Asn Tyr Asp Pro Ala Val Lys Ile Ser Lys Glu Glu Met Thr
            20                  25                  30

Glu Ile Leu Glu Glu Ala Thr Thr Ala Pro Ser Ser Val Asn Ala Gln
        35                  40                  45

Pro Trp Arg Phe Leu Val Ile Asp Ser Pro Glu Gly Lys Glu Lys Leu
    50                  55                  60

Ala Pro Leu Ala Ser Phe Asn Gln Thr Gln Val Thr Thr Ser Ser Ala
65                  70                  75                  80

Val Ile Ala Val Phe Ala Asp Met Asn Asn Ala Asp Tyr Leu Glu Glu
                85                  90                  95

Ile Tyr Ser Lys Ala Val Glu Leu Gly Tyr Met Pro Gln Glu Val Lys
            100                 105                 110

Asp Arg Gln Ile Ala Ala Leu Thr Ala His Phe Glu Lys Leu Pro Ala
        115                 120                 125

Gln Val Asn Arg Glu Thr Ile Leu Ile Asp Gly Gly Leu Val Ser Met
130                 135                 140

Gln Leu Met Leu Thr Ala Arg Ala His Gly Tyr Asp Thr Asn Pro Ile
145                 150                 155                 160

Gly Gly Tyr Asp Lys Glu Asn Ile Ala Glu Thr Phe Gly Leu Asp Lys
                165                 170                 175

Glu Arg Tyr Val Pro Val Met Leu Leu Ser Ile Gly Lys Ala Ala Asp
            180                 185                 190

Glu Gly Tyr Ala Ser Tyr Arg Leu Pro Ile Asp Thr Ile Ala Glu Trp
        195                 200                 205

Lys
```

<210> SEQ ID NO 31
<211> LENGTH: 200
<212> TYPE: PRT
<213> ORGANISM: Pseudomonas aeruginosa
<220> FEATURE:
<221> NAME/KEY: misc_feature
<223> OTHER INFORMATION: strain PA01

<400> SEQUENCE: 31

```
Met His Ile Glu Asp Ala Val Arg Ser Arg Ala Ile Lys Gly Tyr
1               5                   10                  15

Asp Ser Ser Phe Ser Leu Thr Arg Glu Glu Lys Asp His Leu Leu Asp
            20                  25                  30

Leu Ala Leu His Ala Pro Ser Ala Phe Asn Leu Gln His Val Arg Leu
        35                  40                  45

Val Glu Val Ser Asp Pro Gln Leu Arg Val Gln Leu Arg Glu Val Ala
    50                  55                  60

Trp Asp Gln Ala Gln Val Thr Asp Ala Ala Met Leu Val Val Cys
65                  70                  75                  80

Ala Gln Leu Asp Ser Trp Glu Arg Asn Ala Gln Arg Val Trp Asp Gly
                85                  90                  95

Ala Pro Glu Ala Val Gln Ala Phe Met Ala Gly Ala Ile Asp Thr Tyr
            100                 105                 110

Tyr Arg Gly Lys Pro Gln Val Gln Arg Asp Glu Ala Met Arg Ser Cys
        115                 120                 125
```

Gly Leu Leu Ala Gln Thr Leu Met Leu Val Ala Arg Gly Gln Gly Leu
                130                 135                 140

Asp Ser Cys Pro Met Asp Gly Phe Asp Phe Asp Ala Val Ala Arg Leu
145                 150                 155                 160

Ile Asn Leu Pro Asp Asn His Val Ile Gly Leu Met Val Ala Val Gly
                165                 170                 175

Lys Lys Ala Val Glu Pro Trp Pro Arg Ser Gly Lys Leu Pro Arg Glu
                180                 185                 190

Glu Leu Val Ile Arg Asp Arg Phe
                195                 200

<210> SEQ ID NO 32
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 32

Met Thr Pro Thr Thr Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Tyr Phe Leu Gln Cys Ser Ser Ile
            35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
                100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Glu Glu Ser
            210                 215                 220

Arg Pro Ser Ile Leu Asp Tyr Leu His Lys Gln Gly Trp Ala Thr Arg
225                 230                 235                 240

<210> SEQ ID NO 33
<211> LENGTH: 240
<212> TYPE: PRT
<213> ORGANISM: Escherichia coli
<220> FEATURE:
<221> NAME/KEY: misc_feature
<223> OTHER INFORMATION: Strain W3110

<400> SEQUENCE: 33

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Tyr Phe Leu Gln Cys Ser Ser Ile
        35                  40                  45

Ile Arg Ile Thr Asp Lys Ala Leu Arg Glu Glu Leu Val Thr Leu Thr
    50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Gly Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
    130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Lys Glu Ser
    210                 215                 220

Arg Pro Ser Ile Leu Asp Tyr Leu His Lys Gln Gly Trp Ala Thr Arg
225                 230                 235                 240

<210> SEQ ID NO 34
<211> LENGTH: 240
<212> TYPE: PRT
<213> ORGANISM: Escherichia coli
<220> FEATURE:
<221> NAME/KEY: misc_feature
<223> OTHER INFORMATION: Strain W3110

<400> SEQUENCE: 34

Met Thr Pro Thr Thr Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Tyr Phe Leu Gln Cys Ser Ser Ile
        35                  40                  45

Ile Arg Ile Thr Asp Lys Ala Leu Arg Glu Glu Leu Val Thr Leu Thr
    50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala

```
            100                 105                 110
Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
            130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
            165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Lys Glu Ser
            210                 215                 220

Pro Pro Ser Ile Leu Asp Tyr Leu His Lys Gln Gly Trp Ala Thr Arg
225                 230                 235                 240

<210> SEQ ID NO 35
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 35

Met Thr Pro Thr Thr Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Tyr Phe Leu Gln Cys Ser Ser Ile
            35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
            85                  90                  95

Leu Ala Glu Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
            130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
            165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Lys Glu Ser
            210                 215                 220
```

Pro Pro Ser Ile Leu Asp Tyr Leu His Lys Gln Gly Trp Ala Thr Arg
225                 230                 235                 240

<210> SEQ ID NO 36
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 36

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Tyr Phe Leu Gln Cys Ser Ser Ile
        35                  40                  45

Ile Arg Ile Thr Asp Lys Ala Leu Arg Glu Glu Leu Val Thr Leu Thr
50                  55                  60

Gly Gly Gln Lys His Val Ala Gln Ala Glu Phe Trp Val Phe Cys
65              70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Glu Glu Ser
    210                 215                 220

Gly Pro Ser Ile Leu Asp Tyr Leu His Lys Gln Gly Trp Ala Thr Arg
225                 230                 235                 240

<210> SEQ ID NO 37
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 37

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Tyr Phe Leu Gln Cys Ser Ser Ile
        35                  40                  45

```
Ile Arg Ile Thr Asp Lys Ala Leu Arg Glu Glu Leu Val Thr Leu Thr
 50                  55                  60

Gly Gly Gln Lys His Val Ala Gln Ala Ala Glu Phe Trp Val Phe Cys
 65                  70                  75                  80

Ala Asp Phe Asn Arg His Leu Gln Ile Cys Pro Asp Ala Gln Leu Gly
                 85                  90                  95

Leu Ala Gly Gln Leu Leu Met Gly Val Val Asp Thr Ala Met Met Ala
                100                 105                 110

Gln Asn Ala Leu Ile Ala Ala Glu Ser Leu Gly Leu Gly Gly Val Tyr
                115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
                180                 185                 190

Asp Glu Gln Leu Ala Glu Tyr Tyr Leu Thr Arg Gly Ser Asn Asn Arg
                195                 200                 205

Arg Asp Thr Trp Ser Asp His Ile Arg Arg Thr Ile Glu Glu Ser
210                 215                 220

Arg Pro Ser Ile Leu Asp Tyr Leu His Lys Gln Gly Trp Ala Thr Arg
225                 230                 235                 240

<210> SEQ ID NO 38
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 38

Met Thr Pro Thr Ile Glu Leu Ile Cys Gly His Arg Ser Ile Arg His
 1               5                  10                  15

Phe Thr Asp Glu Pro Ile Ser Glu Ala Gln Arg Glu Ala Ile Ile Asn
                 20                  25                  30

Ser Ala Arg Ala Thr Ser Ser Ser Tyr Phe Leu Gln Cys Ser Ser Ile
                 35                  40                  45

Ile Arg Ile Thr Asp Lys Ala Leu Arg Glu Glu Leu Val Thr Leu Thr
 50                  55                  60

Gly Gly Gln Lys His Val Ala Gln Ala Ala Glu Phe Trp Val Phe Cys
 65                  70                  75                  80

Ala Asp Phe Asn Arg His Leu Gln Ile Cys Pro Asp Ala Gln Leu Gly
                 85                  90                  95

Leu Ala Glu Gln Leu Leu Met Gly Val Val Asp Thr Ala Met Met Ala
                100                 105                 110

Gln Asn Ala Leu Ile Ala Ala Glu Ser Leu Gly Leu Gly Gly Val Tyr
                115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175
```

-continued

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Lys Glu Ser
210                 215                 220

Arg Pro Ser Ile Leu Asp Tyr Leu His Lys Gln Gly Trp Ala Thr Arg
225                 230                 235                 240

<210> SEQ ID NO 39
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 39

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Tyr Phe Leu Gln Cys Ser Ser Ile
        35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Lys Glu Ser
210                 215                 220

Gly Pro Ser Ile Leu Asp Tyr Leu His Lys Gln Gly Trp Ala Thr Arg
225                 230                 235                 240

<210> SEQ ID NO 40
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 40

```
Met Thr Pro Thr Thr Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Phe Leu Gln Cys Ser Ser Ile
        35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
                100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
                180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Glu Glu Ser
210                 215                 220

Pro Pro Ser Ile Leu Asp Tyr Leu His Lys Gln Gly Trp Ala Thr Arg
225                 230                 235                 240

<210> SEQ ID NO 41
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 41

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Tyr Phe Leu Gln Cys Ser Ser Ile
        35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
                100                 105                 110

Gln Asn Ala Leu Ile Ala Ala Glu Ser Leu Gly Leu Gly Gly Val Tyr
```

```
                115                 120                 125
Ile Gly Gly Leu Arg Asn Asn Ile Glu Ala Val Thr Lys Leu Leu Lys
            130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Glu Glu Ser
    210                 215                 220

Ala Pro Phe Ile Leu Asp Tyr Leu His Lys Gln Gly Trp Ala Thr Arg
225                 230                 235                 240

<210> SEQ ID NO 42
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 42

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Ser Tyr Phe Leu Gln Cys Ser Ser Ile
            35                  40                  45

Ile Arg Ile Thr Asp Lys Ala Leu Arg Glu Glu Leu Val Thr Leu Thr
        50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
    130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Glu Glu Ser
    210                 215                 220

Arg Pro Phe Ile Leu Asp Tyr Leu His Lys Gln Gly Trp Ala Thr Arg
225                 230                 235                 240
```

-continued

```
<210> SEQ ID NO 43
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 43

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Tyr Phe Leu Gln Cys Ser Ser Ile
        35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Gly Gln Leu Leu Gly Val Val Asp Thr Ala Met Met Ala
            100                 105                 110

Gln Asn Ala Leu Ile Ala Ala Glu Ser Leu Gly Leu Gly Val Tyr
        115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
210                 215                 220

Ala Pro Ser Ile Leu Asp Tyr Leu His Lys Gln Gly Trp Ala Thr Arg
225                 230                 235                 240

<210> SEQ ID NO 44
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 44

Met Thr Pro Thr Thr Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Tyr Phe Leu Gln Cys Ser Ser Ile
        35                  40                  45

Ile Arg Ile Thr Asp Lys Ala Leu Arg Glu Glu Leu Val Thr Leu Thr
50                  55                  60
```

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Lys Glu Ser
210                 215                 220

Gly Pro Ser Ile Leu Asp Tyr Leu His Lys Gln Gly Trp Ala Thr Arg
225                 230                 235                 240

<210> SEQ ID NO 45
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 45

Met Thr Pro Thr Thr Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Tyr Phe Leu Gln Cys Ser Ser Ile
            35                  40                  45

Ile Arg Ile Thr Asp Lys Ala Leu Arg Glu Glu Leu Val Thr Leu Thr
        50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

```
Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Glu Glu Ser
210                 215                 220

Ala Pro Phe Ile Leu Asp Tyr Leu His Lys Gln Gly Trp Ala Thr Arg
225                 230                 235                 240

<210> SEQ ID NO 46
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 46

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Tyr Phe Leu Gln Cys Ser Ser Ile
        35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
210                 215                 220

Ala Pro Ser Ile Leu Asp Tyr Leu His Lys Gln Gly Trp Ala Thr Arg
225                 230                 235                 240

<210> SEQ ID NO 47
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 47

Met Thr Pro Thr Ile Glu Leu Ile Cys Gly His Arg Ser Ile Arg His
1               5                   10                  15
```

Phe Thr Asp Glu Pro Ile Ser Glu Ala Gln Arg Glu Ala Ile Ile Asn
                20                  25                  30

Ser Ala Arg Ala Thr Ser Ser Tyr Phe Leu Gln Cys Ser Ser Ile
        35                  40                  45

Ile Arg Ile Thr Asp Lys Ala Leu Arg Glu Glu Leu Val Thr Leu Thr
 50                  55                  60

Gly Gly Gln Lys His Val Ala Gln Ala Ala Glu Phe Trp Val Phe Cys
 65                  70                  75                  80

Ala Asp Phe Asn Arg His Leu Gln Ile Cys Pro Asp Ala Gln Leu Gly
                85                  90                  95

Leu Ala Gly Gln Leu Leu Met Gly Val Val Asp Thr Ala Met Met Ala
                100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Lys Glu Ser
210                 215                 220

Gly Pro Phe Ile Val Asp Tyr Leu His Lys Gln Gly Trp Ala Thr Arg
225                 230                 235                 240

<210> SEQ ID NO 48
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 48

Met Thr Pro Thr Ile Glu Leu Ile Cys Gly His Arg Ser Ile Arg His
 1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Tyr Phe Leu Gln Cys Ser Ser Ile
        35                  40                  45

Ile Arg Ile Thr Asp Lys Ala Leu Arg Glu Glu Leu Val Thr Leu Thr
 50                  55                  60

Gly Gly Gln Lys His Val Ala Gln Ala Ala Glu Phe Trp Val Phe Cys
 65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
                100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys

```
            130                 135                 140
Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Glu Glu Ser
        210                 215                 220

Arg Pro Ser Ile Val Asp Tyr Leu His Lys Gln Gly Trp Ala Thr Arg
225                 230                 235                 240

<210> SEQ ID NO 49
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 49

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Tyr Phe Leu Gln Cys Ser Ser Ile
            35                  40                  45

Ile Arg Ile Thr Asp Lys Ala Leu Arg Glu Glu Leu Val Thr Leu Thr
        50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
    130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Lys Glu Ser
        210                 215                 220

Ala Pro Ser Ile Leu Asp Tyr Leu His Lys Gln Gly Trp Ala Thr Arg
225                 230                 235                 240

<210> SEQ ID NO 50
<211> LENGTH: 240
```

```
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 50

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Tyr Phe Leu Gln Cys Ser Ser Ile
            35                  40                  45

Ile Arg Ile Thr Asp Lys Ala Leu Arg Glu Glu Leu Val Thr Leu Thr
        50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
                100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
        130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
    210                 215                 220

Gly Pro Phe Ile Val Asp Tyr Leu His Lys Gln Gly Trp Ala Thr Arg
225                 230                 235                 240

<210> SEQ ID NO 51
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 51

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Tyr Phe Leu Gln Cys Ser Ser Ile
            35                  40                  45

Ile Arg Ile Thr Asp Lys Ala Leu Arg Glu Glu Leu Val Thr Leu Thr
        50                  55                  60

Gly Gly Gln Lys His Val Ala Gln Ala Ala Glu Phe Trp Val Phe Cys
65                  70                  75                  80
```

```
Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
            165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Glu Glu Ser
210                 215                 220

Pro Pro Phe Ile Leu Asp Tyr Leu His Lys Gln Gly Trp Ala Thr Arg
225                 230                 235                 240

<210> SEQ ID NO 52
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 52

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Tyr Phe Leu Gln Cys Ser Ser Ile
            35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
            165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205
```

```
Arg Asp Thr Trp Ser Asp His Ile Arg Arg Thr Ile Ile Lys Glu Ser
    210                 215                 220

Pro Pro Phe Ile Leu Asp Tyr Leu His Lys Gln Gly Trp Ala Thr Arg
225                 230                 235                 240
```

<210> SEQ ID NO 53
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 53

```
Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Ser Tyr Phe Leu Gln Cys Ser Ser Ile
            35                  40                  45

Ile Arg Ile Thr Asp Lys Ala Leu Arg Glu Glu Leu Val Thr Leu Thr
    50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
    130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
    210                 215                 220

Gly Pro Ser Ile Val Asp Tyr Leu His Lys Gln Gly Trp Ala Thr Arg
225                 230                 235                 240
```

<210> SEQ ID NO 54
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 54

```
Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30
```

```
Ser Ala Arg Ala Thr Ser Ser Ser Tyr Phe Leu Gln Cys Ser Ser Ile
            35                  40                  45

Ile Arg Ile Thr Asp Lys Ala Leu Arg Glu Glu Leu Val Thr Leu Thr
 50                  55                  60

Gly Gly Gln Lys His Val Ala Gln Ala Ala Glu Phe Trp Val Phe Cys
 65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
            100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Glu Glu Ser
210                 215                 220

Pro Pro Ser Ile Leu Asp Tyr Leu His Lys Gln Gly Trp Ala Thr Arg
225                 230                 235                 240

<210> SEQ ID NO 55
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 55

Met Thr Pro Thr Thr Glu Leu Ile Cys Gly His Arg Ser Ile Arg His
 1               5                  10                  15

Phe Thr Asp Glu Pro Ile Ser Glu Ala Gln Arg Glu Ala Ile Ile Asn
                20                  25                  30

Ser Ala Arg Ala Thr Ser Ser Ser Tyr Phe Leu Gln Cys Ser Ser Ile
            35                  40                  45

Ile Arg Ile Thr Asp Lys Ala Leu Arg Glu Glu Leu Val Thr Leu Thr
 50                  55                  60

Gly Gly Gln Lys His Val Ala Gln Ala Ala Glu Phe Trp Val Phe Cys
 65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
            100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
```

```
                145                 150                 155                 160
Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
                180                 185                 190

Asp Glu Gln Leu Ala Glu Tyr Tyr Leu Thr Arg Gly Ser Asn Asn Arg
                195                 200                 205

Arg Asp Thr Trp Ser Asp His Ile Arg Arg Thr Ile Ile Glu Glu Ser
210                 215                 220

Ala Pro Phe Ile Leu Asp Tyr Leu His Lys Gln Gly Trp Ala Thr Arg
225                 230                 235                 240

<210> SEQ ID NO 56
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 56

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Ser Tyr Phe Leu Gln Cys Ser Ser Ile
                35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
                100                 105                 110

Gln Asn Ala Leu Ile Ala Ala Glu Ser Leu Gly Leu Gly Gly Val Tyr
                115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
                180                 185                 190

Asp Glu Gln Leu Ala Glu Tyr Tyr Leu Thr Arg Gly Ser Asn Asn Arg
                195                 200                 205

Arg Asp Thr Trp Ser Asp His Ile Arg Arg Thr Ile Ile Lys Glu Ser
                210                 215                 220

Gly Pro Ser Ile Leu Asp Tyr Leu His Lys Gln Gly Trp Ala Thr Arg
225                 230                 235                 240

<210> SEQ ID NO 57
<211> LENGTH: 240
<212> TYPE: PRT
<213> ORGANISM: Escherichia coli
<220> FEATURE:
```

```
<221> NAME/KEY: misc_feature
<223> OTHER INFORMATION: strain W3110

<400> SEQUENCE: 57
```

| Met | Thr | Pro | Thr | Thr | Glu | Leu | Ile | Cys | Gly | His | Arg | Ser | Ile | Arg | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | Thr | Asp | Glu | Pro | Ile | Ser | Glu | Ala | Gln | Arg | Glu | Ala | Ile | Ile | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Ala | Arg | Ala | Thr | Ser | Ser | Tyr | Phe | Leu | Gln | Cys | Ser | Ser | Ile |
|-----|-----|-----|-----|-----|-----|-----|-----|-----|-----|-----|-----|-----|-----|-----|
|     |     | 35  |     |     |     |     | 40  |     |     |     |     | 45  |     |     |

| Ile | Arg | Ile | Thr | Asp | Lys | Ala | Leu | Arg | Glu | Glu | Leu | Val | Thr | Leu | Thr |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Gly | Gly | Gln | Lys | His | Val | Ala | Gln | Ala | Ala | Glu | Phe | Trp | Val | Phe | Cys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ala | Asp | Phe | Asn | Arg | His | Leu | Gln | Ile | Cys | Pro | Asp | Ala | Gln | Leu | Gly |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Leu | Ala | Glu | Gln | Leu | Leu | Leu | Gly | Val | Val | Asp | Thr | Ala | Met | Met | Ala |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Gln | Asn | Ala | Leu | Ile | Ala | Ala | Glu | Ser | Leu | Gly | Leu | Gly | Gly | Val | Tyr |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ile | Gly | Gly | Leu | Arg | Asn | Asn | Ile | Glu | Ala | Val | Thr | Lys | Leu | Leu | Lys |
|-----|-----|-----|-----|-----|-----|-----|-----|-----|-----|-----|-----|-----|-----|-----|-----|
| 130 |     |     |     |     | 135 |     |     |     |     | 140 |     |     |     |     |     |

| Leu | Pro | Gln | His | Val | Leu | Pro | Leu | Phe | Gly | Leu | Cys | Leu | Gly | Trp | Pro |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Ala | Asp | Asn | Pro | Asp | Leu | Lys | Pro | Arg | Leu | Pro | Ala | Ser | Ile | Leu | Val |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| His | Glu | Asn | Ser | Tyr | Gln | Pro | Leu | Asp | Lys | Gly | Ala | Leu | Ala | Gln | Tyr |
|-----|-----|-----|-----|-----|-----|-----|-----|-----|-----|-----|-----|-----|-----|-----|-----|
|     |     |     |     | 180 |     |     |     |     | 185 |     |     |     |     | 190 |     |

| Asp | Glu | Gln | Leu | Ala | Glu | Tyr | Tyr | Leu | Thr | Arg | Gly | Ser | Asn | Asn | Arg |
|-----|-----|-----|-----|-----|-----|-----|-----|-----|-----|-----|-----|-----|-----|-----|-----|
|     |     |     | 195 |     |     |     |     | 200 |     |     |     |     | 205 |     |     |

| Arg | Asp | Thr | Trp | Ser | Asp | His | Ile | Arg | Arg | Thr | Ile | Ile | Lys | Glu | Ser |
|-----|-----|-----|-----|-----|-----|-----|-----|-----|-----|-----|-----|-----|-----|-----|-----|
|     |     | 210 |     |     |     |     | 215 |     |     |     |     | 220 |     |     |     |

| Ala | Pro | Ser | Ile | Leu | Asp | Tyr | Leu | His | Lys | Gln | Gly | Trp | Ala | Thr | Arg |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

```
<210> SEQ ID NO 58
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 58
```

| Met | Met | Pro | Thr | Ile | Glu | Leu | Ile | Cys | Gly | His | Arg | Ser | Ile | Arg | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Phe | Thr | Asp | Glu | Pro | Ile | Ser | Glu | Ala | Gln | Arg | Glu | Ala | Ile | Ile | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ser | Ala | Arg | Ala | Thr | Ser | Ser | Tyr | Phe | Leu | Gln | Cys | Ser | Ser | Ile |
|-----|-----|-----|-----|-----|-----|-----|-----|-----|-----|-----|-----|-----|-----|-----|
|     |     | 35  |     |     |     |     | 40  |     |     |     |     | 45  |     |     |

| Ile | Arg | Ile | Thr | Asp | Lys | Ala | Leu | Arg | Glu | Glu | Leu | Val | Thr | Leu | Thr |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Gly | Gly | Gln | Lys | His | Val | Ala | Gln | Ala | Ala | Glu | Phe | Trp | Val | Phe | Cys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ala | Asp | Phe | Asn | Arg | His | Leu | Gln | Ile | Cys | Pro | Asp | Ala | Gln | Leu | Gly |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

```
Leu Ala Glu Gln Leu Leu Leu Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
    130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
    210                 215                 220

Ala Pro Phe Ile Leu Asp Tyr Leu His Lys Gln Gly Trp Ala Thr Arg
225                 230                 235                 240

<210> SEQ ID NO 59
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 59

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Tyr Phe Leu Gln Cys Ser Ser Ile
        35                  40                  45

Ile Arg Ile Thr Asp Lys Ala Leu Arg Glu Glu Leu Val Thr Leu Thr
    50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Gly Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
    130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
    210                 215                 220
```

```
Ala Pro Ser Ile Leu Asp Tyr Leu His Lys Gln Gly Trp Ala Thr Arg
225                 230                 235                 240

<210> SEQ ID NO 60
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 60

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Ser Tyr Phe Leu Gln Cys Ser Ser Ile
            35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
210                 215                 220

Ala Pro Phe Ile Leu Asp Tyr Leu His Lys Gln Gly Trp Ala Thr Arg
225                 230                 235                 240

<210> SEQ ID NO 61
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 61

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Ser Tyr Phe Leu Gln Cys Ser Ser Ile
            35                  40                  45
```

Ile Arg Ile Thr Asp Lys Ala Leu Arg Glu Glu Leu Val Thr Leu Thr
    50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Met Gly Val Val Asp Thr Ala Met Met Ala
                100                 105                 110

Gln Asn Ala Leu Ile Ala Ala Glu Ser Leu Gly Leu Gly Gly Val Tyr
                115                 120                 125

Ile Gly Gly Leu Arg Asn Asn Ile Glu Ala Val Thr Lys Leu Leu Lys
                130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
                180                 185                 190

Asp Glu Gln Leu Ala Glu Tyr Tyr Leu Thr Arg Gly Ser Asn Asn Arg
                195                 200                 205

Arg Asp Thr Trp Ser Asp His Ile Arg Arg Thr Ile Ile Lys Glu Ser
210                 215                 220

Pro Pro Ser Ile Leu Asp Tyr Leu His Lys Gln Gly Trp Ala Thr Arg
225                 230                 235                 240

<210> SEQ ID NO 62
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 62

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Ser Tyr Phe Leu Gln Cys Ser Ser Ile
            35                  40                  45

Ile Arg Ile Thr Asp Lys Ala Leu Arg Glu Glu Leu Val Thr Leu Thr
    50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Gly Gln Leu Leu Met Gly Val Val Asp Thr Ala Met Met Ala
                100                 105                 110

Gln Asn Ala Leu Ile Ala Ala Glu Ser Leu Gly Leu Gly Gly Val Tyr
                115                 120                 125

Ile Gly Gly Leu Arg Asn Asn Ile Glu Ala Val Thr Lys Leu Leu Lys
                130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val

```
            165                 170                 175
His Glu Asn Ser Tyr Gln Pro Leu Asp Lys Gly Ala Leu Ala Gln Tyr
                180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Lys Glu Ser
210                 215                 220

Arg Pro Ser Ile Leu Asp Tyr Leu His Lys Gln Gly Trp Ala Thr Arg
225                 230                 235                 240

<210> SEQ ID NO 63
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 63

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Tyr Phe Leu Gln Cys Ser Ser Ile
        35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Gly Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
210                 215                 220

Pro Pro Ser Ile Leu Asp Tyr Leu His Lys Gln Gly Trp Ala Thr Arg
225                 230                 235                 240

<210> SEQ ID NO 64
<211> LENGTH: 240
<212> TYPE: PRT
<213> ORGANISM: Escherichia coli
<220> FEATURE:
<221> NAME/KEY: misc_feature
<223> OTHER INFORMATION: strain W3110
```

<400> SEQUENCE: 64

Met Thr Pro Thr Thr Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Phe Leu Gln Cys Ser Ser Ile
        35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
210                 215                 220

Arg Pro Phe Ile Leu Asp Tyr Leu His Lys Gln Gly Trp Ala Thr Arg
225                 230                 235                 240

<210> SEQ ID NO 65
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 65

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Tyr Phe Leu Gln Cys Ser Ser Ile
        35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
            100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
    130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
    210                 215                 220

Arg Pro Phe Ile Leu Asp Tyr Leu His Lys Gln Gly Trp Ala Thr Arg
225                 230                 235                 240

<210> SEQ ID NO 66
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 66

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Tyr Phe Leu Gln Cys Ser Ser Ile
        35                  40                  45

Ile Arg Ile Thr Asp Lys Ala Leu Arg Glu Glu Leu Val Thr Leu Thr
    50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Gly Gln Leu Leu Leu Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
    130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
    210                 215                 220

Arg Pro Phe Ile Leu Asp Tyr Leu His Lys Gln Gly Trp Ala Thr Arg
225                 230                 235                 240

<210> SEQ ID NO 67
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 67

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Phe Leu Gln Cys Ser Ser Ile
        35                  40                  45

Ile Arg Ile Thr Asp Lys Ala Leu Arg Glu Glu Leu Val Thr Leu Thr
    50                  55                  60

Gly Gly Gln Lys His Val Ala Gln Ala Glu Phe Trp Val Phe Cys
65              70                  75                  80

Ala Asp Phe Asn Arg His Leu Gln Ile Cys Pro Asp Ala Gln Leu Gly
            85                  90                  95

Leu Ala Glu Gln Leu Leu Met Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
    130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
            165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
    210                 215                 220

Arg Pro Phe Ile Leu Asp Tyr Leu His Lys Gln Gly Trp Ala Thr Arg
225                 230                 235                 240

<210> SEQ ID NO 68
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 68

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Phe Leu Gln Cys Ser Ser Ile
        35                  40                  45

Ile Arg Ile Thr Asp Lys Ala Leu Arg Glu Glu Leu Val Thr Leu Thr
    50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
            100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Glu Glu Ser
210                 215                 220

Arg Pro Phe Ile Leu Asp Tyr Leu His Lys Gln Gly Trp Ala Thr Arg
225                 230                 235                 240

<210> SEQ ID NO 69
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 69

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Ser Phe Leu Gln Cys Ser Ser Ile
            35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
            100                 105                 110

Gln Asn Ala Leu Ile Ala Ala Glu Ser Leu Gly Leu Gly Gly Val Tyr
            115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr

```
                180                 185                 190
Asp Glu Gln Leu Ala Glu Tyr Tyr Leu Thr Arg Gly Ser Asn Asn Arg
            195                 200                 205

Arg Asp Thr Trp Ser Asp His Ile Arg Arg Thr Ile Ile Lys Glu Ser
        210                 215                 220

Ala Pro Phe Ile Leu Asp Tyr Leu His Lys Gln Gly Trp Ala Thr Arg
225                 230                 235                 240

<210> SEQ ID NO 70
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 70

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
            20                  25                  30

Ser Ala Arg Ala Thr Ser Ser Ser Phe Leu Gln Cys Ser Ser Ile
        35                  40                  45

Ile Arg Ile Thr Asp Lys Ala Leu Arg Glu Glu Leu Val Thr Leu Thr
50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
            100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
            180                 185                 190

Asp Glu Gln Leu Ala Glu Tyr Tyr Leu Thr Arg Gly Ser Asn Asn Arg
        195                 200                 205

Arg Asp Thr Trp Ser Asp His Ile Arg Arg Thr Ile Ile Lys Glu Ser
    210                 215                 220

Gly Pro Phe Ile Leu Asp Tyr Leu His Lys Gln Gly Trp Ala Thr Arg
225                 230                 235                 240

<210> SEQ ID NO 71
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 71

Met Thr Pro Thr Ile Glu Leu Ile Cys Gly His Arg Ser Ile Arg His
```

```
            1               5                    10                   15
          Phe Thr Asp Glu Pro Ile Ser Glu Ala Gln Arg Glu Ala Ile Ile Asn
                          20                   25                   30

Ser Ala Arg Ala Thr Ser Ser Ser Phe Leu Gln Cys Ser Ser Ile
                      35                   40                   45

Ile Arg Ile Thr Asp Lys Ala Leu Arg Glu Glu Leu Val Thr Leu Thr
                          50                   55                   60

Gly Gly Gln Lys His Val Ala Gln Ala Ala Glu Phe Trp Val Phe Cys
          65                      70                   75                   80

Ala Asp Phe Asn Arg His Leu Gln Ile Cys Pro Asp Ala Gln Leu Gly
                              85                   90                   95

Leu Ala Glu Gln Leu Leu Leu Gly Val Val Asp Thr Ala Met Met Ala
                          100                  105                  110

Gln Asn Ala Leu Ile Ala Ala Glu Ser Leu Gly Leu Gly Gly Val Tyr
                          115                  120                  125

Ile Gly Gly Leu Arg Asn Asn Ile Glu Ala Val Thr Lys Leu Leu Lys
          130                     135                  140

Leu Pro Gln His Val Leu Pro Leu Phe Gly Leu Cys Leu Gly Trp Pro
          145                     150                  155                  160

Ala Asp Asn Pro Asp Leu Lys Pro Arg Leu Pro Ala Ser Ile Leu Val
                          165                  170                  175

His Glu Asn Ser Tyr Gln Pro Leu Asp Lys Gly Ala Leu Ala Gln Tyr
                          180                  185                  190

Asp Glu Gln Leu Ala Glu Tyr Tyr Leu Thr Arg Gly Ser Asn Asn Arg
                      195                  200                  205

Arg Asp Thr Trp Ser Asp His Ile Arg Arg Thr Ile Ile Lys Glu Ser
          210                     215                  220

Pro Pro Phe Ile Leu Asp Tyr Leu His Lys Gln Gly Trp Ala Thr Arg
          225                     230                  235                  240

<210> SEQ ID NO 72
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 72

Met Thr Pro Thr Ile Glu Leu Ile Cys Gly His Arg Ser Ile Arg His
1               5                    10                   15

Phe Thr Asp Glu Pro Ile Ser Glu Ala Gln Arg Glu Ala Ile Ile Asn
                20                   25                   30

Ser Ala Arg Ala Thr Ser Ser Ser Phe Leu Gln Cys Ser Ser Ile
            35                   40                   45

Ile Arg Ile Thr Asp Lys Ala Leu Arg Glu Glu Leu Val Thr Leu Thr
                50                   55                   60

Gly Gly Gln Lys His Val Ala Gln Ala Ala Glu Phe Trp Val Phe Cys
65                      70                   75                   80

Ala Asp Phe Asn Arg His Leu Gln Ile Cys Pro Asp Ala Gln Leu Gly
                    85                   90                   95

Leu Ala Glu Gln Leu Leu Leu Gly Val Val Asp Thr Ala Met Met Ala
                100                  105                  110

Gln Asn Ala Leu Ile Ala Ala Glu Ser Leu Gly Leu Gly Gly Val Tyr
                115                  120                  125
```

```
Ile Gly Gly Leu Arg Asn Asn Ile Glu Ala Val Thr Lys Leu Leu Lys
        130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
                180                 185                 190

Asp Glu Gln Leu Ala Glu Tyr Tyr Leu Thr Arg Gly Ser Asn Asn Arg
                195                 200                 205

Arg Asp Thr Trp Ser Asp His Ile Arg Arg Thr Ile Ile Lys Glu Ser
        210                 215                 220

Arg Pro Ser Ile Leu Asp Tyr Leu His Lys Gln Gly Trp Ala Thr Arg
225                 230                 235                 240

<210> SEQ ID NO 73
<211> LENGTH: 240
<212> TYPE: PRT
<213> ORGANISM: Escherichia coli
<220> FEATURE:
<221> NAME/KEY: misc_feature
<223> OTHER INFORMATION: strain W3110

<400> SEQUENCE: 73

Met Thr Pro Thr Ile Glu Leu Ile Cys Gly His Arg Ser Ile Arg His
1               5                   10                  15

Phe Thr Asp Glu Pro Ile Ser Glu Ala Gln Arg Glu Ala Ile Ile Asn
                20                  25                  30

Ser Ala Arg Ala Thr Ser Ser Ser Phe Leu Gln Cys Ser Ser Ile
        35                  40                  45

Ile Arg Ile Thr Asp Lys Ala Leu Arg Glu Glu Leu Val Thr Leu Thr
        50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Ala
                100                 105                 110

Gln Asn Ala Leu Ile Ala Ala Glu Ser Leu Gly Leu Gly Gly Val Tyr
        115                 120                 125

Ile Gly Gly Leu Arg Asn Asn Ile Glu Ala Val Thr Lys Leu Leu Lys
        130                 135                 140

Leu Pro Gln His Val Leu Pro Leu Phe Gly Leu Cys Leu Gly Trp Pro
145                 150                 155                 160

Ala Asp Asn Pro Asp Leu Lys Pro Arg Leu Pro Ala Ser Ile Leu Val
                165                 170                 175

His Glu Asn Ser Tyr Gln Pro Leu Asp Lys Gly Ala Leu Ala Gln Tyr
                180                 185                 190

Asp Glu Gln Leu Ala Glu Tyr Tyr Leu Thr Arg Gly Ser Asn Asn Arg
                195                 200                 205

Arg Asp Thr Trp Ser Asp His Ile Arg Arg Thr Ile Ile Lys Glu Ser
        210                 215                 220

Arg Pro Phe Ile Val Asp Tyr Leu His Lys Gln Gly Trp Ala Thr Arg
225                 230                 235                 240

<210> SEQ ID NO 74
```

-continued

```
<211> LENGTH: 240
<212> TYPE: PRT
<213> ORGANISM: Vibrio vulnificus
<220> FEATURE:
<221> NAME/KEY: misc_feature
<223> OTHER INFORMATION: NZ isolate

<400> SEQUENCE: 74
```

Met Asn Ala Val Ile Asp Thr Leu Leu Ser His Arg Ser Ile Arg Lys
1               5                   10                  15

Phe Thr Asp Gln Ala Ile Thr Pro Glu Gln Leu Asp Thr Ile Ile Arg
            20                  25                  30

Thr Gly Leu Ala Ala Ser Ser Ser Leu Leu Gln Val Val Ser Ile
        35                  40                  45

Ile Arg Ile Thr Asp Pro Ala Lys Arg Gln Gln Leu Ala Glu Leu Ala
    50                  55                  60

Gly Pro Gln His Tyr Val Glu Thr Ala Ala Glu Phe Leu Val Phe Cys
65                  70                  75                  80

Ile Asp Tyr Gln Arg His Ala Thr Leu Asn Ser Glu Val Gln Ala Gly
                85                  90                  95

Phe Thr Glu Leu Thr Leu Ile Gly Ala Val Asp Ala Gly Ile Met Ala
            100                 105                 110

Gln Asn Cys Leu Leu Ala Ala Glu Ser Met Gly Leu Gly Gly Val Tyr
        115                 120                 125

Ile Gly Gly Leu Arg Asn Lys Ala Ala Glu Val Asp Ala Leu Leu Glu
    130                 135                 140

Leu Pro Pro Phe Ser Ala Val Leu Phe Gly Met Cys Leu Gly His Pro
145                 150                 155                 160

Asp Gln Asp Pro Asp Leu Lys Pro Arg Leu Pro Ala Glu Val Ile Leu
                165                 170                 175

His Glu Asn His Tyr Gln Pro Leu Asp Leu Asn Lys Val Glu Gln Tyr
            180                 185                 190

Asp Gln Thr Met Leu Asp Tyr Tyr Gly Lys Arg Ser Ser Asn Gln Lys
        195                 200                 205

Gln Ala Ser Trp Ser Glu Gln Val Thr Gly Lys Leu Ala Gly Glu Ser
    210                 215                 220

Arg Pro His Ile Leu Pro Tyr Leu His Ser Lys Gly Leu Ala Thr Lys
225                 230                 235                 240

```
<210> SEQ ID NO 75
<211> LENGTH: 240
<212> TYPE: PRT
<213> ORGANISM: Vibrio vulnificus
<220> FEATURE:
<221> NAME/KEY: misc_feature
<223> OTHER INFORMATION: NZ isolate

<400> SEQUENCE: 75
```

Met Asn Ala Val Ile Asp Thr Leu Leu Ser His Arg Ser Ile Arg Lys
1               5                   10                  15

Phe Thr Asp Gln Ala Ile Thr Pro Glu Gln Leu Asp Thr Ile Ile Arg
            20                  25                  30

Ala Gly Leu Ala Ala Ser Ser Ser Cys Leu Gln Val Val Ser Ile
        35                  40                  45

Ile Arg Ile Thr Asp Pro Ala Lys Arg Gln Gln Leu Ala Glu Leu Ala
    50                  55                  60

Gly Pro Gln His Tyr Val Glu Thr Ala Ala Glu Phe Leu Val Phe Cys
65                  70                  75                  80

```
Ile Asp Tyr Gln Arg His Ala Thr Leu Asn Ser Glu Val Gln Ala Gly
                85                  90                  95

Phe Thr Glu Leu Thr Leu Ile Gly Ala Val Asp Ala Gly Ile Met Ala
            100                 105                 110

Gln Asn Cys Leu Leu Ala Ala Glu Ser Met Gly Leu Gly Gly Val Tyr
        115                 120                 125

Ile Gly Gly Leu Arg Asn Lys Ala Ala Glu Val Asp Ala Leu Leu Glu
    130                 135                 140

Leu Pro Pro Phe Ser Ala Val Leu Phe Gly Met Cys Leu Gly His Pro
145                 150                 155                 160

Asp Gln Asp Pro Asp Leu Lys Pro Arg Leu Pro Ala Glu Val Ile Leu
                165                 170                 175

His Glu Asn His Tyr Gln Pro Leu Asp Leu Asn Lys Val Glu Gln Tyr
            180                 185                 190

Asp Gln Thr Met Leu Asp Tyr Tyr Gly Lys Arg Ser Ser Asn Gln Lys
        195                 200                 205

Gln Ala Ser Trp Ser Glu Gln Val Thr Gly Lys Leu Ala Gly Glu Ser
    210                 215                 220

Arg Pro His Ile Leu Pro Tyr Leu His Ser Lys Gly Leu Ala Thr Lys
225                 230                 235                 240

<210> SEQ ID NO 76
<211> LENGTH: 240
<212> TYPE: PRT
<213> ORGANISM: Vibrio vulnificus
<220> FEATURE:
<221> NAME/KEY: misc_feature
<223> OTHER INFORMATION: NZ isolate

<400> SEQUENCE: 76

Met Asn Ala Val Ile Asp Thr Leu Leu Ser His Arg Ser Ile Arg Lys
1               5                   10                  15

Phe Thr Asp Gln Ala Ile Thr Pro Glu Gln Leu Asp Thr Ile Ile Arg
            20                  25                  30

Ala Gly Leu Ala Ala Ser Ser Ser Met Leu Gln Val Val Ser Ile
        35                  40                  45

Ile Arg Ile Thr Asp Pro Ala Lys Arg Gln Gln Leu Ala Glu Leu Ala
    50                  55                  60

Gly Pro Gln His Tyr Val Glu Thr Ala Ala Glu Phe Leu Val Phe Cys
65                  70                  75                  80

Ile Asp Tyr Gln Arg His Ala Thr Leu Asn Ser Glu Val Gln Ala Gly
                85                  90                  95

Phe Thr Glu Leu Thr Leu Ile Gly Ala Val Asp Ala Gly Ile Met Ala
            100                 105                 110

Gln Asn Cys Leu Leu Ala Ala Glu Ser Met Gly Leu Gly Gly Val Tyr
        115                 120                 125

Ile Gly Gly Leu Arg Asn Lys Ala Ala Glu Val Asp Ala Leu Leu Glu
    130                 135                 140

Leu Pro Pro Phe Ser Ala Val Leu Phe Gly Met Cys Leu Gly His Pro
145                 150                 155                 160

Asp Gln Asp Pro Asp Leu Lys Pro Arg Leu Pro Ala Glu Val Ile Leu
                165                 170                 175

His Glu Asn His Tyr Gln Pro Leu Asp Leu Asn Lys Val Glu Gln Tyr
            180                 185                 190

Asp Gln Thr Met Leu Asp Tyr Tyr Gly Lys Arg Ser Ser Asn Gln Lys
```

195                 200                 205
Gln Ala Ser Trp Ser Glu Gln Val Thr Gly Lys Leu Ala Gly Glu Ser
    210                 215                 220

Arg Pro His Ile Leu Pro Tyr Leu His Ser Lys Gly Leu Ala Thr Lys
225                 230                 235                 240

<210> SEQ ID NO 77
<211> LENGTH: 240
<212> TYPE: PRT
<213> ORGANISM: Vibrio vulnificus
<220> FEATURE:
<221> NAME/KEY: misc_feature
<223> OTHER INFORMATION: NZ isolate

<400> SEQUENCE: 77

Met Asn Ala Val Ile Asp Thr Leu Leu Ser His Arg Ser Ile Arg Lys
1               5                   10                  15

Phe Thr Asp Gln Ala Ile Thr Pro Glu Gln Leu As

```
                20                  25                  30

Ala Gly Leu Ala Ala Ser Ser Ser Leu Leu Gln Val Val Ser Ile
            35                  40                  45

Ile Arg Ile Thr Asp Pro Ala Lys Arg Gln Gln Leu Ala Glu Leu Ala
    50                  55                  60

Gly Pro Gln His Tyr Val Glu Thr Ala Ala Glu Phe Leu Val Phe Cys
65                  70                  75                  80

Ile Asp Tyr Gln Arg His Ala Thr Leu Asn Ser Glu Val Gln Ala Gly
                85                  90                  95

Phe Thr Glu Leu Thr Leu Ile Gly Ala Val Asp Ala Gly Ile Met Ala
            100                 105                 110

Gln Asn Cys Leu Leu Ala Ala Glu Ser Met Gly Leu Gly Gly Val Tyr
        115                 120                 125

Ile Gly Gly Leu Arg Asn Lys Ala Ala Glu Val Asp Ala Leu Leu Glu
    130                 135                 140

Leu Pro Pro Phe Ser Ala Val Leu Phe Gly Met Cys Leu Gly His Pro
145                 150                 155                 160

Asp Gln Asp Pro Asp Leu Lys Pro Arg Leu Pro Ala Glu Val Ile Leu
                165                 170                 175

His Ala Asn His Tyr Gln Pro Leu Asp Leu Asn Lys Val Glu Gln Tyr
            180                 185                 190

Asp Gln Thr Met Leu Asp Tyr Tyr Gly Lys Arg Ser Ser Asn Gln Lys
        195                 200                 205

Gln Ala Ser Trp Ser Glu Gln Val Thr Gly Lys Leu Ala Gly Glu Ser
    210                 215                 220

Arg Pro His Ile Leu Pro Tyr Leu His Ser Lys Gly Leu Ala Thr Lys
225                 230                 235                 240

<210> SEQ ID NO 79
<211> LENGTH: 240
<212> TYPE: PRT
<213> ORGANISM: Vibrio vulnificus
<220> FEATURE:
<221> NAME/KEY: misc_feature
<223> OTHER INFORMATION: NZ isolate

<400> SEQUENCE: 79

Met Asn Ala Val Ile Asp Thr Leu Leu Ser His Arg Ser Ile Arg Lys
1               5                   10                  15

Phe Thr Asp Gln Ala Ile Thr Pro Glu Gln Leu Asp Thr Ile Ile Arg
            20                  25                  30

Ala Gly Leu Ala Ala Ser Ser Ser Leu Leu Gln Val Val Ser Ile
            35                  40                  45

Ile Arg Ile Thr Asp Pro Ala Lys Arg Gln Gln Leu Ala Glu Leu Ala
    50                  55                  60

Gly Pro Gln His Tyr Val Glu Thr Ala Ala Glu Phe Leu Val Phe Cys
65                  70                  75                  80

Ile Asp Tyr Gln Arg His Ala Thr Leu Asn Ser Glu Val Gln Ala Gly
                85                  90                  95

Phe Thr Glu Leu Thr Leu Ile Gly Ala Val Asp Ala Gly Ile Met Ala
            100                 105                 110

Gln Asn Cys Leu Leu Ala Ala Glu Ser Met Gly Leu Gly Gly Val Tyr
        115                 120                 125

Ile Gly Gly Leu Arg Asn Lys Ala Ala Glu Val Asp Ala Leu Leu Glu
    130                 135                 140
```

```
Leu Pro Pro Phe Ser Ala Val Leu Phe Gly Met Cys Leu Gly His Pro
145                 150                 155                 160

Asp Gln Asp Pro Asp Leu Lys Pro Arg Leu Pro Ala Glu Val Ile Leu
            165                 170                 175

His Glu Asn His Tyr Gln Pro Leu Asp Leu Asn Lys Val Glu Gln Tyr
            180                 185                 190

Asp Gln Thr Met Leu Asp Tyr Tyr Gly Lys Arg Ser Ser Asn Gln Lys
            195                 200                 205

Gln Ala Ser Trp Ser Glu Gln Val Thr Gly Lys Asp Ala Gly Glu Ser
    210                 215                 220

Arg Pro His Ile Leu Pro Tyr Leu His Ser Lys Gly Leu Ala Thr Lys
225                 230                 235                 240

<210> SEQ ID NO 80
<211> LENGTH: 239
<212> TYPE: PRT
<213> ORGANISM: Vibrio vulnificus
<220> FEATURE:
<221> NAME/KEY: misc_feature
<223> OTHER INFORMATION: NZ isolate

<400> SEQUENCE: 80

Met Asn Ala Val Ile Asp Thr Leu Leu Ser His Arg Ser Ile Arg Lys
1               5                   10                  15

Phe Thr Asp Gln Ala Ile Thr Pro Glu Gln Leu Asp Thr Ile Ile Arg
            20                  25                  30

Ala Gly Leu Ala Ala Ser Ser Ser Leu Leu Gln Val Val Ser

```
<220> FEATURE:
<221> NAME/KEY: misc_feature
<223> OTHER INFORMATION: NZ isolate

<400> SEQUENCE: 81

Met Asn Ala Val Ile Asp Thr Leu Leu Ser His Arg Ser Ile Arg Lys
1               5                   10                  15

Phe Thr Asp Gln Ala Ile Thr Pro Glu Gln Leu Asp Thr Ile Ile Arg
                20                  25                  30

Ala Gly Leu Ala Ala Ser Ser Ser Leu Leu Gln Val Val Ser Ile
            35                  40                  45

Ile Arg Ile Thr Asp Pro Ala Lys Arg Gln Gln Leu Ala Glu Leu Ala
50                  55                  60

Gly Pro Gln His Tyr Val Glu Thr Ala Ala Glu Phe Leu Val Phe Cys
65                  70                  75                  80

Ile Asp Tyr Gln Arg His Ala Thr Leu Asn Ser Glu Val Gln Ala Gly
                85                  90                  95

Phe Thr Glu Leu Thr Leu Ile Gly Ala Val Asp Ala Gly Ile Met Ala
                100                 105                 110

Gln Asn Cys Leu Leu Ala Ala Glu Ser Met Gly Leu Gly Val Tyr
            115                 120                 125

Ile Gly Gly Leu Arg Asn Lys Ala Ala Glu Val Asp Ala Leu Leu Glu
130                 135                 140

Leu Pro Pro Phe Ser Ala Val Leu Phe Gly Met Cys Leu Gly His Pro
145                 150                 155                 160

Asp Gln Asp Pro Asp Leu Lys Pro Arg Leu Pro Ala Glu Val Ile Leu
                165                 170                 175

His Glu Asn His Tyr Gln Pro Leu Asp Leu Asn Lys Val Glu Gln Tyr
            180                 185                 190

Asp Gln Thr Met Leu Asp Tyr Tyr Gly Lys Arg Ser Ser Asn Gln Lys
            195                 200                 205

Gln Ala Ser Trp Ser Glu Gln Val Thr Gly Lys Leu Ala Gly Glu Val
    210                 215                 220

Arg Pro His Ile Leu Pro Tyr Leu His Ser Lys Gly Leu Ala Thr Lys
225                 230                 235                 240

<210> SEQ ID NO 82
<211> LENGTH: 240
<212> TYPE: PRT
<213> ORGANISM: Vibrio vulnificus
<220> FEATURE:
<221> NAME/KEY: misc_feature
<223> OTHER INFORMATION: NZ isolate

<400> SEQUENCE: 82

Met Asn Ala Val Ile Asp Thr Leu Leu Ser His Arg Ser Ile Arg Lys
1               5                   10                  15

Phe Thr Asp Gln Ala Ile Thr Pro Glu Gln Leu Asp Thr Ile Ile Arg
                20                  25                  30

Ala Gly Leu Ala Ala Ser Ser Ser Leu Leu Gln Val Val Ser Ile
            35                  40                  45

Ile Arg Ile Thr Asp Pro Ala Lys Arg Gln Gln Leu Ala Glu Leu Ala
50                  55                  60

Gly Pro Gln His Tyr Val Glu Thr Ala Ala Glu Phe Leu Val Phe Cys
65                  70                  75                  80

Ile Asp Tyr Gln Arg His Ala Thr Leu Asn Ser Glu Val Gln Ala Gly
                85                  90                  95
```

```
Phe Thr Glu Leu Thr Leu Ile Gly Ala Val Asp Ala Gly Ile Met Ala
                100                 105                 110

Gln Asn Cys Leu Leu Ala Ala Glu Ser Met Gly Leu Gly Gly Val Tyr
            115                 120                 125

Ile Gly Gly Leu Arg Asn Lys Ala Ala Glu Val Asp Ala Leu Leu Glu
        130                 135                 140

Leu Pro Pro Phe Ser Ala Val Leu Phe Gly Met Cys Leu Gly His Pro
145                 150                 155                 160

Asp Gln Asp Pro Asp Leu Lys Pro Arg Leu Pro Ala Glu Val Ile Leu
                165                 170                 175

His Glu Asn His Tyr Gln Pro Leu Asp Leu Asn Lys Val Glu Gln Tyr
            180                 185                 190

Asp Gln Thr Met Leu Asp Tyr Tyr Gly Lys Arg Ser Ser Asn Gln Lys
        195                 200                 205

Gln Ala Ser Trp Ser Glu Gln Val Thr Gly Lys Leu Ala Gly Glu Asp
    210                 215                 220

Arg Pro His Ile Leu Pro Tyr Leu His Ser Lys Gly Leu Ala Thr Lys
225                 230                 235                 240

<210> SEQ ID NO 83
<211> LENGTH: 240
<212> TYPE: PRT
<213> ORGANISM: Salmonella enterica
<220> FEATURE:
<221> NAME/KEY: misc_feature
<223> OTHER INFORMATION: serovar Typhi Ty2

<400> SEQUENCE: 83

Met Ser Pro Thr Ile Glu Leu Leu Cys Gly His Arg Ser Ile Arg His
1               5                   10                  15

Phe Thr Asp Glu Pro Val Thr Asp Ala Gln Arg Glu Ala Ile Ile Ala
                20                  25                  30

Ala Ala Arg Ser Thr Ser Ser Ser Phe Leu Gln Cys Ser Ser Ile
            35                  40                  45

Phe Arg Ile Thr Asp Arg Ala Leu Arg Glu Ala Leu Val Pro Leu Thr
        50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Gly
            100                 105                 110

Gln Asn Ala Leu Thr Ala Ala Glu Ser Leu Gly Leu Gly Gly Val Tyr
        115                 120                 125

Ile Ser Gly Ile Arg Asn Asn Ile Glu Ser Val Thr Glu Leu Leu Lys
    130                 135                 140

Leu Pro Lys His Val Leu Pro Leu Phe Gly Leu Cys Leu Gly Trp Pro
145                 150                 155                 160

Ala Asp Asn Pro Asp Leu Lys Pro Arg Leu Pro Ala Glu Leu Val Val
                165                 170                 175

His Glu Asn Gln Tyr Gln Pro Leu Asp Glu Lys Leu Leu Ala Arg Tyr
            180                 185                 190

Asp Glu Gln Leu Ala Glu Tyr Tyr Leu Thr Arg Gly Ser Asn Thr Arg
        195                 200                 205

Arg Asp Thr Trp Ser Asp His Ile Arg Arg Thr Leu Ile Lys Glu Asn
```

Arg Pro Phe Ile Leu Glu Tyr Leu His Lys Gln Gly Trp Ala Thr Arg
225                 230                 235                 240

<210> SEQ ID NO 84
<211> LENGTH: 240
<212> TYPE: PRT
<213> ORGANISM: Salmonella enterica
<220> FEATURE:
<221> NAME/KEY: misc_feature
<223> OTHER INFORMATION: serovar Typhi Ty2

<400> SEQUENCE: 84

Met Ser Pro Thr Ile Glu Leu Leu Cys Gly His Arg Ser Ile Arg His
1               5                   10                  15

Phe Thr Asp Glu Pro Val Thr Asp Ala Gln Arg Glu Ala Ile Ile Ala
            20                  25                  30

Ala Ala Arg Ser Thr Ser Ser Ser Phe Leu Gln Cys Ser Ser Ile
        35                  40                  45

Ile Arg Ile Thr Asp Arg Ala Leu Arg Glu Ala Leu Val Pro Leu Thr
    50                  55                  60

Gly Gly Gln Lys His Val Ala Gln Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Gly Val Val Asp Thr Ala Met Met Gly
            100                 105                 110

Gln Asn Ala Leu Thr Ala Ala Glu Ser Leu Gly Leu Gly Val Tyr
        115                 120                 125

Ile Gly Gly Ile Arg Asn Asn Ile Glu Ser Val Thr Glu Leu Leu Lys
    130                 135                 140

Leu Pro Lys His Val Leu Pro Leu Phe Gly Leu Cys Leu Gly Trp Pro
145                 150                 155                 160

Ala Asp Asn Pro Asp Leu Lys Pro Arg Leu Pro Ala Glu Leu Val Val
                165                 170                 175

His Glu Asn Gln Tyr Gln Pro Leu Asp Glu Lys Leu Leu Ala Arg Tyr
            180                 185                 190

Asp Glu Gln Leu Ala Glu Tyr Tyr Leu Thr Arg Gly Ser Asn Thr Arg
        195                 200                 205

Arg Asp Thr Trp Ser Asp His Ile Arg Arg Thr Leu Ile Lys Glu Asn
    210                 215                 220

Arg Pro Phe Ile Leu Glu Tyr Leu His Lys Gln Gly Trp Ala Thr Arg
225                 230                 235                 240

<210> SEQ ID NO 85
<211> LENGTH: 240
<212> TYPE: PRT
<213> ORGANISM: Salmonella enterica
<220> FEATURE:
<221> NAME/KEY: misc_feature
<223> OTHER INFORMATION: serovar Typhi Ty2

<400> SEQUENCE: 85

Met Ser Pro Thr Ile Glu Leu Leu Cys Gly His Arg Ser Ile Arg His
1               5                   10                  15

Phe Thr Asp Glu Pro Val Thr Asp Ala Gln Arg Glu Ala Ile Ile Ala
            20                  25                  30

Ala Ala Arg Ser Thr Ser Ser Ser Phe Leu Gln Cys Ser Ser Ile

```
                35                  40                  45
Ile Arg Ile Thr Asp Arg Ala Leu Arg Glu Ala Leu Val Pro Leu Thr
 50                  55                  60
Gly Gly Gln Lys His Val Ala Gln Ala Ala Glu Phe Trp Val Phe Cys
 65                  70                  75                  80
Ala Asp Phe Asn Arg His Leu Gln Ile Cys Pro Asp Ala Gln Leu Gly
                 85                  90                  95
Leu Ala Glu Gln Leu Leu Leu Gly Val Val Asp Thr Ala Met Met Gly
                100                 105                 110
Gln Asn Ala Leu Thr Ala Ala Glu Ser Leu Gly Leu Gly Gly Val Tyr
                115                 120                 125
Ile Ser Gly Ile Ser Asn Asn Ile Glu Ser Val Thr Glu Leu Leu Lys
130                 135                 140
Leu Pro Lys His Val Leu Pro Leu Phe Gly Leu Cys Leu Gly Trp Pro
145                 150                 155                 160
Ala Asp Asn Pro Asp Leu Lys Pro Arg Leu Pro Ala Glu Leu Val Val
                165                 170                 175
His Glu Asn Gln Tyr Gln Pro Leu Asp Glu Lys Leu Leu Ala Arg Tyr
                180                 185                 190
Asp Glu Gln Leu Ala Glu Tyr Tyr Leu Thr Arg Gly Ser Asn Thr Arg
                195                 200                 205
Arg Asp Thr Trp Ser Asp His Ile Arg Arg Thr Leu Ile Lys Glu Asn
210                 215                 220
Arg Pro Phe Ile Leu Glu Tyr Leu His Lys Gln Gly Trp Ala Thr Arg
225                 230                 235                 240

<210> SEQ ID NO 86
<211> LENGTH: 240
<212> TYPE: PRT
<213> ORGANISM: Salmonella enterica
<220> FEATURE:
<221> NAME/KEY: misc_feature
<223> OTHER INFORMATION: serovar Typhi Ty2

<400> SEQUENCE: 86

Met Ser Pro Thr Ile Glu Leu Leu Cys Gly His Arg Ser Ile Arg His
 1                5                  10                  15
Phe Thr Asp Glu Pro Val Thr Asp Ala Gln Arg Glu Ala Ile Ile Ala
                 20                  25                  30
Ala Ala Arg Ser Thr Ser Ser Ser Phe Leu Gln Cys Ser Ser Ile
                 35                  40                  45
Ile Arg Ile Thr Asp Arg Ala Leu Arg Glu Ala Leu Val Pro Leu Thr
 50                  55                  60
Gly Gly Gln Lys His Val Ala Gln Ala Ala Glu Phe Trp Val Phe Cys
 65                  70                  75                  80
Ala Asp Phe Asn Arg His Leu Gln Ile Cys Pro Asp Ala Gln Leu Gly
                 85                  90                  95
Leu Ala Glu Gln Leu Leu Leu Gly Val Val Asp Thr Ala Met Met Gly
                100                 105                 110
Gln Asn Ala Leu Thr Ala Ala Glu Ser Leu Gly Leu Gly Gly Val Tyr
                115                 120                 125
Ile Ser Gly Ile Arg Asn Asn Ile Glu Ser Val Thr Glu Leu Leu Lys
130                 135                 140
Leu Pro Lys His Val Leu Pro Leu Phe Gly Leu Cys Leu Gly Trp Pro
145                 150                 155                 160
```

Ala Asp Asn Pro Asp Leu Lys Pro Arg Leu Pro Ala Glu Leu Val Val
            165                 170                 175

His Glu Asn Gln Tyr Gln Pro Leu Asp Glu Lys Leu Leu Ala Arg Tyr
            180                 185                 190

Asp Glu Gln Leu Ala Glu Tyr Tyr Leu Thr Arg Ala Ser Asn Thr Arg
            195                 200                 205

Arg Asp Thr Trp Ser Asp His Ile Arg Arg Thr Leu Ile Lys Glu Asn
210                 215                 220

Arg Pro Phe Ile Leu Glu Tyr Leu His Lys Gln Gly Trp Ala Thr Arg
225                 230                 235                 240

<210> SEQ ID NO 87
<211> LENGTH: 240
<212> TYPE: PRT
<213> ORGANISM: Salmonella enterica
<220> FEATURE:
<221> NAME/KEY: misc_feature
<223> OTHER INFORMATION: serovar Typhi Ty2

<400> SEQUENCE: 87

Met Ser Pro Thr Ile Glu Leu Leu Cys Gly His Arg Ser Ile Arg His
1               5                   10                  15

Phe Thr Asp Glu Pro Val Thr Asp Ala Gln Arg Glu Ala Ile Ile Ala
            20                  25                  30

Ala Ala Arg Ser Thr Ser Ser Ser Phe Leu Gln Cys Ser Ser Ile
        35                  40                  45

Ile Arg Ile Thr Asp Arg Ala Leu Arg Glu Ala Leu Val Pro Leu Thr
    50                  55                  60

Gly Gly Gln Lys His Val Ala Gln Ala Ala Glu Phe Trp Val Phe Cys
65                  70                  75                  80

Ala Asp Phe Asn Arg His Leu Gln Ile Cys Pro Asp Ala Gln Leu Gly
                85                  90                  95

Leu Ala Glu Gln Leu Leu Leu Gly Val Val Asp Thr Ala Met Met Gly
            100                 105                 110

Gln Asn Ala Leu Thr Ala Ala Glu Ser Leu Gly Leu Gly Gly Val Tyr
        115                 120                 125

Ile Ser Gly Ile Arg Asn Asn Ile Glu Ser Val Thr Glu Leu Leu Lys
130                 135                 140

Leu Pro Lys His Val Leu Pro Leu Phe Gly Leu Cys Leu Gly Trp Pro
145                 150                 155                 160

Ala Asp Asn Pro Asp Leu Lys Pro Arg Leu Pro Ala Glu Leu Val Val
            165                 170                 175

His Glu Asn Gln Tyr Gln Pro Leu Asp Glu Lys Leu Leu Ala Arg Tyr
            180                 185                 190

Asp Glu Gln Leu Ala Glu Tyr Tyr Leu Thr Arg Gly Ser Asn Thr Arg
            195                 200                 205

Arg Asp Thr Trp Ser Asp His Ile Arg Arg Thr Leu Ile Lys Glu Asn
210                 215                 220

Cys Pro Phe Ile Leu Glu Tyr Leu His Lys Gln Gly Trp Ala Thr Arg
225                 230                 235                 240

<210> SEQ ID NO 88
<211> LENGTH: 249
<212> TYPE: PRT
<213> ORGANISM: Bacillus subtilis
<220> FEATURE:
<221> NAME/KEY: misc_feature
<223> OTHER INFORMATION: subspecies subtilis, NZ isolate

<400> SEQUENCE: 88

Met Asn Asn Thr Ile Glu Thr Ile Leu Asn His Arg Ser Ile Arg Ser
1               5                   10                  15

Phe Thr Asp Gln Leu Leu Thr Ala Glu Glu Ile Asp Ile Leu Val Lys
            20                  25                  30

Ser Ala Gln Ala Ala Ser Thr Ser Ser Tyr Val Gln Ala Tyr Ser Ile
        35                  40                  45

Ile Gly Val Ser Asp Pro Glu Lys Lys Arg Glu Leu Ser Val Leu Ala
50                  55                  60

Gly Asn Gln Pro Tyr Val Glu Asn Asn Gly His Phe Phe Val Phe Cys
65                  70                  75                  80

Ala Asp Leu His Arg His Gln Lys Leu Ala Glu Glu Lys Gly Glu Asn
            85                  90                  95

Ile Ser Glu Leu Leu Glu Asn Thr Glu Met Phe Met Val Ser Leu Ile
            100                 105                 110

Asp Ala Ala Leu Ala Ala Gln Asn Met Ser Val Ala Ala Glu Ser Met
            115                 120                 125

Gly Leu Gly Ile Cys Tyr Ile Gly Gly Ile Arg Asn Glu Leu Asp Lys
130                 135                 140

Val Thr Glu Val Leu Gln Thr Pro Asp His Val Leu Pro Leu Phe Gly
145                 150                 155                 160

Leu Ala Val Gly His Pro Ala Asn Leu Ser Gly Lys Lys Pro Arg Leu
                165                 170                 175

Pro Lys Gln Ala Val Tyr His Glu Asn Thr Tyr Asn Val Asn Ala Asp
            180                 185                 190

Asp Phe Arg Asp Thr Met Asn Ala Tyr Asp Gln Thr Ile Ser Asp Tyr
        195                 200                 205

Tyr Arg Glu Arg Thr Asn Gly Gln Arg Glu Leu Thr Trp Ser Asp Gln
210                 215                 220

Ile Leu Asn Phe Met Lys Gln Lys Pro Pro Thr Tyr Leu Asn Asp Tyr
225                 230                 235                 240

Val Lys Glu Lys Gly Phe Asn Lys Asn
            245

<210> SEQ ID NO 89
<211> LENGTH: 249
<212> TYPE: PRT
<213> ORGANISM: Bacillus subtilis
<220> FEATURE:
<221> NAME/KEY: misc_feature
<223> OTHER INFORMATION: subspecies subtilis, NZ isolate

<400> SEQUENCE: 89

Met Asn Asn Thr Ile Glu Thr Ile Leu Asn His Arg Ser Ile Arg Ser
1               5                   10                  15

Phe Thr Asp Gln Leu Leu Thr Ala Glu Glu Ile Asp Ile Leu Val Lys
            20                  25                  30

Ser Ala Gln Ala Ala Ser Thr Ser Ser Tyr Val Gln Ala Tyr Ser Ile
        35                  40                  45

Ile Gly Val Ser Asp Pro Glu Lys Lys Arg Glu Leu Ser Val Leu Ala
50                  55                  60

Gly Asn Gln Pro Tyr Val Glu Asn Asn Gly His Phe Phe Val Phe Cys
65                  70                  75                  80

Ala Asp Leu His Arg His Gln Lys Leu Ala Glu Glu Lys Gly Glu Asn
            85                  90                  95

```
Ile Ser Glu Leu Leu Glu Asn Thr Glu Met Phe Met Val Ser Leu Ile
            100                 105                 110

Asp Ala Ala Leu Ala Ala Gln Asn Met Ser Val Ala Ala Glu Ser Met
            115                 120                 125

Gly Leu Gly Ile Cys Tyr Ile Gly Gly Ile Arg Asn Glu Leu Asp Lys
            130                 135                 140

Val Thr Glu Val Leu Gln Thr Pro Asp His Val Leu Pro Leu Phe Gly
145                 150                 155                 160

Leu Ala Val Gly His Pro Ala Asn Leu Ser Gly Lys Lys Pro Arg Leu
                165                 170                 175

Pro Lys Gln Ala Val Tyr His Glu Asn Thr Tyr Asn Val Asn Ala Asp
            180                 185                 190

Asp Phe Arg Asp Thr Met Asn Ala Tyr Asp Gln Thr Ile Ser Asp Tyr
            195                 200                 205

Tyr Arg Glu Arg Thr Asn Gly Gln Arg Glu Gly Thr Trp Ser Asp Gln
            210                 215                 220

Ile Leu Asn Phe Met Lys Gln Lys Pro Thr Thr Tyr Leu Asn Asp Tyr
225                 230                 235                 240

Val Lys Glu Lys Gly Phe Asn Lys Asn
                245

<210> SEQ ID NO 90
<211> LENGTH: 249
<212> TYPE: PRT
<213> ORGANISM: Bacillus subtilis
<220> FEATURE:
<221> NAME/KEY: misc_feature
<223> OTHER INFORMATION: subspecies subtilis, NZ isolate

<400> SEQUENCE: 90

Met Asn Asn Thr Ile Glu Thr Ile Leu Asn His Arg Ser Ile Arg Ser
1               5                   10                  15

Phe Thr Asp Gln Leu Leu Thr Ala Glu Glu Ile Asp Ile Leu Val Lys
            20                  25                  30

Ser Ala Gln Ala Ala Ser Thr Ser Ser Tyr Val Gln Ala Tyr Ser Ile
            35                  40                  45

Ile Gly Val Ser Asp Pro Glu Lys Lys Arg Glu Leu Ser Val Leu Ala
        50                  55                  60

Gly Asn Gln Pro Tyr Val Glu Asn Asn Gly His Phe Phe Val Phe Cys
65                  70                  75                  80

Ala Asp Leu His Arg His Gln Lys Leu Ala Glu Glu Lys Gly Glu Asn
                85                  90                  95

Ile Ser Glu Leu Leu Glu Asn Thr Glu Met Phe Met Val Ser Leu Ile
            100                 105                 110

Asp Ala Ala Leu Ala Ala Gln Asn Met Ser Val Ala Ala Glu Ser Met
            115                 120                 125

Gly Leu Gly Ile Cys Tyr Ile Gly Gly Ile Arg Asn Glu Leu Asp Lys
            130                 135                 140

Val Thr Glu Val Leu Gln Thr Pro Asp His Val Leu Pro Leu Phe Gly
145                 150                 155                 160

Leu Ala Val Gly His Pro Ala Asn Leu Ser Gly Lys Lys Pro Arg Leu
                165                 170                 175

Pro Lys Gln Ala Val Tyr His Glu Asn Thr Tyr Asn Val Asn Ala Asp
            180                 185                 190

Asp Phe Arg Asp Thr Met Asn Ala Tyr Asp Gln Thr Ile Ser Asp Tyr
```

|     |     |     | 195 |     |     |     | 200 |     |     |     | 205 |     |     |
| --- | --- | --- | --- | --- | --- | --- | --- | --- | --- | --- | --- | --- | --- |
| Tyr | Arg | Glu | Arg | Thr | Asn | Gly | Gln | Arg | Glu | Glu | Thr | Trp | Ser | Asp | Gln |
|     |     |     | 210 |     |     |     | 215 |     |     |     | 220 |     |     |
| Ile | Leu | Asn | Phe | Met | Lys | Gln | Lys | Pro | Leu | Thr | Tyr | Leu | Asn | Asp | Tyr |
| 225 |     |     |     | 230 |     |     |     |     | 235 |     |     |     |     | 240 |
| Val | Lys | Glu | Lys | Gly | Phe | Asn | Lys | Asn |
|     |     |     |     | 245 |

What we claim is:

1. A method of radioimaging of at least one of a cell and a biological agent in a subject, the method comprising the steps of:
   a) introduction of a bacterial NfsA family nitroreductase to a subject; and
   b) introduction of a radiolabeled imaging probe to the subject;
   wherein the method further comprises radioimaging at least one of the cell and biological agent;
   wherein the NfsA family nitroreductase is capable of activating the imaging probe; and
   wherein steps a) and b) may be carried out concurrently or sequentially in any order;
   wherein the radiolabeled imaging probe comprises a radiolabeled 2-nitroimidazole compound.

2. The method of claim 1, further comprising a step of:
   c) introduction of a prodrug to the subject;
   wherein the NfsA family nitroreductase is capable of activating the prodrug and wherein steps a) to c) may be carried out concurrently or sequentially in any order.

3. The method of claim 1 wherein the NfsA family nitroreductase is introduced using gene-directed enzyme prodrug therapy (GDEPT), virus-directed enzyme prodrug therapy (VDEPT), bacterial-directed enzyme prodrug therapy (BDEPT), *Clostridia*-directed enzyme prodrug therapy (CDEPT) or antibody-directed enzyme prodrug therapy (ADEPT).

4. The method of claim 2 wherein the NfsA family nitroreductase is introduced via a transformed cell and/or biological agent that expresses the NfsA family nitroreductase and the sensitivity of the transformed cell and/or biological agent to the prodrug is improved relative to a cell or biological agent that does not express the NfsA family nitroreductase.

5. The method of claim 2 wherein the prodrug comprises a nitroheterocyclic, nitrocarbocyclic, nitroaromatic, mono-nitrobenzamide, dinitrobenzamide or quinone-derived compound.

6. The method of claim 2 wherein the prodrug is selected from the group consisting of NLCQ-1, RSU-1069, RB6145, CI-1010, Misonidazole, Etanidazole, Nimorazole, Metronidazole, Tinidazole, Ornidazole, Nitrofurantoin, Nitrofurazone, Nifuratel, Nifurtimox, Furazolidinone, SN26634, SN27857, KSI 19, LH7, EF5 (pentafluoroetanidazole), EF3 (trifluoroetanidazole), CB 1954, TH-302, PR-104A, SN27686, SN31609, SN32102, SN28065, SN28099, mitomycin C, porfiromycin, E09 and RHI.

7. The method of claim 2 wherein the prodrug and the radiolabeled imaging probe are the same compound.

8. The method of claim 2, wherein introducing said prodrug is used to diagnose and/or treat a disease selected from the group consisting of cancer, Parkinson's disease, Alzheimer's disease, stroke, heart disease, rheumatological diseases and a disease treated by stem-cell transplantation.

9. The method of claim 1 wherein the NfsA nitroreductase is an NfsA family nitroreductase according to SEQ ID NO 1 to 20.

10. The method of claim 1 wherein the NfsA nitroreductase has an S41Y mutation that confers an increased sensitivity to one or more bioreductive substrates.

* * * * *